(12) United States Patent
Mizuochi et al.

(10) Patent No.: US 10,032,069 B2
(45) Date of Patent: Jul. 24, 2018

(54) EXERCISE ANALYSIS APPARATUS, EXERCISE ANALYSIS METHOD, EXERCISE ANALYSIS PROGRAM, AND EXERCISE ANALYSIS SYSTEM

(71) Applicant: Seiko Epson Corporation, Shinjuku-ku (JP)

(72) Inventors: Shunichi Mizuochi, Matsumoto (JP); Kazumi Matsumoto, Shiojiri (JP); Shuji Uchida, Shiojiri (JP); Ken Watanabe, Matsumoto (JP); Daisuke Sugiya, Chino (JP); Akinobu Sato, Fujimi-machi (JP)

(73) Assignee: Seiko Epson Corporation, Tokyo (JP)

( * ) Notice: Subject to any disclaimer, the term of this patent is extended or adjusted under 35 U.S.C. 154(b) by 131 days.

(21) Appl. No.: 14/814,480

(22) Filed: Jul. 30, 2015

(65) Prior Publication Data

US 2016/0030804 A1    Feb. 4, 2016

(30) Foreign Application Priority Data

Jul. 31, 2014 (JP) ................................ 2014-157201
Jul. 31, 2014 (JP) ................................ 2014-157208
Jun. 5, 2015 (JP) ................................ 2015-115213

(51) Int. Cl.
*A63B 24/00* (2006.01)
*G06K 9/00* (2006.01)
*A61B 5/11* (2006.01)

(52) U.S. Cl.
CPC ............ *G06K 9/00342* (2013.01); *A61B 5/11* (2013.01); *G06K 9/0053* (2013.01); *A61B 2503/10* (2013.01)

(58) Field of Classification Search
CPC ....... A63B 24/00; A63B 24/0087; A61B 5/11; A61B 2503/10; G06K 9/00342; G06K 9/0053
See application file for complete search history.

(56) References Cited

U.S. PATENT DOCUMENTS

| 7,653,508 | B1 * | 1/2010 | Kahn | .................... | G01C 22/006 |
|||||| 33/700 |
| 8,042,390 | B2 * | 10/2011 | Pasolini | ............... | G01C 22/006 |
|||||| 702/160 |
| 8,712,723 | B1 * | 4/2014 | Kahn | ..................... | G01B 21/02 |
|||||| 377/24.2 |
| 8,876,738 | B1 * | 11/2014 | Kahn | .................... | A61B 5/1118 |
|||||| 482/8 |

(Continued)

FOREIGN PATENT DOCUMENTS

| JP | 2011-516210 A | 5/2011 |
| JP | 2011-170559 A | 9/2011 |
| JP | 53144224 B | 10/2013 |

*Primary Examiner* — Glenn Richman
(74) *Attorney, Agent, or Firm* — Kilpatrick Townsend & Stockton LLP

(57) ABSTRACT

An exercise analysis apparatus includes a feature point detection unit that detects a feature point in a user's running by using a detection result from an inertial sensor, and an exercise information generation unit that analyzes the user's running with a timing at which the feature point detection unit detects the feature point as a reference by using the detection result from the inertial sensor, so as to generate exercise information of the user.

12 Claims, 60 Drawing Sheets

(56) References Cited

U.S. PATENT DOCUMENTS

| | | | |
|---|---|---|---|
| 2007/0198187 A1* | 8/2007 | Pasolini | G01P 15/125 73/489 |
| 2009/0258710 A1 | 10/2009 | Quatrochi et al. | |
| 2014/0148931 A1 | 5/2014 | Watanabe et al. | |

* cited by examiner

| DETECTION TIME | ACCELERATION | ANGULAR VELOCITY |
|---|---|---|
| t1 | (ax1, ay1, az1) | (ωx1, ωy1, ωz1) |
| t2(=t1+Δt) | (ax2, ay2, az2) | (ωx2, ωy2, ωz2) |
| t3(=t2+Δt) | (ax3, ay3, az3) | (ωx3, ωy3, ωz3) |
| ⋮ | | |

| POSITIONING TIME | POSITION | VELOCITY | POSITIONING ACCURACY (DOP) | SIGNAL INTENSITY | ... |
|---|---|---|---|---|---|
| T1 | (Px1, Py1, Pz1) | (Vx1, Vy1, Vz1) | DP1 | SS1 | |
| T2 | (Px2, Py2, Pz2) | (Vx2, Vy2, Vz2) | DP2 | SS2 | ... |
| T3 | (Px3, Py3, Pz3) | (Vx3, Vy3, Vz3) | DP3 | SS3 | |
| ⋮ | | | | | |

| DETECTION TIME | GEOMAGNETISM |
|---|---|
| t1 | (mx1, my1, mz1) |
| t2(=t1+Δt) | (mx2, my2, mz2) |
| t3(=t2+Δt) | (mx3, my3, mz3) |
| ⋮ | |

FIG. 36

| | SUN | MON | TUE | WED | THU | FRI | SAT | TOTAL |
|---|---|---|---|---|---|---|---|---|
| | | | | | | | 1 21.09km 2:10'00" | 21.09km |
| | 2 | 3 | 4 | 5 15.25km 1:30'00" | 6 | 7 | 8 10.00km 1:00'00" | 25.25km |
| | 5 20.50km 2:00'00" | 10 | 11 | 12 10.00km 1:00'00" | 13 | 14 | 15 5.00km 0:25'00" | 35.50km |
| | 16 42.19km 4:17'01" | 17 | 18 5.00km 0:25'00" | 19 | 20 | 21 | 22 | 47.19km |
| | 23 | 24 | 25 | 26 | 27 | 28 | 29 | 0.00km |
| | 30 | 31 | | | | | | 0.00km |

‹ › 3 March 2014

420

ADVANCING DIRECTION VELOCITY

ADVANCING DIRECTION ACCELERATION

EXERCISE ANALYSIS APPARATUS, EXERCISE ANALYSIS METHOD, EXERCISE ANALYSIS PROGRAM, AND EXERCISE ANALYSIS SYSTEM

BACKGROUND

1. Technical Field

The present invention relates to an exercise analysis apparatus, an exercise analysis method, an exercise analysis program, and an exercise analysis system.

2. Related Art

JP-A-2011-170559 discloses a system in which gait information indicating characteristics of a user's walking action is calculated on the basis of acceleration information of the user's walking action, and presentation information indicating a relationship between a walking location and a walking state is generated on the basis of the calculated gait information and is presented to a presentation apparatus. The gait information is calculated, for example, by performing respective processes such as frequency analysis using fast Fourier transform, autocorrelation analysis, calculation of a root mean square (RMS) value, and calculation of an integral value, on respective acceleration measurement values in an x axis direction, a y axis direction, and a z axis direction.

JP-T-2011-516210 discloses an apparatus which computes biomechanical parameters of a user's stride on the basis of acceleration data and displays the parameters. As the biomechanical parameters, a landing angle of the leg on the ground, a distance by which the gravity center of a runner proceeds during contact of the foot on the ground, and the like, are disclosed.

However, in a system disclosed in JP-A-2011-170559, the gait information indicting the characteristics of the user's walking action does not include information regarding timing of feature points in landing or kicking for each step of the user, and thus it is hard to extract a tendency of the way of moving the user's body. For this reason, the system disclosed in JP-A-2011-170559 can monitor a user's walking state, but is unlikely to assist the user in improving exercise attainments.

The apparatus disclosed in JP-T-2011-516210 does not have a function of detecting slow turnover of the user's legs. The slow turnover of the legs is a phenomenon in which timing of returning a kicking leg is delayed and the leg remains behind even at the next landing timing in running. In the way of the slow turnover of the legs, since muscles under the knee are frequently used, the user becomes tired early, and it takes time to move the rear leg forward. Therefore, the time for the leg to contact the ground is long, and a speed does not increase either. Not only the slow turnover but also a state of a swing leg (a leg which does not contact the ground) when the foot contacts the ground is an important index in evaluating running, but a method of automating and presenting such information has not been proposed until now.

SUMMARY

An advantage of some aspects of the invention is to provide an exercise analysis apparatus, an exercise analysis method, and an exercise analysis program capable of assisting a user in improving exercise attainments.

Another advantage of some aspects of the invention is to provide an exercise analysis apparatus, an exercise analysis system, an exercise analysis method, and an exercise analysis program capable of presenting information regarding a swing leg when a user's foot contacts the ground.

The invention can be implemented as the following forms or application examples.

APPLICATION EXAMPLE 1

An exercise analysis apparatus according to this application example includes: a feature point detection unit that detects a feature point in a user's running by using a detection result from an inertial sensor; and an exercise information generation unit that analyzes the user's running with a timing at which the feature point detection unit detects the feature point as a reference by using the detection result from the inertial sensor, so as to generate exercise information of the user.

According to the exercise analysis apparatus of this application example, since a tendency of the way of moving the user's body is easily extracted by using the feature point of running as a reference, it is possible to assist the user in improving exercise attainments (for example, exercise performance, a score such as time, and unlikelihood of an injury) on the basis of the exercise information which is generated by using the detection result from the inertial sensor with the feature point as a reference.

APPLICATION EXAMPLE 2

In the exercise analysis apparatus according to the application example, the exercise information generation unit may generate the exercise information by using a detection result from the inertial sensor at the timing at which the feature point detection unit detects the feature point.

According to the exercise analysis apparatus of this application example, it is possible to generate exercise information which reflects a state of the user's body in a feature point and is effective in order to improve exercise attainments of the user, by using a detection result from the inertial sensor in the feature point of running.

APPLICATION EXAMPLE 3

In the exercise analysis apparatus according to the application example, the exercise information generation unit may generate the exercise information by using a detection result from the inertial sensor after the feature point detection unit detects the feature point until the feature point detection unit detects the feature point next.

According to the exercise analysis apparatus of this application example, it is possible to generate exercise information which reflects the way of moving the user's body between two feature points and is effective in order to improve exercise attainments of the user, by using a detection result from the inertial sensor between the two feature points.

APPLICATION EXAMPLE 4

In the exercise analysis apparatus according to the application example, the exercise information generation unit may calculate values of a plurality of items indicating an exercise state of the user with a timing at which the feature point detection unit detects the feature point as a reference by using the detection result from the inertial sensor, and may generate the exercise information by combining the values of the plurality of items with each other.

According to the exercise analysis apparatus of this application example, it is possible to generate exercise information which is effective in order to improve exercise attainments of the user, by combining values of a plurality of items in which an exercise state of the user is reflected with each other.

APPLICATION EXAMPLE 5

In the exercise analysis apparatus according to the application example, the exercise information may include information regarding energy efficiency, an energy loss, or a burden on the body in the user's running.

According to the exercise analysis apparatus of this application example, it is possible to present, to the user, information such as whether or not energy which is consumed due to running is efficiently used for the running, or to what extent damage is accumulated in the body due to the running.

APPLICATION EXAMPLE 6

In the exercise analysis apparatus according to the application example, the exercise information may include information regarding directly-below landing, propulsion efficiency, a brake amount in landing, or a ground contact time in the user's running.

According to the exercise analysis apparatus of this application example, it is possible to present, to the user, information used to determine whether or not the efficient running way, the running way of not causing a fatigue, or the running way of not causing an injury is obtained.

APPLICATION EXAMPLE 7

In the exercise analysis apparatus according to the application example, the exercise information generation unit may generate the exercise information separately for left and right sides of the user's body.

According to the exercise analysis apparatus of this application example, it is possible to present, to the user, exercise states of the left and right sides of the user's body in a separate manner.

APPLICATION EXAMPLE 8

In the exercise analysis apparatus according to the application example, the exercise information may include information regarding a left and right balance of the user's body.

According to the exercise analysis apparatus of this application example, it is possible to present, to the user, information regarding to what extent the left and right sides of the user's body are used in well balance.

APPLICATION EXAMPLE 9

In the exercise analysis apparatus according to the application example may further include an advice information generation unit that generates information regarding an advice for improving exercise attainments of the user by using the exercise information.

The exercise attainments may be, for example, exercise performance, a score such as time, and unlikelihood of an injury.

According to the exercise analysis apparatus of this application example, it is possible to assist the user in improving exercise attainments by presenting an advice corresponding to an exercise state of the user.

APPLICATION EXAMPLE 10

In the exercise analysis apparatus according to the application example, the feature point may be at least one of landing, stepping, and taking-off

APPLICATION EXAMPLE 11

An exercise analysis method according to this application example includes: detecting a feature point in a user's running by using a detection result from an inertial sensor; and analyzing the user's running with a timing at which the feature point is detected as a reference by using the detection result from the inertial sensor, so as to generate exercise information of the user.

According to the exercise analysis method of this application example, since a tendency of the way of moving the user's body is easily extracted by using the feature point of running as a reference, it is possible to assist the user in improving exercise attainments on the basis of the exercise information which is generated by using the detection result from the inertial sensor with the feature point as a reference.

APPLICATION EXAMPLE 12

An exercise analysis program according to this application example causes a computer to execute detecting a feature point in a user's running by using a detection result from an inertial sensor; and analyzing the user's running with a timing at which the feature point is detected as a reference by using the detection result from the inertial sensor, so as to generate exercise information of the user.

According to the exercise analysis program of this application example, since a tendency of the way of moving the user's body is easily extracted by using the feature point of running as a reference, it is possible to assist the user in improving exercise attainments on the basis of the exercise information which is generated by using the detection result from the inertial sensor with the feature point as a reference.

APPLICATION EXAMPLE 13

An exercise analysis apparatus according to this application example includes: a calculation unit that generates exercise information of a user by using a detection result from an inertial sensor; and a swing leg information generation unit that generates information regarding a swing leg while the user's foot contacts a ground, by using the exercise information.

The exercise information may include, for example, at least some information regarding an acceleration, an angular velocity, a velocity, a position, and an attitude angle which change due to the user's exercise.

The information regarding the swing leg may be, for example, information regarding an angle formed between a predetermined part (for example, the femur) of the swing leg and a horizontal plane or a vertical plane, and may be information regarding a distance (height) from the horizontal plane to a predetermined part (for example, the knee) of the swing leg.

An angle of the swing leg may be, for example, an angle formed between the femur of the swing leg and the horizontal plane or the vertical plane.

According to the exercise analysis apparatus of this application example, since the inertial sensor can also detect a fine motion of the user, it is possible to generate and present information regarding the swing leg by performing calculation by using a detection result from the inertial sensor.

APPLICATION EXAMPLE 14

In the exercise analysis apparatus according to the application example, the swing leg information generation unit may generate information regarding the swing leg at the time when a predetermined state occurs while the user's foot contacts the ground, and the time when the predetermined state occurs may be the time when the user's foot lands (immediately after landing), the time of mid-stance, the time of stepping, or the time of taking-off (immediately before taking-off).

According to the exercise analysis apparatus of this application example, it is possible to provide, for example, information regarding slow turnover of the legs in the user's exercise.

APPLICATION EXAMPLE 15

In the exercise analysis apparatus according to the application example, the exercise information may include information regarding an attitude angle of the user's body, and the swing leg information generation unit may generate the information regarding the swing leg by using the information regarding the attitude angle.

The information regarding an attitude angle may include, for example, at least one of information pieces regarding a roll angle, a pitch angle, and a yaw angle which change due to the user's exercise.

According to the exercise analysis apparatus of this application example, it is possible to generate information regarding the swing leg while the user's foot contacts the ground with relatively high accuracy by using information regarding an attitude angle which is considered to be correlated with a state of the swing leg.

APPLICATION EXAMPLE 16

In the exercise analysis apparatus according to the application example, the information regarding the swing leg may include information regarding an angle of the swing leg at the time when the predetermined state occurs while the user's foot contacts the ground.

According to the exercise analysis apparatus of this application example, it is possible to generate information regarding an angle of the swing leg while the user's foot contacts the ground with relatively high accuracy.

APPLICATION EXAMPLE 17

In the exercise analysis apparatus according to the application example, the swing leg information generation unit may compute a value of an index correlated with an angle of the swing leg, and may estimate the angle of the swing leg by using the value of the index.

According to the exercise analysis apparatus of this application example, it is possible to estimate an angle of the swing leg with relatively high accuracy by using a value of an index which is correlated with the angle of the swing leg while the user's foot contacts the ground.

APPLICATION EXAMPLE 18

In the exercise analysis apparatus according to the application example may further include a feature point detection unit that detects a feature point in an exercise of the user corresponding to the predetermined state, and the swing leg information generation unit may compute the value of the index by using a detection result of the feature point.

According to the exercise analysis apparatus of this application example, it is possible to compute a value of an index which is correlated with an angle of the swing leg when the user's foot is in a predetermined state, on the basis of the detected feature point.

APPLICATION EXAMPLE 19

In the exercise analysis apparatus according to the application example, the index may be a difference between a time point at which an attitude angle of the user's body satisfies a predetermined condition and a time point at which the predetermined state occurs while the user's foot contacts the ground.

According to the exercise analysis apparatus of this application example, if a value of the index is great, it can be said that there is a tendency that a time period from a predetermined state to the start of the next motion is long, and time is required to return the leg, and thus it is possible to estimate an angle of the swing leg by using the index.

APPLICATION EXAMPLE 20

In the exercise analysis apparatus according to the application example, the index may be a difference between a value of an attitude angle at the time when the attitude angle of the user's body satisfies a predetermined condition and a value of the attitude angle at the time when the predetermined state occurs while the user's foot contacts the ground.

According to the exercise analysis apparatus of this application example, if a value of the index is great, it can be said that there is a tendency that a change in the attitude angle is considerable from a predetermined state to the start of the next motion, and a motion for returning the leg is considerable, and thus it is possible to estimate an angle of the swing leg with high accuracy by using the index.

APPLICATION EXAMPLE 21

In the exercise analysis apparatus according to the application example, the attitude angle may be a yaw angle, and the time when the attitude angle may satisfy the predetermined condition is the time when the yaw angle is the maximum or the minimum between landing and taking-off of the user's foot.

According to the exercise analysis apparatus of this application example, the time when a yaw angle is the maximum or the minimum between landing and taking-off of the user's foot corresponds to the time of starting the next motion, and if a value of the index is great, a time period from a predetermined state to the start of the next motion is long, or a change in the yaw angle is considerable from the predetermined state to the start of the next motion, and time or a motion for returning the leg is considerable, and thus it is possible to estimate an angle of the swing leg with high accuracy by using the index.

APPLICATION EXAMPLE 22

In the exercise analysis apparatus according to the application example, the index may be an attitude angle of the user's body at the time when the predetermined state occurs while the user's foot contacts the ground.

According to the exercise analysis apparatus of this application example, since an attitude angle of the user's body is correlated with an angle of the swing leg when the user's foot is in the predetermined state, it is possible to estimate an angle of the swing leg with high accuracy by using the index.

APPLICATION EXAMPLE 23

In the exercise analysis apparatus according to the application example, the attitude angle may be a pitch angle.

According to the exercise analysis apparatus of this application example, since the swing leg is located backward (at a higher position) as the user's body tilts forward when the user's foot is in the predetermined state, a pitch angle of the user's body is highly correlated with an angle of the swing leg, and thus it is possible to estimate an angle of the swing leg with high accuracy by using the index.

APPLICATION EXAMPLE 24

In the exercise analysis apparatus according to the application example, the inertial sensor may be mounted on the user's body.

According to the exercise analysis apparatus of this application example, since the inertial sensor can also detect a fine motion of the user's body, it is possible to compute (estimate) an angle of the swing leg while the user's foot contacts the ground with high accuracy by performing calculation by using a detection result from the inertial sensor.

APPLICATION EXAMPLE 25

An exercise analysis system according to this application example includes: the exercise analysis apparatus according to according to any one of the application examples described above; and a notification apparatus that acquires the information regarding the swing leg from the exercise analysis apparatus and notifies the user of information regarding an exercise state during the user's exercise.

According to the exercise analysis system of this application example, the user can perform an exercise while being aware of a state of the swing leg on the basis of the information of which a notification is sent.

APPLICATION EXAMPLE 26

An exercise analysis system according to this application example includes: the exercise analysis apparatus according to according to any one of the application examples described above; and an information analysis apparatus that acquires the information regarding the swing leg generated by the exercise analysis apparatus and generates analysis information of exercise performance of the user.

The exercise performance may be, for example, a technical skill and the endurance.

According to the exercise analysis system of this application example, the user can acquire specific information regarding a state of the swing leg on the basis of the analysis information after finishing the exercise.

APPLICATION EXAMPLE 27

An exercise analysis method according to this application example includes: generating exercise information of a user by using a detection result from an inertial sensor; and generating information regarding a swing leg while the user's foot contacts a ground, by using the exercise information.

According to the exercise analysis method of this application example, it is possible to generate and present information regarding the swing leg by performing calculation by using a detection result from the inertial sensor which can detect a fine motion of the user.

APPLICATION EXAMPLE 28

An exercise analysis program according to this application example causes a computer to execute generating exercise information of a user by using a detection result from an inertial sensor; and generating information regarding a swing leg while the user's foot contacts a ground, by using the exercise information.

According to the exercise analysis program of this application example, it is possible to generate and present information regarding the swing leg by performing calculation by using a detection result from the inertial sensor which can detect a fine motion of the user.

BRIEF DESCRIPTION OF THE DRAWINGS

The invention will be described with reference to the accompanying drawings, wherein like numbers reference like elements.

FIG. 3 is a diagram illustrating a configuration example of a sensing data table.

FIG. 4 is a diagram illustrating a configuration example of a GPS data table.

FIG. 5 is a diagram illustrating a configuration example of a geomagnetic data table.

FIG. 36 is a diagram illustrating an example of the whole analysis screen.

DESCRIPTION OF EXEMPLARY EMBODIMENTS

Embodiments

Figure 1:
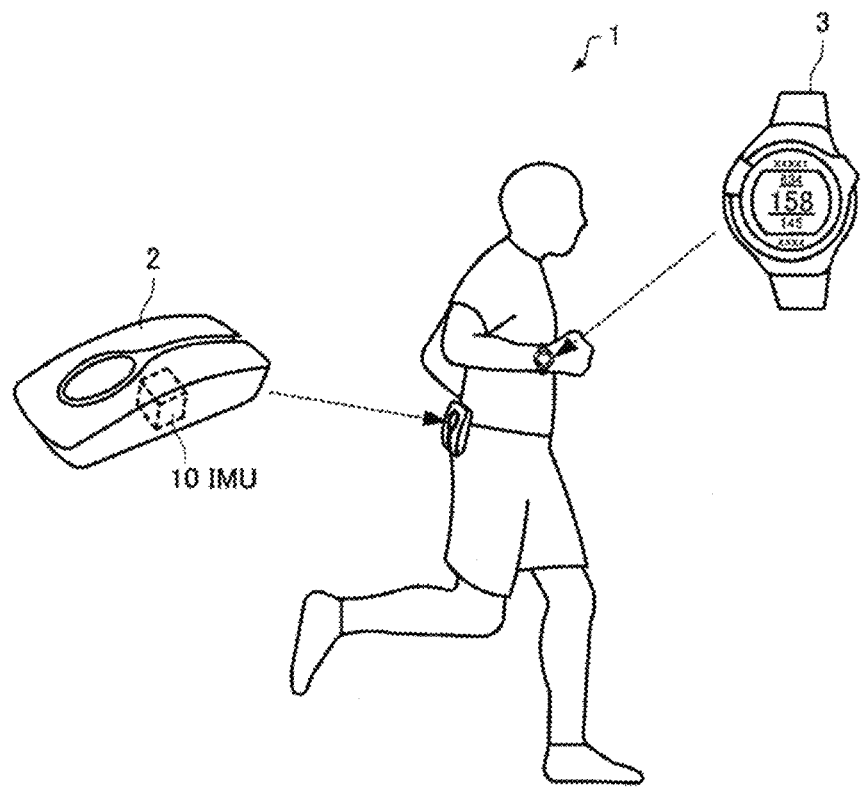
FIG. 1 is a diagram illustrating a summary of an exercise analysis system of a first embodiment.

An exercise analysis apparatus of the present embodiment includes a feature point detection unit that detects a feature point in a user's exercise by using a detection result from an inertial sensor; and an exercise information generation unit that analyzes the user's exercise with a timing at which the feature point detection unit detects the feature point as a reference by using the detection result from the inertial sensor, so as to generate exercise information of the user.

According to the exercise analysis apparatus of the present embodiment, since a tendency of the way of moving the user's body is easily extracted by using the feature point of an exercise as a reference, it is possible to assist the user in improving exercise attainments (for example, exercise performance, a score such as time, and unlikelihood of an injury) on the basis of the exercise information which is generated by using the detection result from the inertial sensor with the feature point as a reference.

In the exercise analysis apparatus of the present embodiment, the exercise information generation unit may generate the exercise information by using a detection result from the inertial sensor at the timing at which the feature point detection unit detects the feature point.

According to the exercise analysis apparatus of the present embodiment, it is possible to generate exercise information which reflects a state of the user's body in a feature point and is effective in order to improve exercise attainments of the user, by using a detection result from the inertial sensor in the feature point of exercise.

In the exercise analysis apparatus of the present embodiment, the exercise information generation unit may generate the exercise information by using a detection result from the inertial sensor after the feature point detection unit detects the feature point until the feature point detection unit detects the feature point next.

According to the exercise analysis apparatus of the present embodiment, it is possible to generate exercise information which reflects the way of moving the user's body between two feature points and is effective in order to improve exercise attainments of the user, by using a detection result from the inertial sensor between the two feature points.

In the exercise analysis apparatus of the present embodiment, the exercise information generation unit may calculate values of a plurality of items indicating an exercise state of the user with a timing at which the feature point detection unit detects the feature point as a reference by using the detection result from the inertial sensor, and may generate the exercise information by combining the values of the plurality of items with each other.

According to the exercise analysis apparatus of the present embodiment, it is possible to generate exercise information which is effective in order to improve exercise attainments of the user, by combining values of a plurality of items in which an exercise state of the user is reflected with each other.

In the exercise analysis apparatus of the present embodiment, the exercise information may include information regarding energy efficiency, an energy loss, or a burden on the body in the user's running.

According to the exercise analysis apparatus of the present embodiment, it is possible to present, to the user, information such as whether or not energy which is consumed due to an exercise is efficiently used for the running, or to what extent damage is accumulated in the body due to the exercise.

In the exercise analysis apparatus of the present embodiment, the exercise information may include information regarding directly-below landing, propulsion efficiency, a brake amount in landing, or a ground contact time in the user's running.

According to the exercise analysis apparatus of the present embodiment, it is possible to present, to the user, information used to determine whether or not the efficient running way, the running way of not causing a fatigue, or the running way of not causing an injury is obtained.

In the exercise analysis apparatus of the present embodiment, the exercise information generation unit may generate the exercise information separately for left and right sides of the user's body.

According to the exercise analysis apparatus of the present embodiment, it is possible to present, to the user, exercise states of the left and right sides of the user's body in a separate manner.

In the exercise analysis apparatus of the present embodiment, the exercise information may include information regarding a left and right balance of the user's body.

According to the exercise analysis apparatus of the present embodiment, it is possible to present, to the user, information regarding to what extent the left and right sides of the user's body are used in well balance.

The exercise analysis apparatus of the present embodiment may further comprise an advice information generation unit that generates information regarding an advice for improving exercise attainments of the user by using the exercise information.

The exercise attainments may be, for example, exercise performance, a score such as time, and unlikelihood of an injury.

According to the exercise analysis apparatus of the present embodiment, it is possible to assist the user in improving exercise attainments by presenting an advice corresponding to an exercise state of the user.

An exercise analysis method of the present embodiment includes detecting a feature point in a user's exercise by using a detection result from an inertial sensor; and analyzing the user's exercise with a timing at which the feature point detection unit detects the feature point as a reference by using the detection result from the inertial sensor, so as to generate exercise information of the user.

According to the exercise analysis method of the present embodiment, since a tendency of the way of moving the user's body is easily extracted by using the feature point of an exercise as a reference, it is possible to assist the user in improving exercise attainments on the basis of the exercise information which is generated by using the detection result from the inertial sensor with the feature point as a reference.

A program of the present embodiment causes a computer to execute detecting a feature point in a user's exercise by using a detection result from an inertial sensor; and analyzing the user's exercise with a timing at which the feature point detection unit detects the feature point as a reference by using the detection result from the inertial sensor, so as to generate exercise information of the user.

According to the program of the present embodiment, since a tendency of the way of moving the user's body is easily extracted by using the feature point of an exercise as a reference, it is possible to assist the user in improving exercise attainments on the basis of the exercise information which is generated by using the detection result from the inertial sensor with the feature point as a reference.

An exercise analysis apparatus of the present embodiment includes a calculation unit that generates exercise information of a user by using a detection result from an inertial sensor; and a swing leg information generation unit that generates information regarding a swing leg while the user's foot contacts a ground, by using the exercise information.

The exercise information may include, for example, at least some information regarding an acceleration, an angular velocity, a velocity, a position, and an attitude angle which change due to the user's exercise.

The information regarding the swing leg may be, for example, information regarding an angle formed between a predetermined part (for example, the femur) of the swing leg and a horizontal plane or a vertical plane, and may be information regarding a distance (height) from the horizontal plane to a predetermined part (for example, the knee) of the swing leg.

An angle of the swing leg may be, for example, an angle formed between the femur of the swing leg and the horizontal plane or the vertical plane.

The time when the predetermined state occurs while the user's foot contacts the ground is the time when the user's foot lands (right after landing), the time of mid-stance, the time of stepping, or the time of taking-off (right before taking-off).

According to the exercise analysis apparatus of the present embodiment, since the inertial sensor can also detect a fine motion of the user, it is possible to generate and present information regarding the swing leg by performing calculation by using a detection result from the inertial sensor.

In the exercise analysis apparatus of the present embodiment, the exercise information may include information regarding an attitude angle of the user's body, and the swing leg information generation unit may generate the information regarding the swing leg by using the information regarding the attitude angle.

The information regarding an attitude angle may include, for example, at least one of information pieces regarding a roll angle, a pitch angle, and a yaw angle which change due to the user's exercise.

According to the exercise analysis apparatus of the present embodiment, it is possible to generate information regarding the swing leg while the user's foot contacts the ground with relatively high accuracy by using information regarding an attitude angle which is considered to be correlated with a state of the swing leg.

In the exercise analysis apparatus of the present embodiment, the information regarding the swing leg may include information regarding an angle of the swing leg at the time when the predetermined state occurs while the user's foot contacts the ground.

According to the exercise analysis apparatus of the present embodiment, it is possible to generate information regarding the swing leg while the user's foot contacts the ground with relatively high accuracy.

In the exercise analysis apparatus of the present embodiment, the swing leg information generation unit may compute a value of an index correlated with an angle of the swing leg, and may estimate the angle of the swing leg by using the value of the index.

According to the exercise analysis apparatus of the present embodiment, it is possible to estimate an angle of the swing leg with relatively high accuracy by using a value of an index which is correlated with the angle of the swing leg while the user's foot contacts the ground.

The exercise analysis apparatus of the present embodiment may further include a feature point detection unit that detects a feature point in an exercise of the user corresponding to the predetermined state, and the swing leg information generation unit may compute the value of the index by using a detection result of the feature point.

According to the exercise analysis apparatus of the present embodiment, it is possible to compute a value of an index which is correlated with an angle of the swing leg when the user's foot is in a predetermined state, on the basis of the detected feature point.

In the exercise analysis apparatus of the present embodiment, the index may be a difference between a time point at which an attitude angle of the user's body satisfies a predetermined condition and a time point at which the predetermined state occurs while the user's foot contacts the ground.

According to the exercise analysis apparatus of the present embodiment, if a value of the index is great, it can be said that there is a tendency that a time period from a predetermined state to the start of the next motion is long, and time is required to return the leg, and thus it is possible to estimate an angle of the swing leg by using the index.

In the exercise analysis apparatus of the present embodiment, the index may be a difference between a value of an attitude angle at the time when the attitude angle of the user's body satisfies a predetermined condition and a value of the attitude angle at the time when the predetermined state occurs while the user's foot contacts the ground.

According to the exercise analysis apparatus of the present embodiment, if a value of the index is great, it can be said that there is a tendency that a change in the attitude angle is considerable from a predetermined state to the start of the next motion, and a motion for returning the leg is considerable, and thus it is possible to estimate an angle of the swing leg with high accuracy by using the index.

In the exercise analysis apparatus of the present embodiment, the attitude angle may be a yaw angle, and the time when the attitude angle satisfies the predetermined condition may be the time when the yaw angle is the maximum or the minimum between landing and taking-off of the user's foot.

According to the exercise analysis apparatus of the present embodiment, the time when a yaw angle is the maximum or the minimum between landing and taking-off of the user's foot corresponds to the time of starting the next motion, and if a value of the index is great, there is a tendency that a time period from a predetermined state to the start of the next motion is long, or a change in the yaw angle is considerable from the predetermined state to the start of the next motion, and time or a motion for returning the leg is considerable, and thus it is possible to estimate an angle of the swing leg with high accuracy by using the index.

In the exercise analysis apparatus of the present embodiment, the index may be an attitude angle of the user's body at the time when the predetermined state occurs while the user's foot contacts the ground.

According to the exercise analysis apparatus of the present embodiment, since an attitude angle of the user's body is correlated with an angle of the swing leg when the user's foot is in the predetermined state, it is possible to estimate an angle of the swing leg with high accuracy by using the index.

In the exercise analysis apparatus of the present embodiment, the attitude angle may be a pitch angle.

According to the exercise analysis apparatus of the present embodiment, since the swing leg is located backward (at a higher position) as the user's body tilts forward when the user's foot is in the predetermined state, a pitch angle of the user's body is highly correlated with an angle of the swing leg, and thus it is possible to estimate an angle of the swing leg with high accuracy by using the index.

In the exercise analysis apparatus of the present embodiment, the time when the predetermined state occurs while the user's foot contacts the ground may be the time when the user's foot lands.

According to the exercise analysis apparatus of the present embodiment, it is possible to provide, for example, information regarding slow turnover of the legs in the user's exercise.

In the exercise analysis apparatus of the present embodiment, the inertial sensor may be mounted on the user's body.

According to the exercise analysis apparatus of the present embodiment, since the inertial sensor can also detect a fine motion of the user's body, it is possible to compute (estimate) an angle of the swing leg while the user's foot contacts the ground with high accuracy by performing calculation by using a detection result from the inertial sensor.

An exercise analysis system of the present embodiment includes any one of the exercise analysis apparatuses; and a notification apparatus that acquires information regarding the swing leg from the exercise analysis apparatus and notifies the user of information regarding an exercise state during the user's exercise.

According to the exercise analysis system of the present embodiment, the user can perform an exercise while being aware of a state of the swing leg on the basis of the information of which a notification is sent.

An exercise analysis system of the present embodiment includes any one of the exercise analysis apparatuses; and an information analysis apparatus that acquires information regarding the swing leg generated by the exercise analysis apparatus and generates analysis information of exercise performance of the user.

The exercise performance may be, for example, a technical skill and the endurance.

According to the exercise analysis system of the present embodiment, the user can acquire specific information regarding a state of the swing leg on the basis of the analysis information after finishing the exercise.

An exercise analysis method of the present embodiment includes generating exercise information of a user by using a detection result from an inertial sensor; and generating information regarding a swing leg at the time when a predetermined state occurs while the user's foot contacts a ground, by using the exercise information.

According to the exercise analysis method of the present embodiment, it is possible to generate and present information regarding the swing leg by performing calculation by using a detection result from the inertial sensor which can detect a fine motion of the user.

A program of the present embodiment causes a computer to perform generating exercise information of a user by using a detection result from an inertial sensor; and generating information regarding a swing leg while the user's foot contacts a ground, by using the exercise information.

According to the program of the present embodiment, it is possible to generate and present information regarding the swing leg by performing calculation by using a detection result from the inertial sensor which can detect a fine motion of the user.

Hereinafter, preferred embodiments of the invention will be described in detail with reference to the drawings. The embodiments described below are not intended to improperly limit the configuration of the invention disclosed in the appended claims. It cannot be said that all constituent elements described below are essential constituent elements of the invention.

1. First Embodiment
1-1 Summary of Exercise Analysis System
FIG. 1 is a diagram for explaining a summary of an exercise analysis system 1 according to a first embodiment.

As illustrated in FIG. 1, the exercise analysis system 1 of the first embodiment includes an exercise analysis apparatus 2 and a notification apparatus 3. The exercise analysis apparatus 2 is mounted on a body part (for example, a right waist, a left waist, or a central part of the waist) of a user. The exercise analysis apparatus 2 has an inertial measurement unit (IMU) 10 built thereinto, recognizes a motion of the user in running (including walking), computes velocity, a position, attitude angles (a roll angle, a pitch angle, and a yaw angle), and the like, and analyzes a user's exercise so as to generate exercise analysis information. In the present embodiment, the exercise analysis apparatus 2 is mounted on the user so that one detection axis (hereinafter, referred to as a z axis) of the inertial measurement unit (IMU) 10 substantially matches the gravitational acceleration direction (vertically downward direction) in a state in which the user stands still. The exercise analysis apparatus 2 transmits at least a part of the generated exercise analysis information to the notification apparatus 3.

The notification apparatus 3 is a wrist type (wristwatch type) portable information apparatus and is mounted on a user's wrist or the like. However, the notification apparatus 3 may be a portable information apparatus such as a head mounted display (HMD) or a smart phone. The user operates the notification apparatus 3 before running or during running, so as to instruct the exercise analysis apparatus 2 to start or finish measurement (an inertial navigation calculation process or an exercise analysis process which will be described later). The user operates the notification apparatus 3 after the running, so as to instruct the exercise analysis apparatus 2 to start or finish a running analysis process (which will be described later). The notification apparatus 3 transmits a command for instructing measurement to be started or finished, a command for instructing the running analysis process to be started or finished, and the like to the exercise analysis apparatus 2. The notification apparatus 3 may be a display apparatus.

If a command for starting measurement is received, the exercise analysis apparatus 2 causes the inertial measurement unit (IMU) 10 to start measurement, and analyzes a user's running on the basis of a measurement result so as to generate exercise analysis information. The exercise analysis apparatus 2 transmits the generated exercise analysis information to the notification apparatus 3. The notification apparatus 3 receives the exercise analysis information, and presents the received exercise analysis information to the user in various forms such as text, graphics, sound, and vibration. The user can recognize the exercise analysis information via the notification apparatus 3 during running.

If a command for instructing the running analysis process to be started is received, the exercise analysis apparatus 2 analyzes past running by using exercise analysis information generated during the past running, and transmits information regarding an analysis result to the notification apparatus 3 or an information apparatus such as a personal computer or a smart phone (not illustrated). The notification apparatus 3 or the information apparatus receives the information regarding the analysis result, and presents the received exercise analysis information to the user in various forms such as text, graphics, sound, and vibration. The user can recognize the analysis result of the past running via the notification apparatus 3 or the information apparatus.

Data communication between the exercise analysis apparatus 2 and the notification apparatus 3 may be wireless communication or wired communication.

In the present embodiment, hereinafter, as an example, a detailed description will be made of a case where the exercise analysis apparatus 2 generates exercise analysis information during the user's running exercise (running), but the exercise analysis system 1 of the present embodiment is also applicable to a case where exercise analysis information is generated in exercises other than running.

1-2. Coordinate Systems

Coordinate systems necessary in the following description are defined.

Figure 2:
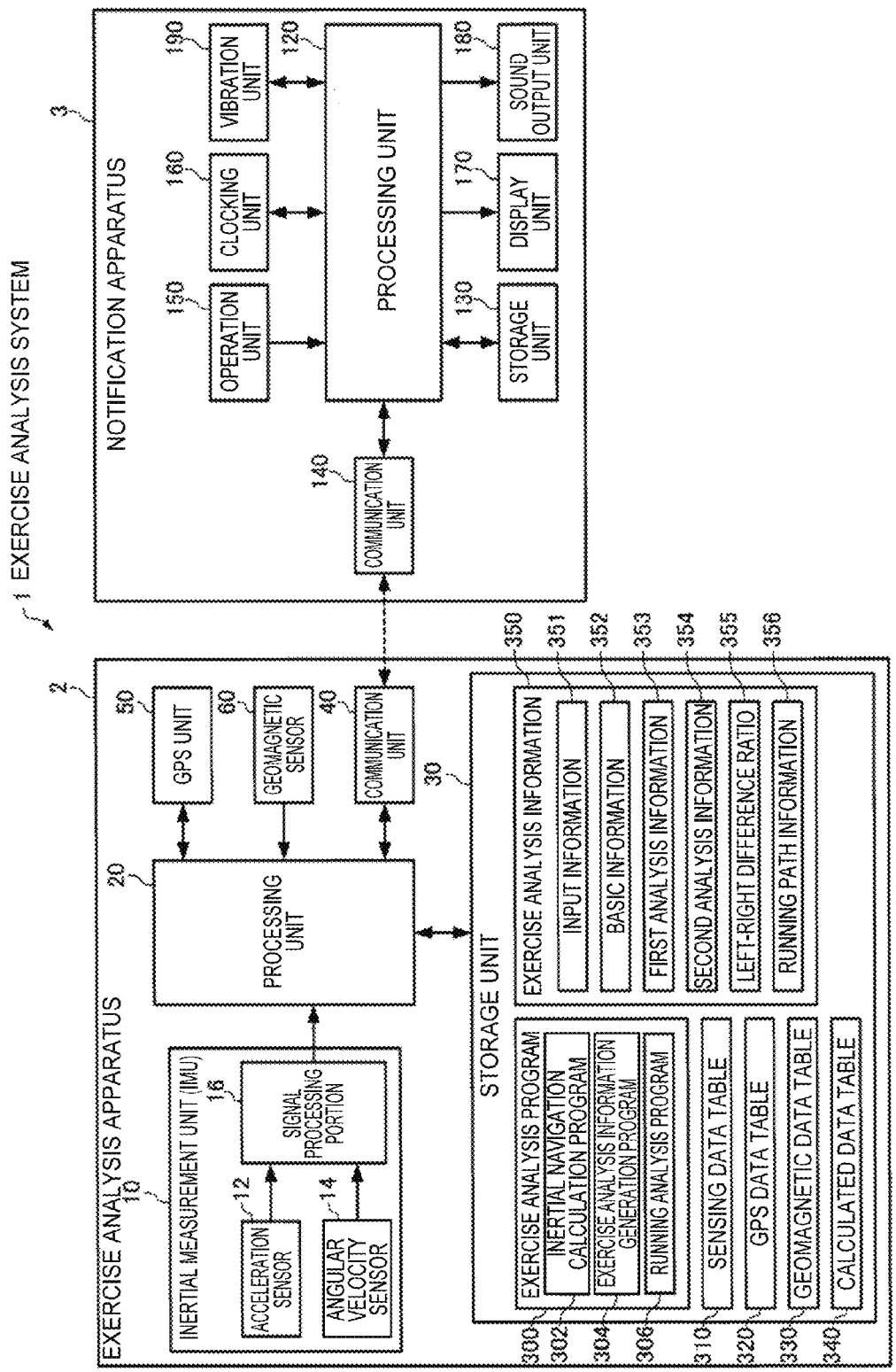
FIG. 2 is a functional block diagram illustrating a configuration example of an exercise analysis apparatus and a notification apparatus in the first embodiment.

Earth centered earth fixed frame (e frame): right handed three-dimensional orthogonal coordinates in which the center of the earth is set as an origin, and a z axis is taken so as to be parallel to the axis of the earth Navigation frame (n frame): three-dimensional orthogonal coordinates in which a moving body (user) is set as an origin, and an x axis is set to the north, a y axis is set to the east, and a z axis is set to the gravitational direction Body frame (b frame): three-dimensional orthogonal coordinates using a sensor (the inertial measurement unit (IMU) 10) as a reference Moving frame (m frame): right handed three-dimensional orthogonal coordinates in which a moving body (user) is set as an origin, and an advancing direction of the moving body (user) is set as an x axis 1-3. Configuration of Exercise Analysis System FIG. 2 is a functional block diagram illustrating a configuration example of the exercise analysis apparatus 2 and the notification apparatus 3 in the first embodiment. As illustrated in FIG. 2, the exercise analysis apparatus 2 includes the inertial measurement unit (IMU) 10, a processing unit 20, a storage unit 30, a communication unit 40, a global positioning system (GPS) unit 50, and a geomagnetic sensor 60. However, the exercise analysis apparatus 2 of the present embodiment may have a configuration in which some of the constituent elements are deleted or changed, or other constituent elements may be added thereto.

The inertial measurement unit 10 (an example of an inertial sensor) includes an acceleration sensor 12, an angular velocity sensor 14, and a signal processing portion 16.

The acceleration sensor 12 detects respective accelerations in the three-axis directions which intersect each other (ideally, perpendicular to each other), and outputs a digital signal (acceleration data) corresponding to magnitudes and directions of the detected three-axis accelerations.

The angular velocity sensor 14 detects respective angular velocities in the three-axis directions which intersect each other (ideally, perpendicular to each other), and outputs a digital signal (angular velocity data) corresponding to magnitudes and directions of the detected three-axis angular velocities.

The signal processing portion 16 receives the acceleration data and the angular velocity data from the acceleration sensor 12 and the angular velocity sensor 14, respectively, adds time information thereto, stores the data items and the time information in a storage unit (not illustrated), generates sensing data in which the stored acceleration data, angular velocity data and time information conform to a predetermined format, and outputs the sensing data to the processing unit 20.

The acceleration sensor 12 and the angular velocity sensor 14 are ideally installed so as to match three axes of a sensor coordinate system (b frame) with the inertial measurement unit 10 as a reference, but, in practice, an error occurs in an installation angle. Therefore, the signal processing portion 16 performs a process of converting acceleration data and the angular velocity data into data of the sensor coordinate system (b frame) by using a correction parameter which is calculated in advance according to the installation angle error. Instead of the signal processing portion 16, the processing unit 20 to be described later may perform the process.

The signal processing portion 16 may perform a temperature correction process on the acceleration sensor 12 and the angular velocity sensor 14. Instead of the signal processing portion 16, the processing unit 20 to be described later may perform the temperature correction process, and a temperature correction function may be incorporated into the acceleration sensor 12 and the angular velocity sensor 14.

The acceleration sensor 12 and the angular velocity sensor 14 may output analog signals, and, in this case, the signal processing portion 16 may A/D convert an output signal from the acceleration sensor 12 and an output signal from the angular velocity sensor 14 so as to generate sensing data.

The GPS unit 50 receives a GPS satellite signal which is transmitted from a GPS satellite which is one type of positioning satellite, performs positioning computation by using the GPS satellite signal so as to calculate a position and velocity (which is a vector including a magnitude and a direction) of the user in n frames, and outputs GPS data in which time information or positioning accuracy information is added to the calculated results to the processing unit 20. A method of calculating a position or velocity or a method of generating by using GPS is well known, and thus detailed description thereof will be omitted.

The geomagnetic sensor 60 detects respective geomagnetisms in the three-axis directions which intersect each other (ideally, perpendicular to each other), and outputs a digital signal (geomagnetic data) corresponding to magnitudes and directions of the detected three-axis geomagnetisms. Here, the geomagnetic sensor 60 may output an analog signal, and, in this case, the processing unit 20 may A/D converts an output signal from the geomagnetic sensor 60 so as to generate geomagnetic data.

The processing unit 20 is constituted of, for example, a central processing unit (CPU), a digital signal processor (DSP), or an application specific integrated circuit (ASIC), and performs various calculation processes or control processes according to various programs stored in the storage unit 30. Particularly, the processing unit 20 receives sensing data, GPS data, and geomagnetic data from the inertial measurement unit 10, the GPS unit 50, and the geomagnetic sensor 60, respectively, and calculates a velocity, a position, an attitude angle, and the like of the user by using the data. The processing unit 20 performs various calculation processes by using the calculated information so as to analyze exercise of the user and to generate various pieces of exercise analysis information which will be described later. The processing unit 20 transmits some (output information during running or output information after running which will be described later) of the generated pieces of exercise analysis information to the notification apparatus 3 via the communication unit 40, and the notification apparatus 3 outputs the received exercise analysis information in a form of text, an image, sound, vibration, or the like.

The storage unit 30 is constituted of, for example, recording media including various IC memories such as a read only memory (ROM), a flash ROM, and a random access memory (RAM), a hard disk, and a memory card.

Figure 41:
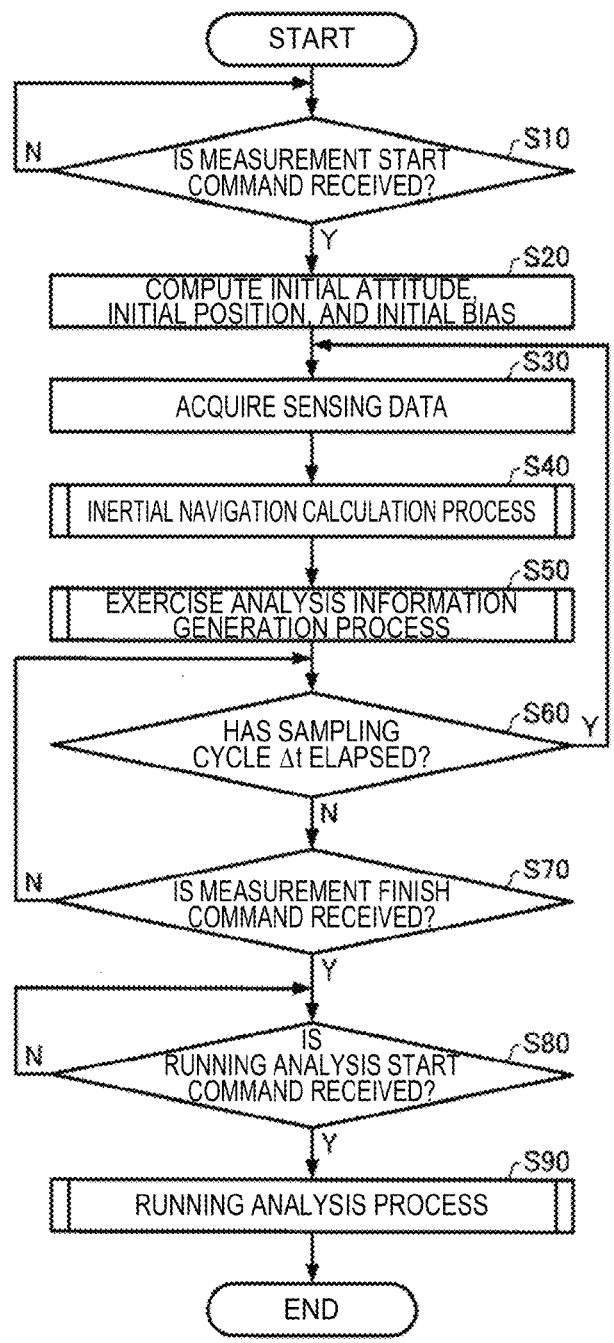
FIG. 41 is a flowchart illustrating an example of procedures of an exercise analysis process in the first embodiment.

The storage unit 30 stores an exercise analysis program 300 which is read by the processing unit 20 and is used to perform an exercise analysis process (refer to FIG. 41). The exercise analysis program 300 includes, as sub-routines, an inertial navigation calculation program 302 for performing an inertial navigation calculation process (refer to FIG. 42), an exercise analysis information generation program 304 for performing an exercise analysis information generation process (refer to FIG. 44), and a running analysis program 306 for performing a running analysis process (refer to FIG. 45).

The storage unit 30 stores a sensing data table 310, a GPS data table 320, a geomagnetic data table 330, a calculated data table 340, exercise analysis information 350, and the like.

The sensing data table 310 is a data table which stores sensing data (a detection result in the inertial measurement unit 10) received by the processing unit 20 from the inertial measurement unit 10 in a time series. FIG. 3 is a diagram illustrating a configuration example of the sensing data table 310. As illustrated in FIG. 3, the sensing data table 310 is configured so that sensing data items in which the detection time 311 in the inertial measurement unit 10, an acceleration 312 detected by the acceleration sensor 12, and an angular velocity 313 detected by the angular velocity sensor 14 are correlated with each other are arranged in a time series. When measurement is started, the processing unit 20 adds new sensing data to the sensing data table 310 whenever a sampling cycle Δt (for example, 20 ms or 10 ms) elapses. The processing unit 20 corrects an acceleration bias and an angular velocity bias which are estimated according to error estimation (which will be described later) using the extended Karman filter, and updates the sensing data table 310 by overwriting the corrected acceleration and angular velocity to the sensing data table.

The GPS data table 320 is a data table which stores GPS data (a detection result in the GPS unit (GPS sensor) 50) received by the processing unit 20 from the GPS unit 50 in a time series. FIG. 4 is a diagram illustrating a configuration example of the GPS data table 320. As illustrated in FIG. 4, the GPS data table 320 is configured so that GPS data items in which the time 321 at which the GPS unit 50 performs positioning computation, a position 322 calculated through the positioning computation, a velocity 323 calculated through the positioning computation, positioning accuracy (dilution of precision (DOP)) 323, a signal intensity 325 of a received GPS satellite signal, and the like are correlated with each other are arranged in a time series. When measurement is started, the processing unit 20 adds GPS data whenever the GPS data is acquired (for example, every second in an asynchronous manner with acquisition timing of sensing data) so as to update the GPS data table 320.

The geomagnetic data table 330 is a data table which stores geomagnetic data (a detection result in the geomagnetic sensor) received by the processing unit 20 from the geomagnetic sensor 60 in a time series. FIG. 5 is a diagram illustrating a configuration example of the geomagnetic data table 330. As illustrated in FIG. 5, the geomagnetic data table 330 is configured so that geomagnetic data items in which the detection time 331 in the geomagnetic sensor 60 and a geomagnetism 332 detected by the geomagnetic sensor 60 are correlated with each other are arranged in a time series. When measurement is started, the processing unit 20 adds new geomagnetic data to the geomagnetic data table 330 whenever the sampling cycle Δt (for example, 10 ms) elapses.

Figure 6:
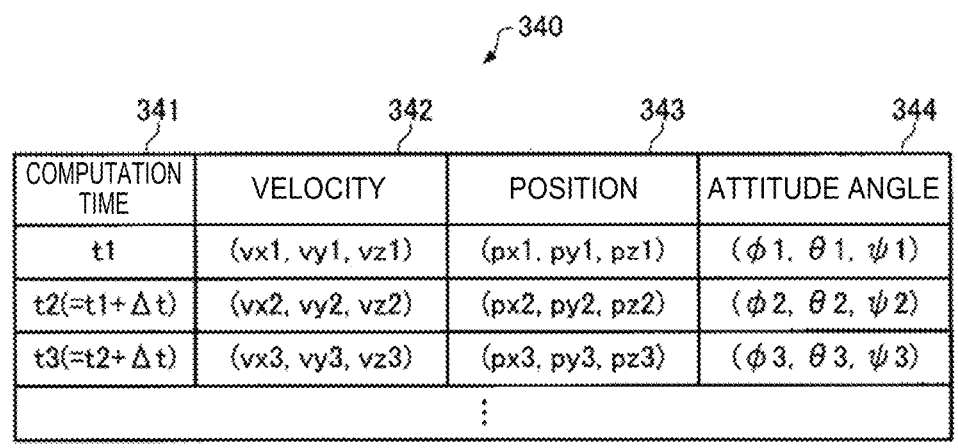
FIG. 6 is a diagram illustrating a configuration example of a calculated data table.

The calculated data table 340 is a data table which stores a velocity, a position, and an attitude angle calculated by the processing unit 20 by using the sensing data in a time series. FIG. 6 is a diagram illustrating a configuration example of the calculated data table 340. As illustrated in FIG. 6, the calculated data table 340 is configured so that calculated data items in which the time 341 at which the processing unit 20 performs computation, a velocity 342, a position 343, and an attitude angle 344 are correlated with each other are arranged in a time series. When measurement is started, the processing unit 20 calculates a velocity, a position, and an attitude angle whenever new sensing data is acquired, that is, the sampling cycle Δt elapses, and adds new calculated data to the calculated data table 340. The processing unit 20 corrects a velocity, a position, and an attitude angle by using a velocity error, a position error, and an attitude angle error which are estimated according to error estimation using the extended Karman filter, and updates the calculated data table 340 by overwriting the corrected velocity, position and attitude angle to the calculated data table.

The exercise analysis information 350 is various information pieces regarding the exercise of the user, and includes each item of input information 351, each item of basic information 352, each item of first analysis information 353, each item of second analysis information 354, each item of left-right difference ratio 355, running path information 356, and the like, generated by the processing unit 20. Details of the various information pieces will be described later.

FIG. 2 is referred to again. The communication unit 40 performs data communication with a communication unit 140 of the notification apparatus 3, and performs a process of receiving some exercise analysis information (output information during running or output information after running to be described later) generated by the processing unit 20 and transmitting the exercise analysis information to the notification apparatus 3, a process of receiving a command (a command for starting or finishing measurement, a command for starting or finishing the running analysis process, or the like) transmitted from the notification apparatus 3 and sending the command to the processing unit 20, and the like.

The notification apparatus 3 includes a processing unit 120, a storage unit 130, the communication unit 140, an operation unit 150, a clocking unit 160, a display unit 170, a sound output unit 180, and a vibration unit 190. However, the notification apparatus 3 of the present embodiment may have a configuration in which some of the constituent elements are deleted or changed, or other constituent elements may be added thereto.

The processing unit 120 is constituted of, for example, a CPU, a DSP, or an ASIC, and performs various calculation processes or control processes according to a program stored in the storage unit 130. For example, the processing unit 120 performs various processes (a process of sending a command for starting or finishing measurement or a command for starting or finishing the running analysis process to the communication unit 140, a process of performing display or outputting sound corresponding to the operation data, and the like) corresponding to operation data received from the operation unit 150; a process of receiving output information during running or output information after running from the communication unit 140 and sending text data or image data corresponding to the output information during running or the output information after running to the display unit 170; a process of sending sound data corresponding to the output information during running or the output information after running to the sound output unit 180; and a process of sending vibration data corresponding to the output information during running to the vibration unit 190. The processing unit 120 performs a process of generating time image data corresponding to time information received from the clocking unit 160 and sending the time image data to the display unit 170, and the like.

The storage unit 130 is constituted of a recording medium such as a ROM, a flash ROM, a hard disk, or a memory card which stores a program or data required for the processing unit 120 to perform various processes, and a RAM (for example, various IC memories) serving as a work area of the processing unit 120.

The communication unit 140 performs data communication with the communication unit 40 of the exercise analysis apparatus 2, and performs a process of receiving a command (a command for starting or finishing measurement, a command for starting or finishing the running analysis process, or the like) corresponding to operation data from the processing unit 120 and transmitting the command to the communication unit 40 of the exercise analysis apparatus 2, a process of receiving output information during running or output information after running transmitted from the communication unit 40 of the exercise analysis apparatus 2 and sending the information to the processing unit 120, and the like.

The operation unit 150 performs a process of acquiring operation data (operation data such as starting or finishing of measurement or selection of display content) from the user and sending the operation data to the processing unit 120. The operation unit 150 may be, for example, a touch panel type display, a button, a key, or a microphone.

The clocking unit 160 performs a process of generating time information such as year, month, day, hour, minute, and second. The clocking unit 160 is implemented by, for example, a real time clock (RTC) IC.

The display unit 170 displays image data or text data sent from the processing unit 120 as text, a graph, a table, animation, or other images. The display unit 170 is implemented by, for example, a display such as a liquid crystal display (LCD), an organic electroluminescent (EL) display, or an electrophoretic display (EPD), and may be a touch panel type display. A single touch panel type display may implement functions of the operation unit 150 and the display unit 170.

The sound output unit 180 outputs sound data sent from the processing unit 120 as sound such as voice or buzzer sound. The sound output unit 180 is implemented by, for example, a speaker or a buzzer.

The vibration unit 190 vibrates in response to vibration data sent from the processing unit 120. This vibration is transmitted to the notification apparatus 3, and the user wearing the notification apparatus 3 can feel the vibration. The vibration unit 190 is implemented by, for example, a vibration motor.

1-4. Functional Configuration of Processing Unit

Figure 7:
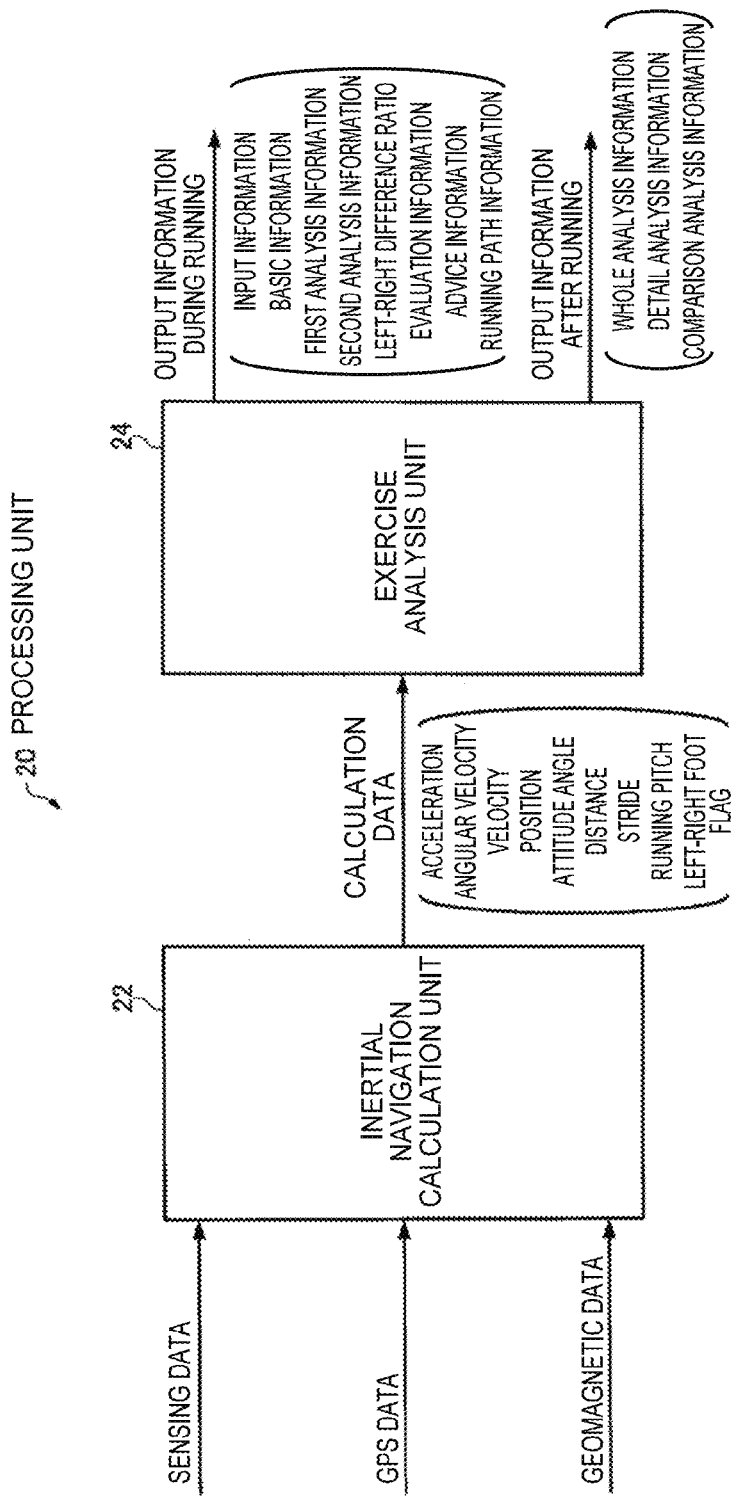
FIG. 7 is a functional block diagram illustrating a configuration example of a processing unit of the exercise analysis apparatus in the first embodiment.

FIG. 7 is a functional block diagram illustrating a configuration example of the processing unit 20 of the exercise analysis apparatus 2 in the first embodiment. In the present embodiment, the processing unit 20 functions as an inertial navigation calculation unit 22 and an exercise analysis unit 24 by executing the exercise analysis program 300 stored in the storage unit 30.

The inertial navigation calculation unit 22 performs inertial navigation calculation by using sensing data (a detection result in the inertial measurement unit 10), GPS data (a detection result in the GPS unit 50), and geomagnetic data (a detection result in the geomagnetic sensor 60), so as to calculate an acceleration, an angular velocity, a velocity, a position, an attitude angle, a distance, a stride, and a running pitch, and outputs calculation data including the calculation results. The calculation data output from the inertial navigation calculation unit 22 is stored in the storage unit 30. Details of the inertial navigation calculation unit 22 will be described later.

The exercise analysis unit 24 analyzes the exercise of the user by using the calculation data (the calculation data stored in the storage unit 30) output from the inertial navigation calculation unit 22, and generates a plurality of exercise information pieces (each item of input information, each item of basic information, each item of first analysis information, each item of second analysis information, each item of left-right difference ratio, running path information, and the like, which will be described later) for improving running attainments (example of exercise attainments) of the user. The running attainments may be, for example, running performance, score of time or the like, or unlikelihood of an injury. The exercise analysis unit 24 generates the output information during running which is output during running by using one or more items of the plurality of exercise information pieces. The exercise analysis information including the plurality of exercise information pieces is stored in the storage unit 30. The exercise analysis unit 24 performs the running analysis process by using the exercise analysis information after the user finishes the running, and generates the output information after running which is output after the running is finished. Details of the exercise analysis unit 24 will be described later.

1-5. Functional Configuration of Inertial Navigation Calculation Unit

Figure 8:
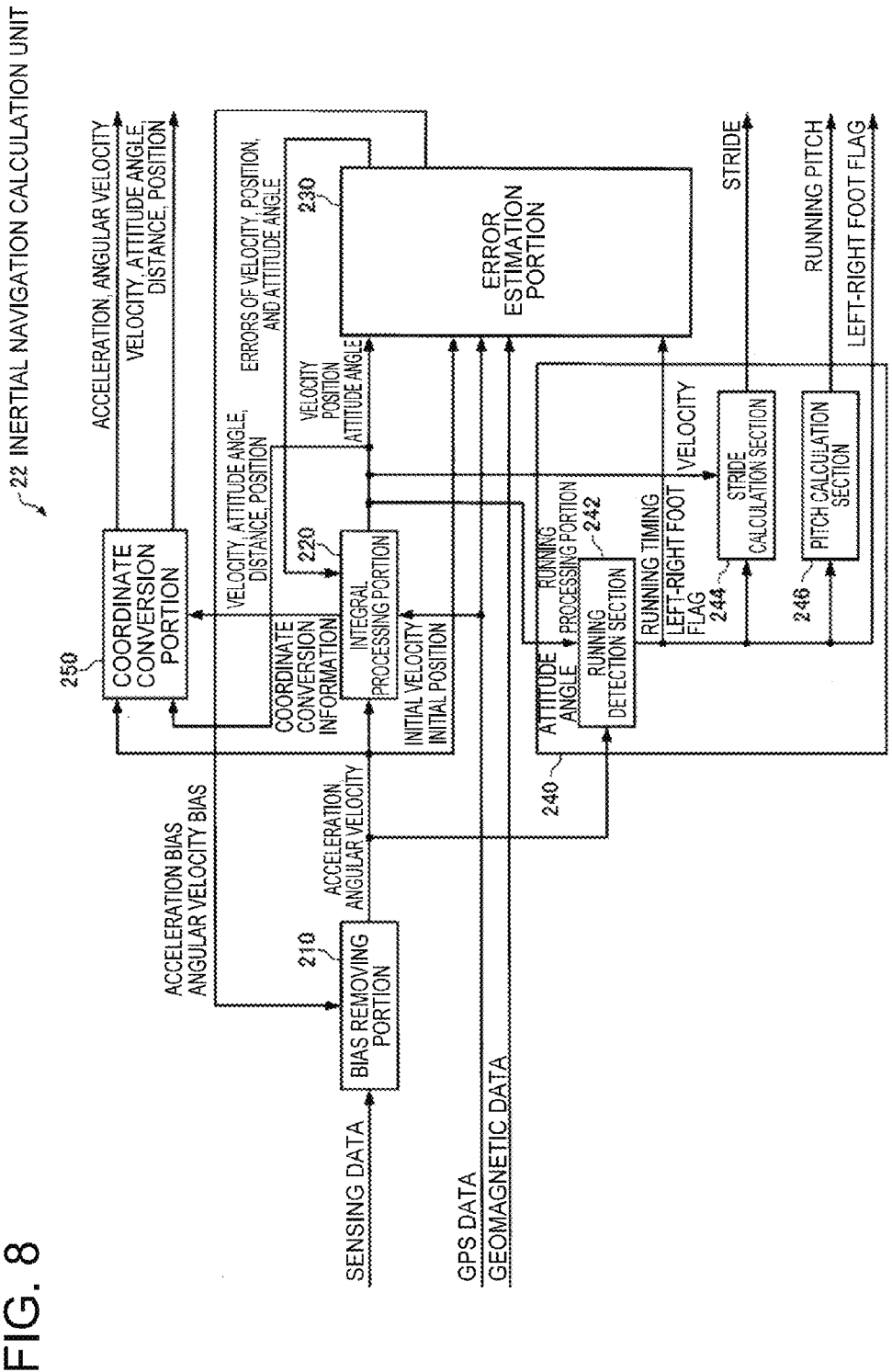
FIG. 8 is a functional block diagram illustrating a configuration example of an inertial navigation calculation unit.

FIG. 8 is a functional block diagram illustrating a configuration example of the inertial navigation calculation unit 22. In the present embodiment, the inertial navigation calculation unit 22 includes a bias removing portion 210, an integral processing portion 220, an error estimation portion 230, a running processing portion 240, and a coordinate conversion portion 250. However, the inertial navigation calculation unit 22 of the present embodiment may have a configuration in which some of the constituent elements are deleted or changed, or other constituent elements may be added thereto.

The bias removing portion 210 subtracts an acceleration bias $b_a$ and an angular velocity bias $b_\omega$ estimated by the error estimation portion 230 from three-axis accelerations and three-axis angular velocities included newly acquired sensing data, so as to perform a process of correcting the three-axis accelerations and the three-axis angular velocities. Since estimated values of the acceleration bias $b_a$ and the angular velocity bias $b_\omega$ are present in an initial state right after measurement is started, the bias removing portion 210 computes initial biases by using sensing data from the inertial measurement unit (IMU) 10 assuming that an initial state of the user is a stoppage state.

The integral processing portion 220 performs a process of calculating a velocity $v^e$, a position $p^e$, and attitude angles (a roll angle $\phi_{be}$, a pitch angle $\theta_{be}$, and a yaw angle $\psi_{be}$) of the e frame on the basis of the accelerations and the angular velocities corrected by the bias removing portion 210. Specifically, first, the integral processing portion 220 sets an initial velocity to zero assuming that an initial state of the user is a stoppage state, or calculates an initial velocity by using the velocity included in the GPS data and also calculates an initial position by using the position included in the GPS data. The integral processing portion 220 specifies a gravitational acceleration direction on the basis of the three-axis accelerations of the b frame corrected by the bias removing portion 210 so as to calculate initial values of the roll angle $\phi_{be}$ and the pitch angle $\theta_{be}$, also calculates an initial value of the yaw angle $\psi_{be}$ on the basis of the velocity including the GPS data, and sets the calculated initial values as initial attitude angles of the e frame. In a case where the GPS data cannot be obtained, an initial value of the yaw angle $\psi_{be}$ is set to, for example, zero. The integral processing portion 220 calculates an initial value of a coordinate conversion matrix (rotation matrix) $C_b^e$ from the b frame into the e frame, expressed by Equation (1) on the basis of the calculated initial attitude angles.

$$C_b^e = \begin{bmatrix} \cos\theta_{be}\cdot\cos\varphi_{be} & \cos\theta_{be}\cdot\sin\varphi_{be} & -\sin\theta_{be} \\ \sin\phi_{be}\cdot\sin\theta_{be}\cdot\cos\varphi_{be} - \cos\phi_{be}\cdot\sin\varphi_{be} & \sin\phi_{be}\cdot\sin\theta_{be}\cdot\sin\varphi_{be} + \cos\phi_{be}\cdot\cos\varphi_{be} & \sin\phi_{be}\cdot\cos\theta_{be} \\ \cos\phi_{be}\cdot\sin\theta_{be}\cdot\cos\varphi_{be} + \sin\phi_{be}\cdot\sin\varphi_{be} & \cos\phi_{be}\cdot\sin\theta_{be}\cdot\sin\varphi_{be} - \sin\phi_{be}\cdot\cos\varphi_{be} & \cos\phi_{be}\cdot\cos\theta_{be} \end{bmatrix} \quad (1)$$

Then, the integral processing portion 220 integrates the three-axis angular velocities corrected by the bias removing portion 210 so as to calculate the coordinate conversion matrix $C_b^e$, and calculates attitude angles by using Equation (2).

$$\begin{bmatrix} \phi_{be} \\ \theta_{be} \\ \varphi_{be} \end{bmatrix} = \begin{bmatrix} \arctan2(C_b^e(2,3), C_b^e(3,3)) \\ -\arcsin C_b^e(1,3) \\ \arctan2(C_b^e(1,2), C_b^e(1,1)) \end{bmatrix} \quad (2)$$

The integral processing portion 220 converts the three-axis accelerations of the b frame corrected by the bias removing portion 210 into three-axis accelerations of the e frame by using the coordinate conversion matrix $C_b^e$, and removes an gravitational acceleration component therefrom for integration so as to calculate the velocity $v^e$ of the e frame. The integral processing portion 220 integrates the velocity $v^e$ of the e frame so as to calculate the position $p^e$ of the e frame.

The integral processing portion 220 performs a process of correcting the velocity $v^e$, the position $p^e$, and the attitude angles by using a velocity error $\delta v^e$, a position error $\delta p^e$, and attitude angle errors $\varepsilon^e$ estimated by the error estimation portion 230, and also performs a process of computing a distance by integrating the corrected velocity $v^e$.

The integral processing portion 220 also calculates a coordinate conversion matrix $C_b^m$ from the b frame into the m frame, a coordinate conversion matrix $C_e^m$ from the e frame into the m frame, and a coordinate conversion matrix $C_e^n$ from the e frame into the n frame. The coordinate conversion matrices are used for a coordinate conversion process in the coordinate conversion portion 250 which will be described later as coordinate conversion information.

The error estimation portion 230 estimates an error of an index indicating a state of the user by using the velocity and/or the position, and the attitude angles calculated by the integral processing portion 220, the acceleration or the angular velocity corrected by the bias removing portion 210, the GPS data, the geomagnetic data, and the like. In the present embodiment, the error estimation portion 230 uses the velocity, the attitude angles, the acceleration, the angular velocity, and the position as indexes indicating a state of the user, and estimates errors of the indexes by using the extended Karman filter. In other words, the error estimation portion 230 uses an error (velocity error) $\delta v^e$ of the velocity $v^e$ calculated by the integral processing portion 220, errors (attitude angle errors) $\varepsilon^e$ of the attitude angles calculated by the integral processing portion 220, the acceleration bias $b_a$, the angular velocity bias $b_\omega$, and an error (position error) $\delta p^e$ of the position $p^e$ calculated by the integral processing portion 220, as state variables of the extended Karman filter, and a state vector X is defined as in Equation (3).

$$X = \begin{bmatrix} \delta v^e \\ \varepsilon^e \\ b_a \\ b_\omega \\ \delta p^e \end{bmatrix} \quad (3)$$

The error estimation portion 230 predicts state variables (errors of the indexes indicating a state of the user) included in the state vector X by using a predication formula of the extended Karman filter. The predication formulae of the extended Karman filter are expressed as in Equation (4). In Equation (4), the matrix Φ is a matrix which associates the previous state vector X with the present state vector X, and is designed so that some elements thereof change every moment while reflecting attitude angles, a position, and the like. Q is a matrix indicating process noise, and each element thereof is set to an appropriate value. P is an error covariance matrix of the state variables.

$$X = \Phi X$$

$$P = \Phi P \Phi^T + Q \quad (4)$$

The error estimation portion 230 updates (corrects) the predicted state variables (errors of the indexes indicating a state of the user) by update formulae of the extended Karman filter. The update formulae of the extended Karman filter are expressed as in Equation (5). Z and H are respectively an observation vector and an observation matrix, and the update formulae (5) indicate that the state vector X is corrected by using a difference between the actual observation vector Z and a vector HX predicted from the state vector X. R is a covariance matrix of observation errors, and may have predefined constant values, and may be dynamically changed. K is a Karman gain, and K increases as R decreases. From Equation (5), as K increases (R decreases), a correction amount of the state vector X increases, and thus P decreases.

$$K = PH^T(HPH^T + R)^{-1}$$

$$X = X + K(Z - HX) \quad (5)$$

$$P = (I - KH)P$$

An error estimation method (a method of estimating the state vector X) may include, for example, the following methods.

Figure 9:
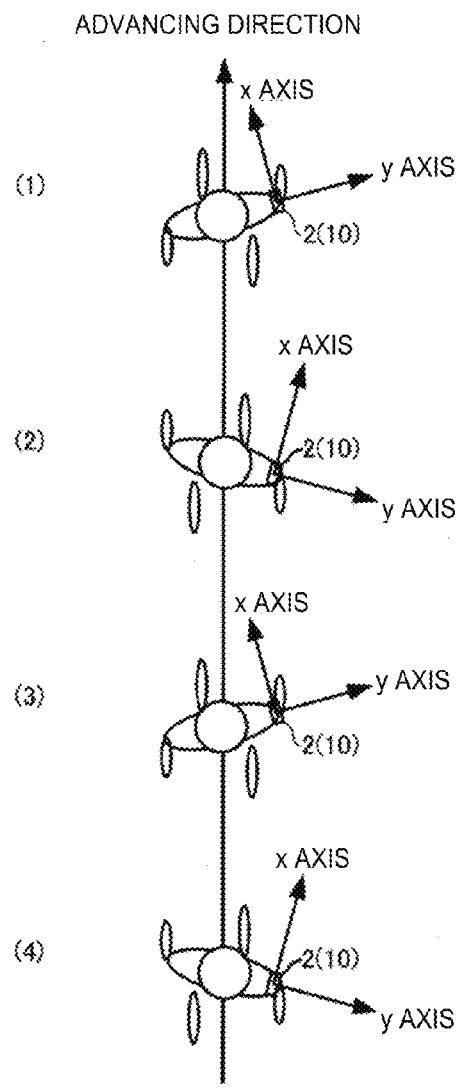
FIG. 9 is a diagram illustrating an attitude during a user's running.
Figure 10:
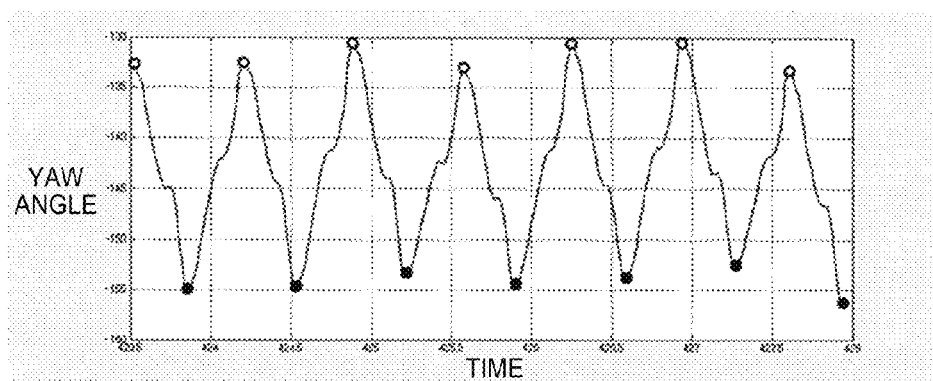
FIG. 10 is a diagram illustrating a yaw angle during the user's running.

An error estimation method using correction on the basis of attitude angle errors:

FIG. 9 is an overhead view of movement of the user in a case where the user wearing the exercise analysis apparatus 2 on the user's right waist performs a running operation (going straight). FIG. 10 is a diagram illustrating an example of a yaw angle (azimuth angle) calculated by using a detection result in the inertial measurement unit 10 in a case where there user performs the running operation (going straight), in which an transverse axis expresses time, and a longitudinal axis expresses a yaw angle (azimuth angle).

An attitude of the inertial measurement unit 10 relative to the user changes at any time due to the running operation of the user. In a state in which the user takes a step forward with the left foot, as illustrated in (1) or (3) of FIG. 9, the inertial measurement unit 10 is tilted to the left side with respect to the advancing direction (the x axis of the m frame). In contrast, in a state in which the user takes a step forward with the right foot, as illustrated in (2) or (4) of FIG. 9, the inertial measurement unit 10 is tilted to the right side with respect to the advancing direction (the x axis of the m frame). In other words, the attitude of the inertial measurement unit 10 periodically changes every two left and right steps due to the running motion of the user. In FIG. 10, for example, the yaw angle is the maximum in a state in which the user takes a step forward with the right foot (O in FIG. 10), and is the minimum in a state in which the user takes a step forward with the left foot (● in FIG. 10). Therefore, an error can be estimated assuming that the previous (two steps before) attitude angle is the same as the present attitude angle, and the previous attitude angle is a true attitude angle. In this method, the observation vector Z of Equation (5) is a difference between the previous attitude angle and the present attitude angle calculated by the integral processing portion 220, and the state vector X is corrected on the basis of a difference between the attitude angle error $\varepsilon^e$ and an observed value according to the update formulae (5) so that an error is estimated.

An error estimation method using correction based on the angular velocity bias:

This method is a method of estimating an error assuming that the previous (two steps before) attitude angle is the same as the present attitude angle, and the previous attitude angle is not required to be a true attitude angle. In this method, the observation vector Z of Equation (5) is an angular velocity bias by using the previous attitude angle and the present attitude angle calculated by the integral processing portion 220, and the state vector X is corrected on the basis of a difference between the angular velocity bias $b_\omega$ and an observed value according to the update formulae (5).

An error estimation method using correction based on azimuth angle error:

This method is a method of estimating an error assuming that the previous (two steps before) yaw angle (azimuth angle) is the same as the present yaw angle (azimuth angle), and the previous yaw angle (azimuth angle) is a true yaw angle (azimuth angle). In this method, the observation vector Z of Equation (5) is a difference between the previous yaw angle and the present yaw angle calculated by the integral processing portion 220, and the state vector X is corrected on the basis of a difference between an azimuth angle error $\varepsilon_z^e$ and an observed value according to the update formulae (5) so that an error is estimated.

An error estimation method using correction based on stoppage:

This method is a method of estimating an error assuming that a velocity is zero when the user stops. In this method, the observation vector Z is a difference between a velocity $v^e$ calculated by the integral processing portion 220 and zero, and the state vector X is corrected on the basis of the velocity error $\delta v^e$ according to the update formulae (5) so that an error is estimated.

An error estimation method using correction based on stoppage:

This method is a method of estimating an error assuming that a velocity is zero and an attitude change is also zero when the user stops. In this method, the observation vector Z is an error of the velocity $v^e$ calculated by the integral processing portion 220 and a difference between the previous attitude angle and the present attitude angle calculated by the integral processing portion 220, and the state vector X is corrected on the basis of the velocity error $\delta v^e$ and the attitude angle error $\varepsilon^e$ according to the update formulae (5) so that an error is estimated.

An error estimation method using correction based on an observed value of GPS:

This method is a method of estimating an error assuming that the velocity $v^e$, the position $p^e$, or the yaw angle $\psi_{be}$ calculated by the integral processing portion 220 is the same as a velocity, a position, or an azimuth angle (a velocity, a position, or an azimuth angle after being converted into the e frame) which is calculated by using GPS data. In this method, the observation vector Z is a difference between a velocity, a position, or a yaw angle calculated by the integral processing portion 220 and a velocity, a positional velocity, or an azimuth angle calculated by using the GPS data, and the state vector X is corrected on the basis of a difference between the velocity error $\delta v^e$, the position error $\delta p^e$, or the azimuth angle errors $\varepsilon_z^e$, and an observed value according to the update formulae (5) so that an error is estimated.

An error estimation method using correction based on an observed value in geomagnetic sensor:

This method is a method of estimating an error assuming that the yaw angle $\psi_{be}$ calculated by the integral processing portion 220 is the same as an azimuth angle (an azimuth angle after being converted into the e frame) calculated from the geomagnetic sensor. In this method, the observation vector Z is a difference between a yaw angle calculated by the integral processing portion 220 and an azimuth angle calculated by using geomagnetic data, and the state vector X is corrected on the basis of a difference between the azimuth angle errors $\varepsilon_z^e$ and an observed value according to the update formulae (5) so that an error is estimated.

Figure 11:
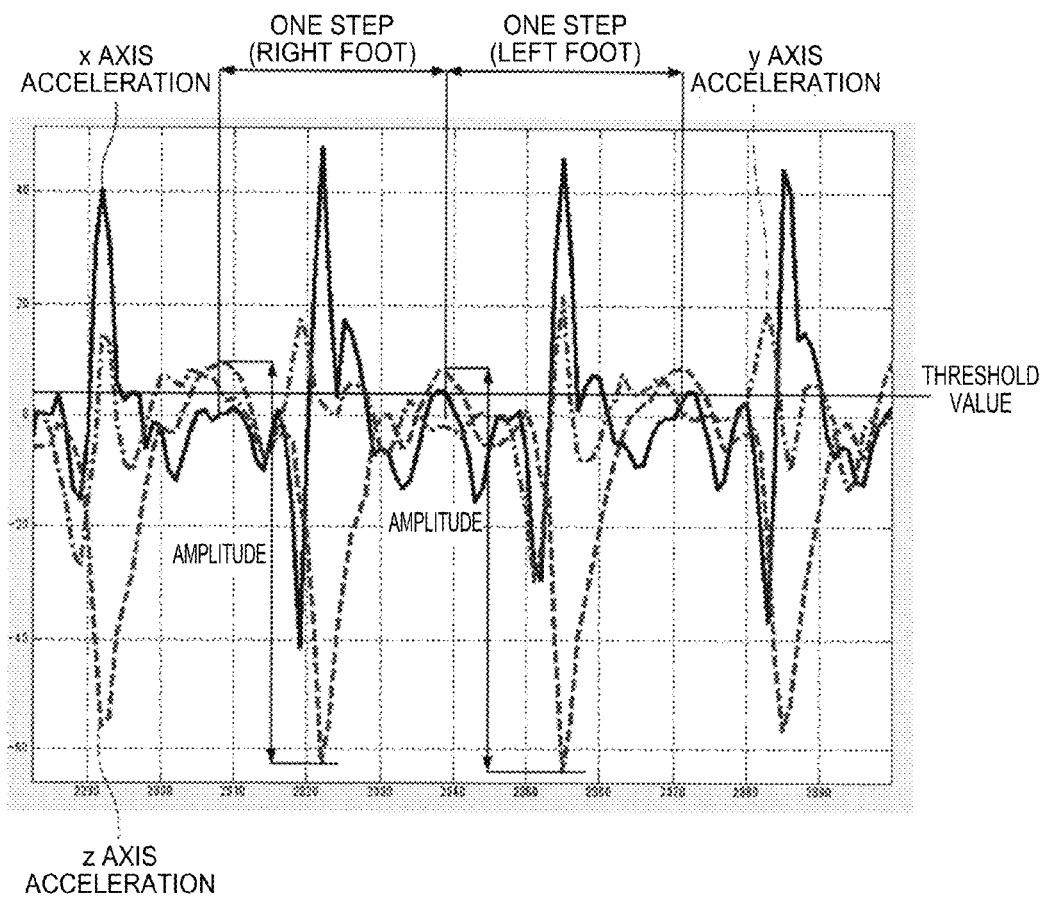
FIG. 11 is a diagram illustrating an example of three-axis accelerations during the user's running.

Referring to FIG. 8 again, the running processing portion 240 includes a running detection section 242, a stride calculation section 244, and a pitch calculation section 246. The running detection section 242 performs a process of detecting a running cycle (running timing) of the user by using a detection result (specifically, sensing data corrected by the bias removing portion 210) in the inertial measurement unit 10. As described with reference to FIGS. 9 and 10, since the user's attitude periodically changes (every two left and right steps) while the user is running, an acceleration detected by the inertial measurement unit 10 also periodically changes. FIG. 11 is a diagram illustrating an example of three-axis accelerations detected by the inertial measurement unit 10 during the user's running. In FIG. 11, a transverse axis expresses time, and a longitudinal axis expresses an acceleration value. As illustrated in FIG. 11, the three-axis accelerations periodically change, and, particularly, it can be seen that the z axis (the axis in the gravitational direction) acceleration changes periodically and regularly. The z axis acceleration reflects an acceleration obtained when the user moves vertically, and a time period from the time when the z axis acceleration becomes the maximum value which is equal to or greater than a predetermined threshold value to the time when the z axis acceleration becomes the maximum value which is equal to or greater than the predetermined threshold value next corresponds to a time period of one step. One step in a state in which the user takes a step forward with the right foot and one step in a state in which the user takes a step forward with the left foot are alternately taken in a repeated manner.

Therefore, in the present embodiment, the running detection section 242 detects a running cycle whenever the z axis acceleration (corresponding to an acceleration obtained when the user moves vertically) detected by the inertial measurement unit 10 becomes the maximum value which is equal to or greater than the predetermined threshold value. In other words, the running detection section 242 outputs a timing signal indicating that a running cycle is detected whenever the z axis acceleration detected by the inertial measurement unit 10 becomes the maximum value which is equal to or greater than the predetermined threshold value. In practice, since a high frequency noise component is included in the three-axis accelerations detected by the inertial measurement unit 10, the running detection section 242 applies a low-pass filter to the three-axis accelerations, and detects a running cycle by using a z axis acceleration from which noise is removed.

The running detection section 242 determines which one of the left and right running cycles corresponds to the detected running cycle, and outputs left-right foot flag (for example, an ON flag for the right foot, and an OFF flag for the left foot) indicating the corresponding running cycle. For example, as illustrated in FIG. 10, since the yaw angle is the maximum in a state in which the user takes a step forward with the right foot (O in FIG. 10), and is the minimum in a state in which the user takes a step forward with the left foot (● in FIG. 10), the running detection section 242 can determine a left foot running cycle or a right foot running cycle by using attitude angles (especially, a yaw angle) calculated by the integral processing portion 220. As illustrated in FIG. 9, when viewed from the head of the user, the inertial measurement unit 10 is rotated in a clockwise direction from a state in which the user takes a step forward with the left foot (the state (1) or (3) in FIG. 9) to a state in which the user takes a step forward with the right foot (the state (2) or (4) in FIG. 9). In contrast, the inertial measurement unit 10 is rotated in a counterclockwise direction from a state in which the user takes a step forward with the right foot to a state in which the user takes a step forward with the left foot. Therefore, for example, the running detection section 242 may determine a left foot running cycle or a right foot running cycle on the basis of a polarity of the z axis angular velocity. In this case, in practice, since a high frequency noise component is included in the three-axis angular velocities detected by the inertial measurement unit 10, the running detection section 242 applies a low-pass filter to the three-axis angular velocities, and determines a left foot running cycle or a right foot running cycle by using a z axis angular velocity from which noise is removed.

Since it may not be known whether the user starts to run from the right foot or the left foot, and a wrong running cycle may be detected during running, the running detection section 242 preferably comprehensively determines whether a running cycle is a left foot running cycle or a right foot running cycle by also using information (for example, attitude angles) other than the z axis acceleration.

The stride calculation section 244 calculates a stride for each of the left and right foots by using a timing signal for the running cycle and the left-right foot flag output from the running detection section 242, and a velocity or a position calculated by the integral processing portion 220, and outputs the stride for each of the left and right foots. In other words, the stride calculation section 244 integrates a velocity for each sampling cycle Δt in a time period from the start of the running cycle to the start of the next running cycle (alternatively, computes a difference between a position at the time when the running cycle is started and a position at the time when the next running cycle is started) so as to calculate and output a stride.

The pitch calculation section 246 performs a process of calculating the number of steps for one minute by using the timing signal for the running cycle output from the running detection section 242, and outputting the number of steps as a running pitch. In other words, the pitch calculation section 246 computes the number of steps per second by taking an inverse number of the running cycle, and calculates the number of steps for one minute (running pitch) by multiplying the number of steps per second by 60.

The coordinate conversion portion 250 performs a coordinate conversion process of converting the three-axis accelerations and the three-axis angular velocities of the b frame corrected by the bias removing portion 210 into three-axis accelerations and three-axis angular velocities of the m frame, respectively, by using the coordinate conversion information (coordinate conversion matrix $C_b^m$) from the b frame into the m frame, calculated by the integral processing portion 220. The coordinate conversion portion 250 performs a coordinate conversion process of converting the velocities in the three-axis directions, the attitude angles about the three axes, and the distances in the three-axis directions of the e frame calculated by the integral processing portion 220 into velocities in the three-axis directions, attitude angles about the three axes, and distances in the three-axis directions of the m frame, respectively, by using the coordinate conversion information (coordinate conversion matrix $C_e^m$) from the e frame into the m frame, calculated by the integral processing portion 220. The coordinate conversion portion 250 performs a coordinate conversion process of converting the position of the e frame calculated by the integral processing portion 220 into a position of the n frame, respectively, by using the coordinate conversion information (coordinate conversion matrix $C_e^n$) from the e frame into the n frame, calculated by the integral processing portion 220.

The inertial navigation calculation unit 22 outputs calculation data (stores the calculation data in the storage unit 30) including information regarding the accelerations, the angular velocities, the velocities, the position, the attitude angles, and the distances having undergone the coordinate conversion in the coordinate conversion portion 250, and the stride, the running pitch, and the left-right foot flag calculated by the running processing portion 240.

1-6. Functional Configuration of Exercise Analysis Unit

Figure 12:
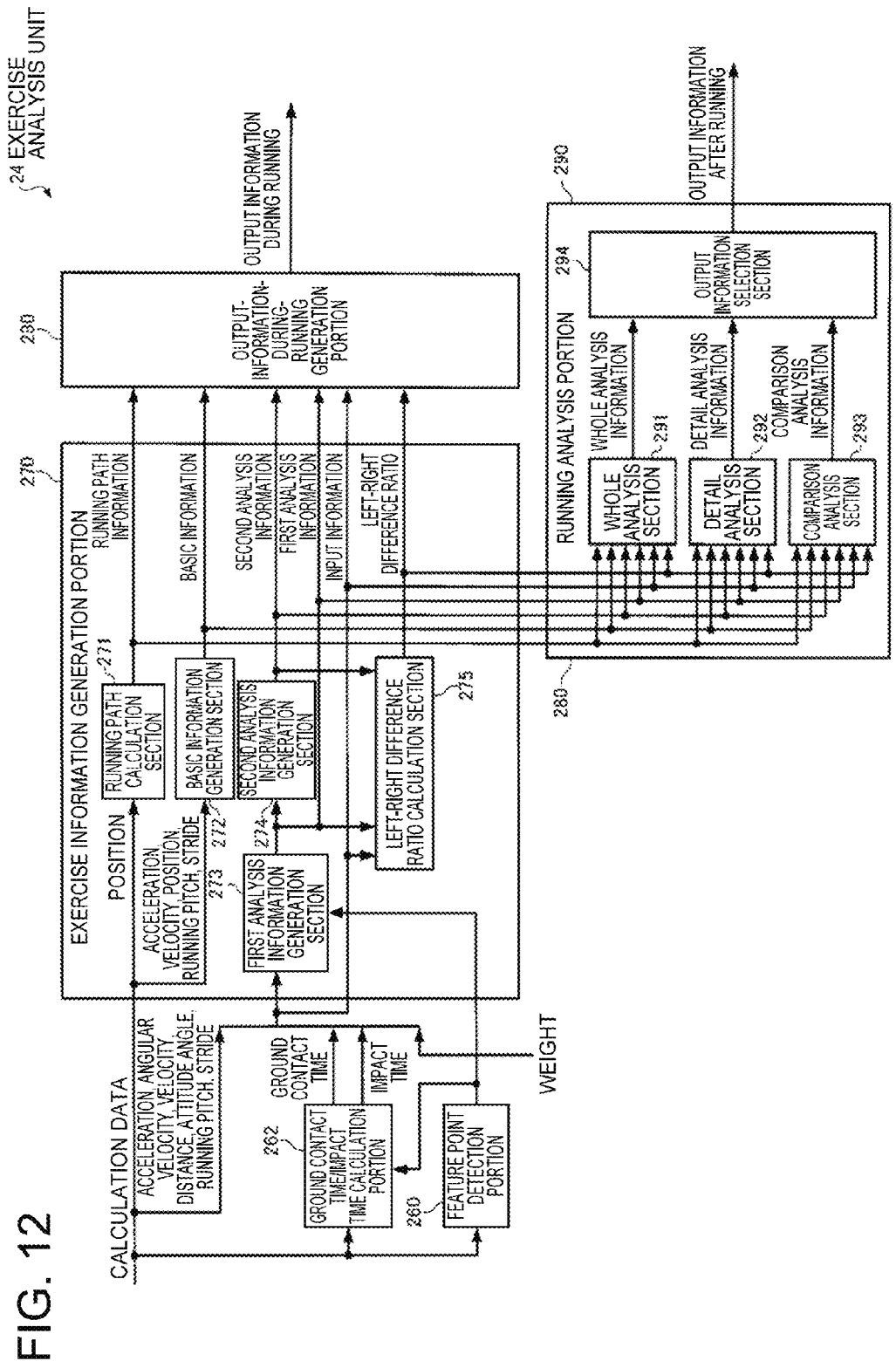
FIG. 12 is a functional block diagram illustrating a configuration example of an exercise analysis unit in the first embodiment.

FIG. 12 is a functional block diagram illustrating a configuration example of the exercise analysis unit 24 in the first embodiment. In the present embodiment, the exercise analysis unit 24 includes a feature point detection portion 260, a ground contact time/impact time calculation portion 262, an exercise information generation portion 270, an output-information-during-running generation portion 280, and a running analysis portion 290. However, the exercise analysis unit 24 of the present embodiment may have a configuration in which some of the constituent elements are deleted or changed, or other constituent elements may be added thereto.

The feature point detection portion 260 performs a process of detecting a feature point in the running exercise of the user by using the calculation data. The feature point in the running exercise of the user is a data part corresponding to a feature portion of the running exercise of the user, and is, for example, landing (which may be set as appropriate such as a time point at which a part of the sole contacts the ground, a time point at which the entire sole contacts the ground, any time point between the time when the heel of the foot contact the ground and the time when the toe of the foot leaves the ground, any time point between the time when the toe of the foot contact the ground and the time when the heel of the foot leaves the ground, or a time period in which the entire sole is contacting the ground), stepping (a state in which the user's weight is applied to the foot most), or taking-off (which may be set as appropriate such as a time point at which a part of the sole leaves the ground, a time point at which the entire sole leaves the ground, any time point between the time when the toe of the foot contact the ground and the time when the heel of the fool leaves the ground, or any time point between the time when the heel of the foot contact the ground and the time when the toe of the foot leaves the ground). Specifically, the feature point detection portion 260 separately detects a feature point at the running cycle for the right foot and a feature point at the running cycle for the left foot by using the left-right foot flag included in the calculation data. For example, the feature point detection portion 260 may detect landing at a timing at which the vertical acceleration (a detected value on the z axis in the acceleration sensor) changes from a positive value to a negative value, may detect stepping at a time point at which the acceleration in the advancing direction has a peak after the vertical acceleration has a peak in the negative direction from the landing, and may detect taking-off at a time point at which the vertical acceleration changes from a negative value to a positive value.

The ground contact time/impact time calculation portion 262 performs a process of calculating each value of a ground contact time and an impact time with the timing at which the feature point is detected by the feature point detection portion 260 as a reference, by using the calculation data. For example, the ground contact time/impact time calculation portion 262 determines whether the present calculation data corresponds to calculation data for the right foot running cycle or calculation data for the left foot running cycle on the basis of the left-right foot flag included in the calculation data, and calculates each value of the ground contact time and the impact time with the timing at which the feature point is detected by the feature point detection portion 260 as a reference, for each of the right foot running cycle and the left foot running cycle. Details of definition and a calculation method of the ground contact time and the impact time will be described later.

The exercise information generation portion 270 includes a running path calculation section 271, a basic information generation section 272, a first analysis information generation section 273, a second analysis information generation section 274, and a left-right difference ratio calculation section 275, and performs a process of analyzing exercise of the user so as to generate a plurality of exercise information pieces for improving running attainments of the user, by using some calculation data or input information. Here, the input information is information which is input to the first analysis information generation section 273, and includes respective items of the running pitch, the stride, the accelerations in the three-axis directions of the m frame, the angular velocities about the three axes thereof, the velocities in the three-axis directions thereof, the distances in the three-axis directions thereof, and the attitude angles about the three axes thereof, included in the calculation data, the ground contact time and the impact time calculated by the ground contact time/impact time calculation portion 262, and a user's weight. Specifically, the exercise information generation portion 270 performs a process of analyzing exercise of the user with a timing at which the feature point is detected by the feature point detection portion 260 as a reference by using the input information, and of generating, as exercise information pieces, each item of the basic information, each item of the first analysis information, each item of the second analysis information, each item of the left-right difference ratio, the running path information, and the like.

The running path calculation section 271 performs a process of calculating a running path of the user in n frames by using time-series information regarding positions of the n frames included in the calculation data and of generating running path information which is one of the exercise information pieces.

The basic information generation section 272 performs a process of generating basic information regarding the exercise of the user by using the information regarding the acceleration, the velocity, the position, the stride, and the running pitch included in the calculation data. Here, the basic information includes respective items such as the running pitch, the stride, the running velocity, the elevation, the running distance, and the running time (lap time). Each item of the basic information is a single exercise information piece. Specifically, the basic information generation section 272 outputs the running pitch and the stride included in the calculation data as a running pitch and a stride of the basic information. The basic information generation section 272 calculates exercise information such as the present value or an average value during running of the running velocity, the elevation, the running distance, and the running time (lap time) by using some or all of the acceleration, the velocity, the position, the running pitch, and the stride included in the calculation data.

The first analysis information generation section 273 performs a process of analyzing the exercise of the user with the timing at which the feature point is detected by the feature point detection portion 260 as a reference, by using the input information, so as to generate first analysis information. Here, the first analysis information includes respective items such as brake amounts in landing (a brake amount 1 in landing and a brake amount 2 in landing), directly-below landing ratios (a directly-below landing ratio 1, a directly-below landing ratio 2, and a directly-below landing ratio 3), propulsion forces (a propulsion force 1 and a propulsion force 2), propulsion efficiency (propulsion efficiency 1, propulsion efficiency 2, propulsion efficiency 3, and propulsion efficiency 4), an amount of energy consumption, a landing impact, running performance, a forward tilt angle, and timing coincidence. Each item of the first analysis information indicates a running state (an example of an exercise state) of the user, and is a single piece of exercise information. Details of the content of each item and a computation method of the first analysis information will be described later.

In the present embodiment, the first analysis information generation section 273 calculates values of some of the items of the first analysis information by using the input information at the timing at which the feature point is detected by the feature point detection portion 260. The first analysis information generation section 273 calculates values of at least some of the items of the first analysis information by using the input information at a timing at which the next feature point is detected after the feature point is detected by the feature point detection portion 260 (the timing may be a time period between the two same feature points (for example, between landing and the next landing) or between two different feature points (for example, between landing and taking-off)).

The first analysis information generation section 273 calculates a value of each item of the first analysis information for the respective left and right sides of the user's body. Specifically, the first analysis information generation section 273 calculates each item included in the first analysis information for the right foot running cycle and the left foot running cycle depending on whether the feature point detection portion 260 has detected the feature point at the right foot running cycle or the feature point at the left foot running cycle. The first analysis information generation section 273 calculates an average value or a total value of the left and right sides for each item included in the first analysis information.

The second analysis information generation section 274 performs a process of generating second analysis information by using the first analysis information generated by the first analysis information generation section 273. Here, the second analysis information includes respective items such as energy loss, energy efficiency, and a burden on the body. Each item of the second analysis information is a single exercise information piece. Details of the content of each item and a calculation method of the second analysis information will be described later. The second analysis information generation section 274 calculates a value of each item of the second analysis information for the right foot running cycle and the left foot running cycle. The second analysis information generation section 274 calculates an average value or a total value of the left and right sides for each item included in the second analysis information.

The left-right difference ratio calculation section 275 performs a process of calculating a left-right difference ratio which is an index indicating a balance between the left and right sides of the user's body by using values at the right foot running cycle and values at the left foot running cycle with respect to the running pitch, the stride, the ground contact time, and the impact time included in the input information, all the items of the first analysis information, and all the items of the second analysis information. The left-right difference ratio of each item is a single exercise information piece. Details of the content and a computation method of the left-right difference ratio will be described later.

The output-information-during-running generation portion 280 performs a process of generating output information during running which is information which is output during the user's running, by using a plurality of exercise information pieces including the running path information, each item of the basic information, each item of the input information, each item of the first analysis information, each item of the second analysis information, the left-right difference ratio of each item, and the like.

The output-information-during-running generation portion 280 may generate the output information during running on the basis of at least one exercise information piece which satisfies a predetermined condition among the plurality of exercise information pieces. As the predetermined condition, a running state of the user may be better than a criterion, and a running state of the user may be worse than a criterion. For example, the output-information-during-running generation portion 280 may output only the best items, and, conversely, may output the worst items, as the output information during running. Alternatively, each item may be divided in stages and may be evaluated, and, as the output information during running, only items with the highest evaluation (for example, a rank 1 of ranks 1 to 5) may be output, and, conversely, only items with the lowest evaluation (for example, a rank 5 of ranks 1 to 5) may be output. The output-information-during-running generation portion 280 may include, as the output information during running, evaluation information (evaluation in stages, or the like) for evaluating a running state of the user, or advice information regarding an advice for improving running attainments of the user or an advice for improving a running state of the user.

For example, in a case where a value of the propulsion efficiency included in the first analysis information satisfies a predetermined condition (within a reference range or out of the reference range), the output-information-during-running generation portion 280 may generate output information during running including information for performing a notification that a numerical value of the propulsion efficiency or the propulsion efficiency is higher (lower) than a reference value, or may generate output information during running including evaluation information indicating that the propulsion efficiency is high or advice information for improving the propulsion efficiency.

The output-information-during-running generation portion 280 may generate output information during running by processing some or all of the various information pieces without being changed, and may generate output information during running by combining some or all of the various information pieces with each other.

The processing unit 20 transmits the output information during running to the notification apparatus 3. The notification apparatus 3 receives the output information during running so as to generate data such as corresponding to images, sound, or vibration, and presents (delivers) the data to the user via the display unit 170, the sound output unit 180, and the vibration unit 190.

The running analysis portion 290 includes a whole analysis section 291, a detail analysis section 292, a comparison analysis section 293, and an output information selection section 294, and performs a process of generating output information after running which is information which is output after the user finishes running, on the basis of at least one exercise information piece of the plurality of exercise information pieces (the running path information, each item of the basic information, each item of the input information, each item of the first analysis information, each item of the second analysis information, the left-right difference ratio of each item, and the like) stored in the storage unit 30.

The whole analysis section 291 performs a process of wholly analyzing (generally analyzing) past running of the user by using the various exercise information pieces stored in the storage unit 30, so as to generate whole analysis information which is information indicating an analysis result. Specifically, the whole analysis section 291 performs an average value calculation process, a process of selecting a final value when running is finished, a process of determining whether or not the value is better (or worse) than a reference value or whether or not an improvement ratio is higher (or lower) than a reference value, and the like, on some or all exercise information pieces in running on the date selected by the user. The whole analysis section 291 performs a process or the like of calculating (or selecting) an average value (or a final value) for each running date, on a predetermined item which is set in advance or an item selected by the user. The whole analysis section 291 performs a process or the like of selecting running path information in running on the date selected by the user.

The detail analysis section 292 performs a process of analyzing past running of the user in detail by using the various exercise information pieces stored in the storage unit 30, so as to generate detail analysis information which is information indicating an analysis result. Specifically, the detail analysis section 292 performs a process of selecting values of some or all of the items of the various exercise information pieces at a time point selected by the user or a process of generating time-series data of an item selected by the user, on running on the date selected by the user. The detail analysis section 292 performs a process of selecting running path information in running on the date selected by the user, a process of calculating a running position at a time point selected by the user, or a process of calculating time-series data of the left-right difference ratio of a predetermined item or an item selected by the user. The detail analysis section 292 (an example of an advice information generation section) performs a process or the like of evaluating running attainments in running on the date selected by the user and of generating information regarding an evaluation result or information regarding advices of a method for improving a running type, a method for reducing time, or a training instruction.

The comparison analysis section 293 performs a process or the like of comparing a plurality of past running results of the user with each other for analysis, or comparing a past running result of the user with a running result of another user for analysis, by using the various exercise information pieces stored in the storage unit 30, so as to generate comparison analysis information which is information indicating an analysis result. Specifically, the comparison analysis section 293 performs a process of generating comparison analysis information which is the same as the detail analysis information on running for each of a plurality of dates selected by the user, or a process of generating comparison analysis information which is the same as detail analysis information on running on the date selected by the user and past running of another user.

The output information selection section 294 performs a process of selecting any one of the whole analysis information, the detail analysis information, and the comparison analysis information in response to a user's selection operation and of outputting the selected information as output information after running.

The output information after running may include exercise information which is not output during the user's running among the plurality of exercise information pieces, that is, exercise information which is not included in the output information during running. Alternatively, the output information after running may include exercise information which is output during the user's running among the plurality of exercise information pieces, that is, exercise information included in the output information during running. The output information after running may include information regarding an advice for improving running attainments of the user or an advice for improving a running state of the user. The output information after running may include information (information other than exercise information generated by the exercise information generation portion 270 during the user's running) which is generated by the running analysis portion 290 after the user finishes running.

The processing unit 20 transmits the output information after running to the notification apparatus 3 or an information apparatus such a personal computer or a smart phone (neither thereof illustrated). The notification apparatus 3 or the information apparatus receives the output information after running so as to generate data such as corresponding to images, sound, or vibration, and presents (delivers) the data to the user via the display unit, the sound output unit, and the vibration unit.

1-7. Detection of Feature Point

During the user's running, the user repeatedly performs operations such as landing by taking a step forward with the right foot, stepping, taking-off (kicking), then, landing by taking a step forward with the left, stepping, and taking-off (kicking). Therefore, the landing, the stepping, and the taking-off (kicking) may be understood as feature points of running. The exercise can be evaluated on the basis of input information in such feature points or input information from the feature point to the next feature point. Therefore, in the present embodiment, the feature point detection portion 260 detects three feature points including the landing, the stepping, and the taking-off (kicking) in the user's running, and the ground contact time/impact time calculation portion 262 calculates the ground contact time or the impact time on the basis of a timing of the landing or the taking-off (kicking). The first analysis information generation section 273 calculates some items of the first analysis information by using input information in the feature point or input information from the feature point to the next feature point.

Figure 13:
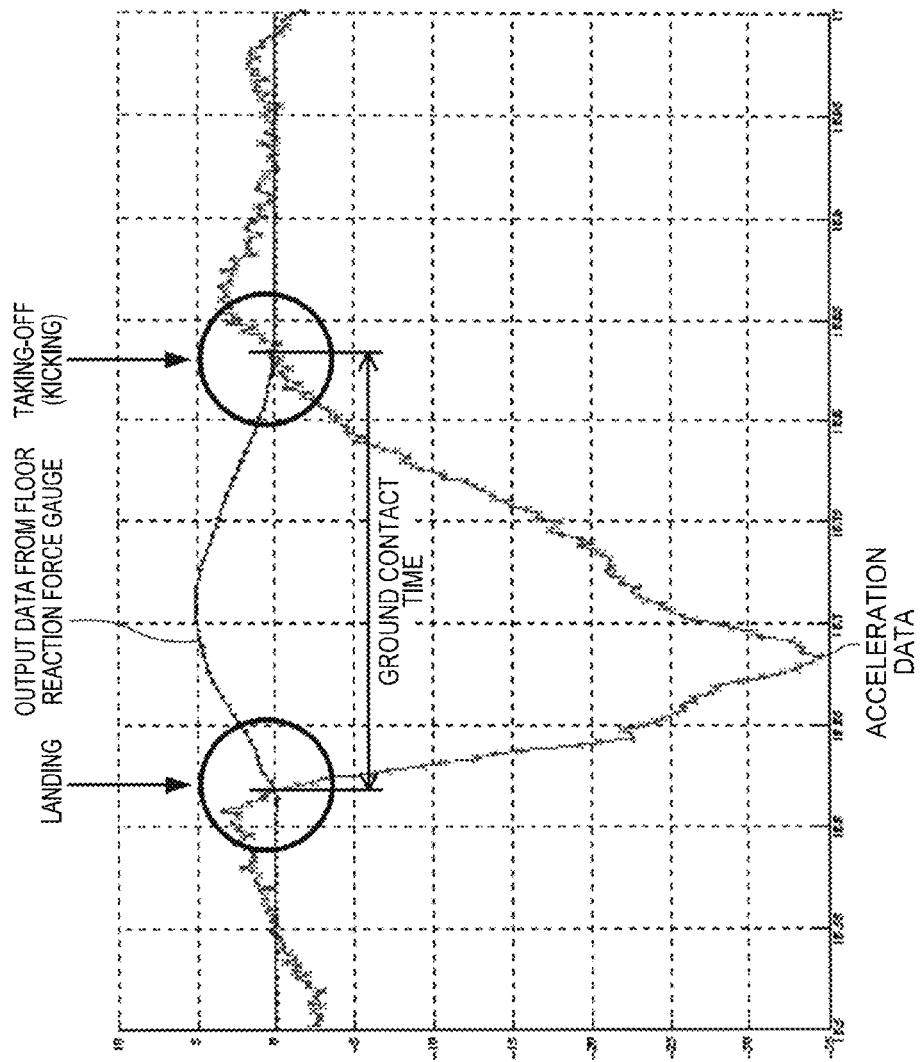
FIG. 13 is a diagram illustrating a method of determining timings of landing and taking-off (kicking).

A method of determining timings of the landing and the taking-off (kicking) will be described with reference to FIG. 13. FIG. 13 is a graph of acceleration data acquired when a floor reaction force gauge is installed on the ground, and a subject wearing an apparatus into which a three-axis acceleration sensor is built on the subject's waist runs. In FIG. 13, a transverse axis expresses time, and a longitudinal axis expresses acceleration. In FIG. 13, output date of the floor reaction force gauge is also displayed in parallel. Since a detected value of the floor reaction force gauge changes only when the foot contacts the ground, when data of the floor reaction force gauge is compared with acceleration data, it can be seen from FIG. 13 that a landing timing can be determined as being a point where a vertical acceleration (a detected value in the z axis of the acceleration sensor) changes from a positive value to a negative value. A taking-off (kicking) timing can be determined as being a point where a vertical acceleration (a detected value in the z axis of the acceleration sensor) changes from a negative value to a positive value. As illustrated in FIG. 13, the ground contact time can be computed as a difference between a time point of the taking-off and a time point of the landing.

Figure 14:
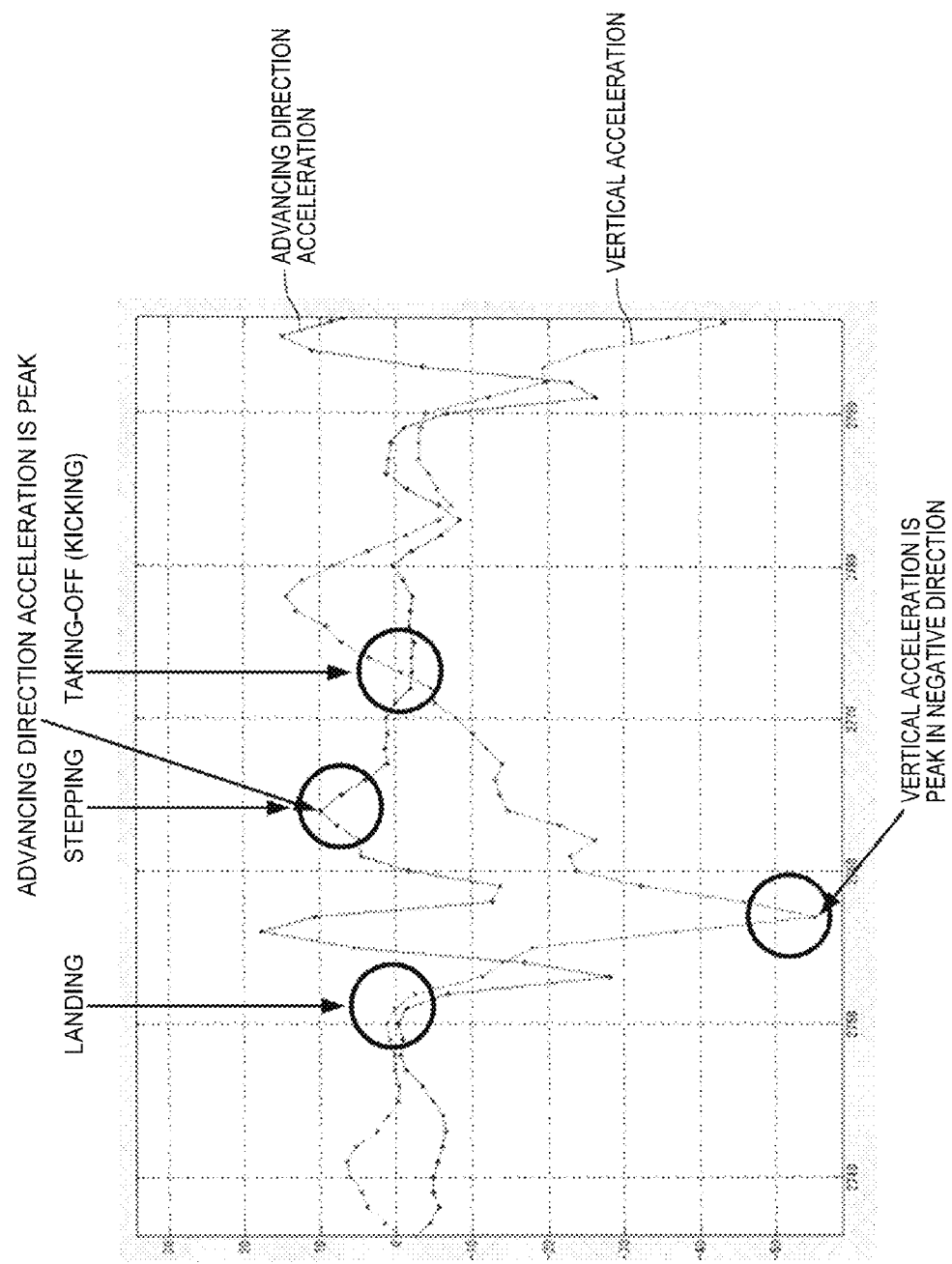
FIG. 14 is a diagram illustrating a method of determining a timing of stepping.

With reference to FIG. 14, a description will be made of a method of determining a stepping timing. In FIG. 14, a transverse axis expresses time, and a longitudinal axis expresses acceleration. As illustrated in FIG. 14, after the landing (a point where a vertical acceleration changes from a positive value to a negative value), a point where an advancing direction acceleration has a peak from a point where the vertical acceleration has a peak in the negative direction can be determined as being the stepping timing.

Figure 15:
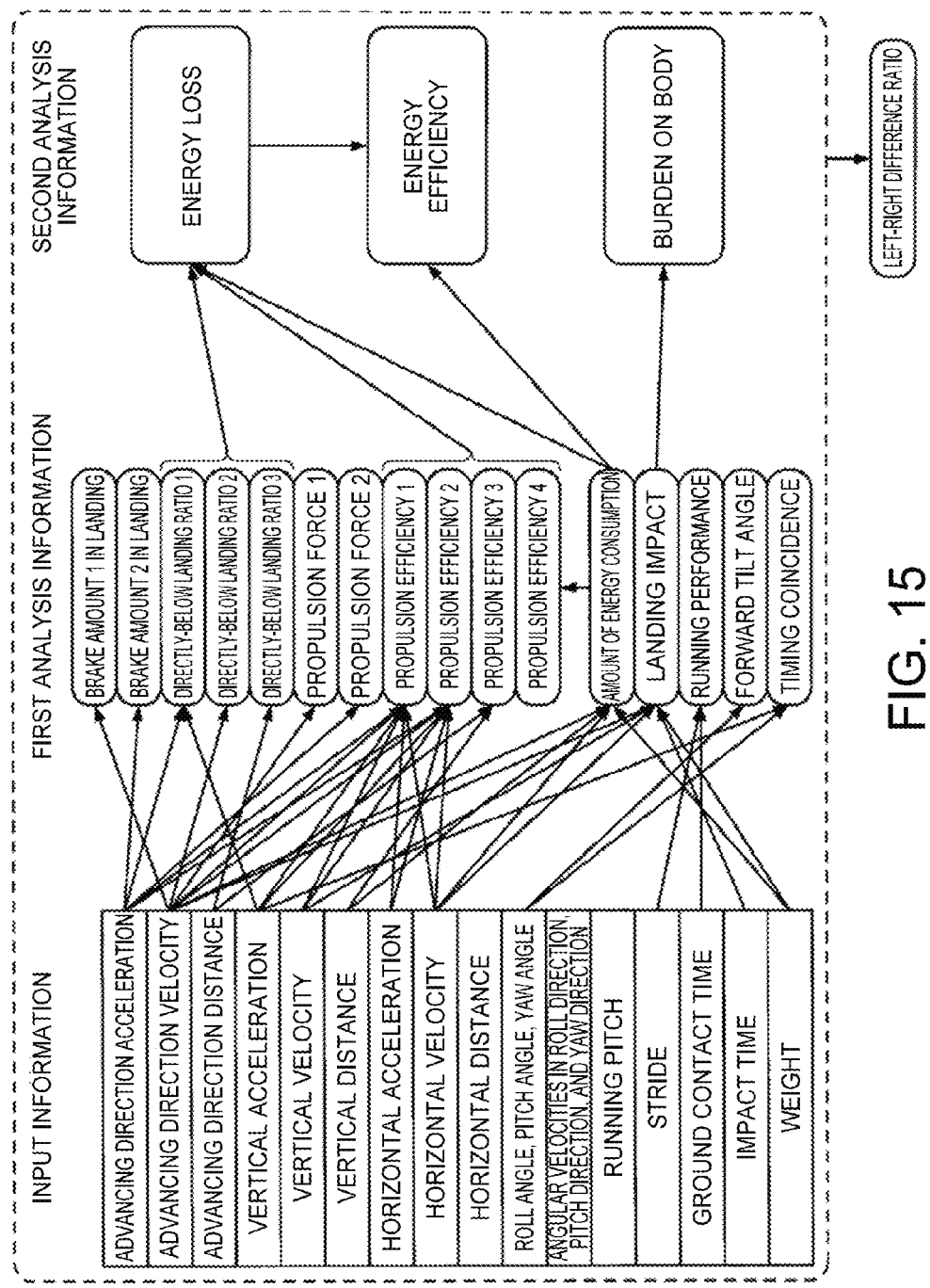
FIG. 15 is a diagram illustrating a relationship between input information and analysis information.

1-8. Details of Input Information and Analysis Information
1-8-1. Relationship Between Input Information and Analysis Information FIG. 15 is a diagram illustrating a relationship between input information and analysis information (the first analysis information, the second analysis information, and the left-right difference ratio).

The input information includes respective items such as the "advancing direction acceleration", the "advancing direction velocity", the "advancing direction distance", the "vertical acceleration", the "vertical velocity", the "vertical distance", the "horizontal acceleration", the "horizontal velocity", the "horizontal distance", the "attitude angles (a roll angle, a pitch angle, and a yaw angle)", the "angular velocities (in a roll direction, a pitch direction, and a yaw direction)", the "running pitch", the "stride", the "ground contact time", the "impact time", and the "weight".

The first analysis information include items such as the "break amount 1 in landing", the "break amount 2 in landing", the "directly-below landing ratio 1", the "directly-below landing ratio 2", the "directly-below landing ratio 3", the "propulsion force 1", the "propulsion force 2", the "propulsion efficiency 1", the "propulsion efficiency 2", the "propulsion efficiency 3", "propulsion efficiency 4", the "amount of energy consumption", the "landing impact", the "running performance", the "forward tilt angle", and "timing coincidence". The respective items excluding the "propulsion efficiency 4" included in the first analysis information are calculated by using at least one item of the input information. The "propulsion efficiency 4" is calculated by using the amount of energy consumption. FIG. 15 shows the items of the first analysis information, which are calculated by using the items of the input information with the arrows. For example, the "directly-below landing ratio 1" is calculated by using the advancing direction acceleration and the vertical velocity.

The second analysis information includes items such as the "energy loss", the "energy efficiency", and the "burden on the body". The respective items included in the second analysis information are calculated by using at least one item of the first analysis information. FIG. 15 shows the items of the second analysis information, which are calculated by using the items of the first analysis information with the arrows. For example, the "energy loss" is calculated by using the "directly-below landing ratios (directly-below landing ratios 1 to 3)" and the "propulsion efficiency (propulsion efficiency 1 to 4)".

The left-right difference ratio is an index indicating a balance between the left and right sides of the user's body, and is calculated for the "running pitch", the "stride", the "ground contact time", the "impact time", all of the items of the first analysis information, and all of the items of the second analysis information.

1-8-2. Input Information

Hereinafter, a description will be made of details of each item of the input information.

Figure 16:
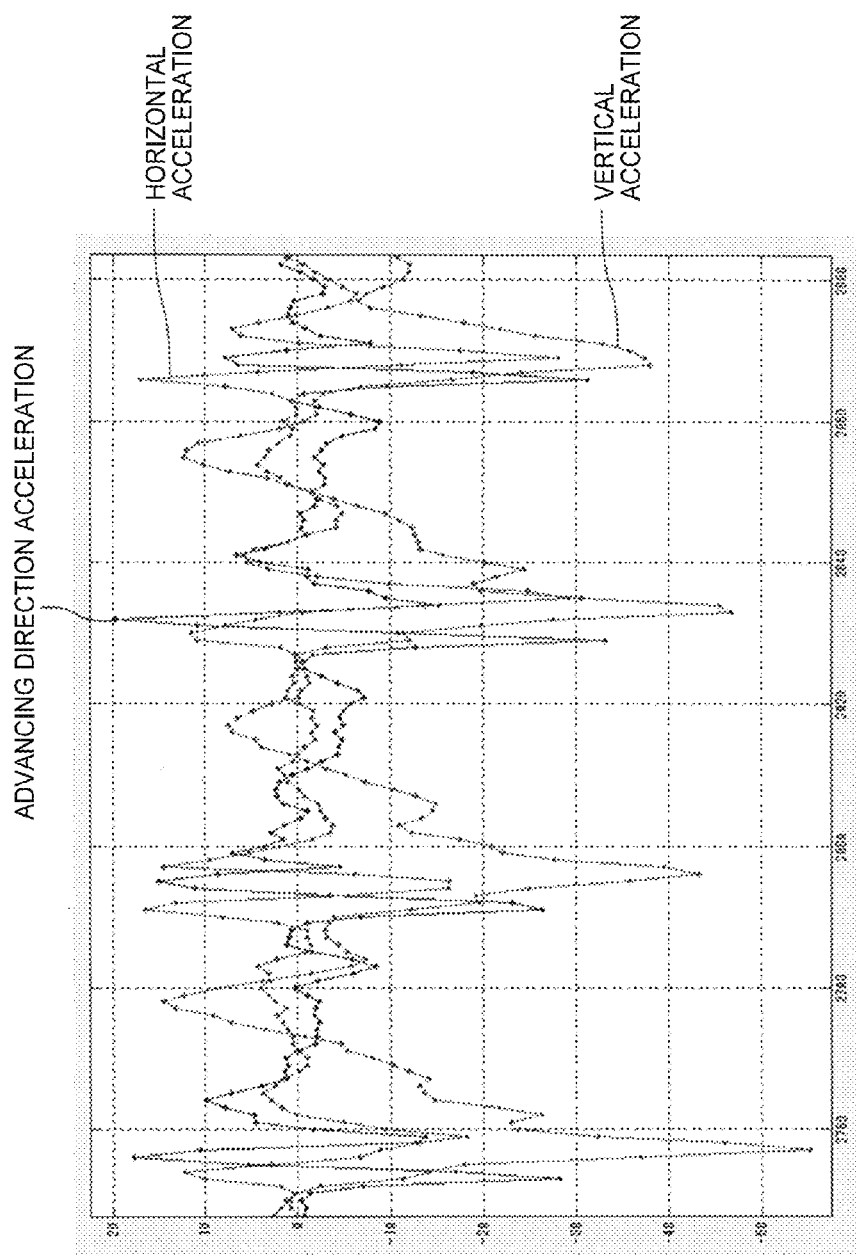
FIG. 16 illustrates an example of an advancing direction acceleration, a vertical acceleration, and a horizontal acceleration.

Advancing Direction Acceleration, Vertical Acceleration, and Horizontal Acceleration The "advancing direction" is an advancing direction (the x axis direction of the m frame) of the user, the "vertical direction" is a perpendicular direction (the z axis direction of the m frame), and the "horizontal direction" is a direction (the y axis direction of the m frame) perpendicular to both the advancing direction and the vertical direction. The advancing direction acceleration, the vertical acceleration, and the horizontal acceleration are respectively an acceleration in the x axis direction of the m frame, an acceleration in the z axis direction thereof, and an acceleration in the y axis direction thereof, and are calculated by the coordinate conversion portion 250. FIG. 16 illustrates an example of a graph in which the advancing direction acceleration, the vertical acceleration, and the horizontal acceleration during the user's running are calculated at a cycle of 10 ms.

Advancing Direction Velocity, Vertical Velocity, and Horizontal Velocity

Figure 17:
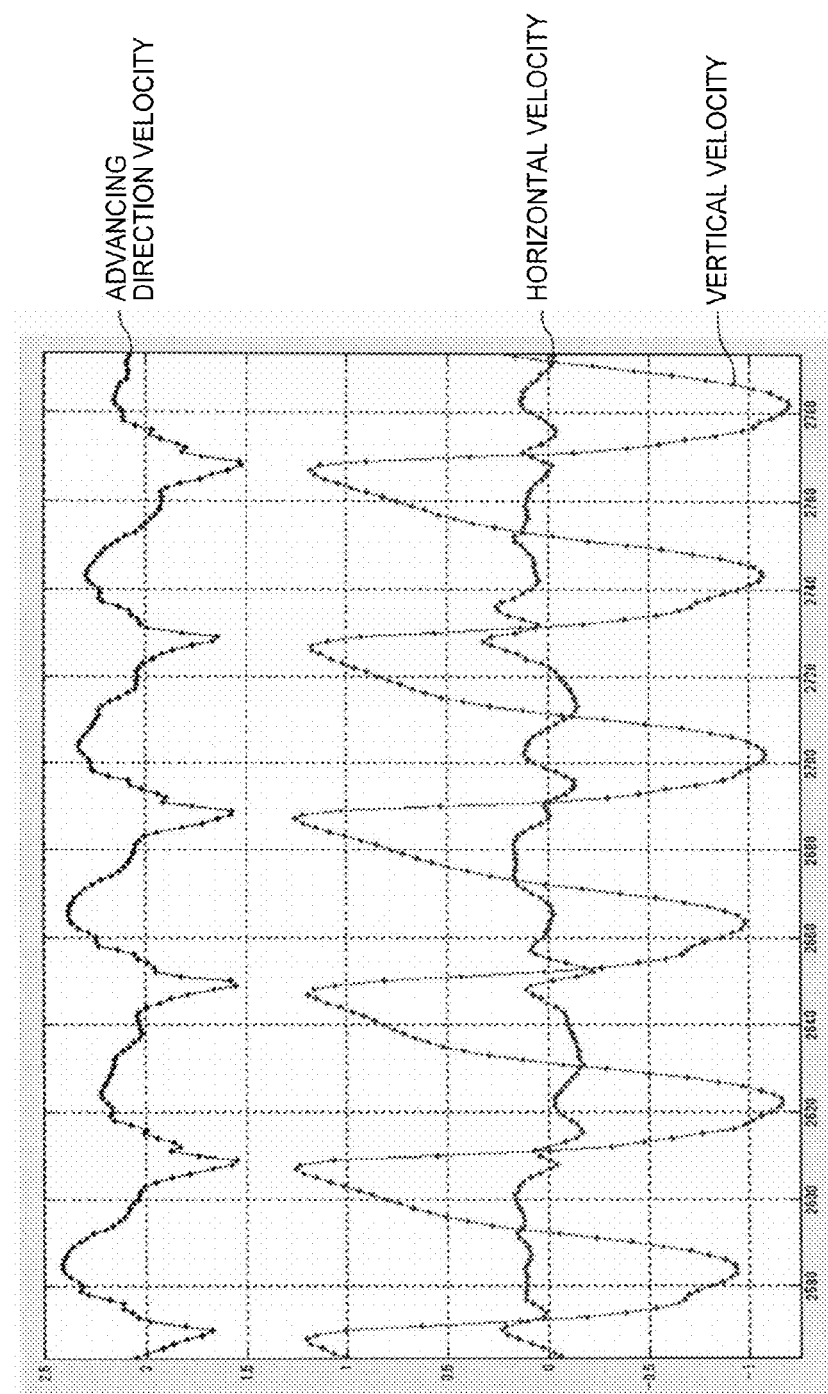
FIG. 17 illustrates an example of an advancing direction velocity, a vertical velocity, and a horizontal velocity.

The advancing direction velocity, the vertical velocity, and the horizontal velocity are respectively a velocity in the x axis direction of the m frame, a velocity in the z axis direction thereof, and a velocity in the y axis direction thereof, and are calculated by the coordinate conversion portion 250. Alternatively, the advancing direction velocity, the vertical velocity, and the horizontal velocity may be respectively calculated by integrating the advancing direction acceleration, the vertical acceleration, and the horizontal acceleration. FIG. 17 illustrates an example of a graph in which the advancing direction velocity, the vertical velocity, and the horizontal velocity during the user's running are calculated at a cycle of 10 ms.

Angular Velocities (in Roll Direction, Pitch Direction, and Yaw Direction)

Figure 18:
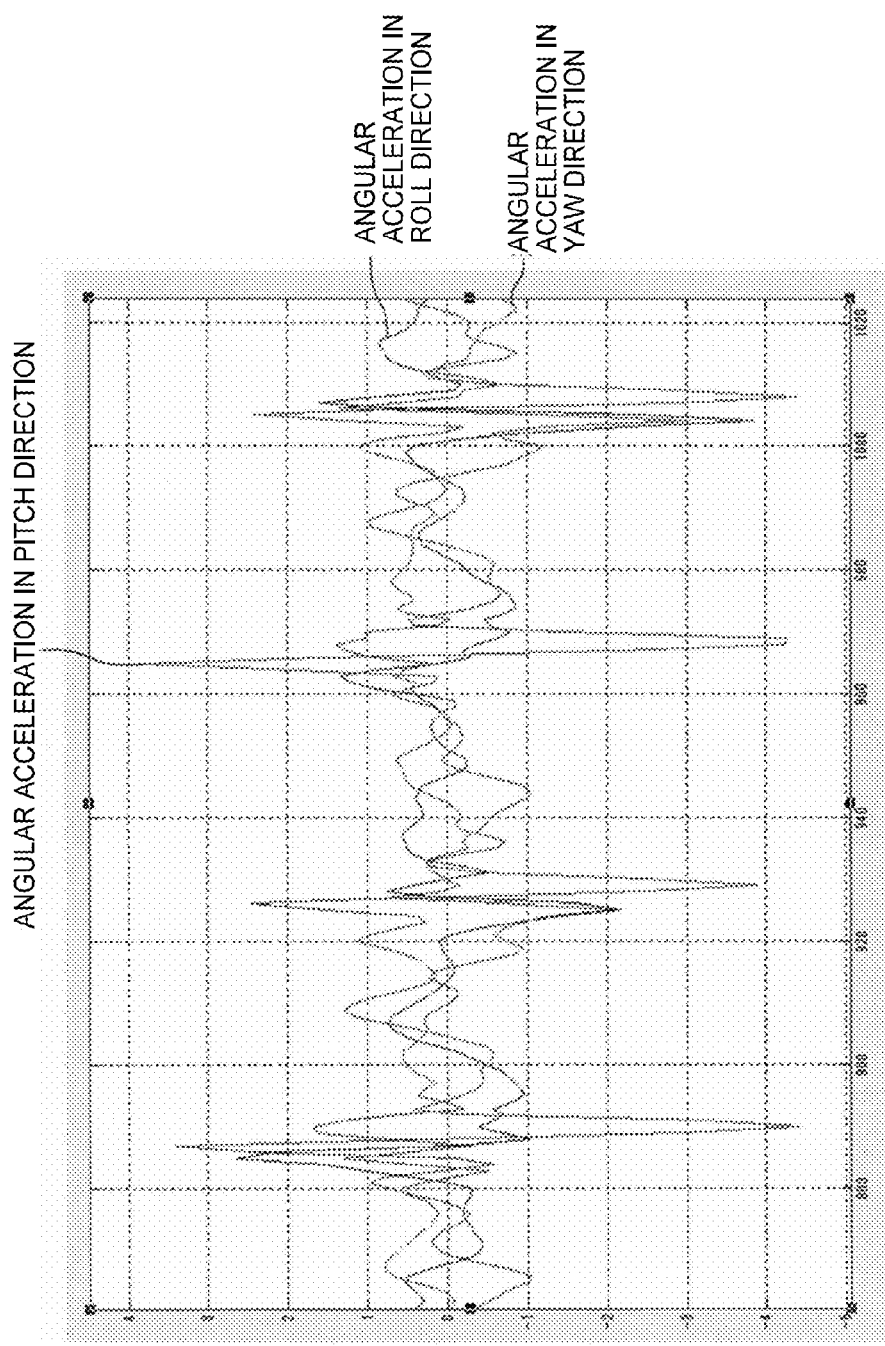
FIG. 18 is a diagram illustrating an example of an acceleration in a roll angle, an acceleration in a pitch angle, and an acceleration in a yaw angle.

The angular velocity in the roll direction, the angular velocity in the pitch direction, and the angular velocity in the yaw direction are respectively an angular velocity about the x axis of the m frame, an angular velocity about the y axis thereof, and an angular velocity about the z axis thereof, and are calculated by the coordinate conversion portion 250. FIG. 18 illustrates an example of a graph in which the angular velocity in the roll direction, the angular velocity in the pitch direction, and the angular velocity in the yaw direction during the user's running are calculated at a cycle of 10 ms.

Attitude Angles (Roll Angle, Pitch Angle, and Yaw Angle)

Figure 19:
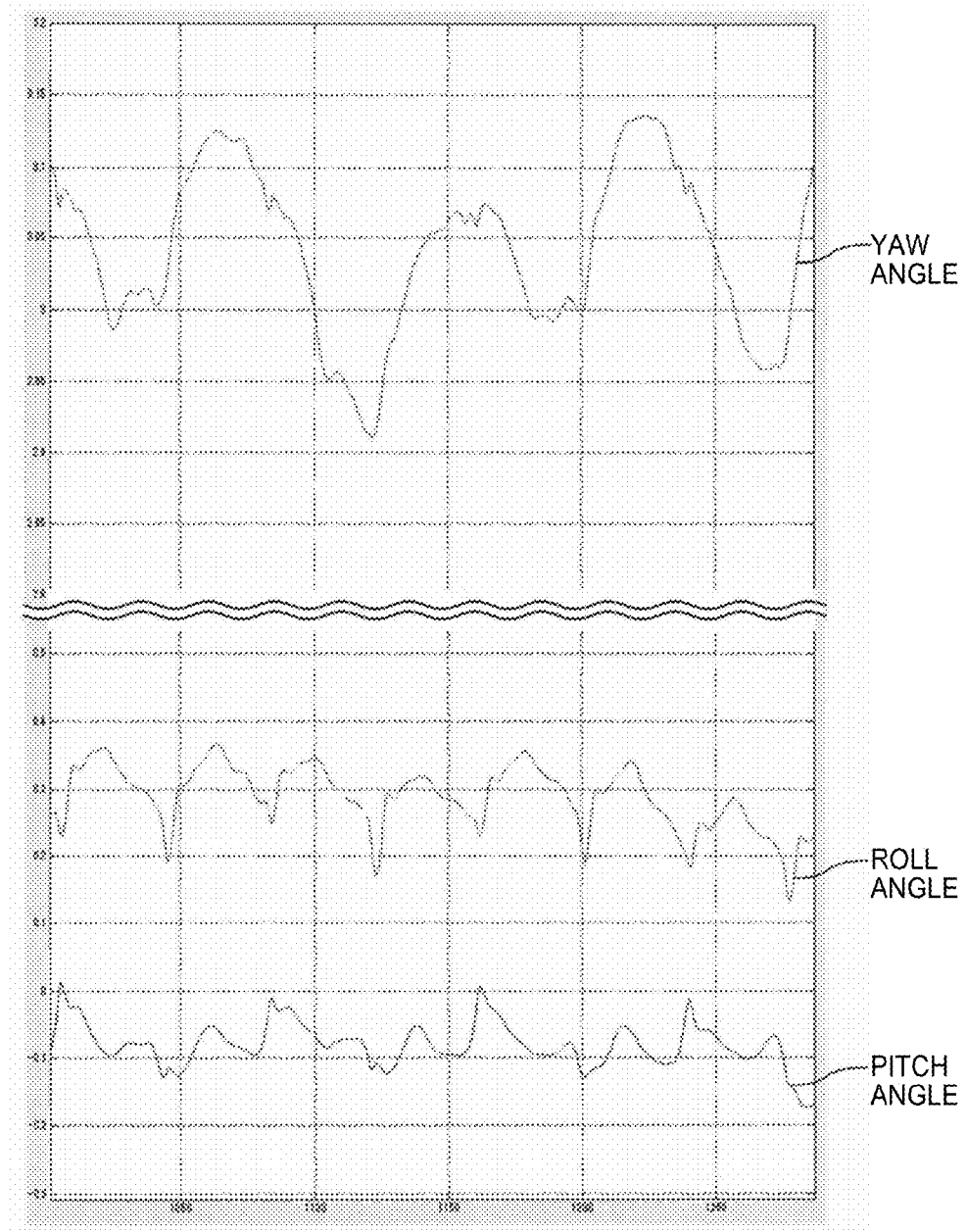
FIG. 19 is a diagram illustrating an example of a roll angle, a pitch angle, and a yaw angle.

The roll angle, the pitch angle, and the yaw angle are respectively an attitude angle about the x axis of the m frame, an attitude angle about the y axis thereof, and an attitude angle about the z axis thereof, output from the coordinate conversion portion 250, and are calculated by the coordinate conversion portion 250. Alternatively, the roll angle, the pitch angle, and the yaw angle may be respectively calculated by integrating (by performing rotation calculation on) the angular velocity in the roll direction, the angular velocity in the pitch direction, and the angular velocity in the yaw direction. FIG. 19 illustrates an example of a graph in which the roll angle, the pitch angle, and the yaw angle during the user's running are calculated at a cycle of 10 ms.

Advancing Direction Distance, Vertical Distance, and Horizontal Distance

Figure 20:
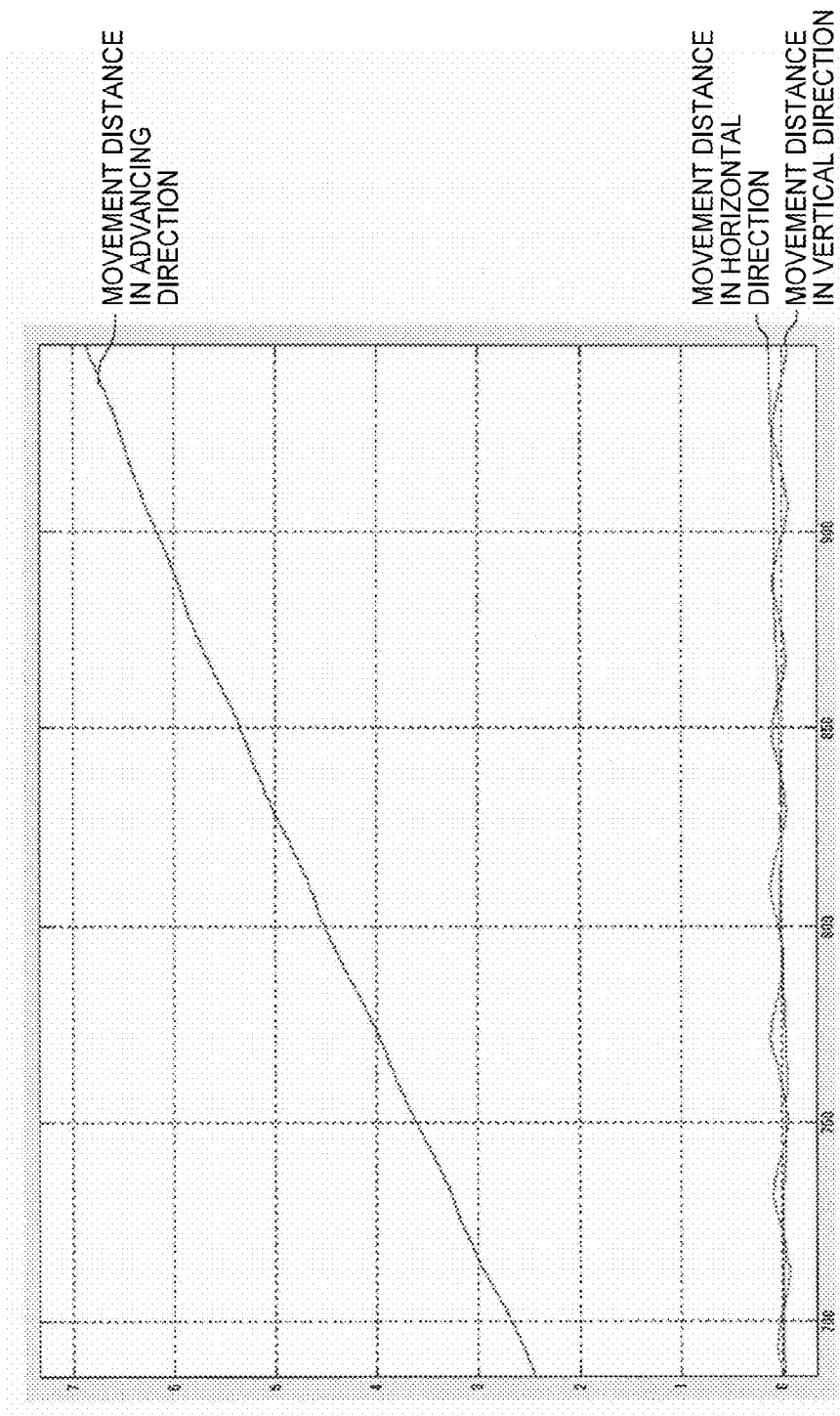
FIG. 20 is a diagram illustrating an example of an advancing direction distance, a vertical distance, and a horizontal distance.

The advancing direction distance, the vertical distance, and the horizontal distance are respectively a movement distance in the x axis direction of the m frame, a movement distance in the y axis direction thereof, and a movement distance in the z direction thereof from a desired position (for example, a position right before the user's running), and are calculated by the coordinate conversion portion 250. FIG. 20 illustrates an example of a graph in which the advancing direction distance, the vertical distance, and the horizontal distance during the user's running are calculated at a cycle of 10 ms.

Running Pitch

The running pitch is an exercise index defined as the number of steps per one minute, and is calculated by the pitch calculation section 246. Alternatively, the running pitch may be calculated by dividing an advancing direction distance for one minute by the number of steps.

Stride

The stride is an exercise index defined as one step, and is calculated by the stride calculation section 244. Alternatively, the stride may be calculated by dividing an advancing direction distance for one minute by the running pitch.

Ground Contact Time

The ground contact time is an exercise index defined as time taken from landing to taking-off (kicking) (refer to FIG. 13), and is calculated by the ground contact time/impact time calculation portion 262. The taking-off (kicking) indicates the time when the toe leaves the ground. The ground contact time has a high correlation with a running speed, and may thus be used as running performance of the first analysis information.

Impact Time

Figure 21:
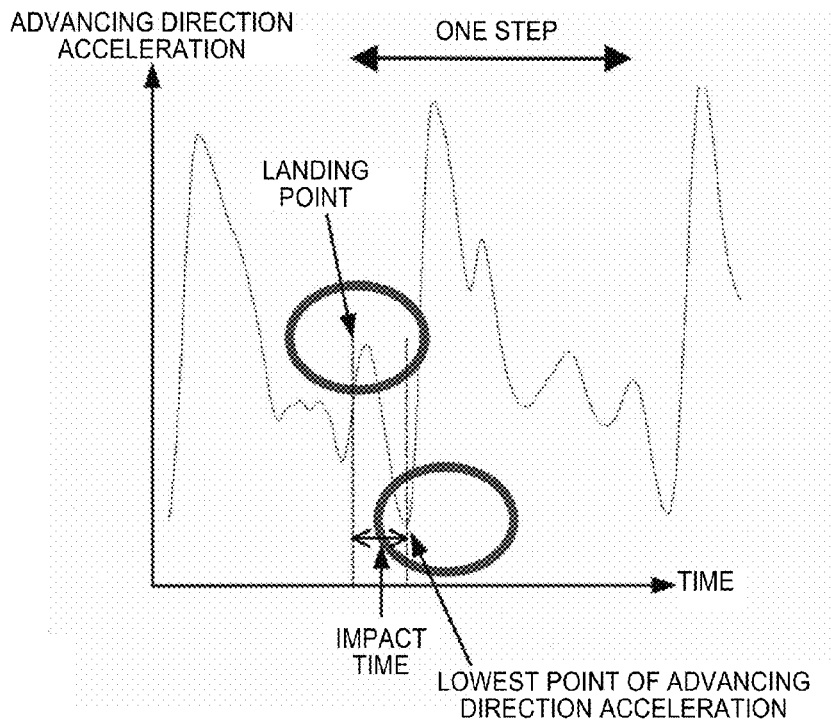
FIG. 21 is a diagram illustrating a method of computing an impact time.

The impact time is an exercise index defined as time when an impact caused by landing is being applied to the body, and is calculated by the ground contact time/impact time calculation portion 262. A method of computing the impact time will be described with reference to FIG. 21. In FIG. 21, a transverse axis expresses time, and a longitudinal axis expresses advancing direction acceleration. As illustrated in FIG. 21, the impact time may be computed as the impact time=(time point at which advancing direction acceleration is the minimum during one step–a time point of landing).

Weight

The weight is a user's weight, and a numerical value thereof is input by the user operating the operation unit 150 before running.

1-8-3. First Analysis Information

Hereinafter, a description will be made of details of each item of the first analysis information calculated by the first analysis information generation section 273.

Brake Amount 1 in Landing

Figure 22:
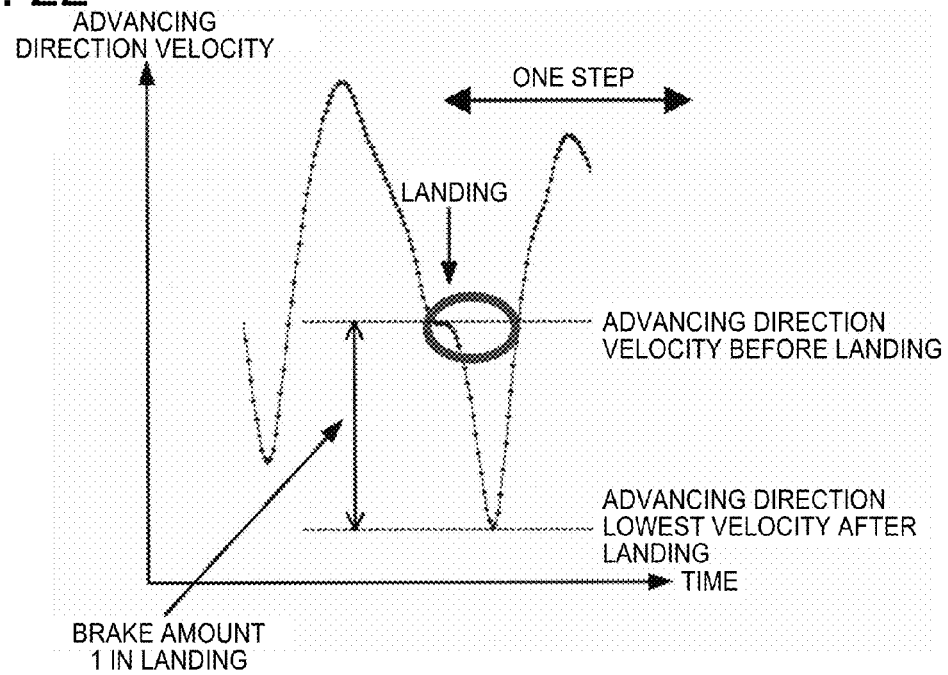
FIG. 22 is a diagram illustrating a method of computing a brake amount 1 in landing.

The brake amount 1 in landing is an exercise index defined as an amount of velocity which is reduced due to landing. A method of computing the brake amount 1 in landing will be described with reference to FIG. 22. In FIG. 22, a transverse axis expresses time, and a longitudinal axis expresses advancing direction velocity. As illustrated in FIG. 22, the brake amount 1 in landing may be computed as (advancing direction velocity before landing)–(advancing direction lowest velocity after landing). The velocity in the advancing direction is reduced due to landing, and the lowest point in the advancing direction velocity after the landing during one step is the advancing direction lowest velocity.

Brake Amount 2 in Landing

Figure 23:
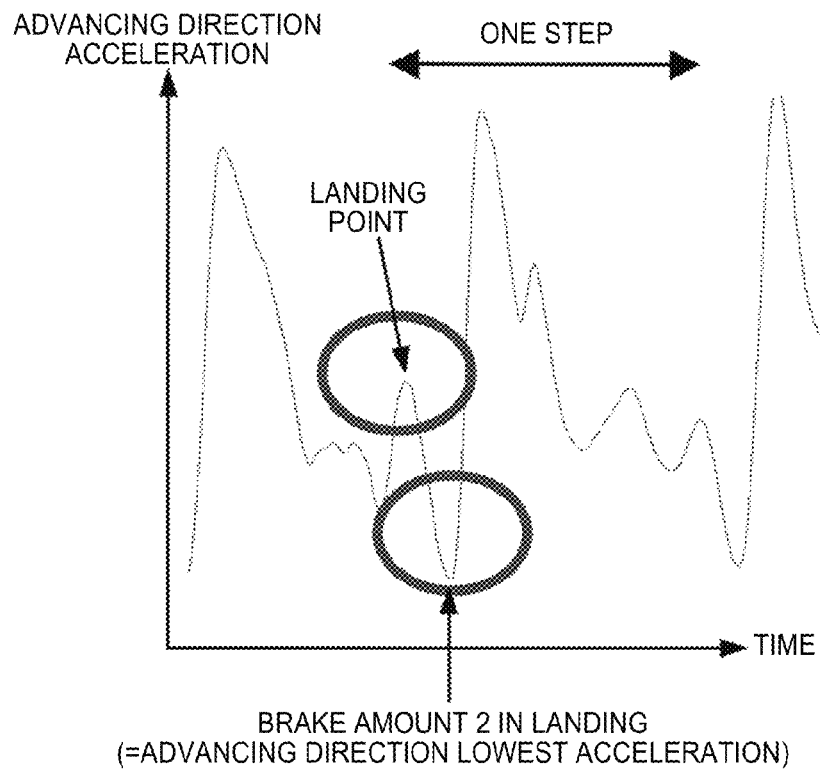
FIG. 23 is a diagram illustrating a method of computing a brake amount 2 in landing.

The brake amount 2 in landing is an exercise index defined as an amount of the lowest acceleration in the advancing direction, caused by landing. A description will be made of a method of computing the brake amount 2 in landing with reference to FIG. 23. In FIG. 23, a transverse axis expresses time, and a longitudinal axis expresses advancing direction acceleration. As illustrated in FIG. 23, the brake amount 2 in landing matches the advancing direction lowest acceleration after landing during one step. The lowest point of the advancing direction acceleration after landing during one step is the advancing direction lowest acceleration.

Directly-Below Landing Ratio 1

Figure 24:
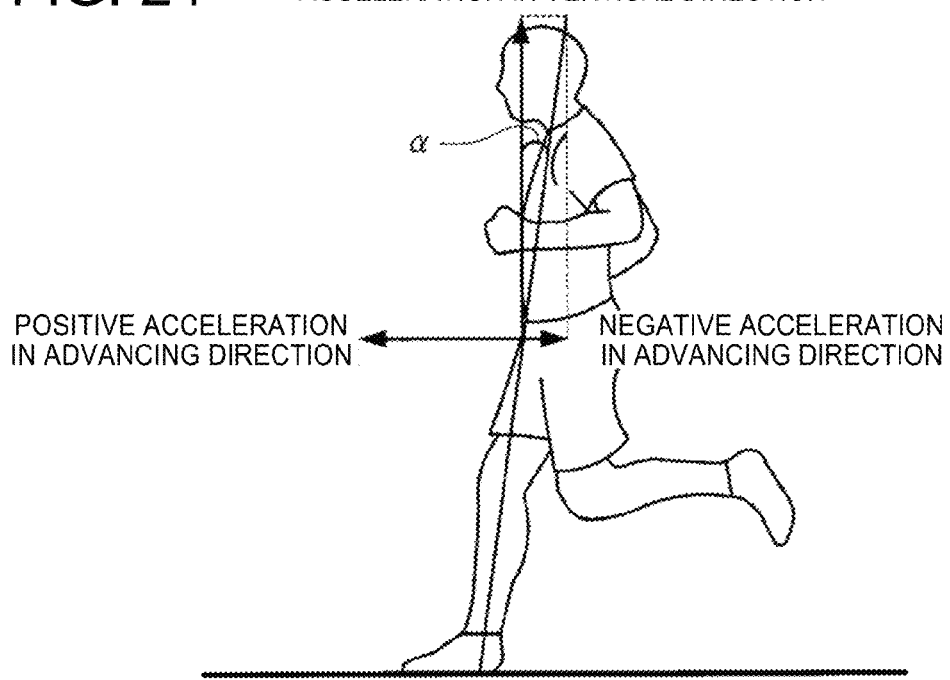
FIG. 24 is a diagram illustrating a method of computing a directly-below landing ratio 1.

The directly-below landing ratio 1 is an exercise index which expresses whether landing is performed directly below the body. If the landing is performed directly under the body, a brake amount is reduced at the time of landing, and thus efficient running can be performed. Typically, since a brake amount increases according to velocity, only the brake amount is not sufficient as indexes, but the directly-below landing ratio 1 is an index which can be expressed in a ratio, and thus the same evaluation can be performed even if velocity changes by using the directly-below landing ratio 1. A description will be made of method of computing the directly-below landing ratio 1 with reference to FIG. 24. As illustrated in FIG. 24, if the advancing direction acceleration (negative acceleration) and the vertical acceleration in landing are used, and $\alpha$ is set as $\alpha$=arctan(advancing direction acceleration in landing/vertical acceleration in landing), the directly-below landing ratio 1 may be computed as the directly-below landing ratio 1=cos $\alpha\times$100(%). Alternatively, an ideal angle $\alpha'$ may be calculated by using data of a plurality of people who run fast, and the directly-below landing ratio 1 may be computed as the directly-below landing ratio 1=$\{1-|(\alpha'-\alpha)/\alpha'|\}\times$100(%).

Directly-Below Landing Ratio 2

Figure 25:
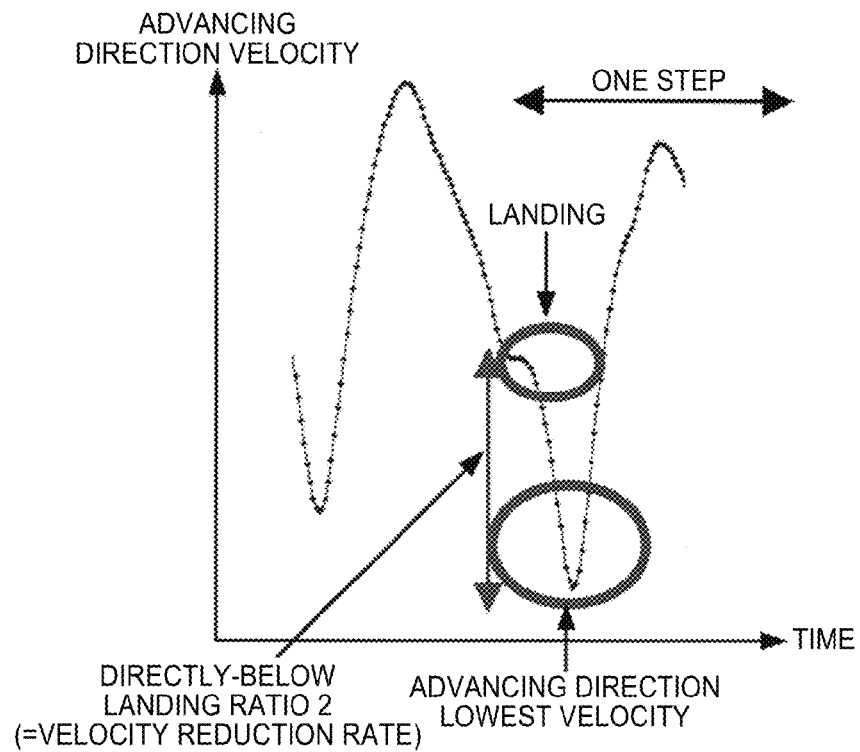
FIG. 25 is a diagram illustrating a method of computing a directly-below landing ratio 2.

The directly-below landing ratio 2 is an exercise index which expresses whether or not landing is performed directly below the body as the extent in which velocity is reduced in landing. A description will be made of a method of computing the directly-below landing ratio 2 with reference to FIG. 25. In FIG. 25, a transverse axis expresses time, and a longitudinal axis expresses advancing direction velocity. As illustrated in FIG. 25, the directly-below landing ratio 2 is computed as the directly-below landing ratio 2=(advancing direction lowest velocity after landing/advancing direction velocity right before landing)$\times$100(%).

Directly-Below Landing Ratio 3

Figure 26:
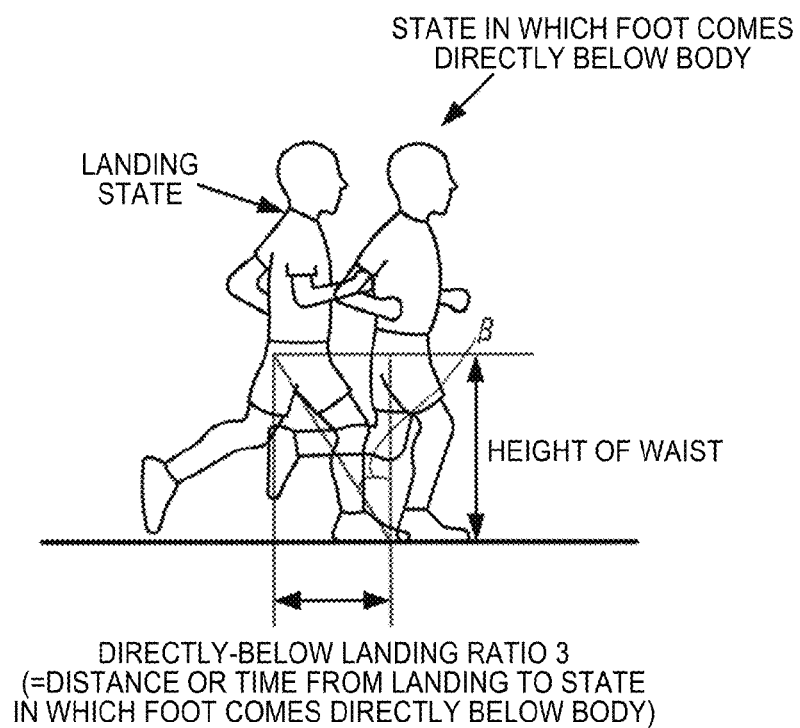
FIG. 26 is a diagram illustrating a method of computing a directly-below landing ratio 3.

The directly-below landing ratio 3 is an exercise index which expresses whether or not landing is performed directly below the body as a distance or time until the foot comes directly under the body from landing. A description will be made of a method of computing the directly-below landing ratio 3 with reference to FIG. 26. As illustrated in FIG. 26, the directly-below landing ratio 3 may be computed as the directly-below landing ratio 3=(advancing direction distance when the foot comes directly below the body)–(advancing direction distance in landing), or the directly-below landing ratio 3=(time point when the foot comes directly below the body)–(time point in landing). Here, as illustrated in FIG. 14, there is a timing at which the vertical acceleration has a peak in the negative direction after landing (a point where the vertical acceleration changes from a positive value to a negative value), and this timing may be determined as being a timing (time point) at which the foot comes directly below the body.

In addition, as illustrated in FIG. 26, the directly-below landing ratio 3 may be defined as the directly-below landing ratio 3=$\beta$=arctan(the distance until the foot comes directly below the body/the height of the waist). Alternatively, the directly-below landing ratio 3 may be defined as the directly-below landing ratio 3=(1–the distance until the foot comes directly below the body/a movement distance from landing to kicking)$\times$100(%) (a ratio occupied by the distance until the foot comes directly below the body in the movement distance during the foot's contact on the ground). Alternatively, the directly-below landing ratio 3 may be defined as the directly-below landing ratio 3=(1–the time until the foot comes directly below the body/movement time from landing to kicking)$\times$100(%) (a ratio occupied by the time until the foot comes directly below the body in the movement time during the foot's contact on the ground).

Propulsion Force 1

Figure 27:
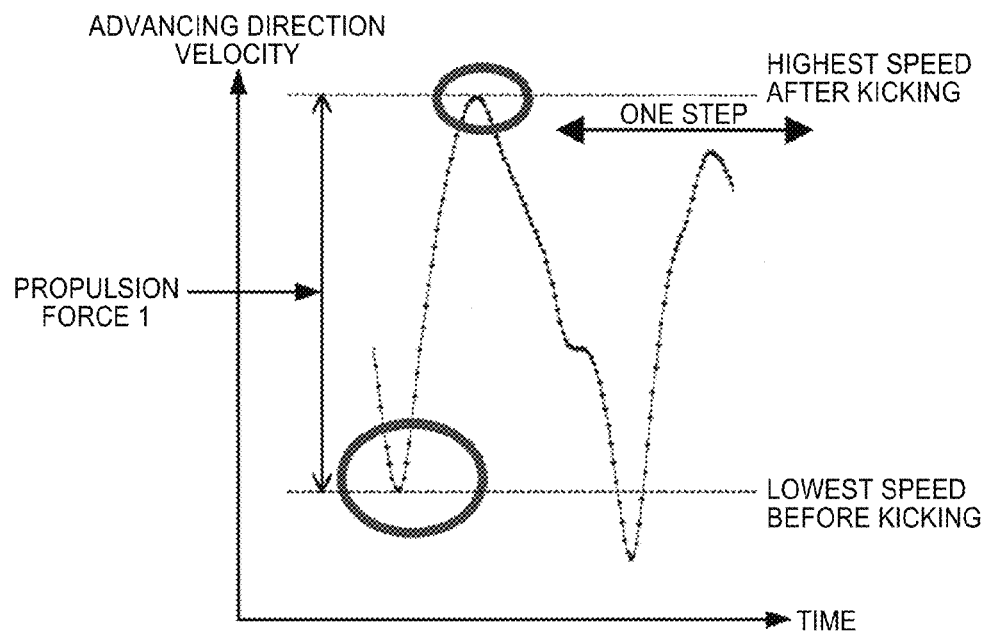
FIG. 27 is a diagram illustrating a method of computing a propulsion force 1.

The propulsion force 1 is an exercise index defined as a velocity amount which is increased in the advancing direction by kicking the ground. A description will be made of a method of computing the propulsion force 1 with reference to FIG. 27. In FIG. 27, a transverse axis expresses time, and a longitudinal axis expresses advancing direction velocity. As illustrated in FIG. 27, the propulsion force 1 may be computed as the propulsion force 1=(advancing direction highest velocity after kicking)–(advancing direction lowest velocity before kicking).

Propulsion Force 2

Figure 28:
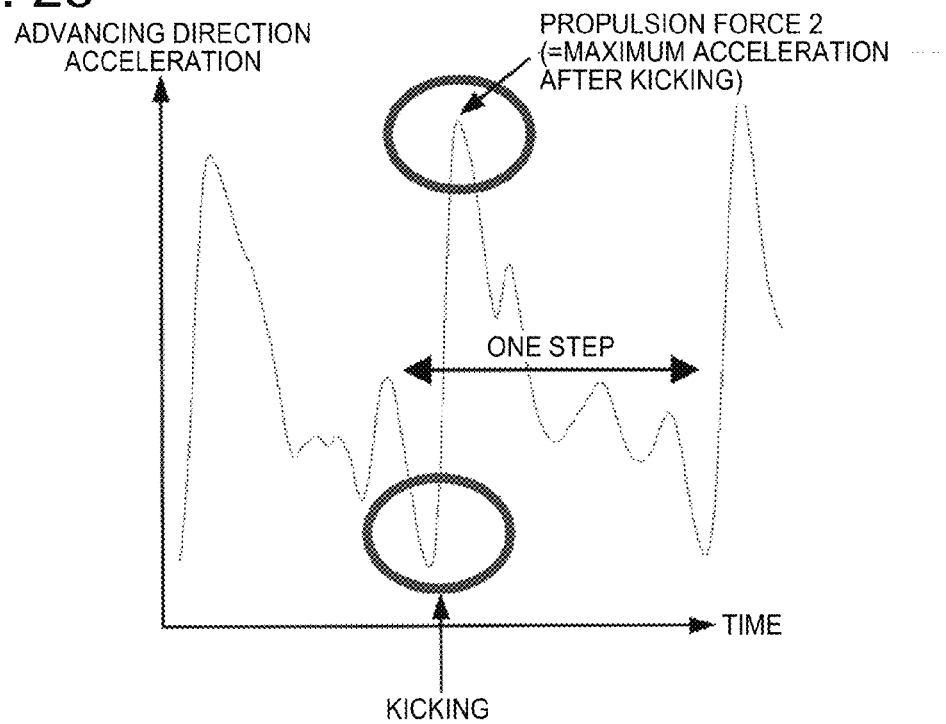
FIG. 28 is a diagram illustrating a method of computing a propulsion force 2.

The propulsion force 2 is an exercise index defined as the maximum acceleration which is increased in the advancing direction by kicking the ground. A description will be made of a method of computing the propulsion force 2 with reference to FIG. 28. In FIG. 28, a transverse axis expresses time, and a longitudinal axis expresses advancing direction acceleration. As illustrated in FIG. 28, the propulsion force 2 matches the advancing direction maximum acceleration after kicking during one step.

Propulsion Efficiency 1

Figure 29:
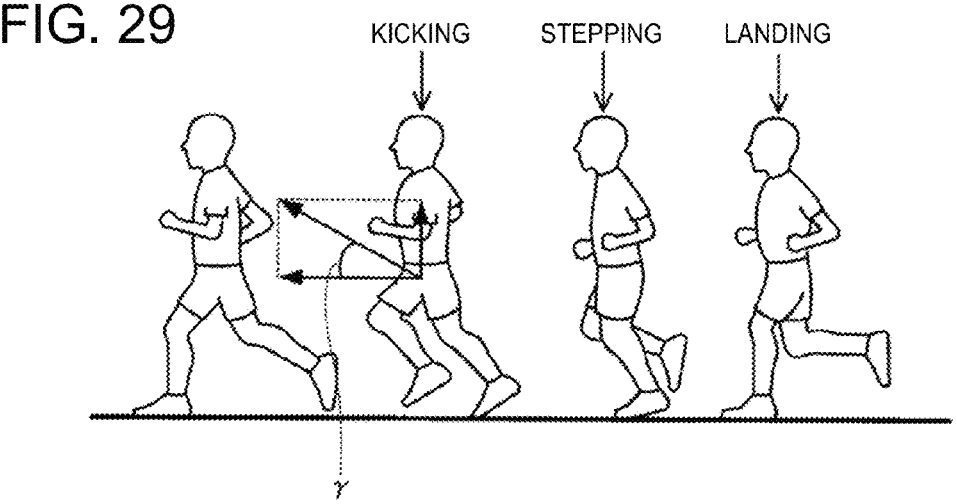
FIG. 29 is a diagram illustrating a method of computing propulsion efficiency 1.

The propulsion efficiency 1 is an exercise index indicating whether or not a kicking force is efficiently converted into a propulsion force. If a useless vertical movement and a useless horizontal movement are removed, efficient running is possible. Generally, since the vertical movement and the horizontal movement increase according to velocity, only the vertical movement and the horizontal movement are not sufficient, but the propulsion efficiency 1 is an index which can be expressed in a ratio, and thus the same evaluation can be performed even if velocity changes by using the propulsion efficiency 1. The propulsion efficiency 1 is computed for each of the vertical direction and the horizontal direction. A description will be made of a method of computing the propulsion efficiency 1 with reference to FIG. 29. As illustrated in FIG. 29, if the vertical acceleration and the advancing direction acceleration in kicking are used, and $\gamma$ is set as $\gamma$=arctan(vertical acceleration in kicking/advancing direction acceleration in kicking), the vertical propulsion efficiency 1 may be computed as the propulsion efficiency 1=cos $\gamma \times 100(\%)$. Alternatively, an ideal angle $\gamma'$ may be calculated by using data of a plurality of people who run fast, and the vertical propulsion efficiency 1 may be computed as the vertical propulsion efficiency 1=1−|($\gamma'$−$\gamma$)/$\gamma'$|×100(%). Similarly, if the horizontal acceleration and the advancing direction acceleration in kicking are used, and $\delta$ is set as $\delta$=arctan(horizontal acceleration in kicking/advancing direction acceleration in kicking), the horizontal propulsion efficiency 1 may be computed as the propulsion efficiency 1=cos $\delta \times 100(\%)$. Alternatively, an ideal angle $\delta'$ may be calculated by using data of a plurality of people who run fast, and the horizontal propulsion efficiency 1 may be computed as horizontal propulsion efficiency 1={1−|($\delta'$−$\delta$)/$\delta'$|}×100 (%).

In addition, the vertical propulsion efficiency 1 may be calculated by replacing $\gamma$ with arctan(vertical velocity in kicking/advancing direction velocity in kicking). Similarly, the horizontal propulsion efficiency 1 may be calculated by replacing $\delta$ with arctan(horizontal velocity in kicking/advancing direction velocity in kicking).

Propulsion Efficiency 2

Figure 30:
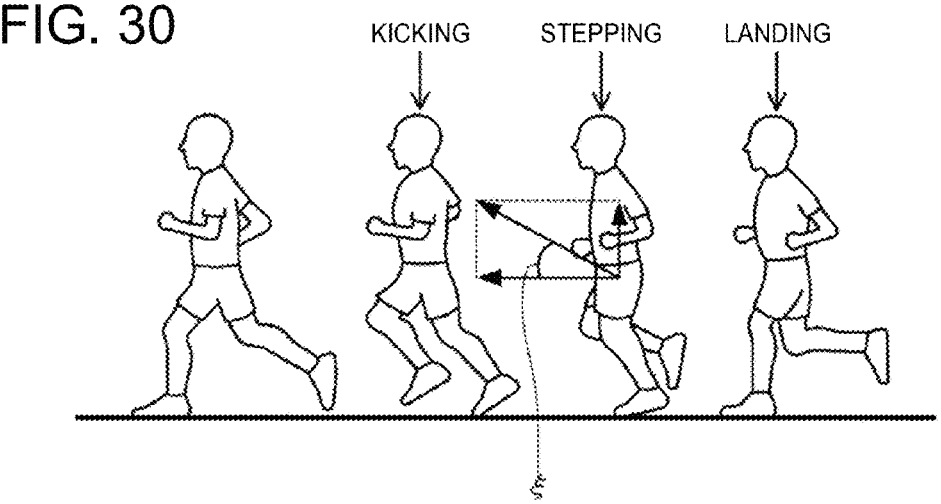
FIG. 30 is a diagram illustrating a method of computing propulsion efficiency 2.

The propulsion efficiency 2 is an exercise index indicating whether or not a kicking force is efficiently converted into a propulsion force by using an angle of acceleration in stepping. A description will be made of a method of computing the propulsion efficiency 2 with reference to FIG. 30. As illustrated in FIG. 30, if the vertical acceleration and the advancing direction acceleration in stepping are used, and $\xi$ is set as $\xi$=arctan(vertical acceleration in stepping/advancing direction acceleration in stepping), the vertical propulsion efficiency 2 may be computed as the propulsion efficiency 2=cos $\xi \times 100(\%)$. Alternatively, an ideal angle $\xi'$ may be calculated by using data of a plurality of people who run fast, and the vertical propulsion efficiency 2 may be computed as the vertical propulsion efficiency 2={1−|($\xi'$−$\xi$)/$\xi'$|}×100(%). Similarly, if the horizontal acceleration and the advancing direction acceleration in kicking are used, and $\eta$ is set as $\eta$=arctan(horizontal acceleration in stepping/advancing direction acceleration in stepping), the horizontal propulsion efficiency 2 may be computed as the propulsion efficiency 2=cos $\eta \times 100(\%)$. Alternatively, an ideal angle $\eta'$ may be calculated by using data of a plurality of people who run fast, and the horizontal propulsion efficiency 2 may be computed as the horizontal propulsion efficiency 2={1−|($\eta'$−$\eta$)/$\eta'$|}×100(%).

In addition, the vertical propulsion efficiency 2 may be calculated by replacing $\xi$ with arctan (vertical velocity in stepping/advancing direction velocity in stepping). Similarly, the horizontal propulsion efficiency 2 may be calculated by replacing $\eta$ with arctan(horizontal velocity in stepping/advancing direction velocity in stepping).

Propulsion Efficiency 3

Figure 31:
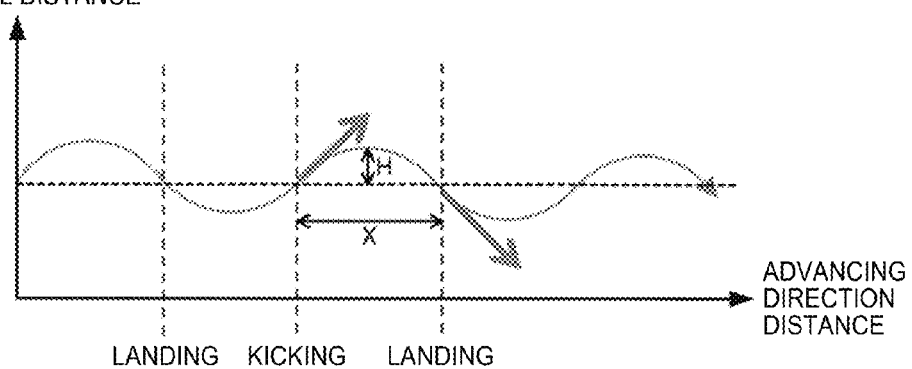
FIG. 31 is a diagram illustrating a method of computing propulsion efficiency 3.

The propulsion efficiency 3 is an exercise index indicating whether or not a kicking force is efficiently converted into a propulsion force by using an angle of rushing. A description will be made of a method of computing the propulsion efficiency 3 with reference to FIG. 31. In FIG. 31, a transverse axis expresses an advancing direction distance, and a longitudinal axis expresses a vertical distance. As illustrated in FIG. 31, if the highest arrival point (½ of the amplitude of the vertical distance) in the vertical direction during one step is denoted by H, and an advancing direction distance from kicking to landing is denoted by X, the propulsion efficiency 3 may be computed by using Equation (6).

$$\text{Propulsion Efficiency 3} = \arcsin\left(\sqrt{\frac{16H^2}{X^2 + 16H^2}}\right) \quad (6)$$

Propulsion Efficiency 4

The propulsion efficiency 4 is an exercise index indicating whether or not a kicking force is efficiently converted into a propulsion force by using a ratio of energy used to go forward in the advancing direction to total energy which is generated during one step. The propulsion efficiency 4 is computed as the propulsion efficiency 4=(energy used to go forward in the advancing direction/energy used for one step)×100(%). This energy is a sum of potential energy and kinetic energy.

Amount of Energy Consumption

The amount of energy consumption is an exercise index defined as an amount of energy which is consumed for one-step advancing, and also indicates a result obtained by integrating an amount of energy consumed for one-step advancing for a running period. The amount of energy consumption is computed as the amount of energy consumption=(an amount of energy consumption in the vertical direction)+(an amount of energy consumption in the advancing direction)+(an amount of energy consumption in the horizontal direction). Here, the amount of energy consumption in the vertical direction is computed as the amount of energy consumption in the vertical direction=(weight×gravity×vertical distance). The amount of energy consumption in the advancing direction is computed as the amount of energy consumption in the advancing direction=[weight×{(advancing direction highest velocity after kicking)−(advancing direction lowest velocity after landing)$^2$}/2]. The amount of energy consumption in the horizontal direction is computed as the amount of energy consumption in the horizontal direction=[weight×{(horizontal direction highest velocity after kicking)$^2$−(horizontal direction lowest velocity after landing)$^2$}/2].

Landing Impact

The landing impact is an exercise index indicating to what extent an impact is applied to the body due to landing. The landing impact is computed as the landing impact=(an impact force in the vertical direction)+(an impact force in the advancing direction)+(an impact force in the horizontal direction). Here, the impact force in the vertical direction is computed as the impact force in the vertical direction= (weight×vertical velocity in landing/impact time). The impact force in the advancing direction is computed as the impact force in the advancing direction={weight×(advancing direction velocity before landing−advancing direction lowest velocity after landing)/impact time}. The impact force in the horizontal direction is computed as the impact force in the horizontal direction={weight×(horizontal velocity before landing−horizontal lowest velocity after landing)/impact time}.

Running Performance

The running performance is an exercise index indicating a user's running force. For example, it is known that there is a correlation between a ratio of a stride and ground contact time, and a running record (time) ("As for Ground Contact Time and Taking-Off Time in Race on 100 m Track", Journal of Research and Development for Future Athletics. 3(1):1-4, 2004.). The running performance is computed as the running performance=(stride/ground contact time).

Forward Tilt Angle

Figure 32:
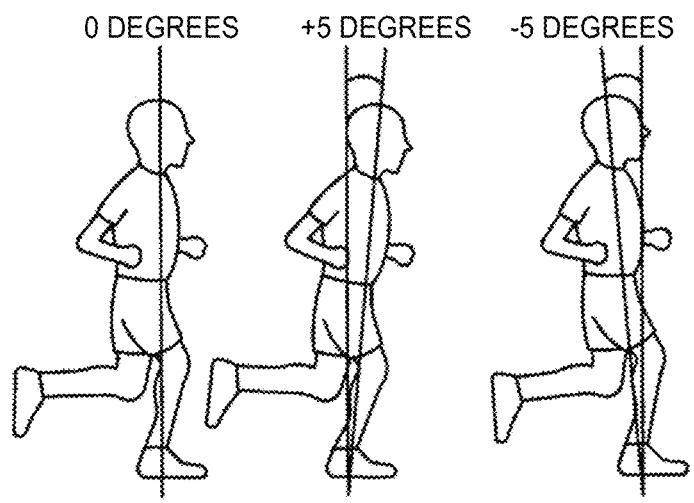
FIG. 32 is a diagram illustrating a forward tilt angle.

The forward tilt angle is an exercise index indicating to what extent the user's body is tilted with respect to the ground. As illustrated in FIG. 32, if the forward tilt angle is set to 0 degrees when the user stands vertically to the ground (the left part), the forward tilt angle has a positive value when the user bends forward (the central part), and the forward tilt angle has a negative value when the user bends backward (the right part). The forward tilt angle is obtained by converting a pitch angle of the m frame so as to cause the same specification. Since the exercise analysis apparatus 2 (the inertial measurement unit 10) is mounted on the user, and may be already tilted at this time, the forward tilt angle is assumed to be 0 degrees in the left part of FIG. 32 during stoppage, and may be computed by using an amount of change therefrom.

Timing Coincidence

Figure 33A:
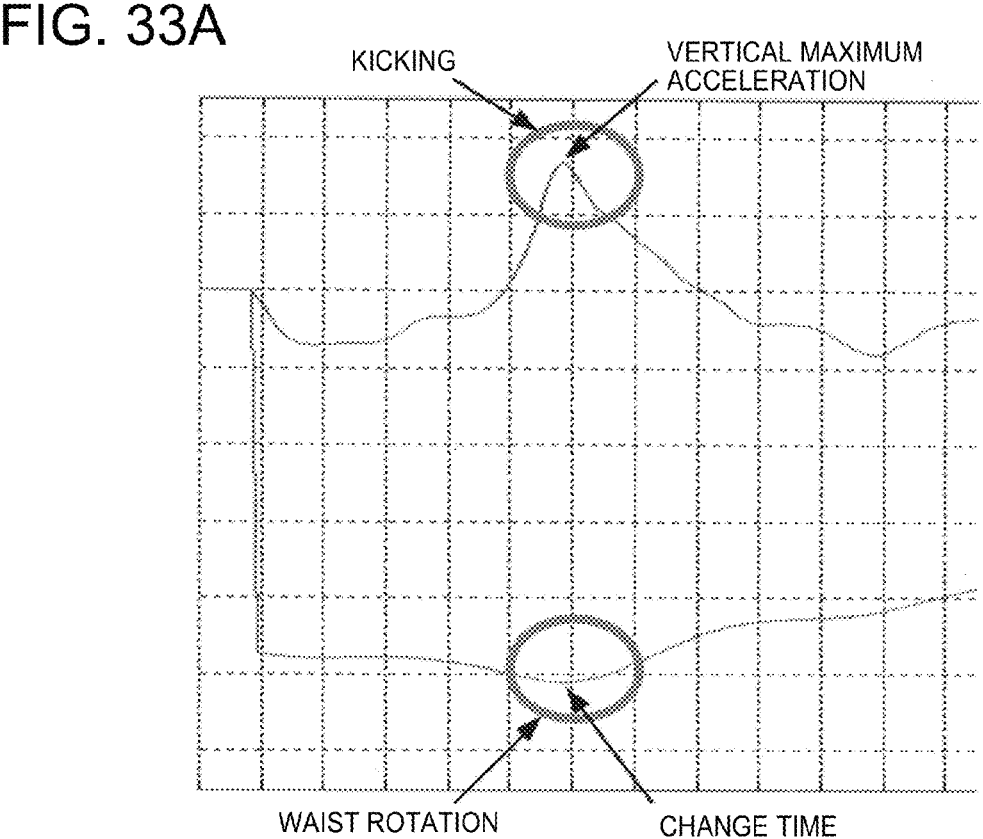
FIGS. 33A and 33B illustrate examples of a relationship between a waist rotation timing and a kicking timing.
Figure 33B:
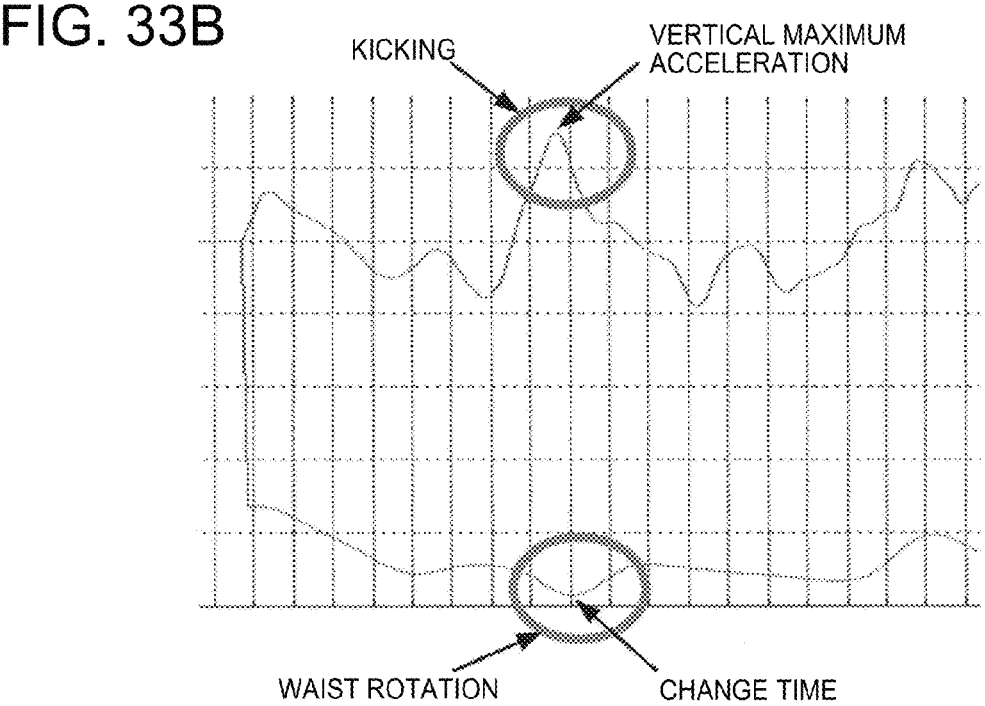

The timing coincidence is an exercise index indicating how close to a good timing a timing of a user's feature point is. For example, an exercise index indicating how close to a kicking timing a timing of waist rotation is. In the way of the slow turnover of the legs, since, when one leg reaches the ground, the other leg remains behind the body still, a case where a waist rotation timing comes after kicking may be determined as being the slow turnover the legs. In FIG. 33A, a waist rotation timing substantially matches a kicking timing, and thus this can be said to be good running. On the other hand, in FIG. 33B, a waist rotation timing is later than a kicking timing, and thus this can be said to be in the way of the slow turnover of the legs.

1-8-4. Second Analysis Information

Hereinafter, a description will be made of details of each item of the second analysis information calculated by the second analysis information generation section 274.

Energy Loss

The energy loss is an exercise index indicating an amount of energy which is wastefully used with respect to an amount of energy consumed for one-step advancing, and also indicates a result obtained by integrating an amount of energy which is wastefully used with respect to an amount of energy consumed for one-step advancing for a running period. The energy loss is computed as the energy loss={amount of energy consumption×(100−directly-below landing ratio)×(100−propulsion efficiency)}. Here, the directly-below landing ratio is any one of the directly-below landing ratios 1 to 3, and the propulsion efficiency is any one of the propulsion efficiency 1 to the propulsion efficiency 4.

Energy Efficiency

The energy efficiency is an exercise index indicating whether or not the energy consumed for one-step advancing is efficiently used as energy for going forward in the advancing direction, and also indicates a result obtained by integrating the energy for a running period. The energy efficiency is computed as the energy efficiency={(amount of energy consumption−energy loss)/(amount of energy consumption)}.

Burden on Body

The burden on the body is an exercise index indicating to what extent impacts are accumulated in the body by accumulating a landing impact. An injury occurs due to accumulation of impacts, and thus likelihood of an injury can be determined by evaluating the burden on the body. The burden on the body is computed as the burden on the body=(burden on right leg+burden on left leg). The burden on the right leg may be computed by integrating landing impacts on the right leg. The burden on the left leg may be computed by integrating landing impacts on the left leg. Here, as the integration, both integration during running and integration from the past are performed.

1-8-5. Left-Right Difference Ratio (Left-Right Balance)

The left-right difference ratio is an exercise index indicating to what extent there is a difference between the left and right sides of the body for the running pitch, the stride, the ground contact time, the impact time, each item of the first analysis information, and each item of the second analysis information, and is assumed to indicate to what extent the left leg is deviated relative to the right leg. The left-right difference ratio is computed as the left-right difference ratio=(numerical value for left leg/numerical value for right leg×100(%)). The numerical value is a numerical value of each of the running pitch, the stride, the ground contact time, the impact time, the brake amount, the propulsion force, the directly-below landing ratio, the propulsion efficiency, the velocity, the acceleration, the movement distance, the forward tilt angle, the waist rotation angle, the waist rotation angular velocity, the amount of being tilted toward the left and right sides, the impact time, the running performance, the amount of energy consumption, the energy loss, the energy efficiency, the landing impact, and the burden on the body. The left-right difference ratio also includes an average value or a variance of the respective numerical values.

1-9. Feedback During Running 1-9-1. Feedback Information

The output-information-during-running generation portion 280 outputs the basic information such as the running pitch, the stride, the running velocity, the elevation, the running distance, and the running time, as the output information during running. The output-information-during-running generation portion 280 outputs, as the output information during running, each value of the present information such as the ground contact time, the brake amount in landing, the directly-below landing ratio, the propulsion efficiency, the ground contact time, the forward tilt angle, the timing coincidence, the running performance, the energy efficiency, and the left-right difference ratio, or an average value (movement average value) corresponding to several steps (for example, ten steps). The output-information-during-running generation portion 280 outputs, as the output information during running, information in which the numerical values are graphed in a time series, and time-series information of the amount of energy consumption and the burden on the body (accumulated damage). The output-information-during-running generation portion 280 outputs, as the output information during running, information for evaluating a running state of the user, advice information for improving a running state of the user, advice information for improving running attainments of the user, running path information, and the like. The output information during running is presented (feedback) to the user during the user's running.

1-9-2. Feedback Timing

The output-information-during-running generation portion 280 may output the output information during running at all time during running. Alternatively, in a case where a numerical value of a predetermined item exceeds a threshold value (reference value), the output-information-during-running generation portion 280 may output information regarding the exceeding state, the item whose numerical value exceeds the threshold value, or the worst item. Alternatively, in a case where a numerical value of a predetermined item does not exceed a threshold value (reference value), the output-information-during-running generation portion 280 may output information regarding a state in which the numerical value does not exceed the threshold value, the item whose numerical value does not exceed the threshold value, or the best item. Alternatively, the output-information-during-running generation portion 280 may output information selected by the user at all times during running. Alternatively, in a case where information selected by the user exceeds a threshold value (reference value), the output-information-during-running generation portion 280 may output the exceeding state and a numerical value thereof. Alternatively, in a case where information selected by the user does not exceed a threshold value, the output-information-during-running generation portion 280 may output a state in which the information does not exceed the threshold value, and a numerical value thereof.

1-9-3. Feedback Method

The output information during running output from the output-information-during-running generation portion 280 may be displayed on a screen of the display unit 170 of the notification apparatus 3 so as to be fed back to the user. Alternatively, the output information during running may be fed back in voice from the sound output unit 180 of the notification apparatus 3. Alternatively, the content regarding a timing such as a waist rotation timing, a pitch, or a kicking timing may be fed back in short sound such as "beep beep" from the sound output unit 180 of the notification apparatus 3. Alternatively, the user may be instructed to view the content displayed on the display unit 170 by using sound or vibration from the sound output unit 180 or the vibration unit 190 of the notification apparatus 3.

1-9-4. Specific Examples of Feedback

Running Pitch

For example, a numerical value of the present running pitch or an average value corresponding to several steps may be displayed on the display unit 170, and sound of a tempo or a length corresponding to the running pitch, or music corresponding to the running pitch may be output from the sound output unit 180. For example, an inverse number of the running pitch (time per step) may be calculated, and short sound for each step may be output.

Alternatively, it may be determined whether or not the running pitch is within a reference range (equal to or higher than a lower limit threshold value, or equal to or lower than an upper limit threshold value) which is set in advance, and, in a case where the running pitch is lower than the lower limit threshold value, display or voice such as the content that "the pitch is decreasing" may be performed on the display unit 170 or may be output from the sound output unit 180, and, in a case where the running pitch is higher than the upper limit threshold value, display or voice such as the content that the content that "the pitch is increasing" may be performed on the display unit 170 or may be output from the sound output unit 180. Alternatively, in a case where the running pitch is lower than the lower limit threshold value, sound or vibration of a slow tempo may be output from the sound output unit 180 or the vibration unit 190, and in a case where the running pitch is higher than the upper limit threshold value, sound or vibration of a fast tempo may be output, so that a tempo of sound or vibration switches in each case.

Alternatively, if the running pitch is not included in the reference range, display or voice of an advice for causing the running pitch to enter the reference range, such as the content that "the pitch is decreasing; intentionally increase the pitch by slightly narrowing a stride", or "the pitch is increasing; intentionally decrease the pitch by slightly widening a stride", may be performed on the display unit 170 or may be output from the sound output unit 180.

Stride

For example, a numerical value of the present stride or an average value corresponding to several steps may be displayed on the display unit 170, and sound of a tempo or a length corresponding to the stride, or music corresponding to the stride may be output from the sound output unit 180.

Alternatively, it may be determined whether or not the stride is within a reference range (equal to or higher than a lower limit threshold value, or equal to or lower than an upper limit threshold value) which is set in advance, and, in a case where the stride is lower than the lower limit threshold value, display or voice such as the content that "stride is shortening" may be performed on the display unit 170 or may be output from the sound output unit 180, and, in a case where the stride is higher than the upper limit threshold value, display or voice such as the content that the content that "stride is lengthening" may be performed on the display unit 170 or may be output from the sound output unit 180. Alternatively, in a case where the stride is lower than the lower limit threshold value, sound or vibration of a slow tempo may be output from the sound output unit 180 or the vibration unit 190, and in a case where the running pitch is higher than the upper limit threshold value, sound or vibration of a fast tempo may be output, so that a tempo of sound or vibration switches in each case.

Alternatively, if the stride is not included in the reference range, display or voice of an advice for causing the stride to enter the reference range, such as the content that "the stride is decreasing; intentionally increase the stride by slightly widening the stride", or "the stride is increasing; intentionally decrease the stride by slightly narrowing the stride", may be performed on the display unit 170 or may be output from the sound output unit 180.

Ground Contact Time

For example, the present ground contact time or an average value corresponding to several steps may be displayed on the display unit 170, and sound of a tempo or a length corresponding to the ground contact time, or music corresponding to the ground contact time may be output from the sound output unit 180. However, since the user recognizes a numerical value of the ground contact time but hardly determines whether this numerical value indicates a right state or a wrong state, for example, it may be determined to which level of, for example, 10 levels a numerical value of the ground contact time belongs by using, for example, a predefined threshold value, and a level the ground contact time of the user may be fed back as 1 to 10.

Alternatively, in a case where an average value of the ground contact time improves during running, display or voice of an advice that "the running performance increases; let's exercise continuously in this state" may be performed on the display unit 170 or may be output from the sound output unit 180.

Brake Amount 1 in Landing

For example, a numerical value of the present brake amount 1 in landing or an average value corresponding to several steps may be displayed on the display unit 170, and sound with a volume corresponding to the brake amount 1 in landing may be output from the sound output unit 180.

Alternatively, in a case where the brake amount 1 in landing is compared with a threshold value which is set in advance, and is higher than the threshold value, it may be determined that the brake amount is too large, and display or voice such as the content that "the brake amount is increasing; there is a possibility of waist-falling running way", may be performed on the display unit 170 or may be output from the sound output unit 180. Alternatively, in a case where the brake amount 1 in landing is higher than the threshold value, sound or vibration other than voice may be output.

Alternatively, in a case where the brake amount 1 in landing is higher than the threshold value, display or voice of an advice such as the content that "the brake amount is increasing; if the brake amount is large, efficiency is reduced, and thus danger of being injured also increases" or "there is a possibility of waist-falling running way; pay attention to the pelvis, and set the foot directly below the body so that the waist falls in landing" may be performed on the display unit 170 or may be output from the sound output unit 180.

Brake Amount 2 in Landing

In the same manner as in the brake amount 1 in landing, a numerical value of the brake amount 2 in landing or an average value corresponding to several steps is fed back, or in a case where the brake amount 2 in landing is higher than a threshold value, it is fed back that the brake amount is too large. Alternatively, in a case where the brake amount 2 in landing is higher than the threshold value, the same advice as in the brake amount 1 in landing may be fed back.

Directly-Below Landing Ratio 1

For example, a numerical value of the present directly-below landing ratio 1 or an average value corresponding to several steps may be displayed on the display unit 170, and sound with a volume corresponding to the directly-below landing ratio 1 may be output from the sound output unit 180.

Alternatively, in a case where the directly-below landing ratio 1 is compared with a threshold value which is set in advance, and is lower than the threshold value, it may be determined that directly-below landing is not performed, and display or voice such as the content that "the directly-below landing ratio is decreasing" or "directly-below landing is not performed" may be performed on the display unit 170 or may be output from the sound output unit 180. Alternatively, in a case where the directly-below landing ratio 1 is lower than the threshold value, sound or vibration other than voice may be output.

Alternatively, in a case where the directly-below landing ratio 1 is lower than the threshold value, display or voice of an advice such as the content that "the directly-below landing ratio is decreasing; if the directly-below landing is not performed, this causes an increase in the brake amount and an increase in vertical movement, and thus efficiency of running is reduced; intentionally put the waist firmly by stretching the backbone", may be performed on the display unit 170 or may be output from the sound output unit 180.

Directly-Below Landing Ratio 2

In the same manner as in the directly-below landing ratio 1, a numerical value of the directly-below landing ratio 2 or an average value corresponding to several steps is fed back, or in a case where the directly-below landing ratio 2 is lower than a threshold value, it is fed back that the directly-below landing is not performed. Alternatively, in a case where the directly-below landing ratio 2 is lower than the threshold value, the same advice as in the directly-below landing ratio 1 may be fed back.

Directly-Below Landing Ratio 3

In the same manner as in the directly-below landing ratio 1, a numerical value of the directly-below landing ratio 3 or an average value corresponding to several steps is fed back, or in a case where the directly-below landing ratio 3 is lower than a threshold value, it is fed back that the directly-below landing is not performed. Alternatively, in a case where the directly-below landing ratio 3 is lower than the threshold value, the same advice as in the directly-below landing ratio 1 may be fed back.

Propulsion Force 1

For example, a numerical value of the present propulsion force 1 or an average value corresponding to several steps may be displayed on the display unit 170, and sound with a volume corresponding to the propulsion force 1 may be output from the sound output unit 180.

Alternatively, in a case where the propulsion force 1 is compared with a threshold value which is set in advance, and is lower than the threshold value, it may be determined that propulsion force decreases, and display or voice such as the content that "the propulsion force is decreasing" or "there is a possibility that a kicking force may act upward" may be performed on the display unit 170 or may be output from the sound output unit 180. Alternatively, in a case where the propulsion force 1 is lower than the threshold value, sound or vibration other than voice may be output.

Alternatively, in a case where the propulsion force 1 is lower than the threshold value, display or voice of an advice such as the content that "there is a possibility that a kicking force may act upward; run in such a state of capturing the ground with the entire sole instead of kicking", may be performed on the display unit 170 or may be output from the sound output unit 180.

Propulsion Force 2

In the same manner as in the propulsion force 1, a numerical value of the propulsion force 2 or an average value corresponding to several steps is fed back, or in a case where the propulsion force 2 is lower than a threshold value, it is fed back that the propulsion force decreases. Alternatively, in a case where the propulsion force 2 is lower than the threshold value, the same advice as in the propulsion force 1 may be fed back.

Propulsion Efficiency 1

For example, the present propulsion efficiency 1 or an average value corresponding to several steps may be displayed on the display unit 170, and sound with a volume corresponding to the propulsion efficiency 1 may be output from the sound output unit 180. However, since the user recognizes a numerical value of the propulsion efficiency 1 but hardly determines whether this numerical value indicates a right state or a wrong state, for example, a direction corresponding to the present propulsion efficiency 1 of the user and a direction corresponding to ideal propulsion efficiency 1 (about 45 degrees) may be displayed so as to overlap each other (or may be displayed in parallel to each other).

Alternatively, in a case where the propulsion efficiency 1 is compared with a threshold value which is set in advance, and is lower than the threshold value, it may be determined that the vertical movement or the horizontal movement is too large, and display or voice such as the content that "the propulsion efficiency is decreasing" or "the vertical movement or the horizontal movement is large", may be performed on the display unit 170 or may be output from the sound output unit 180. Alternatively, in a case where the propulsion efficiency 1 is lower than the threshold value, sound or vibration other than voice may be output.

Alternatively, in a case where the propulsion efficiency 1 is lower than the threshold value, display or voice such as the content that "the vertical movement or the horizontal movement is large; if you kicks excessively, you takes such a form as springing up, and a burden on the calves increases; therefore, run in such a state of capturing the ground with the entire sole", may be performed on the display unit 170 or may be output from the sound output unit 180.

Propulsion Efficiency 2

In the same manner as in the propulsion efficiency 1, a numerical value of the propulsion efficiency 2 or an average value corresponding to several steps is fed back, or in a case where the propulsion efficiency 2 is lower than a threshold value, it is fed back that the vertical movement or the horizontal movement is too large. Alternatively, in a case where the propulsion efficiency 2 is lower than the threshold value, the same advice as in the propulsion efficiency 1 may be fed back.

Propulsion Efficiency 3

In the same manner as in the propulsion efficiency 1, a numerical value of the propulsion efficiency 3 or an average value corresponding to several steps is fed back, or in a case where the propulsion efficiency 3 is lower than a threshold value, it is fed back that the vertical movement or the horizontal movement is too large. Alternatively, in a case where the propulsion efficiency 3 is lower than the threshold value, the same advice as in the propulsion efficiency 1 may be fed back.

Propulsion Efficiency 4

In the same manner as in the propulsion efficiency 1, a numerical value of the propulsion efficiency 4 or an average value corresponding to several steps is fed back, or in a case where the propulsion efficiency 4 is lower than a threshold value, it is fed back that the vertical movement or the horizontal movement is too large. Alternatively, in a case where the propulsion efficiency 4 is lower than the threshold value, the same advice as in the propulsion efficiency 1 may be fed back.

Amount of Energy Consumption

For example, the amount of energy consumption hitherto may be displayed on the display unit 170, and sound with a volume corresponding to the amount of energy consumption may be output from the sound output unit 180.

Alternatively, in a case where the amount of energy consumption is compared with a threshold value which is set in advance, and is higher than the threshold value, it may be determined that the amount of useless energy consumption is too large, and display or voice such as the content that "the amount of energy consumed for one step is increasing", may be performed on the display unit 170 or may be output from the sound output unit 180. Alternatively, in a case where the amount of energy consumption is higher than the threshold value, sound or vibration other than voice may be output.

Alternatively, in a case where the amount of energy consumption is higher than the threshold value, for example, display or voice of an advice such as the content that "the amount of energy consumed for one step is increasing; minimize useless energy consumption through efficient running", may be performed on the display unit 170 or may be output from the sound output unit 180.

Landing Impact

For example, a numerical value of the present landing impact or an average value corresponding to several steps may be displayed on the display unit 170, and sound with a volume corresponding to the landing impact may be output from the sound output unit 180.

Alternatively, in a case where the landing impact is compared with a threshold value which is set in advance, and is higher than the threshold value, it may be determined that the level of useless landing impact is too high, and display or voice such as the content that "the level of landing impact is high", may be performed on the display unit 170 or may be output from the sound output unit 180. Alternatively, in a case where the level of landing impact is higher than the threshold value, sound or vibration other than voice may be output.

Alternatively, in a case where the landing impact is higher than the threshold value, for example, display or voice of an advice such as the content that "the landing impact is serious; if impacts are accumulated, this may lead to an injury; carefully run so as to minimize the vertical movement and to cause the foot to land directly below the body", may be performed on the display unit 170 or may be output from the sound output unit 180.

Running Performance

For example, a numerical value of the present running performance or an average value corresponding to several steps may be displayed on the display unit 170, and sound with a volume corresponding to the propulsion force 1 may be output from the sound output unit 180. However, since the user recognizes a numerical value of the running performance but hardly determines whether this numerical value indicates a right state or a wrong state, for example, it may be determined to which level of, for example, 10 levels a numerical value of the running performance belongs by using, for example, a predefined threshold value, and a level the running performance of the user may be fed back as 1 to 10.

Alternatively, in a case where an average value of the running performance improves during running, display or voice of an advice that "the running performance increases; let's exercise continuously in this state" may be performed on the display unit 170 or may be output from the sound output unit 180.

Forward Tilt Angle

For example, a numerical value of the present forward tilt angle or an average value corresponding to several steps may be displayed on the display unit 170, and sound with a volume corresponding to the forward tilt angle may be output from the sound output unit 180. However, since the user recognizes a numerical value of the forward tilt angle but hardly determines whether this numerical value indicates a right state or a wrong state, for example, an image showing the present attitude of the user and an image showing an ideal attitude (an attitude tilted forward by about 5 degrees to 10 degrees) may be displayed so as to overlap each other (or may be displayed in parallel to each other).

Alternatively, it may be determined whether or not the forward tilt angle is within a reference range (equal to or higher than a lower limit threshold value, or equal to or lower than an upper limit threshold value) which is set in advance, and, in a case where the forward tilt angle is lower than the lower limit threshold value, display or voice such as the content that "you are running in a state of being tilted backward" may be performed on the display unit 170 or may be output from the sound output unit 180, and, in a case where the forward tilt angle is higher than the upper limit threshold value, display or voice such as the content that the content that "you are running in a state of being tilted forward much" may be performed on the display unit 170 or may be output from the sound output unit 180. Alternatively, in a case where the forward tilt angle is lower than the lower limit threshold value, sound with a small volume or weak vibration may be output from the sound output unit 180 or the vibration unit 190, and in a case where the forward tilt angle is higher than the upper limit threshold value, sound with a large volume or strong vibration may be output, so that a volume or vibration strength switches in each case.

Alternatively, if the forward tilt angle is not included in the reference range, display or voice of an advice for causing the forward tilt angle to enter the reference range, such as the content that "you are running in a state of being tilted backward; there is a possibility of stooping slightly; intentionally put the body directly on the top of the pelvis and move the centroid to the stepping foot", may be performed on the display unit 170 or may be output from the sound output unit 180.

Timing Coincidence

For example, a numerical value of the present timing coincidence or an average value corresponding to several steps may be displayed on the display unit 170, and sound with a volume corresponding to the timing coincidence may be output from the sound output unit 180.

Alternatively, it may be determined whether or not the timing coincidence is within a reference range (equal to or higher than a lower limit threshold value, or equal to or lower than an upper limit threshold value) which is set in advance, and, in a case where the timing coincidence is not included in the reference range, display or voice indicating that the timing coincidence is not included in the reference range may be performed on the display unit 170 or may be output from the sound output unit 180. Alternatively, in a case where the timing coincidence is not included in the reference range, a volume or vibration strength may be output in a switching manner from the sound output unit 180 or the vibration unit 190.

Alternatively, if the timing coincidence is not included in the reference range, display or voice of an advice for causing the timing coincidence to enter the reference range may be performed on the display unit 170 or may be output from the sound output unit 180.

As an example, regarding the timing coincidence between a waist rotation timing and a kicking timing, for example, a numerical value (a positive or negative numerical value) of a difference between the present waist rotation timing and the kicking timing or an average value corresponding to several steps may be displayed, or sound with a volume corresponding to the numerical value of the difference may be output. Alternatively, in a case where the difference between the waist rotation timing and the kicking timing is higher than an upper limit threshold value, it may be determined that the user is in the way of the slow turnover of the legs, and display or voice such as the content that "you are in the way of the slow turnover of the legs" may be performed or may be output. Alternatively, in a case where the difference between the waist rotation timing and the kicking timing is higher than the upper limit threshold value, for example, display or voice of an advice such as the content that "you are in the way of the slow turnover of the legs; power under the knee is used for running, and thus the calves may become tired soon; intentionally increase a speed of pulling the kicking leg", may be performed or may be output.

Energy Loss

For example, a numerical value of the present energy loss or an average value corresponding to several steps may be displayed on the display unit 170, and sound with a volume corresponding to the energy loss may be output from the sound output unit 180.

Alternatively, in a case where the amount of energy loss is compared with a threshold value which is set in advance, and is higher than the threshold value, it may be determined that the amount of useless energy loss is too large, and display or voice such as the content that "the amount of energy consumed for one step is increasing", may be performed on the display unit 170 or may be output from the sound output unit 180. Alternatively, in a case where the amount of energy loss is higher than the threshold value, sound or vibration other than voice may be output.

Alternatively, in a case where the amount of energy loss is higher than the threshold value, for example, display or voice of an advice such as the content that "the amount of energy consumed for one step is increasing; minimize useless energy consumption through efficient running", may be performed on the display unit 170 or may be output from the sound output unit 180.

Energy Efficiency

In the same manner as in the energy loss, a numerical value of the energy efficiency is fed back, or in a case where the energy efficiency is higher than a threshold value, it is fed back that the amount of useless energy consumption is too large. Alternatively, in a case where the energy loss is higher than the threshold value, the same advice as in the energy loss may be fed back.

Burden on Body

For example, a numerical value of the burden on the body (accumulated damage) hitherto may be displayed on the display unit 170, and sound with a volume corresponding to the burden on the body may be output from the sound output unit 180.

Alternatively, in a case where the burden on the body is compared with a threshold value which is set in advance, and is higher than the threshold value, it may be determined that the level of burden on the body is too high, and display or voice such as the content that "the burden on the body is increasing", may be performed on the display unit 170 or may be output from the sound output unit 180. Alternatively, in a case where the level of burden on the body is higher than the threshold value, sound or vibration other than voice may be output.

Alternatively, in a case where the level of burden on the body is higher than the threshold value, for example, display or voice of an advice such as the content that "the burden on the body is increasing; take a break; excessive burdens may cause an injury; carefully run so as to minimize the vertical movement and to cause the foot to land directly below the body", may be performed on the display unit 170 or may be output from the sound output unit 180.

Left-Right Difference Ratio

For example, a numerical value of the present left-right difference ratio or an average value corresponding to several steps for the above-described items may be displayed on the display unit 170, and sound with a volume corresponding to the left-right difference ratio may be output from the sound output unit 180.

Alternatively, it may be determined whether or not the left-right difference ratio is within a reference range (equal to or higher than a lower limit threshold value (for example, 70%), or equal to or lower than an upper limit threshold value (for example, 130%)) which is set in advance, and, in a case where the timing coincidence is not included in the reference range, display or voice such as the content that "the left and right balance is not good" may be performed on the display unit 170 or may be output from the sound output unit 180.

Alternatively, in a case where the left-right difference ratio is not included in the reference range, display or voice of an advice such as the content that "the bad left and right balance causes an injury; in order to reduce the difference between the left and right sides, you obtain uniform flexibility through stretching or train the muscles or the gluteus medius of the trunk" may be performed on the display unit 170 or may be output from the sound output unit 180.

1-9-5. Display Examples

Figure 34A:
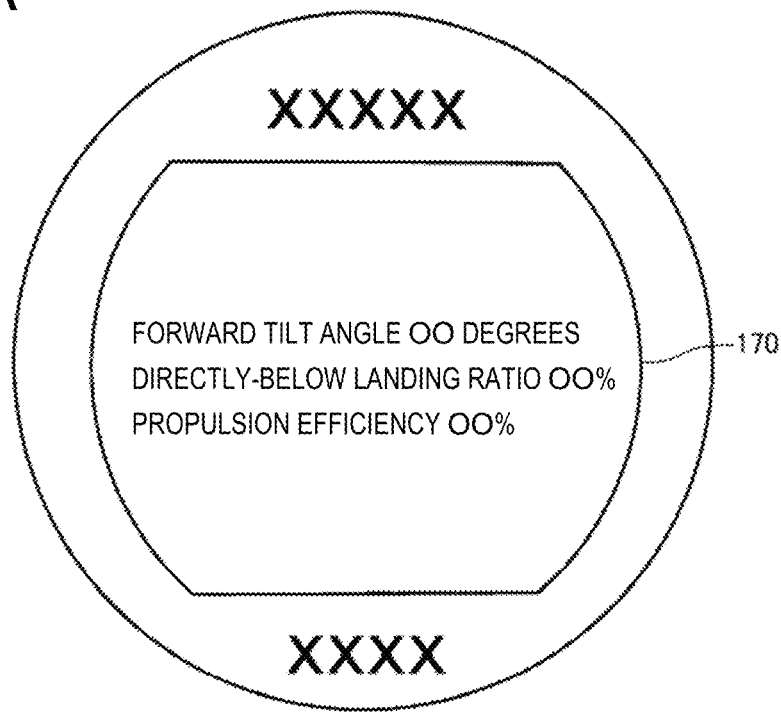
FIGS. 34A and 34B illustrate examples of a screen which is displayed during the user's running.
Figure 34B:
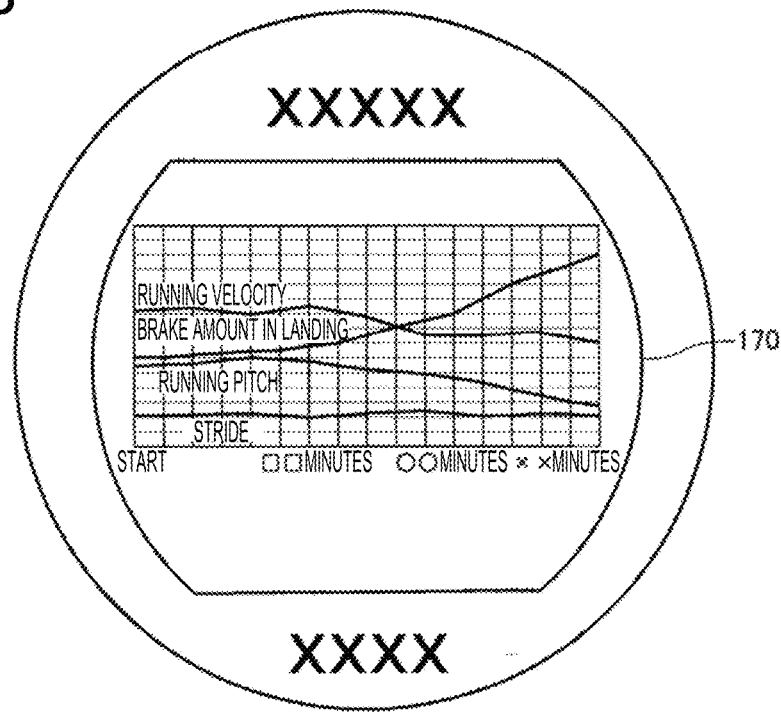

FIGS. 34A and 34B illustrate examples of screens displayed on the display unit 170 of the wrist watch type notification apparatus 3 during the user's running. In the example illustrated in FIG. 34A, respective numerical values of the "forward tilt angle", the "directly-below landing ratio", and the "propulsion efficiency" are displayed on the display unit 170. In the example illustrated in FIG. 34B, a time-series graph is displayed in which a transverse axis expresses time from starting of running, and a longitudinal axis expresses numerical values of respective items such as the "running velocity", the "running pitch", the "brake amount in landing", and the "stride". The numerical values of the respective items of FIG. 34A or the graphs of the respective items of FIG. 34B are updated in real time during the user's running. In response to a user's operation, numerical values of other items may be displayed, and the graphs may be scrolled. The items displayed on the screen of FIG. 34A or the screen of FIG. 34B may be items (for example, items within a reference range or items out of the reference range) satisfying a predetermined condition, items of which a notification is performed, or items which are designated by the user in advance. The screen on which the numerical values of the items are displayed as in FIG. 34A and the screen on which the numerical values of the items are displayed as in FIG. 34B may switch through an user's input operation.

The user can run while viewing the screen as in the screen of FIG. 34A or 34B so as to check the present running state. For example, the user can continue to run while being aware of the running way which causes a numerical value of each item to be favorable or the running way which causes an item with a numerical value to be improved, or while objectively recognizing a fatigue state.

1-10. Feedback after Running 1-10-1. Feedback Information

The running analysis portion 290 outputs, as the output information after running, some or all of the various exercise information pieces generated by the exercise information generation portion 270 during the user's running. In other words, among the plurality of exercise information pieces, exercise information which is not output during the user's running or exercise information which is output during the user's running is fed back after the user finishes running. The running analysis portion 290 outputs information generated after the user finishes running, by using the plurality of exercise information pieces. For example, information regarding an advice for improving running attainments of the user or an advice for improving a running state of the user is fed back after the user's running. Specifically, in the present embodiment, any one of whole analysis information, detail analysis information, and comparison analysis information is selected as the output information after running through a user's selection operation.

1-10-2. Feedback Timing

The running analysis portion 290 outputs the output information after running after the user's running in response to a user's input operation. Specifically, if running which is desired to be analyzed is selected by the user from past running history, the running analysis portion 290 transitions to a whole analysis mode so as to perform whole analysis of the running selected by the user, and generates and outputs the whole analysis information as the output information after running. If the user performs an operation of selecting detail analysis, the running analysis portion 290 transitions to a detail analysis mode so as to perform detail analysis corresponding to the subsequent user's operation, and generates and outputs the detail analysis information as the output information after running. If the user performs an operation of selecting comparison analysis, the running analysis portion 290 transitions to a comparison analysis mode so as to perform comparison analysis corresponding to the subsequent user's operation, and generates and outputs the comparison analysis information as the output information after running. If the user performs an operation of selecting whole analysis in the detail analysis mode or the comparison analysis mode, the running analysis portion 290 transitions to the whole analysis mode so as to output the whole analysis information as the output information after running. The running analysis portion 290 may store whole analysis information, detail analysis information, and comparison analysis information generated in the past in the storage unit 30, for example, in a first-in first-out (FIFO) method, and may read the analysis information stored in the storage unit 30 without performing analysis again and may out the analysis information in a case where information regarding an analysis result is stored in the storage unit 30 when whole analysis, detail analysis, or comparison analysis is performed.

1-10-3. Feedback Method

The output information after running output from the running analysis portion 290 may be displayed on a screen of the display unit 170 of the notification apparatus 3 so as to be fed back to the user. Alternatively, evaluation or an advice regarding the user's running may be fed back in voice from the sound output unit 180 of the notification apparatus 3.

1-10-4. Display Examples

Whole Analysis Screen

Figure 35:
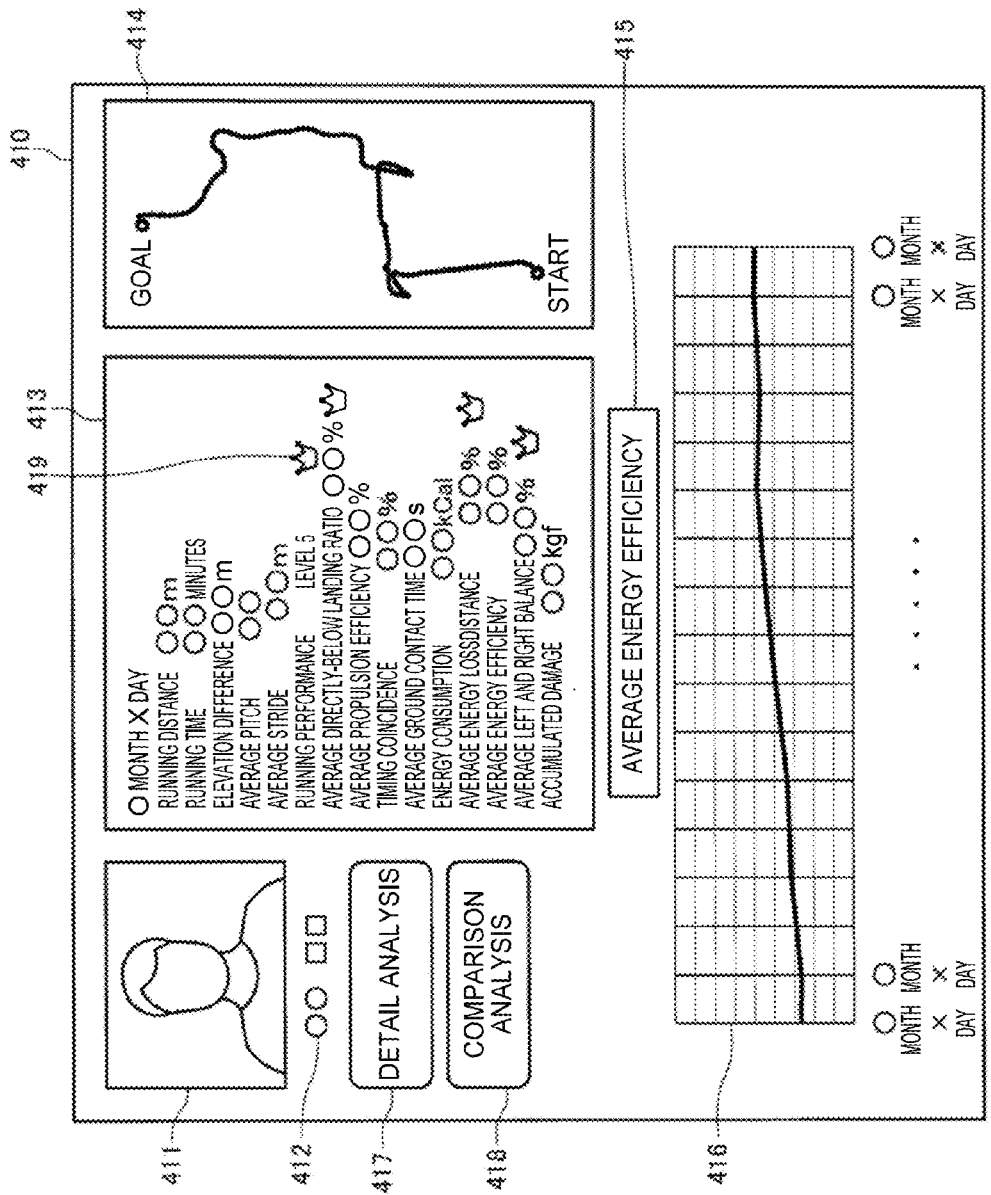
FIG. 35 is a diagram illustrating an example of a whole analysis screen.

FIGS. 35 and 36 illustrate examples of a screen (whole analysis screen) of the whole analysis information displayed on the display unit 170 of the notification apparatus 3. For example, FIG. 35 illustrates a screen of the first page, and FIG. 36 illustrates a screen of the second page. The user may select the screen of FIG. 35 or the screen of FIG. 36 which is then displayed on the display unit 170, by performing a screen scroll operation.

In the example illustrated in FIG. 35, a whole analysis screen 410 (first page) includes a user image 411 and a user name 412 which are registered in advance by the user, a summary image 413 displaying an analysis result of past running selected by the user, a running path image 414 displaying a running path from the start to the goal, an item name 415 of an item selected by the user and time-series data 416 thereof, a detail analysis button 417, and a comparison analysis button 418.

The summary image 413 includes respective numerical values of a "running distance", a "running time", an "elevation difference (between the start and the goal)", an "average pitch (an average value of running pitches)", an "average stride (an average value of strides)" "running performance", an "average directly-below landing ratio (an average value of directly-below landing ratios)", an "average propulsion efficiency (an average value of propulsion efficiency)", "timing coincidence", an "average ground contact time (an average value of ground contact times)", "energy consumption", an "average energy loss (an average value of energy losses)", "average energy efficiency (an average value of energy efficiency)", an "average left and right balance (an average value of left-right difference ratios)", and an "accumulated damage (burden on the body)", on the date on which past running was performed and which is selected by the user, and in this running. When analysis is started after running, a whole analysis screen of the latest running data stored in the storage unit 30 may be displayed.

In the summary image 413, a predetermined mark 419 is added beside an item whose numerical value is better than a reference value. In the example illustrated in FIG. 35, the mark 419 is added to the "running performance", the "average directly-below landing ratio", the "average energy loss", and the "average left and right balance". A predetermined mark may be added to an item whose numerical value is worse than a reference value, or an item whose improvement ratio is higher or lower than a reference value.

The running path image 414 is an image which displays a running path (running corresponding to the summary image 413) from the start point to the goal point in past running selected by the user.

The item name 415 indicates an item selected by the user from the items included in the summary image 413, and the time-series data 416 generates numerical values of the item indicated by the item name 415 as a graph in a time series. In the example illustrated in FIG. 35, the "average energy efficiency" is selected, and a time-series graph is displayed in which a transverse axis expresses the running date, and a longitudinal axis expresses a numerical value of the average energy efficiency. If the user selects one date on the transverse axis of the time-series data 416, an analysis result of the running on the selected date is displayed on the summary image 413.

The detail analysis button 417 is a button for transition from the whole analysis mode to the detail analysis mode, and if the user performs a selection operation (pressing operation) of the detail analysis button 417, transition to the detail analysis mode occurs, and a detail analysis screen is displayed.

The comparison analysis button 418 is a button for transition from the whole analysis mode to the comparison analysis mode, and if the user performs a selection operation (pressing operation) of the comparison analysis button 418, transition to the comparison analysis mode occurs, and a comparison analysis screen is displayed.

In the example illustrated in FIG. 36, history of running which was performed in the past by the user is displayed on a whole analysis screen 420 (second page). In the example illustrated in FIG. 36, a calendar image is displayed as the whole analysis screen 420, today's date (Mar. 24, 2014) is shown by a thick region, and a running distance and a running time are written on the date when the user performed running. A sum value of running distances and a sum value of running time of each week are written on a right column. If the user selects one of the past running items on the whole analysis screen 420, the whole analysis screen 410 illustrated in FIG. 35 changes to a screen which displays a result of whole analysis on the date selected by the user.

By checking the attainments of the running performed in the past while viewing the whole analysis screen illustrated in FIG. 35 or 36, the user can recognize an advantage or a disadvantage of the user's running way, and can practice the running way for improving running attainments or the running way for improving a running state in the next running and thereafter.

Detail Analysis Screen

Figure 37:
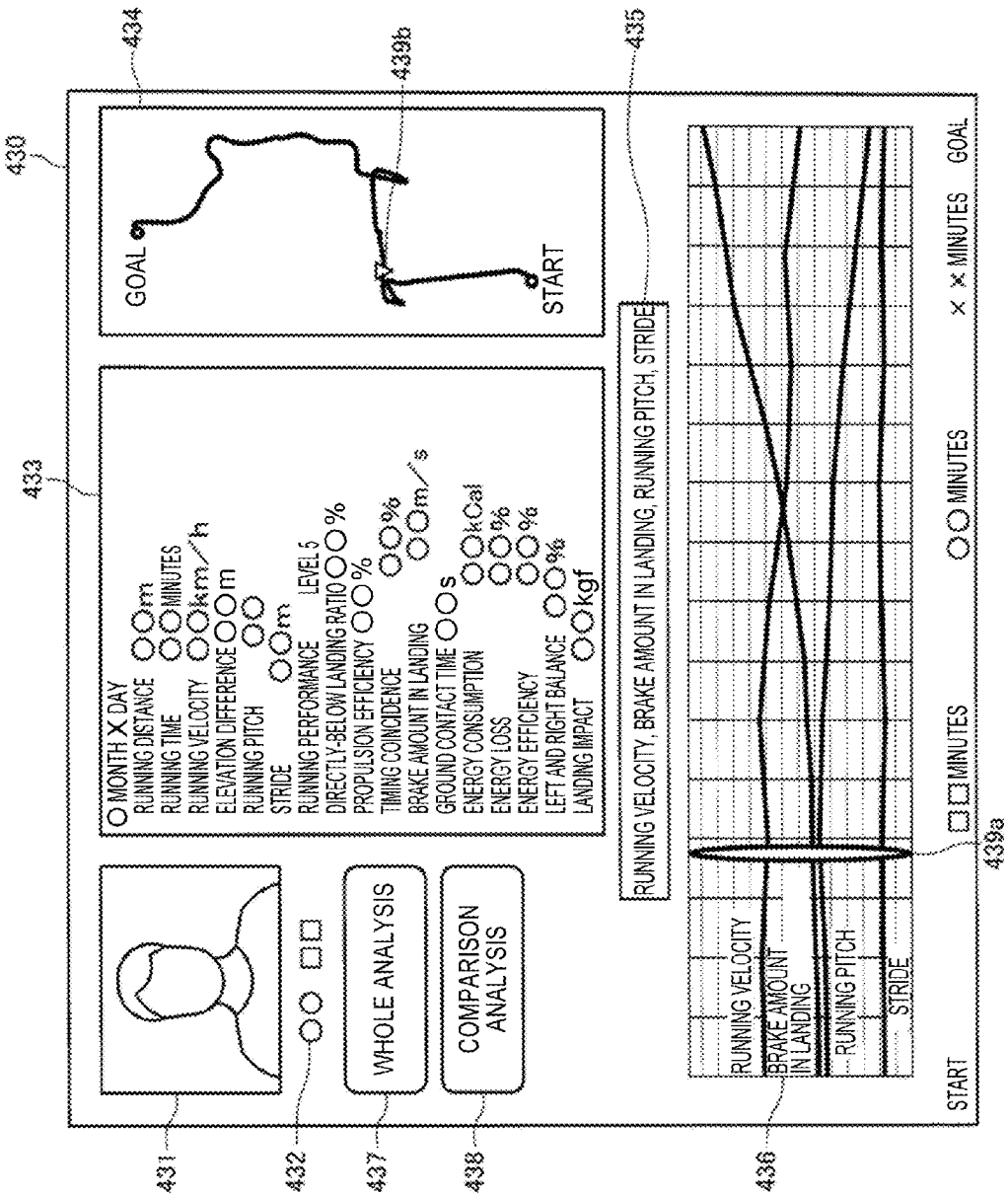
FIG. 37 is a diagram illustrating an example of a detail analysis screen.
Figure 38:
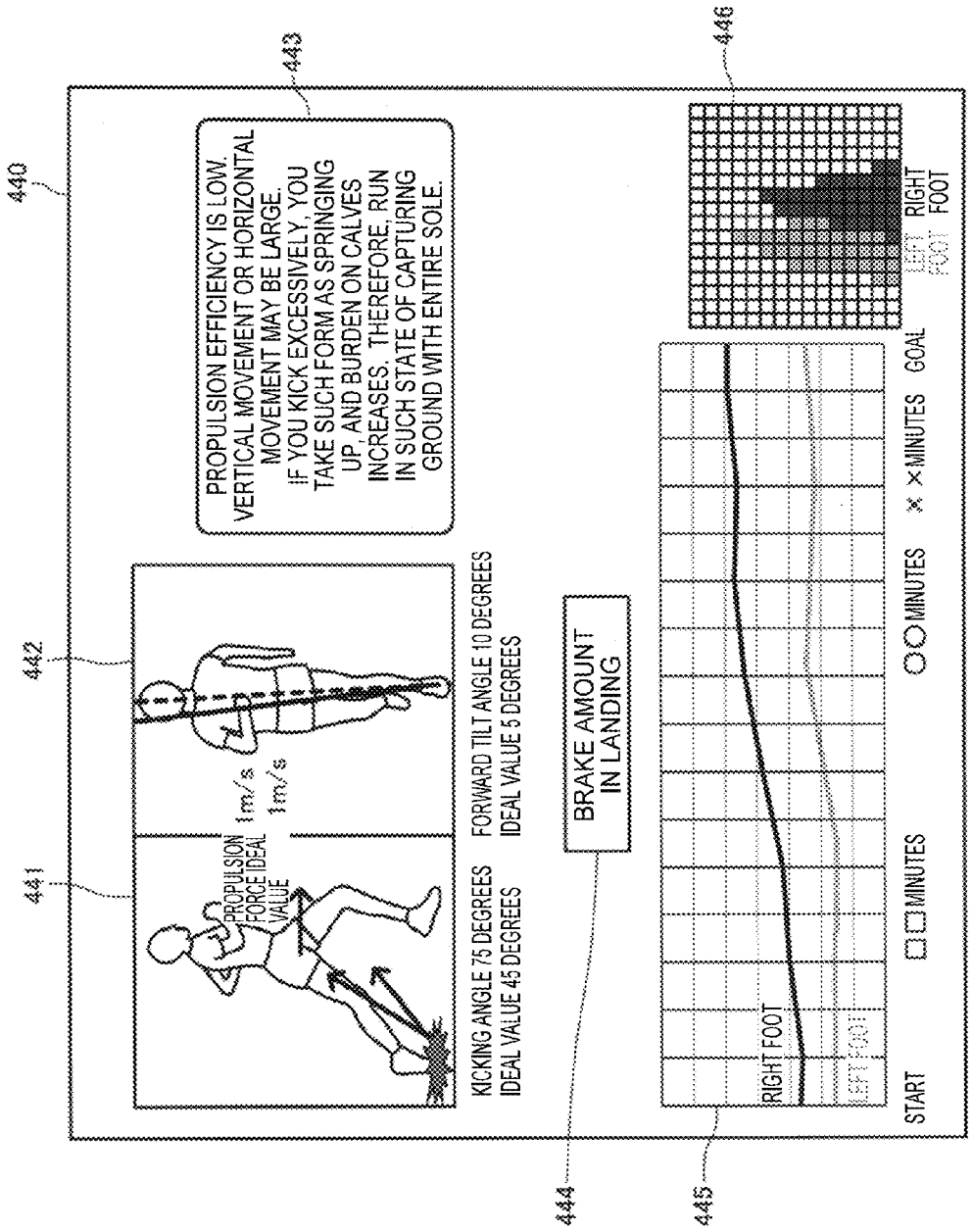
FIG. 38 is a diagram illustrating an example of the detail analysis screen.
Figure 39:
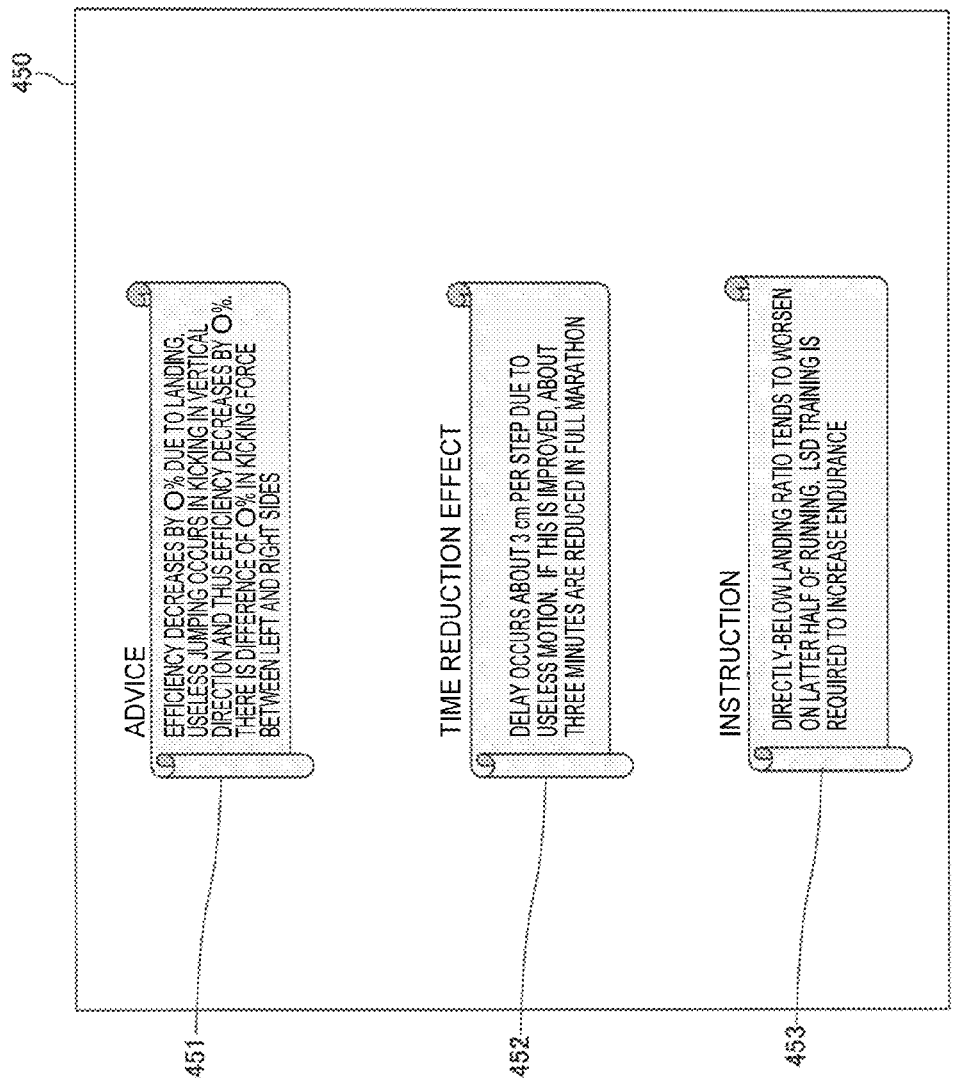
FIG. 39 is a diagram illustrating an example of the detail analysis screen.

FIGS. 37 to 39 illustrate examples of a screen (detail analysis screen) of detail analysis information displayed on the display unit 170 of the notification apparatus 3. The detail analysis screen preferably presents more detailed information than the whole analysis screen. For example, information regarding items more than the whole analysis screen may be presented. Alternatively, the number of items displayed on a single page may be reduced more than on the whole analysis screen, and thus finer duration, a finer numerical value, or the like may be displayed. For example, FIG. 37 illustrates a screen of the first page, FIG. 38 illustrates a screen of the second page, and FIG. 39 illustrates a screen of the third page. The user can select the screen of FIG. 37, the screen of FIG. 38, or the screen of FIG. 39 by performs a screen scroll operation or the like, and can display the selected screen on the display unit 170.

In the example illustrated in FIG. 37, a detail analysis screen 430 (first page) includes a user image 431 and a user name 432 which are registered in advance by the user, a summary image 433 displaying an analysis result at a time point selected by the user in past running selected by the user, a running path image 434 displaying a running path from the start to the goal, an item name 435 of an item selected by the user and time-series data 436 thereof, a whole analysis button 437, and a comparison analysis button 438.

The summary image 433 includes respective numerical values of a "running distance (from the start to a time point selected by the user)", a "running time (from the start to the time point selected by the user)", a "running velocity", an "elevation difference (between the start point and a running position at the selected time point)", a "running pitch", a "stride", "running performance", a "directly-below landing ratio", "propulsion efficiency", "timing coincidence", a "brake amount in landing", a "ground contact time", "energy consumption", a "energy loss", "energy efficiency", an "left and right balance (left-right difference ratio)", and a "landing impact", at the time point (from the start) selected by the user on the date on which past running was performed and which is selected by the user, and in this running.

The running path image 434 is an image which displays a running path (running corresponding to the summary image 433) from the start point to the goal point in past running selected by the user, and a running position at the time point selected by the user is shown by a predetermined mark 439b.

The item name 435 indicates an item selected by the user from the items included in the summary image 433, and the time-series data 436 generates numerical values of the item indicated by the item name 435 as a graph in a time series. In the example illustrated in FIG. 37, the "running velocity", the "brake amount in landing", the "running pitch", and the "stride" are selected, and a time-series graph is displayed in which a transverse axis expresses time from the start of running, and a longitudinal axis expresses a numerical value of each of the items. A sliding bar 439*a* which can be moved in the horizontal direction is displayed on the time-series data 436, and the user can select a time point from the start of running by moving the sliding bar 439*a*. A numerical value of each item of the summary image 433 or a position of a mark 439*b* of the running path image 434 changes in interlocking with a position (a time point selected by the user) of the sliding bar 439*a*.

The whole analysis button 437 is a button for transition from the detail analysis mode to the whole analysis mode, and if the user performs a selection operation (pressing operation) of the whole analysis button 437, transition to the whole analysis mode occurs, and a whole analysis screen is displayed.

The comparison analysis button 438 is a button for transition from the detail analysis mode to the comparison analysis mode, and if the user performs a selection operation (pressing operation) of the comparison analysis button 438, transition to the comparison analysis mode occurs, and a comparison analysis screen is displayed.

In the example illustrated in FIG. 38, a detail analysis screen 440 (second page) includes animation images 441 and 442 of the running selected by the user, a message image 443, an item name 444 of an item selected by the user, and a line graph 445 and a histogram 446 which show numerical values related to the right foot and the left foot of the item name 444 in a time series.

The animation image 441 is an image obtained when the user is viewed from the side, and the animation image 442 is an image obtained when the user is viewed from the front. The animation image 441 also includes comparison display between a propulsion force or a kicking angle of the user and an ideal propulsion force or kicking angle. Similarly, the animation image 442 also includes comparison display between a forward tilt angle of the user and an ideal forward tilt angle.

The message image 443 displays evaluation information for a result of the user's running, a message for improving running attainments, or the like. In the example illustrated in FIG. 38, a message of evaluation and an advice is displayed, such as the content that "the propulsion efficiency is low; the vertical movement or the horizontal movement may be large; if you kicks excessively, you takes such a form as springing up, and a burden on the calves increases; therefore, run in such a state of capturing the ground with the entire sole".

The item name 444 indicates an item selected by the user from the items included in the summary image 433 illustrated in FIG. 37, and the line graph 445 and the histogram 446 generate numerical values related to the right foot and the left foot of the item indicated by the item name 444 as a graph by arranging the numerical values in a time series. In the example illustrated in FIG. 38, the "brake amount in landing" is selected, and the line graph 445 is displayed in which a transverse axis expresses time from the start of running, and a longitudinal axis expresses a numerical value related to the left and right feet. The histogram 446 is displayed in which a transverse axis expresses the brake amount in landing, and a longitudinal axis expresses a frequency in which the left foot and the right foot are differentiated from each other by colors.

In the example illustrated in FIG. 39, a detail analysis screen 450 (third page) includes message images 451, 452 and 453 based on an analysis result of the running selected by the user.

In the example illustrated in FIG. 39, the message image 451 displays a message of evaluation or an advice such as the content that "the efficiency decreases by O% due to landing; useless jumping occurs in kicking and thus the efficiency decreases by O%; there is a difference of O% in a kicking force between the left and right sides". The message image 452 displays a message of an advice for obtaining a time reduction effect, such as the content that "delay occurs about 3 cm per step due to useless motion; if this is improved, about three minutes are reduced in full marathon". The message image 453 displays a message of an instruction such as the content that "the directly-below landing ratio tends to worsen on the latter half of the running; LSD training is required to increase the endurance".

By checking the details, the advices, or the like of the running performed in the past while viewing the detail analysis screens illustrated in FIGS. 37 to 39, the user can recognize an advantage or a disadvantage of the user's running way, and can practice the running way for improving running attainments or the running way for improving a running state in the next running and thereafter.

Comparison Analysis Screen

Figure 40:
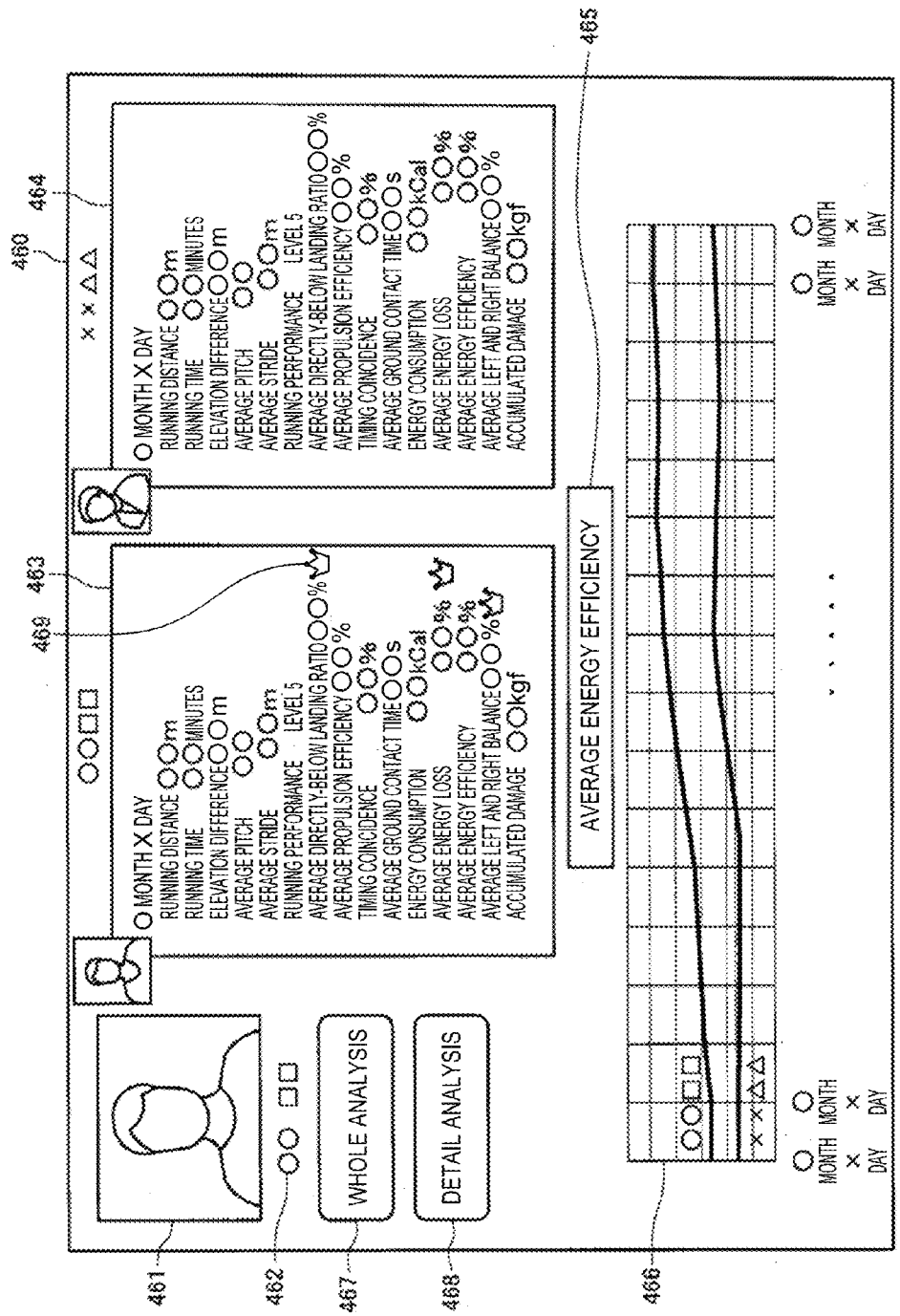
FIG. 40 is a diagram illustrating an example of a comparison analysis screen.

FIG. 40 illustrates an example of a screen (comparison analysis screen) of comparison analysis information displayed on the display unit 170 of the notification apparatus 3.

In the example illustrated in FIG. 40, a comparison analysis screen 460 includes a user image 461 and a user name 462 which are registered in advance by the user, a summary image 463 displaying an analysis result of past running selected by the user, a summary image 464 displaying an analysis result of past running of another user, an item name 465 of an item selected by the user and time-series data 466 thereof, a whole analysis button 467, and a detail analysis button 468.

The summary image 463 includes respective numerical values of a "running distance", a "running time", an "elevation difference (between the start and the goal)", an "average pitch (an average value of running pitches)", an "average stride (an average value of strides)" "running performance", an "average directly-below landing ratio (an average value of directly-below landing ratios)", an "average propulsion efficiency (an average value of propulsion efficiency)", "timing coincidence", an "average ground contact time (an average value of ground contact times)", "energy consumption", an "average energy loss (an average value of energy losses)", "average energy efficiency (an average value of energy efficiency)", an "average left and right balance (an average value of left-right difference ratios)", and an "accumulated damage (burden on the body)", on the date on which past running was performed and which is selected by the user, and in this running.

In the summary image 463, a predetermined mark 469 is added beside an item whose numerical value is better than a reference value. In the example illustrated in FIG. 40, the mark 469 is added to the "average directly-below landing ratio", the "average energy loss", and the "average left and right balance". A predetermined mark may be added to an item whose numerical value is worse than a reference value, or an item whose improvement ratio is higher or lower than a reference value.

The summary image 464 includes the date on which another user performed past running, and numerical values of the same items as the items included in the summary image 463. In FIG. 40, the name and an image of another user are displayed around the summary image 464.

The item name 465 indicates an item selected by the user from the items included in the summary image 463, and the time-series data 466 generates numerical values of the item indicated by the item name 465 as a graph in a time series. In the example illustrated in FIG. 40, the "average energy efficiency" is selected, and a time-series graph is displayed in which a transverse axis expresses the running date, and a longitudinal axis expresses numerical values of the average energy efficiency of the user and another user. If the user selects one date on the transverse axis of the time-series data 466, an analysis result of the running (for example, the closest running if running is not present on the selected date) of the user and another user on the selected date is displayed on the summary image 463 and the summary image 464.

The whole analysis button 467 is a button for transition from the comparison analysis mode to the whole analysis mode, and if the user performs a selection operation (pressing operation) of the whole analysis button 467, transition to the whole analysis mode occurs, and a whole analysis screen is displayed.

The detail analysis button 468 is a button for transition from the comparison analysis mode to the detail analysis mode, and if the user performs a selection operation (pressing operation) of the detail analysis button 468, transition to the detail analysis screen is displayed.

By checking the comparison results of the attainments of the running performed in the past and the running attainments of another user while viewing the comparison analysis screen illustrated in FIG. 40, the user can recognize an advantage or a disadvantage of the user's running way, and can practice the running way for improving running attainments or the running way for improving a running state in the next running and thereafter.

1-11. Usage Examples of Exercise Analysis System

The user can use the exercise analysis system 1 of the present embodiment for usage as exemplified below.

Usage Examples During Running

The user displays a running pitch or a stride in a time series from the start of running, and performs a running exercise while checking how the running pitch or the stride changes from the start of running.

The user displays a brake amount in landing or a directly-below landing ratio in a time series from the start of running, and performs a running exercise while checking how the brake amount in landing or the directly-below landing ratio changes from the start of running.

The user displays a propulsion force or propulsion efficiency in a time series from the start of running, and performs a running exercise while checking how the propulsion force or the propulsion efficiency changes from the start of running.

The user displays running performance in a time series from the start of running, and performs a running exercise while checking to what extent the running performance changes from the start of running.

The user displays a forward tilt angle in a time series from the start of running, and performs a running exercise while checking how the forward tilt angle changes relative to an ideal value from the start of running.

The user displays timing coincidence of waist rotation in a time series from the start of running, and performs a running exercise while checking how a timing of waist rotation changes relative to an ideal timing from the start of running.

The user displays an amount of energy consumption, an energy loss, energy efficiency, a landing impact, or a left-right difference ratio in a time series from the start of running, and observes, as a reference of running, to what extent the amount of energy consumption for one step, the energy loss for one step, the energy efficiency for one step, the landing impact, or the left-right difference ratio changes. The user displays an accumulated damage (burden on the body) and determines a break timing by referring to the accumulated damage (burden on the body) from the start of running.

Usage Examples after Running

The user selects a whole analysis screen, displays an average pitch or an average stride in a plurality of past running items in a time series in order of the date, and checks the progress, for example, how the pitch or the stride changes relative to an ideal running pitch or stride as a reference of a running exercise. Alternatively, the user selects a detail analysis screen, displays a running pitch or a stride in a certain single running item in a time series in order of time points from the start of the running, and checks how the running pitch or the stride changes in the single running item as a reference of a running exercise.

The user selects a whole analysis screen, displays an average brake amount in landing and an average directly-below landing ratio in a plurality of past running items in a time series in order of the date, and checks the progress, for example, how the brake amount in landing or the directly-below landing ratio changes relative to an ideal value, or whether or not the brake amount in landing is reduced due to improvement in the directly-below landing ratio as a reference of a running exercise. Alternatively, the user selects a detail analysis screen, displays a brake amount in landing and a directly-below landing ratio in a certain single running item in a time series in order of time points from the start of the running, and checks to what extent the brake amount in landing or the directly-below landing ratio changes in the single running item as a reference of a running exercise.

The user selects a whole analysis screen, displays an average propulsion force and average propulsion efficiency in a plurality of past running items in a time series in order of the date, and checks the progress, for example, how the propulsion force or the propulsion efficiency changes relative to an ideal value, or whether or not the propulsion force increases due to improvement in the propulsion efficiency as a reference of a running exercise. Alternatively, the user selects a detail analysis screen, displays a propulsion force and a propulsion efficiency in a certain single running item in a time series in order of time points from the start of the running, and checks to what extent the propulsion force or the propulsion efficiency changes in the single running item as a reference of a running exercise.

The user selects a whole analysis screen, displays running performance in a plurality of past running items in a time series in order of the date, checks the progress of the running performance from the past, and enjoys improvement in the performance. Alternatively, the user selects a comparison analysis screen, displays running performance of the user and running performance of a user's friend in a time series, and enjoys improvement in the performance through comparison. Alternatively, the user selects a detail analysis screen, displays running performance in a certain single running item in a time series in order of time points from the start of the running, and checks to what extent the running performance changes in the single running item as a reference of a running exercise.

The user selects a whole analysis screen, displays an average forward tilt angle in a plurality of past running items in a time series in order of the date, and checks the progress, for example, how the forward tilt angle changes relative to an ideal value as a reference of a running exercise. Alternatively, the user selects a detail analysis screen, displays a forward tilt angle in a certain single running item in a time series in order of time points from the start of the running, and checks how the forward tilt angle changes in the single running item as a reference of a running exercise.

The user selects a whole analysis screen, displays timing coincidence of waist rotation in a plurality of past running items in a time series in order of the date, and checks the progress, for example, how a timing of waist rotation changes relative to an ideal timing as a reference of a running exercise. Alternatively, the user selects a detail analysis screen, displays timing coincidence of waist rotation in a certain single running item in a time series in order of time points from the start of the running, and checks how the timing coincidence changes in the single running item as a reference of a running exercise.

The user selects a whole analysis screen, displays energy consumption, an average energy loss, average energy efficiency and an average directly-below landing ratio, or average propulsion efficiency in a plurality of past running items in a time series in order of the date, and checks whether or not an efficient running state is achieved by comparing an amount of energy consumption, an energy loss, or energy efficiency with the directly-below landing ratio or the propulsion efficiency. Alternatively, the user selects a detail analysis screen, displays an amount of energy consumption, an energy loss, or energy efficiency in a certain single running item in a time series in order of time points from the start of the running, and checks how the amount of energy consumption for one step, the energy loss for one step, or the energy efficiency for one step changes in the single running item as a reference of a running exercise.

The user selects a whole analysis screen, displays an landing impact and an average directly-below landing ratio, or average propulsion efficiency in a plurality of past running items in a time series in order of the date, and checks whether or not a danger of injury is reduced by comparing the landing impact with the directly-below landing ratio or the propulsion efficiency. Alternatively, the user selects a detail analysis screen, displays a landing impact in a certain single running item in a time series in order of time points from the start of the running, and checks to what extent the landing impact changes in the single running item as a reference of a running exercise.

The user selects a whole analysis screen, displays an average left-right difference ratio (an average left and right balance) in a plurality of past running items in a time series in order of the date, and observes and enjoys the progress, for example, to what extent the left-right difference ratio improves from the past. Alternatively, the user selects a detail analysis screen, displays a left-right difference ratio in a certain single running item in a time series in order of time points from the start of the running, and checks how the left-right difference ratio changes in the single running item as a reference of a running exercise.

1-12. Procedure of Process

FIG. 41 is a flowchart illustrating an example (an example of an exercise analysis method) of procedures of the exercise analysis process performed by the processing unit 20 of the exercise analysis apparatus 2 in the first embodiment during the user's running. The processing unit 20 of the exercise analysis apparatus 2 (an example of a computer) performs the exercise analysis process according to the procedures of the flowchart illustrated in FIG. 41 by executing the exercise analysis program 300 stored in the storage unit 30.

As illustrated in FIG. 41, the processing unit 20 waits for a command for starting measurement to be received (N in step S10), and if the command for starting measurement is received (Y in step S10), first, the processing unit 20 computes an initial attitude, an initial position, and an initial bias by using sensing data and GPS data measured by the inertial measurement unit 10 assuming that the user stops (step S20).

Next, the processing unit 20 acquires the sensing data from the inertial measurement unit 10, and adds the acquired sensing data to the sensing data table 310 (step S30).

Next, the processing unit 20 performs an inertial navigation calculation process so as to generate calculation data including various information pieces (step S40). An example of procedures of the inertial navigation calculation process will be described later.

Next, the processing unit 20 performs an exercise analysis information generation process by using the calculation data generated in step S40 so as to generate exercise analysis information and output information during running, and transmits the output information during running to the notification apparatus 3 (step S50). An example of procedures of the exercise analysis information generation process will be described later. The output information during running transmitted to the notification apparatus 3 is fed back in real time during the user's running. In the present specification, the "real time" indicates that processing is started at a timing at which processing target information is acquired. Therefore, the "real time" also includes some time difference between acquisition of information and completion of processing of the information.

The processing unit 20 repeatedly performs the processes in step S30 and the subsequent steps whenever the sampling cycle Δt elapses (Y in step S60) from the acquisition of the previous sensing data until a command for finishing the measurement is received (N in step S60 and N in step S70). If the command for finishing the measurement is received (Y in step S70), the processing unit 20 waits for a running analysis starting command for giving an instruction for starting a running analysis process (N in step S80).

If the running analysis starting command is received (Y in step S80), the processing unit 20 performs a running analysis process on the user's past running by using the exercise analysis information generated in step S50 or exercise analysis information which was generated during the past running and was stored in the storage unit 30, and transmits information regarding an analysis result to the notification apparatus 3 or other information apparatuses (step S90). An example of procedures of the running analysis process will be described later. If the running analysis process is completed, the processing unit 20 finishes the exercise analysis process.

Figure 42:
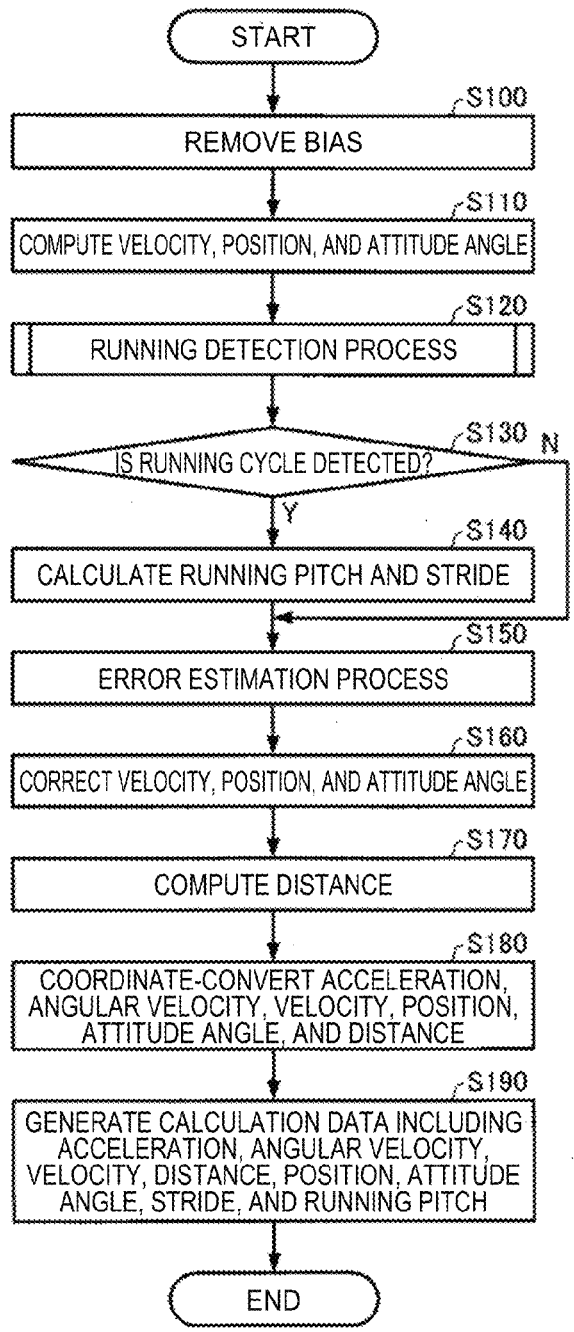
FIG. 42 is a flowchart illustrating an example of procedures of an inertial navigation calculation process.

FIG. 42 is a flowchart illustrating an example of procedures of the inertial navigation calculation process (the process in step S40 of FIG. 41). The processing unit 20 (the inertial navigation calculation unit 22) performs the inertial navigation calculation process according to the procedures of the flowchart illustrated in FIG. 42 by executing the inertial navigation calculation program 302 stored in the storage unit 30.

As illustrated in FIG. 42, first, the processing unit 20 removes biases from acceleration and angular velocity included in the sensing data acquired in step S30 of FIG. 41 by using the initial bias calculated in step S20 of FIG. 41 (by using the acceleration bias $b_a$ and an angular velocity bias $b_\omega$ after the acceleration bias $b_a$ and the angular velocity bias $b_\omega$ are estimated in step S150 to be described later) so as to correct the acceleration and the angular velocity, and updates the sensing data table 310 by using the corrected acceleration and velocity (step S100).

Next, the processing unit 20 integrates the sensing data corrected in step S100 so as to compute a velocity, a position, and an attitude angle, and adds calculated data including the computed velocity, position, and attitude angle to the calculated data table 340 (step S110).

Next, the processing unit 20 performs a running detection process (step S120). An example of procedures of the running detection process will be described later.

Next, in a case where a running cycle is detected through the running detection process (step S120) (Y in step S130), the processing unit 20 computes a running pitch and a stride (step S140). If a running cycle is not detected (N in step S130), the processing unit 20 does not perform the process in step S140.

Next, the processing unit 20 performs an error estimation process so as to estimate a velocity error $\delta v^e$, an attitude angle errors $\varepsilon^e$, a acceleration bias $b_a$, an angular velocity bias $b_\omega$, and a position error $\delta p^e$ (step S150).

Next, the processing unit 20 corrects the velocity, the position, and the attitude angle by using the velocity error $\delta v^e$, the attitude angle errors $\varepsilon^e$, and the position error $\delta p^e$ estimated in step S150, and updates the calculated data table 340 by using the corrected velocity, position and attitude angle (step S160). The processing unit 20 integrates the velocity corrected in step S160 so as to compute a distance of the e frame (step S170).

Next, the processing unit 20 performs coordinate-converts the sensing data (the acceleration and the angular velocity of the b frame) stored in the sensing data table 310, the calculated data (the velocity, the position, and the attitude angle of the e frame) stored in the calculated data table 340, and the distance of the e frame calculated in step S170 into acceleration, angular velocity, velocity, a position, an attitude angle, and a distance of the m frame, respectively (step S180).

The processing unit 20 generates calculation data including the acceleration, the angular velocity, the velocity, the position, and the attitude angle of the m frame having undergone the coordinate conversion in step S180, and the stride and the running pitch calculated in step S140 (step S190). The processing unit 20 performs the inertial navigation calculation process (the processes in steps S100 to S190) whenever sensing data is acquired in step Storage unit 30 of FIG. 41.

Figure 43:
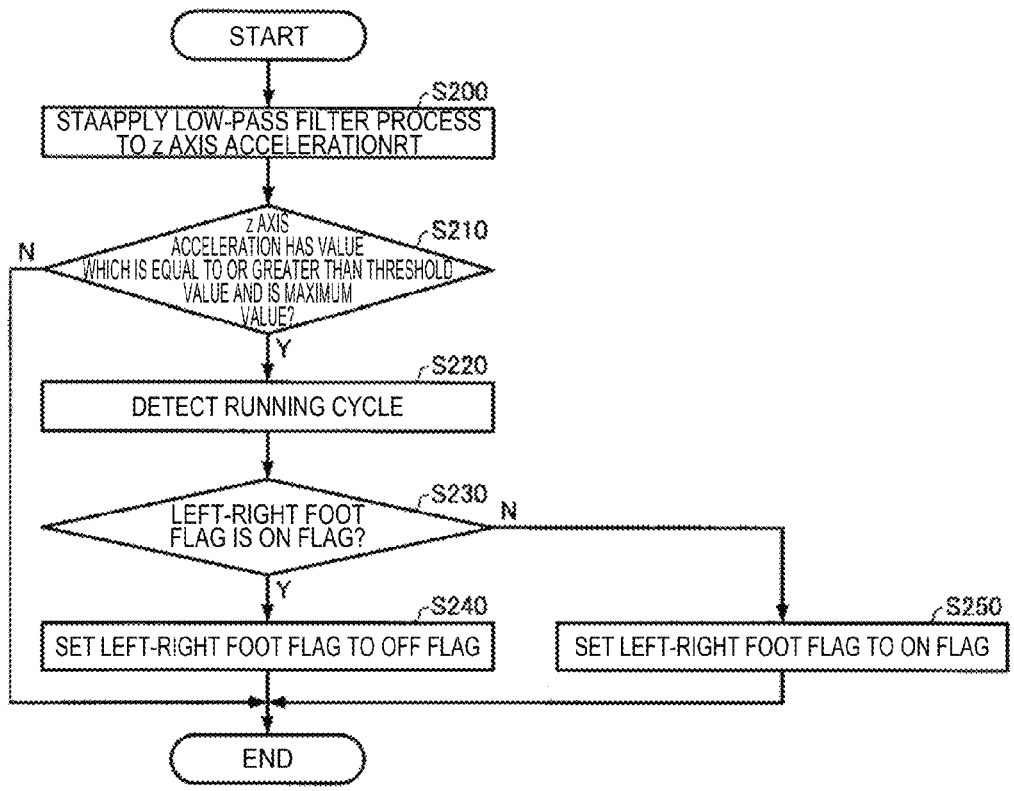
FIG. 43 is a flowchart illustrating an example of procedures of a running detection process in the first embodiment.

FIG. 43 is a flowchart illustrating an example of procedures of the running detection process (the process in step S120 of FIG. 42) in the first embodiment. The processing unit 20 (the running detection section 242) performs the running detection process according to the procedures of the flowchart illustrated in FIG. 43.

As illustrated in FIG. 43, the processing unit 20 performs a low-pass filter process on a z axis acceleration included in the acceleration corrected in step S100 of FIG. 42 (step S200) so as to remove noise therefrom.

Next, if the z axis acceleration having undergone the low-pass filter process in step S200 has a value which is equal to or greater than a threshold value and is the maximum value (Y in step S210), the processing unit 20 detects a running cycle at this timing (step S220).

If a left-right foot flag is an ON flag (Y in step S230), the processing unit 20 sets the left-right foot flag to an OFF flag (step S240), and if the left-right foot flag is not an ON flag (N in step S230), the processing unit 20 sets the left-right foot flag to an ON flag (step S250), and finishes the running detection process. If the z axis acceleration has a value which is smaller than the threshold value or is not the maximum value (N in step S210), the processing unit 20 does not perform the processes in steps S220 and the subsequent steps and finishes the running detection process.

Figure 44:
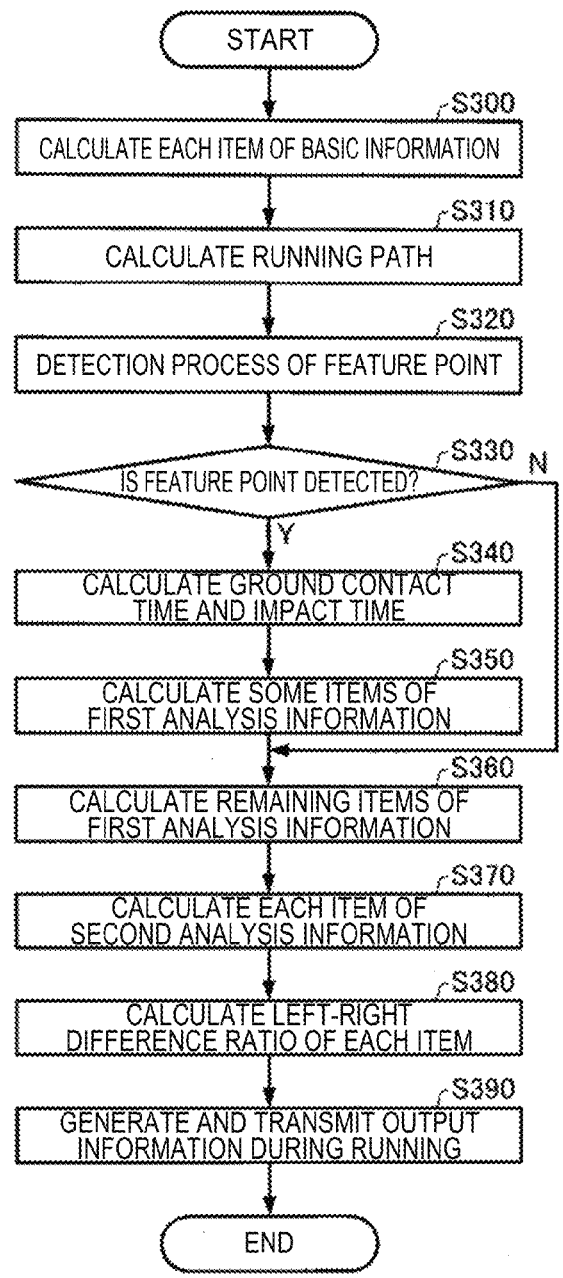
FIG. 44 is a flowchart illustrating an example of procedures of an exercise analysis information generation process in the first embodiment.

FIG. 44 is a flowchart illustrating an example of procedures of the exercise analysis information generation process (the process in step S50 of FIG. 41) in the first embodiment. The processing unit 20 (the exercise analysis unit 24) performs the exercise analysis information generation process according to the procedures of the flowchart illustrated in FIG. 44 by executing the exercise analysis information generation program 304 stored in the storage unit 30.

As illustrated in FIG. 44, first, the processing unit 20 calculates each item of the basic information by using the calculation data generated through the inertial navigation calculation process of the step S40 of FIG. 41 (step S300). The processing unit 20 calculates a running path by using the calculation data so as to generate running path information (step S310).

Next, the processing unit 20 performs a process of detecting a feature point (landing, stepping, taking-off, or the like) in the running exercise of the user by using the calculation data (step S320).

If the feature point is detected through the process in step S320 (Y in step S330), the processing unit 20 calculates a ground contact time and an impact time on the basis of the timing of detecting the feature point (step S340). The processing unit 20 calculates some items (which require information regarding the feature point in order to calculate the items) of the first analysis information on the basis of the timing of detecting the feature point by using some of the calculation data and the ground contact time and the impact time generated in step S340 as input information (step S350). If a feature point is not detected through the process in step S320 (N in step S330), the processing unit 20 does not the processes in steps S340 and S350.

Next, the processing unit 20 calculates remaining items (which does not require the information regarding the feature point in order to calculate the items) of the first analysis information by using the input information (step S360).

Next, the processing unit 20 calculates each item of the second analysis information by using the first analysis information (step S370).

Next, the processing unit 20 calculates a left-right difference ratio for each item of the input information, each item of the first analysis information, and each item of the second analysis information (step S380). The processing unit 20 stores the input information, the basic information, the first analysis information, the second analysis information, the left-right difference ratio, and the running path information in the storage unit 30 as the exercise analysis information 350.

Next, the processing unit 20 generates output information during running by using the input information, the basic information, the first analysis information, the second analysis information, the left-right difference ratio, and the running path information, transmits the generated output information during running to the notification apparatus 3 (step S390), and finishes the exercise analysis information generation process.

Figure 45:
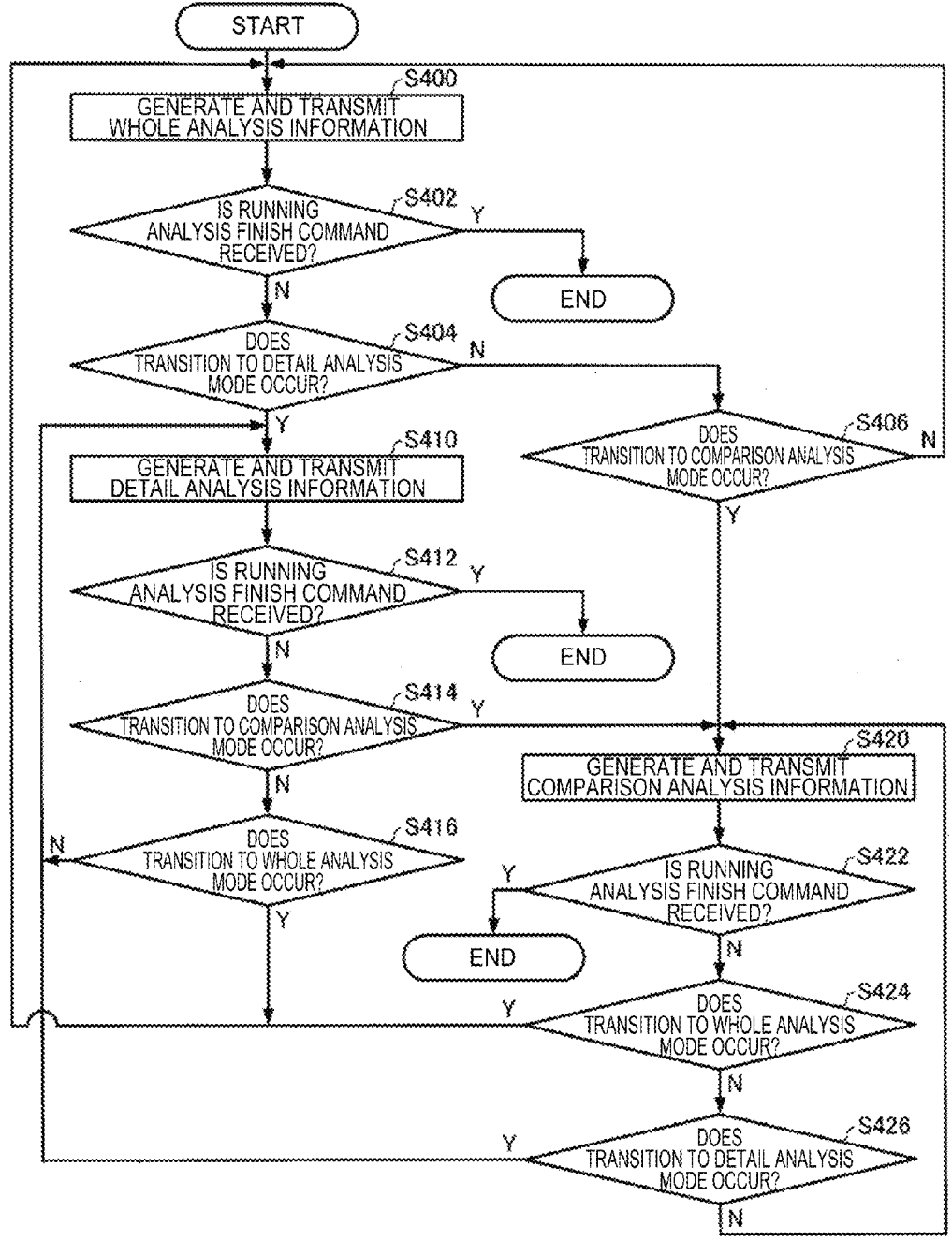
FIG. 45 is a flowchart illustrating an example of procedures of a running analysis process.

FIG. 45 is a flowchart illustrating an example of procedures of the running analysis process (the process in step S90 of FIG. 41). The processing unit 20 (the running analysis portion 290) performs the running analysis process according to the procedures of the flowchart illustrated in FIG. 45 by executing the running analysis program 306 stored in the storage unit 30.

As illustrated in FIG. 45, the processing unit 20 selects the whole analysis mode, the processing unit 20 performs whole analysis on past running of the user so as to generate whole analysis information by using the exercise analysis information generated through the exercise analysis process in step S50 of FIG. 41 or exercise analysis information which was generated during the past running and was stored in the storage unit 30, and transmits the whole analysis information to the notification apparatus 3 or other information apparatuses as output information after running (step S400).

If a running analysis finishing command for giving an instruction for finishing the running analysis process is received in the whole analysis mode (Y in step S402), the processing unit 20 finishes the running analysis process. If the running analysis finishing command is not received (N in step S402), and transition to the detail analysis mode or the comparison analysis mode does not occur (N in step S404 and N in step S406), the processing unit 20 repeatedly performs the whole analysis process (step S400).

If transition occurs from the whole analysis mode to the detail analysis mode (Y in step S404), the processing unit 20 performs detail analysis so as to generate detail analysis information, and transmits the generated detail analysis information to the notification apparatus 3 or other information apparatuses as the output information after running (step S410). The transition from the whole analysis mode to the detail analysis mode occurs, for example, when the user performs a selection operation (pressing operation) of the detail analysis button 417 included in the whole analysis screen 410 illustrated in FIG. 35.

If the running analysis finishing command is received in the detail analysis mode (Y in step S412), the processing unit 20 finishes the running analysis process. If the running analysis finishing command is not received (N in step S412), and transition to the comparison analysis mode or the whole analysis mode does not occur (N in step S414 and N in step S416), the processing unit 20 repeatedly performs the detail analysis process in response to a user's operation (step S410).

If transition occurs from the whole analysis mode to the comparison analysis mode (Y in step S406), or transition occurs from the detail analysis mode to the comparison analysis mode (Y in step S414), the processing unit 20 performs comparison analysis so as to generate comparison analysis information, and transmits the generated comparison analysis information to the notification apparatus 3 or other information apparatuses as the output information after running (step S420). The transition from the whole analysis mode to the comparison analysis mode occurs, for example, when the user performs a selection operation (pressing operation) of the comparison analysis button 418 included in the whole analysis screen 410 illustrated in FIG. 35. The transition from the detail analysis mode to the comparison analysis mode occurs, for example, when the user performs a selection operation (pressing operation) of the comparison analysis button 438 included in the detail analysis screen 430 illustrated in FIG. 37.

If the running analysis finishing command is received in the comparison analysis mode (Y in step S422), the processing unit 20 finishes the running analysis process. If the running analysis finishing command is not received (N in step S422), and transition to the whole analysis mode or the detail analysis mode does not occur (N in step S424 and N in step S426), the processing unit 20 repeatedly performs the comparison analysis process in response to a user's operation (step S420).

If transition occurs from the detail analysis mode to the whole analysis mode (Y in step S416), or transition occurs from the comparison analysis mode to the whole analysis mode (Y in step S424), the processing unit 20 performs the whole analysis process in step S400. The transition from the detail analysis mode to the whole analysis mode occurs, for example, when the user performs a selection operation (pressing operation) of the whole analysis button 437 included in the detail analysis screen 430 illustrated in FIG. 37. The transition from the comparison analysis mode to the whole analysis mode occurs, for example, when the user performs a selection operation (pressing operation) of the whole analysis button 467 included in the comparison analysis screen 460 illustrated in FIG. 40.

If transition occurs from the comparison analysis mode to the detail analysis mode (Y in step S426), the processing unit 20 performs the detail analysis process in step S410. The transition from the comparison analysis mode to the detail analysis mode occurs, for example, when the user performs a selection operation (pressing operation) of the detail analysis button 468 included in the comparison analysis screen 460 illustrated in FIG. 40.

1-3. Effects

In the first embodiment, the exercise analysis apparatus 2 calculates a ground contact time, an impact time, and some items of the first analysis information which cause a tendency of the way of moving the body during the user's running to be easily extracted with a feature point such as landing, stepping, or taking-off (kicking) of an exercise in the running of the user as a reference by using a detection result from the inertial measurement unit 10. In the first embodiment, the exercise analysis apparatus 2 calculates remaining items of the first analysis information, each item of the second analysis information, and a left-right difference ratio of each item so as to generate various exercise information pieces, and presents output information during running or output information after running which is generated by using the exercise information pieces, to the user. Therefore, according to the first embodiment, it is possible to assist the user in improving running attainments.

Particularly, in the first embodiment, the exercise analysis apparatus 2 generates exercise information which reflects a state of the user's body in a feature point or the way of moving the user's body between two feature points and is effective in order to improve running attainments of the user, by using a detection result from the inertial measurement unit 10 in the feature point in the user's running, or a detection result from the inertial measurement unit 10 between the two feature points, and presents the exercise information to the user. Therefore, according to the first embodiment, the user can check the presented information and can efficiently improve running attainments.

In the first embodiment, the exercise analysis apparatus 2 combines a plurality of items of the first analysis information so as to generate each item (energy efficiency, an energy loss, and a burden on the body) of the second analysis information which reflects the way of moving the user's body during running and which causes the user to easily recognize a running state, and presents each item of the second analysis information to the user. Therefore, according to the first embodiment, the user can continuously run while recognizing whether or not an efficient running way is obtained, or whether or not a risk of injury is low, or can perform checking thereof after running.

In the first embodiment, the exercise analysis apparatus 2 calculates a left-right difference ratio for each item of the input information, the first analysis information, and the second analysis information, and presents the item to the user. Therefore, according to the first embodiment, the user can examine training for improving left and right balance in consideration of a risk of injury.

In the first embodiment, the exercise analysis apparatus 2 generates information regarding various evaluation types or advices corresponding to a running state of the user and presents the information the user while the user is running or after the user finishes the running. Therefore, according to the first embodiment, the user can promptly and accurately recognize an advantage or a disadvantage of the user's running way, and can thus efficiently improve running attainments.

In the first embodiment, the exercise analysis apparatus 2 presents information which is generated on the basis of exercise information satisfying a predetermined condition according to a running state to the user during the user's running, and thus the user can easily utilize the presented information. The exercise analysis apparatus 2 presents information which is based on some of the exercise information generated during the user's running, to the user after running, and thus the user can also easily utilize the presented information after running. Therefore, according to the first embodiment, it is possible to assist the user in improving running attainments.

In the first embodiment, the exercise analysis apparatus 2 presents an item in which a running state is good or an item in which a running state is bad, to the user during the user's running. Therefore, according to the first embodiment, the user can run while recognizing an advantage or a disadvantage of the user's running way.

According to the present embodiment, the exercise analysis apparatus 2 also presents information which is not presented during the user's running, after running is finished, and thus it is possible to assist the user in improving running attainments.

According to the first embodiment, the exercise analysis apparatus 2 also presents information which is presented during the user's running, after the running is finished, and thus the user can recognize a running state which cannot be recognized during the running, after the running. Therefore, it is possible to assist the user in improving running attainments.

2. Second Embodiment

In a second embodiment, the same constituent elements as those of the first embodiment are given the same reference numerals and will not be described or will be described briefly, and the content which is different from that of the first embodiment will be described in detail.

2-1. Configuration of Exercise Analysis System

Figure 46:
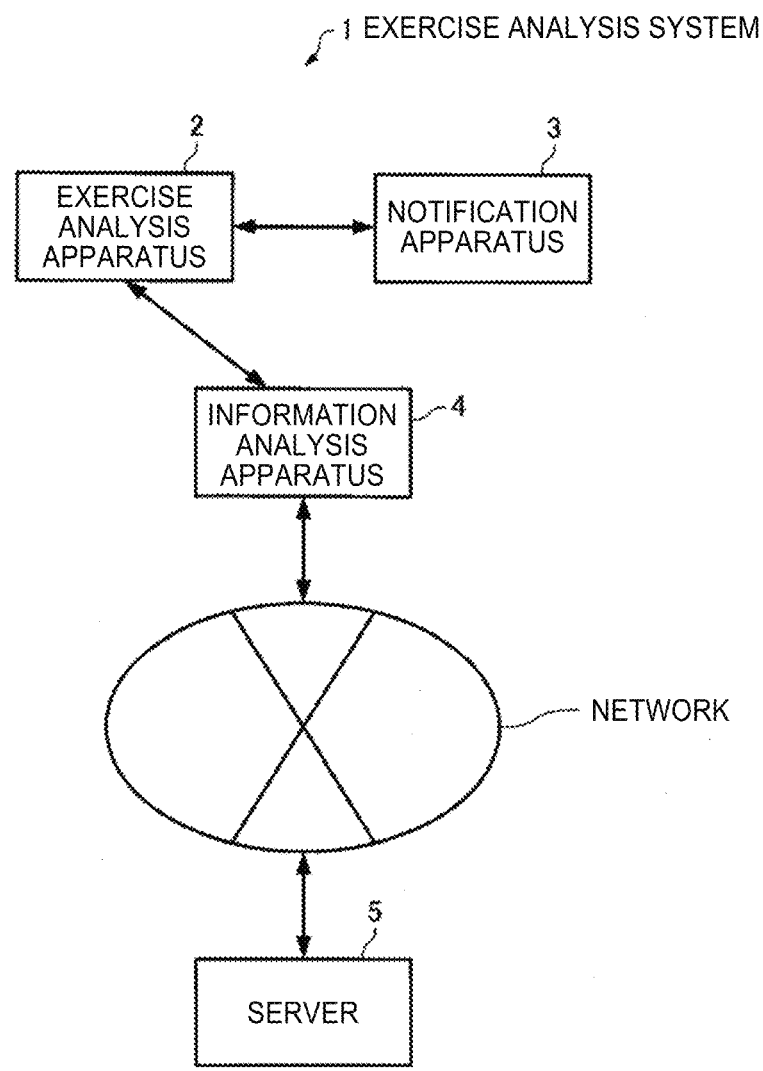
FIG. 46 is a diagram illustrating a configuration example of an exercise analysis system of the second embodiment.

Hereinafter, as an example, a description will be made of an exercise analysis system which analyzes an exercise during a user's running (including walking), but the exercise analysis system of the second embodiment is also applicable to exercise analysis systems which analyze exercises other than running. FIG. 46 is a diagram illustrating a configuration example of an exercise analysis system 1 of the second embodiment. As illustrated in FIG. 46, the exercise analysis system 1 of the second embodiment includes an exercise analysis apparatus 2, a notification apparatus 3, and an information analysis apparatus 4. The exercise analysis apparatus 2 is an apparatus which analyzes an exercise during a user's running, and the notification apparatus 3 is an apparatus which notifies the user of a state of the exercise during running or information regarding a running result. The information analysis apparatus 4 is an apparatus which analyzes a running result after the user finishes the running, and presents the analyzed result to the user. Also in the second embodiment, in the same manner as in the first embodiment, as illustrated in FIG. 1, the exercise analysis apparatus 2 has an inertial measurement unit (IMU) 10 built thereinto, and is mounted on a body part (for example, a right waist, a left waist, or a central part of the waist) of the user so that one detection axis (hereinafter, referred to as a z axis) of the inertial measurement unit (IMU) 10 substantially matches the gravitational acceleration direction (vertically downward direction) in a state in which the user stands still. The notification apparatus 3 is a wrist type (wristwatch type) portable information apparatus and is mounted on a user's wrist or the like. However, the notification apparatus 3 may be a portable information apparatus such as a head mounted display (HMD) or a smart phone.

The user operates the notification apparatus 3 when starting running, so as to instruct the exercise analysis apparatus 2 to start measurement (an inertial navigation calculation process or an exercise analysis process), and operates the notification apparatus 3 after the running, so as to instruct the exercise analysis apparatus 2 to finish the measurement. The notification apparatus 3 transmits a command for starting or finishing the measurement to the exercise analysis apparatus 2 in response to a user's operation.

If the command for starting the measurement, the exercise analysis apparatus 2 causes the inertial measurement unit (IMU) 10 to start the measurement, computes values of various exercise indexes which are indexes related to the user's running performance (an example of exercise performance) by using a measurement result, and generates exercise analysis information including the values of the various exercise indexes as information regarding an analysis result of the user's running exercise. The exercise analysis apparatus 2 generates information (output information during running) which is output during the user's running by using the generated exercise analysis information, and transmits the exercise analysis information to the notification apparatus 3. The notification apparatus 3 receives the output information during running from the exercise analysis apparatus 2, compares each value of the various exercise indexes included in the output information during running with each target value which is set in advance, and notifies the user of goodness and badness of each exercise index by using sound or vibration. Consequently, the user can run while recognizing goodness and badness of each exercise index.

If the command for finishing the measurement is received, the exercise analysis apparatus 2 causes the inertial measurement unit (IMU) 10 to finish the measurement, generates information (running result information: a running distance and running velocity) regarding a result of the user's running, and transmits the running result information to the notification apparatus 3. The notification apparatus 3 receives the running result information from the exercise analysis apparatus 2, and notifies the user of the running result information as text or an image. Consequently, the user can immediately recognize the running result information. Alternatively, the notification apparatus 3 may generate running result information on the basis of the output information during running and may notify the user of the running result information as text or an image.

Data communication between the exercise analysis apparatus 2 and the notification apparatus 3 may be wireless communication or wired communication.

As illustrated in FIG. 46, in the present embodiment, the exercise analysis system 1 includes a server 5 connected to a network such as the Internet or a local area network (LAN). The information analysis apparatus 4 is an information apparatus such as a personal computer or a smart phone and can perform data communication with the server 5 via the network. The information analysis apparatus 4 acquires exercise analysis information in the user's past running from the exercise analysis apparatus 2, and transmits the exercise analysis information to the server 5 via the network. However, an apparatus which is different from the information analysis apparatus 4 may acquire the exercise analysis information from the exercise analysis apparatus 2 and may transmit the exercise analysis information to the server 5, and the exercise analysis apparatus 2 may directly transmit the exercise analysis information to the server 5. The server 5 receives the exercise analysis information and stores the exercise analysis information in a database built into a storage unit (not illustrated).

The information analysis apparatus 4 acquires the exercise analysis information of the user from the database of the server 5 via the network so as to analyze the user's running performance, and displays information regarding an analysis result on a display unit (not illustrated in FIG. 46). It is possible to evaluate the user's running performance on the basis of the analysis information displayed on the display unit of the information analysis apparatus 4.

In the exercise analysis system 1, the exercise analysis apparatus 2, the notification apparatus 3, the information analysis apparatus 4 may be separately provided; the exercise analysis apparatus 2 and the notification apparatus 3 may be integrally provided, and the information analysis apparatus 4 may be separately provided; the notification apparatus 3 and the information analysis apparatus 4 may be integrally provided, and the exercise analysis apparatus 2 may be separately provided; the exercise analysis apparatus 2 and the information analysis apparatus 4 may be integrally provided, and the notification apparatus 3 may be separately provided; and the exercise analysis apparatus 2, the notification apparatus 3, and the information analysis apparatus 4 may be integrally provided. The exercise analysis apparatus 2, the notification apparatus 3, and the information analysis apparatus 4 may have any combination.

1-2. Coordinate Systems

Coordinate systems which are necessary in the following description are defined in the same manner as in "1-2. Coordinate Systems" of the first embodiment.

Figure 47:
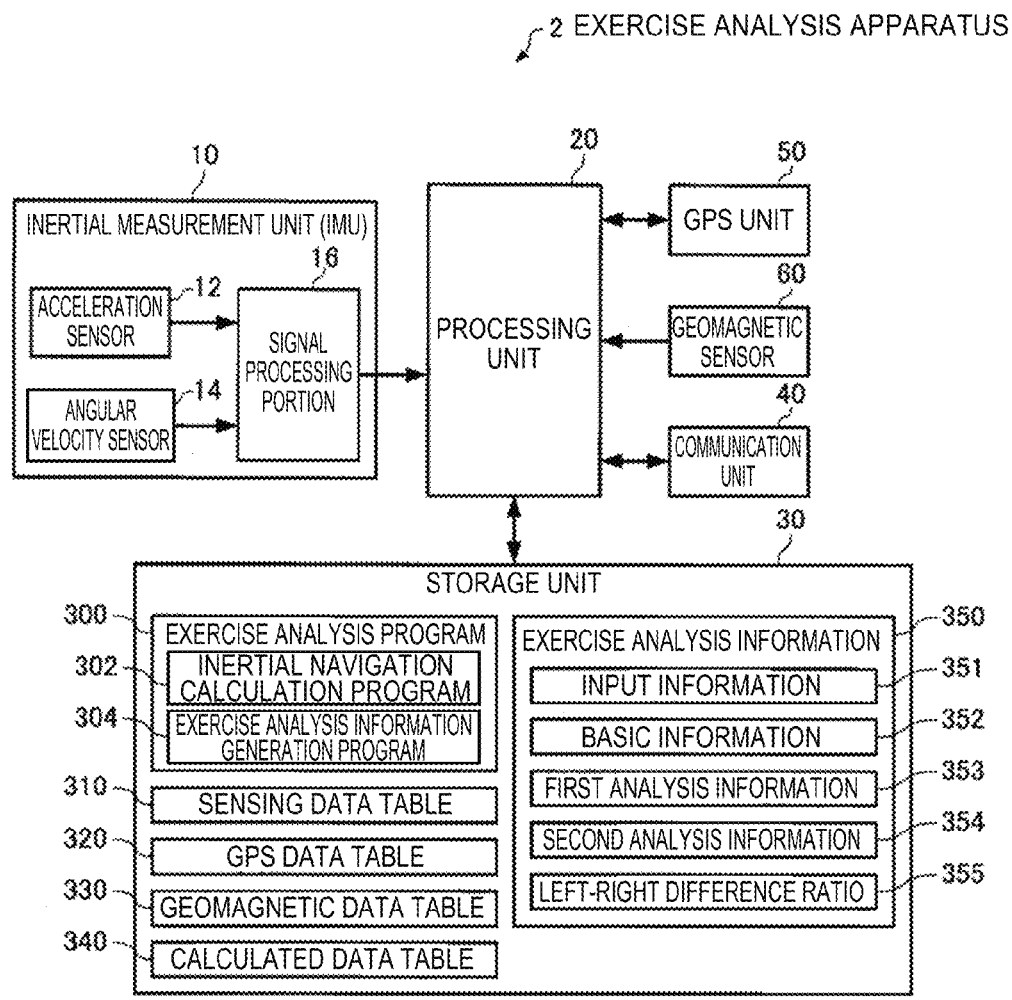
FIG. 47 is a functional block diagram illustrating a configuration example of an exercise analysis apparatus of the second embodiment.

2-3. Exercise Analysis Apparatus 2-3-1. Configuration of Exercise Analysis Apparatus FIG. 47 is a functional block diagram illustrating a configuration example of the exercise analysis apparatus 2 of the second embodiment. As illustrated in FIG. 47, the exercise analysis apparatus 2 of the second embodiment includes the inertial measurement unit (IMU) 10, a processing unit 20, a storage unit 30, a communication unit 40, a GPS unit 50, and a geomagnetic sensor 60 in the same manner as in the first embodiment. However, the exercise analysis apparatus 2 of the present embodiment may have a configuration in which some of the constituent elements are deleted or changed, or other constituent elements may be added thereto.

A function and a configuration of the inertial measurement unit (IMU) 10 are the same as in the first embodiment (FIG. 2), and thus description thereof will be omitted. Functions of the GPS unit 50 and the geomagnetic sensor 60 are also the same as in the first embodiment, and thus description thereof will be omitted.

The communication unit 40 performs data communication with a communication unit 140 (refer to FIG. 62) of the notification apparatus 3 or a communication unit 540 (refer to FIG. 65) of the information analysis apparatus 4, and performs a process of receiving commands (commands for starting and finishing measurement) transmitted from the communication unit 140 of the notification apparatus 3 and sending the commands to the processing unit 20, a process of receiving output information during running or running result information generated by the processing unit 20 and transmitting the information to the communication unit 140 of the notification apparatus 3, and a process of receiving a transmission request command of exercise analysis information from the communication unit 540 of the information analysis apparatus 4, sending the command to the processing unit 20, receiving the exercise analysis information from the processing unit 20, and transmitting the exercise analysis information to the communication unit 540 of the information analysis apparatus 4.

The processing unit 20 is constituted of, for example, a CPU, a DSP, or an ASIC, and performs various calculation processes or control processes according to a program stored in the storage unit 30 (recording medium). Particularly, if the command for starting measurement is received from the notification apparatus 3 via the communication unit 40, the processing unit 20 receives sensing data, GPS data, and geomagnetic data from the inertial measurement unit 10, the GPS unit 50, and the geomagnetic sensor 60, respectively, until receiving the command for finishing the measurement, and calculates a velocity or a position of the user, an attitude angle of the body, and the like by using the data. The processing unit 20 performs various calculation processes by using the calculated information so as to analyze exercise of the user and to generate various pieces of exercise analysis information which are then stored in the storage unit 30. The processing unit 20 performs a process of generating output information during running or running result information by using the generated exercise analysis information, and sending the information to the communication unit 40.

If the transmission request command of exercise analysis information is received from the information analysis apparatus 4 via the communication unit 40, the processing unit 20 performs a process of reading exercise analysis information designated by the transmission request command from the storage unit 30, and sending the exercise analysis information to the communication unit 540 of the information analysis apparatus 4 via the communication unit 40.

The storage unit 30 is constituted of, for example, recording media including a ROM, a flash ROM, a hard disk, and a memory card which store a program or data, and a RAM serving as a work area of the processing unit 20. The storage unit 30 (any one of recording media) stores an exercise analysis program 300 which is read by the processing unit 20 and is used to perform an exercise analysis process (refer to FIG. 56). The exercise analysis program 300 includes, as sub-routines, an inertial navigation calculation program 302 for performing an inertial navigation calculation process (refer to FIG. 42), and an exercise analysis information generation program 304 for performing an exercise analysis information generation process (refer to FIG. 58).

In the same manner as in the first embodiment, the storage unit 30 stores a sensing data table 310, a GPS data table 320, a geomagnetic data table 330, a calculated data table 340, exercise analysis information 350, and the like. Configurations of the sensing data table 310, the GPS data table 320, the geomagnetic data table 330, and the calculated data table 340 are the same as in the first embodiment (FIGS. 3 to 6), and illustration and description thereof will be omitted.

The exercise analysis information 350 is various information pieces regarding the exercise of the user, and includes each item of input information 351, each item of basic information 352, each item of first analysis information 353, each item of second analysis information 354, each item of left-right difference ratio 355, and the like, generated by the processing unit 20.

2-3-2. Functional Configuration of Processing Unit

Figure 48:
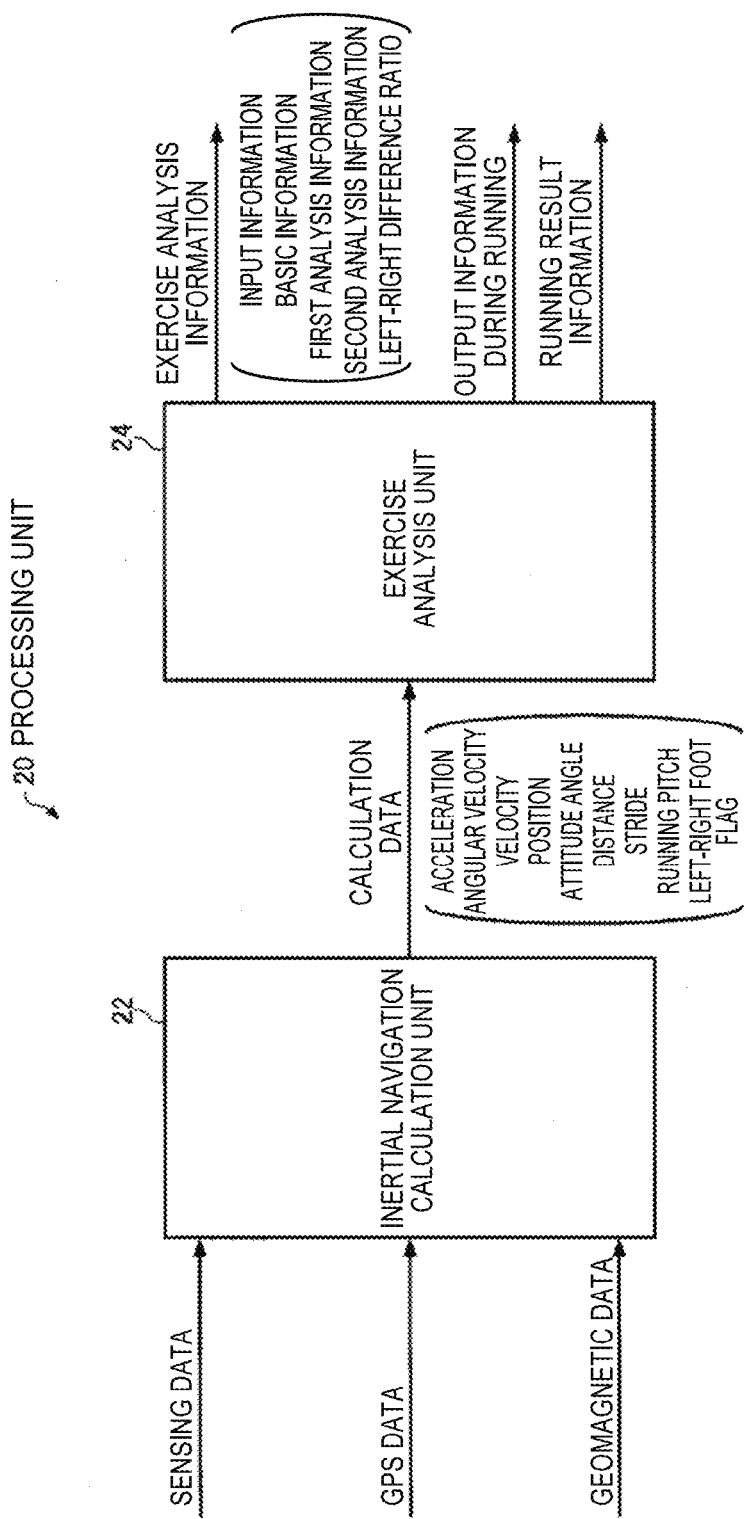
FIG. 48 is a functional block diagram illustrating a configuration example of a processing unit of the exercise analysis apparatus in the second embodiment.

FIG. 48 is a functional block diagram illustrating a configuration example of the processing unit 20 of the exercise analysis apparatus 2 in the second embodiment. In the same manner as in the first embodiment, also in the second embodiment, the processing unit 20 functions as an inertial navigation calculation unit 22 and an exercise analysis unit 24 by executing the exercise analysis program 300 stored in the storage unit 30. However, the processing unit 20 may receive the exercise analysis program 300 stored in any storage device (recording medium) via the network and may execute the exercise analysis program.

In the same manner as in the first embodiment, the inertial navigation calculation unit 22 (an example of a calculation unit) performs inertial navigation calculation by using sensing data (a detection result in the inertial measurement unit 10), GPS data (a detection result in the GPS unit 50), and geomagnetic data (a detection result in the geomagnetic sensor 60), so as to calculate an acceleration, an angular velocity, a velocity, a position, an attitude angle, a distance, a stride, and a running pitch, and outputs calculation data (example of exercise information the user) including the calculation results. The calculation data output from the inertial navigation calculation unit 22 is stored in the storage unit 30 in order of time points.

The exercise analysis unit 24 analyzes an exercise during the user's running by using calculation data (the calculation data stored in the storage unit 30) output from the inertial navigation calculation unit 22, so as to generate exercise analysis information (input information, basic information, first analysis information, second analysis information, a left-right difference ratio, and the like) which is information regarding an analysis result. The exercise analysis information generated by the exercise analysis unit 24 is stored in the storage unit 30 in order of time points during the user's running.

The exercise analysis unit 24 generates output information during running which is output during the user's running (specifically, until the inertial measurement unit 10 finishes the measurement after starting the measurement) by using the generated exercise analysis information. The output information during running generated by the exercise analysis unit 24 is transmitted to the notification apparatus 3 via the communication unit 40.

The exercise analysis unit 24 generates running result information which is information regarding a running result when the user finishes the running (specifically, when the inertial measurement unit 10 finishes the measurement), by using the exercise analysis information which is generated during the running. The running result information generated by the exercise analysis unit 24 is transmitted to the notification apparatus 3 via the communication unit 40.

2-3-3. Functional Configuration of Inertial Navigation Calculation Unit

A configuration example of the inertial navigation calculation unit 22 of the second embodiment is the same as in the first embodiment (FIG. 8), and thus description thereof will be omitted. In the same manner as in the first embodiment, also in the second embodiment, the inertial navigation calculation unit 22 includes a bias removing portion 210, an integral processing portion 220, an error estimation portion 230, a running processing portion 240, and a coordinate conversion portion 250. Functions of the constituent elements are the same as in the first embodiment, and thus description thereof will be omitted.

2-3-4. Functional Configuration of Exercise Analysis Unit

Figure 49:
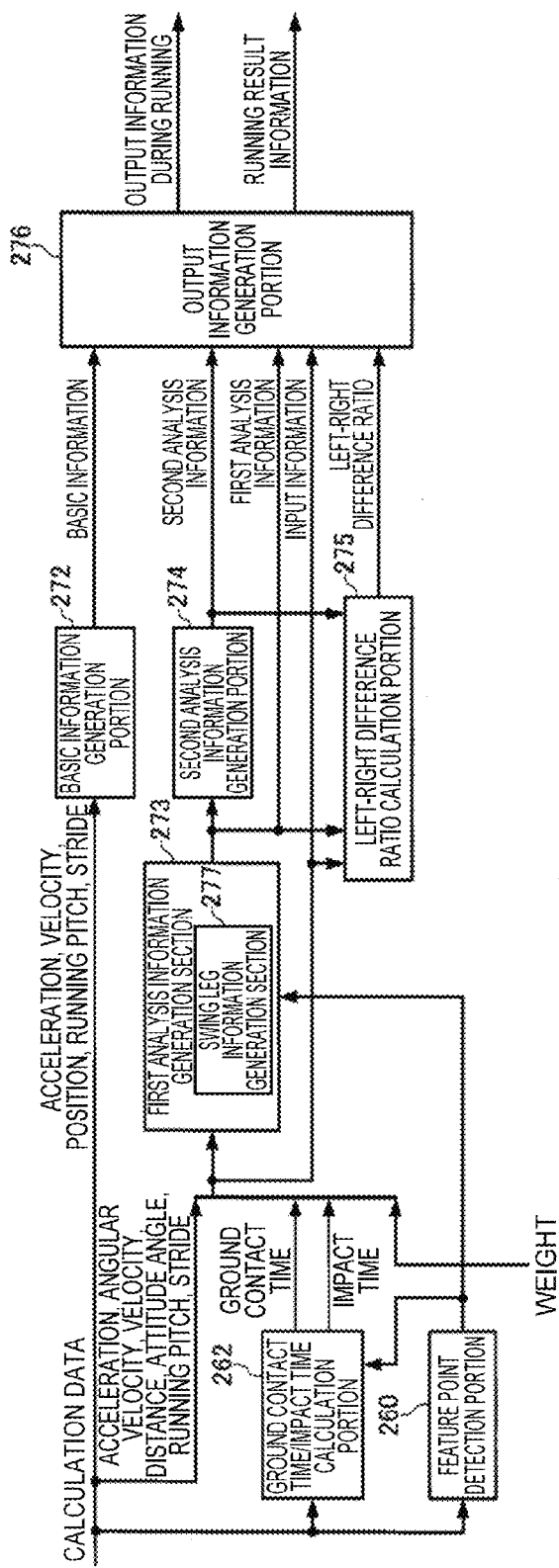
FIG. 49 is a functional block diagram illustrating a configuration example of an exercise analysis unit of the second embodiment.

FIG. 49 is a functional block diagram illustrating a configuration example of the exercise analysis unit 24. In the present embodiment, the exercise analysis unit 24 includes a feature point detection portion 260, a ground contact time/impact time calculation portion 262, a basic information generation portion 272, a first analysis information generation portion 273, a second analysis information generation portion 274, a left-right difference ratio calculation portion 275, and an output information generation portion 276. However, the exercise analysis unit 24 of the present embodiment may have a configuration in which some of the constituent elements are deleted or changed, or other constituent elements may be added thereto.

Respective functions of the feature point detection portion 260, the ground contact time/impact time calculation portion 262, and the basic information generation portion 272 are the same as in the first embodiment, and thus description thereof will be omitted. In the same manner as in the first embodiment, also in the present embodiment, basic information generated by the basic information generation portion 272 includes respective items such as a running pitch, a stride, a running velocity, an elevation, a running distance, and a running time (lap time).

The first analysis information generation portion 273 performs a process of analyzing the exercise of the user with a timing at which a feature point is detected by the feature point detection portion 260 as a reference, by using input information, so as to generate first analysis information.

Here, in the same manner as in the first embodiment, the input information includes respective items such as an advancing direction acceleration, an advancing direction velocity, an advancing direction distance, a vertical acceleration, a vertical velocity, a vertical distance, a horizontal acceleration, a horizontal velocity, a horizontal distance, attitude angles (a roll angle, a pitch angle, and a yaw angle), angular velocities (in a roll direction, a pitch direction, and a yaw direction), a running pitch, a stride, a ground contact time, an impact time, and a weight.

In the same manner as in the first embodiment, the first analysis information includes respective items such as brake amounts in landing (a brake amount 1 in landing and a brake amount 2 in landing), directly-below landing ratios (a directly-below landing ratio 1, a directly-below landing ratio 2, and a directly-below landing ratio 3), propulsion forces (a propulsion force 1 and a propulsion force 2), propulsion efficiency (propulsion efficiency 1, propulsion efficiency 2, propulsion efficiency 3, and propulsion efficiency 4), an amount of energy consumption, a landing impact, running performance, a forward tilt angle, and timing coincidence, and also includes an item such as slow turnover of the legs.

The first analysis information generation portion 273 calculates a value of each item of the first analysis information for the respective left and right sides of the user's body. Specifically, the first analysis information generation portion 273 calculates each item included in the first analysis information for the right foot running cycle and the left foot running cycle depending on whether the feature point detection portion 260 has detected the feature point at the right foot running cycle or the feature point at the left foot running cycle. The first analysis information generation portion 273 calculates an average value or a total value of the left and right sides for each item included in the first analysis information.

Particularly, in the present embodiment, the first analysis information generation portion 273 includes a swing leg information generation section 277. The swing leg information generation section 277 performs a process of generating information regarding a swing leg while the user's foot contacts the ground, by using the calculation data. The information regarding a swing leg may be, for example, information regarding an angle formed between a predetermined part (for example, the femur) of the swing leg and a horizontal plane or a vertical plane, and may be information regarding a distance (height) from the horizontal plane to a predetermined part (for example, the knee) of the swing leg. The swing leg information generation section 277 may compute an angle of the swing leg (an angle of the femur) when the user's foot is in a predetermined state, by using a detection result of a feature point detected by the feature point detection portion 260 and corresponding to the predetermined state while the user's foot contacts the ground.

Hereinafter, in the present embodiment, a description will be made assuming that the time when the predetermined state occurs while the user's foot contacts the ground is the time when the user's foot lands (right after landing), and the information regarding a swing leg is an angle (hereinafter, simply referred to as an "angle of the femur") formed between the femur of the swing leg and the horizontal plane or the vertical plane. In other words, the swing leg information generation section 277 performs a process of computing an angle of the swing leg (angle of the femur) when the user's foot lands (in landing). The first analysis information generation portion 273 sets a value of the angle of the swing leg in landing, computed by the swing leg information generation section 277, as a value of the "slow turnover of the legs" included in the first analysis information.

For example, the swing leg information generation section 277 may compute an angle of the swing leg in landing by using the attitude angles (a roll angle, a pitch angle, and a yaw angle) of the m frame included in the calculation data. Specifically, the swing leg information generation section 277 computes a value of an index correlated with an angle of the swing leg in landing, and estimates the angle of the swing leg in landing by using the value of the index.

For example, the index correlated with an angle of the swing leg in landing may be a difference between a time point at which an attitude angle of the user's body satisfies a predetermined condition and a time point in landing. For example, the attitude angle is a yaw angle, and the time when the attitude angle satisfies a predetermined condition may be the time when the yaw angle is the maximum between landing and taking-off of the user's right foot, or may be the time when the yaw angle is the minimum between landing and taking-off of the user's left foot. In other words, an index correlated with an angle of the swing leg in landing may be a difference between a time point at which a yaw angle of the user's body is the maximum or the minimum between landing and taking-off of the user's right foot to taking-off and a time point in landing of the user's right foot or left foot (hereinafter, this index is referred to as a first index). In other words, the first index is a difference between a time point at which the user's waist rotates to the maximum in the yaw direction (the time of starting the next one-step operation) and a time point in landing. In a case where a value of the first index is great, it can be said that a time period from landing to the start of the next one-step operation is long, and time is required to return the leg, and thus a phenomenon of slow turnover of the legs occurs.

Figure 50:
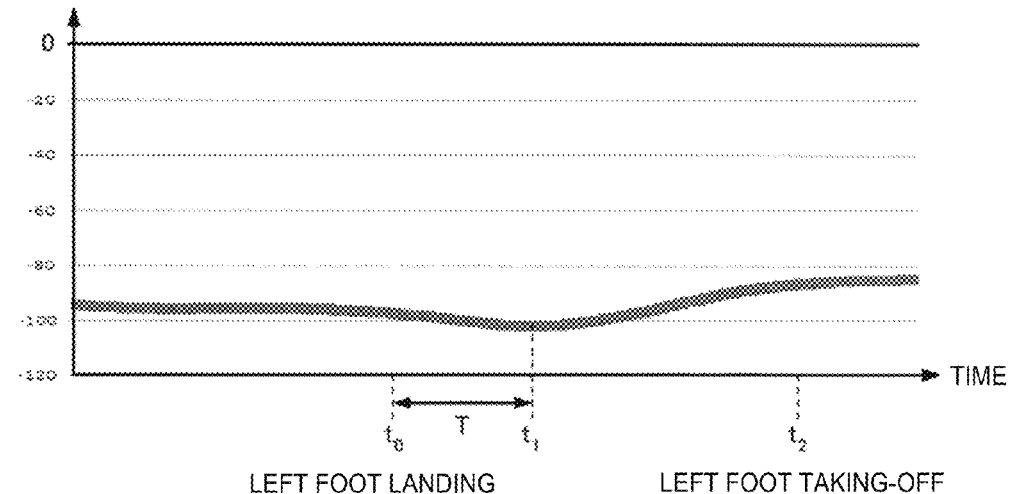
FIG. 50 is a diagram illustrating a first index correlated with an angle of a swing leg in landing.

FIG. 50 illustrates an example of a graph showing a state in which a yaw angle of the user's waist changes over time, in which a transverse axis expresses time, and a longitudinal axis expresses a yaw angle. In FIG. 50, a time difference T between a time point $t_1$ at which the yaw angle is the minimum from a landing time point $t_0$ of the left foot to a taking-off time point $t_2$ thereof, and the time point $t_0$ of the left foot corresponds to the first index. In the present embodiment, since the inertial measurement unit (IMU) 10 is mounted on the user's body part (for example, the right waist, the left waist, or the central part of the waist), a timing at which a yaw angle of the user's waist is the maximum or the minimum at a walking cycle substantially matches a timing at which a yaw angle of the m frame is the maximum or the minimum. Therefore, the swing leg information generation section 277 can acquire a measurement time point in landing of the right foot (or the left foot) detected by the feature point detection portion 260, and a measurement time point at which a yaw angle of the m frame has the maximum value (or the minimum value) between landing and taking-off of the right foot (left foot), and can compute a difference between the two measurement time points as the first index.

Figure 51:
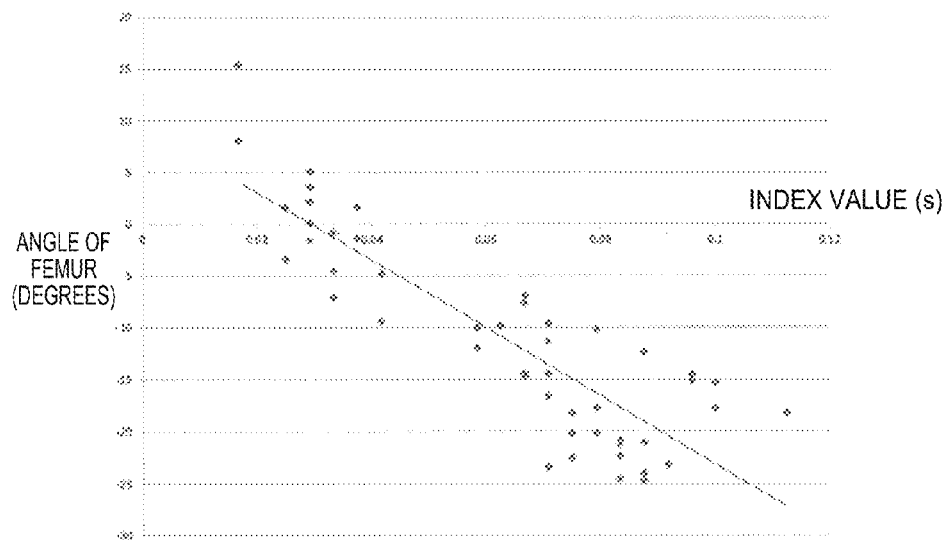
FIG. 51 is a diagram illustrating the first index correlated with an angle of the swing leg in landing.

FIG. 51 is a diagram in which a relationship between a value of the first index and an angle of the femur (an angle formed between the femur and the vertical plane) of the swing leg in landing is plotted in plurality, in which a transverse axis expresses the first index (unit: second), and a longitudinal axis expresses an angle of the femur (unit: degree). As illustrated in FIG. 51, an angle of the femur of the swing leg in landing is highly correlated with the first index value. Therefore, the swing leg information generation section 277 can estimate (compute) an angle of the femur of the swing leg in landing by assigning a value of the first index to a correlation represented by a straight line in the figure which is approximated by applying the least square method to the plotted relationships.

For example, an index correlated with an angle of the swing leg in landing may be a difference between a value of an attitude angle when the attitude angle of the user's body satisfies a predetermined condition and a value of the attitude angle in landing. For example, the attitude angle is a yaw angle, and the time when the attitude angle satisfies a predetermined condition may be the time when the yaw angle is the maximum between landing and taking-off of the user's right foot, or may be the time when the yaw angle is the minimum between landing and taking-off of the user's left foot. In other words, an index correlated with an angle of the swing leg in landing may be a difference between a value of a yaw angle when the yaw angle of the user's body is the maximum or the minimum between landing and taking-off of the user's right foot to taking-off and a value of the yaw angle in landing of the user's right foot or left foot (hereinafter, this index is referred to as a second index). In other words, the second index is a difference between a value of a yaw angle when the user's waist rotates to the maximum in the yaw direction (the time of starting the next one-step operation) and a value of the yaw angle in landing. In a case where a value of the second index is great, it can be said that a change in a yaw angle is considerable from landing to the start of the next one-step operation, and a motion for returning the leg after landing is considerable, and thus a phenomenon of slow turnover of the legs occurs.

Figure 52:
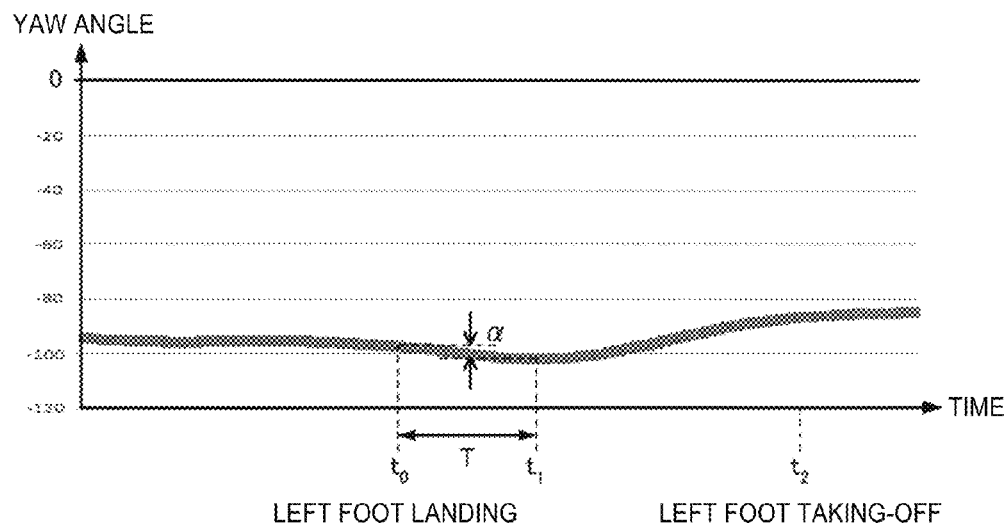
FIG. 52 is a diagram illustrating a second index correlated with an angle of the swing leg in landing.

FIG. 52 illustrates an example of a graph showing a state in which a yaw angle of the user's waist changes over time, in which a transverse axis expresses time, and a longitudinal axis expresses a yaw angle. In FIG. 52, a yaw angle difference α between a yaw angle at a time point $t_1$ at which the yaw angle is the minimum from a landing time point $t_0$ of the left foot to a taking-off time point $t_2$ thereof, and a yaw angle at the time point $t_0$ of the left foot corresponds to the second index. Therefore, the swing leg information generation section 277 can acquire a yaw angle of the m frame in landing of the right foot (or the left foot) detected by the feature point detection portion 260, and the maximum value (or the minimum value) of a yaw angle of the m frame between landing and taking-off of the right foot (left foot), and can compute a difference between the two yaw angles as a value of the second index.

Figure 53:
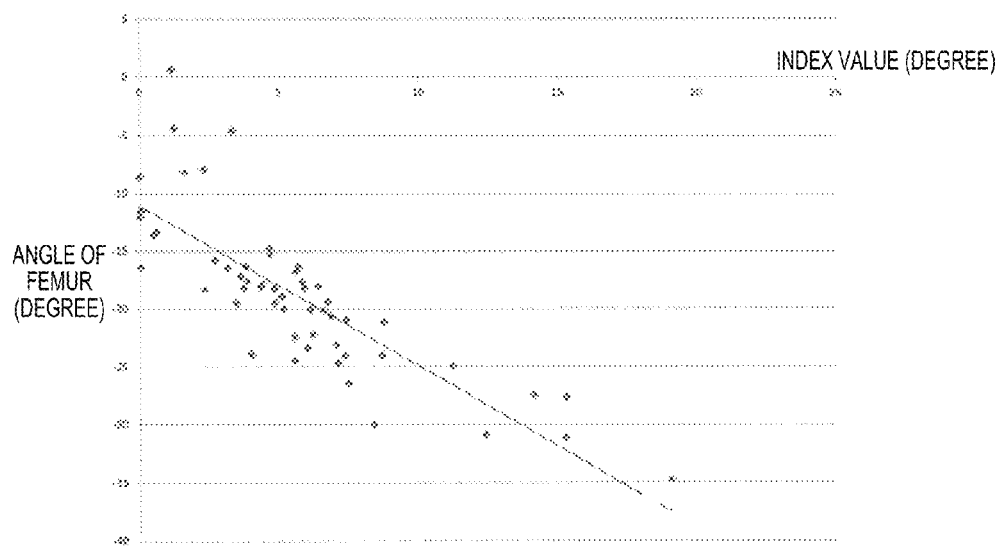
FIG. 53 is a diagram illustrating the second index correlated with an angle of the swing leg in landing.

FIG. 53 is a diagram in which a relationship between a value of the second index and an angle of the femur (an angle formed between the femur and the vertical plane) of the swing leg in landing is plotted in plurality, in which a transverse axis expresses the second index (unit: degree), and a longitudinal axis expresses an angle of the femur (unit: degree). As illustrated in FIG. 53, an angle of the femur of the swing leg in landing is highly correlated with the second index value. Therefore, the swing leg information generation section 277 can estimate (compute) an angle of the femur of the swing leg in landing by assigning a value of the second index to a correlation represented by a straight line in the figure which is approximated by applying the least square method to the plotted relationships.

Figure 54:
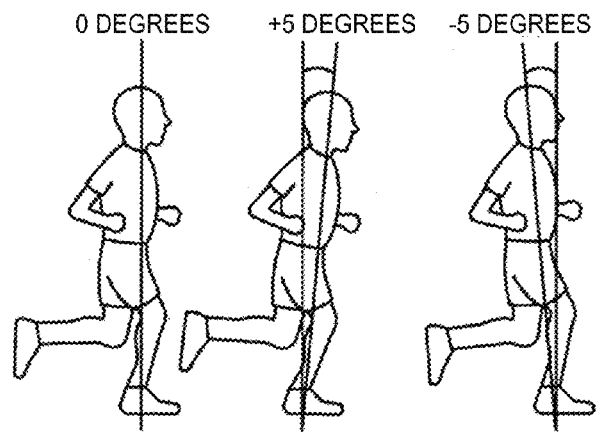
FIG. 54 is a diagram illustrating a third index correlated with an angle of the swing leg in landing.

For example, an index correlated with an angle of the swing leg in landing may be an attitude angle of the user's body in landing. For example, an index correlated with an angle of the swing leg in landing may be a pitch angle of the user's body when the user's right foot or left foot lands (hereinafter, this index is referred to as a third index). As illustrated in FIG. 54, a pitch angle (third index) of the user's body is, for example, an angle formed between the user's body and the vertical plane, and has a positive value when the user tilts forward, zero when the user stands upright, and a negative value when the user tilts backward. In a case where the leg lies high backward, the body is tilted forward, and thus a pitch angle increases. Therefore, if a value of the third index is great, a phenomenon of slow turnover of the legs occurs. Therefore, the swing leg information generation section 277 acquires a pitch angle of the m frame in landing of the right foot (or the left foot) detected by the feature point detection portion 260, and converts the pitch angle so that the pitch angle has the same specification as illustrated in FIG. 54 so as to be used as a value of the third index.

Figure 55:
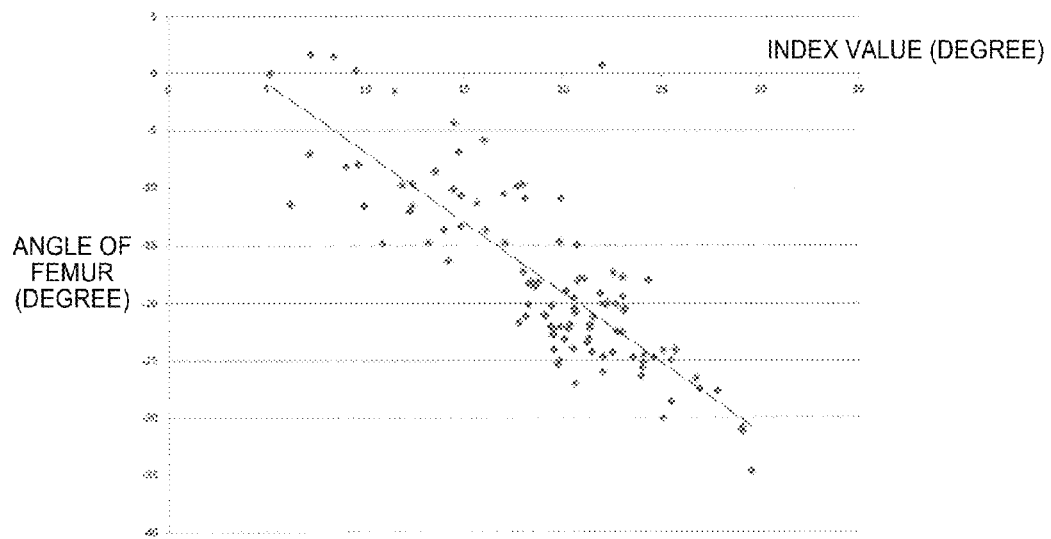
FIG. 55 is a diagram illustrating the third index correlated with an angle of the swing leg in landing.

FIG. 55 is a diagram in which a relationship between a value of the third index and an angle of the femur (an angle formed between the femur and the vertical plane) of the swing leg in landing is plotted in plurality, in which a transverse axis expresses the third index (unit: degree), and a longitudinal axis expresses an angle of the femur (unit: degree). As illustrated in FIG. 55, an angle of the femur of the swing leg in landing is highly correlated with the third index value. Therefore, the swing leg information generation section 277 can estimate (compute) an angle of the femur of the swing leg in landing by assigning a value of the third index to a correlation represented by a straight line in the figure which is approximated by applying the least square method to the plotted relationships.

Referring to FIG. 49 again, the second analysis information generation portion 274 performs a process of generating second analysis information by using the first analysis information generated by the first analysis information generation portion 273. Here, the second analysis information includes respective items such as energy loss, energy efficiency, and a burden on the body in the same manner as in the first embodiment. The second analysis information generation portion 274 calculates a value of each item of the second analysis information for the right foot running cycle and the left foot running cycle. The second analysis information generation portion 274 calculates an average value or a total value of the left and right sides for each item included in the second analysis information.

The left-right difference ratio calculation portion 275 performs a process of calculating a left-right difference ratio which is an index indicating a balance between the left and right sides of the user's body by using values at the right foot running cycle and values at the left foot running cycle with respect to the running pitch, the stride, the ground contact time, and the impact time included in the input information, all the items of the first analysis information, and all the items of the second analysis information.

The output information generation portion 276 performs a process of generating output information during running which is information which is output during the user's running, by using the basic information, the input information, the first analysis information, the second analysis information, the left-right difference ratio, and the like. The "running pitch", the "stride", the "ground contact time", and the "impact time" included in the input information, all items of the first analysis information, all items of the second analysis information, and the left-right difference ratio are exercise indexes used to evaluate a running technique of the user, and the output information during running includes information regarding values of some or all of the exercise indexes. The exercise index included in the output information during running may be predefined, and may be selected by the user operating the notification apparatus 3. The output information during running may include some or all of the running velocity, the elevation, the running distance, and the running time (lap time) included in the basic information.

The output information generation portion 276 generates running result information which is information regarding a running result of the user by using the basic information, the input information, the first analysis information, the second analysis information, the left-right difference ratio, and the like. For example, the output information generation portion 276 may generate the running result information including information regarding an average value of each exercise index during the user's running (during measurement in the inertial measurement unit 10). The running result information may include some or all of the running velocity, the elevation, the running distance, and the running time (lap time).

The output information generation portion 276 transmits the output information during running to the notification apparatus 3 via the communication unit 40 during the user's running, and transmits the running result information to the notification apparatus 3 when the user finishes the running.

2-3-5. Input Information

Details of each item of the input information have been described in the first embodiment, and thus description thereof will be omitted here.

2-3-6. First Analysis Information

Among the respective items of the first analysis information calculated by the first analysis information generation portion 273, details of each item except for the "slow turnover of the legs" have been described in the first embodiment, and thus description thereof will be omitted here.

Slow Turnover of Legs

The slow turnover of the legs is an exercise index indicating to what extent a leg (swing leg) remains behind at the next landing point of the kicking leg. As described above, the slow turnover of the legs is computed as an angle of the swing leg (an angle of the femur) when the user lands. For example, an index correlated with the slow turnover of the legs (an angle of the swing leg) is computed, and an angle of the swing leg (an angle of the femur) when the user's leg contacts the ground can be estimated by using a correlation which is obtained in advance on the basis of the index.

2-3-7. Second Analysis Information

Details of each item of the second analysis information calculated by the second analysis information generation portion 274 have been described in the first embodiment, and thus description thereof will be omitted here.

2-3-8. Left-Right Difference Ratio (Left and Right Balance)

The left-right difference ratio is an exercise index indicating to what extent there is a difference between the left and right sides of the body for the running pitch, the stride, the ground contact time, the impact time, each item of the first analysis information, and each item of the second analysis information, and is assumed to indicate to what extent the left leg is deviated relative to the right leg. The left-right difference ratio is computed as the left-right difference ratio=(numerical value for left leg/numerical value for right leg×100(%)). The numerical value is a numerical value of each of the running pitch, the stride, the ground contact time, the impact time, the brake amount, the propulsion force, the directly-below landing ratio, the propulsion efficiency, the velocity, the acceleration, the movement distance, the forward tilt angle, the slow turnover of the legs, the waist rotation angle, the waist rotation angular velocity, the amount of being tilted toward the left and right sides, the impact time, the running performance, the amount of energy consumption, the energy loss, the energy efficiency, the landing impact, and the burden on the body. The left-right difference ratio also includes an average value or a variance of the respective numerical values.

2-3-9. Procedure of Process

Figure 56:
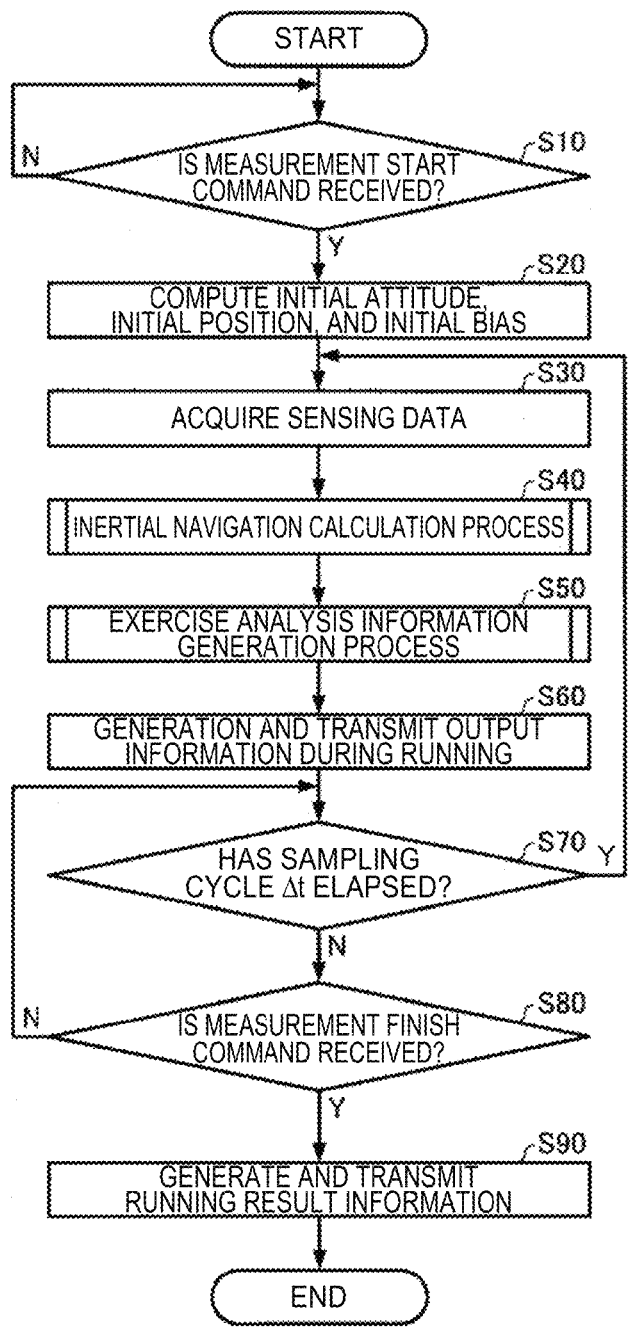
FIG. 56 is a flowchart illustrating an example of procedures of an exercise analysis process performed in the second embodiment.

FIG. 56 is a flowchart illustrating an example of procedures of the exercise analysis process performed by the processing unit 20 of the exercise analysis apparatus 2 in the second embodiment. The processing unit 20 of the exercise analysis apparatus 2 (an example of a computer) performs the exercise analysis process according to the procedures of the flowchart illustrated in FIG. 56 by executing the exercise analysis program 300 stored in the storage unit 30.

As illustrated in FIG. 56, the processing unit 20 waits for a command for starting measurement to be received (N in step S10), and if the command for starting measurement is received (Y in step S10), first, the processing unit 20 computes an initial attitude, an initial position, and an initial bias by using sensing data and GPS data measured by the inertial measurement unit 10 assuming that the user stops (step S20).

Next, the processing unit 20 acquires the sensing data from the inertial measurement unit 10, and adds the acquired sensing data to the sensing data table 310 (step S30).

Next, the processing unit 20 performs an inertial navigation calculation process so as to generate calculation data including various information pieces (step S40). Details of procedures of the inertial navigation calculation process are the same as in the first embodiment (FIG. 42), and thus illustration and description thereof will be omitted.

Next, the processing unit 20 performs an exercise analysis information generation process by using the calculation data generated in step S40 so as to generate exercise analysis information (step S50). An example of procedures of the exercise analysis information generation process will be described later.

Next, the processing unit 20 generates output information during running by using the exercise analysis information generated in step S40 and transmits the exercise analysis information to the notification apparatus 3 (step S60).

The processing unit 20 repeatedly performs the processes in step S30 and the subsequent steps whenever the sampling cycle Δt elapses (Y in step S70) from the acquisition of the previous sensing data until a command for finishing the measurement is received (N in step S70 and N in step S80).

If the command for finishing the measurement is received (Y in step S80), the processing unit 20 generates running result information by using the exercise analysis information generated in step S50, transmits the running result information to the notification apparatus 3 (step S90), and finishes the exercise analysis process.

Figure 57:
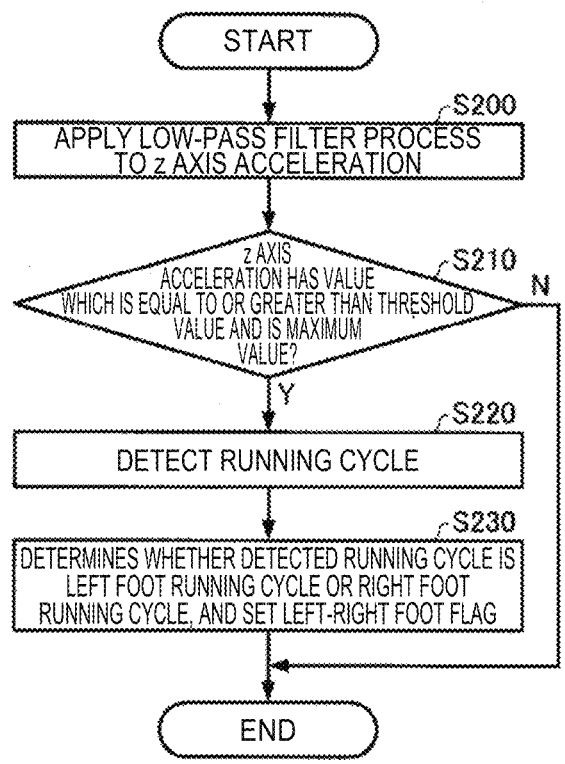
FIG. 57 is a flowchart illustrating an example of procedures of a running detection process in the second embodiment.

FIG. 57 is a flowchart illustrating an example of procedures of the running detection process (the process in step S120 of FIG. 42) in the second embodiment. The processing unit 20 (the running detection section 242) performs the running detection process according to, for example, the procedures of the flowchart illustrated in FIG. 57.

As illustrated in FIG. 57, the processing unit 20 performs a low-pass filter process on a z axis acceleration included in the acceleration corrected in step S100 of FIG. 42 (step S200) so as to remove noise therefrom.

Next, if the z axis acceleration having undergone the low-pass filter process in step S200 has a value which is equal to or greater than a threshold value and is the maximum value (Y in step S210), the processing unit 20 detects a running cycle at this timing (step S220).

Next, the processing unit 20 determines whether the running cycle detected in step S220 is a left foot running cycle or a right foot running cycle, sets a left-right foot flag (step S230), and finishes the running detection process. If the z axis acceleration has a value which is smaller than the threshold value or is not the maximum value (N in step S210), the processing unit 20 does not perform the processes in steps S220 and the subsequent steps and finishes the running detection process.

Figure 58:
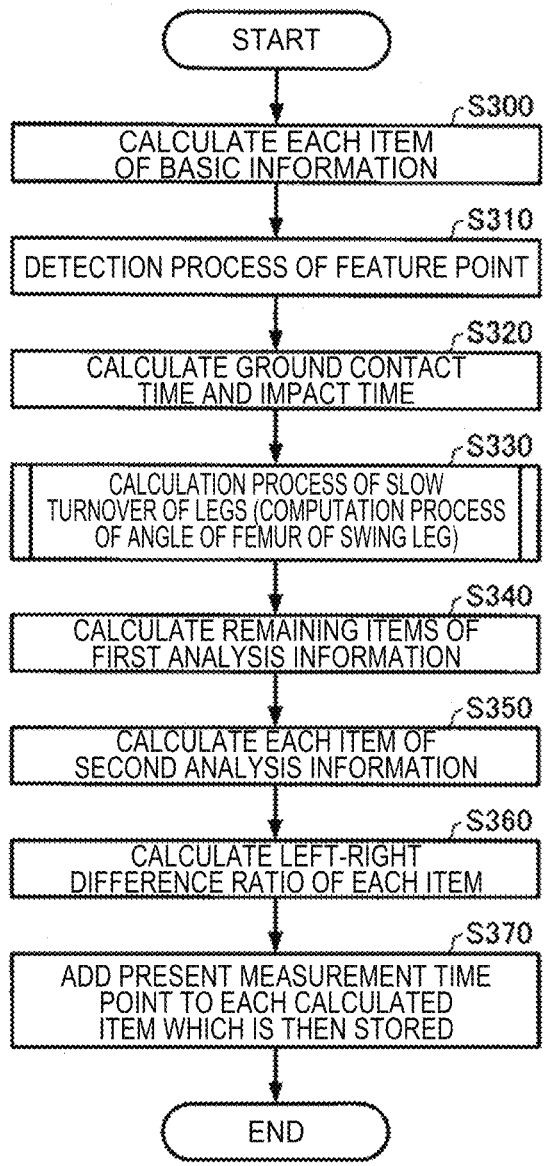
FIG. 58 is a flowchart illustrating an example of procedures of an exercise analysis information generation process in the second embodiment.

FIG. 58 is a flowchart illustrating an example of procedures of the exercise analysis information generation process (the process in step S50 of FIG. 56) in the second embodiment. The processing unit 20 (the exercise analysis unit 24) performs the exercise analysis information generation process according to, for example, the procedures of the flowchart illustrated in FIG. 58 by executing the exercise analysis information generation program 304 stored in the storage unit 30.

As illustrated in FIG. 58, first, the processing unit 20 calculates each item of the basic information by using the calculation data generated through the inertial navigation calculation process of the step S40 of FIG. 56 (step S300).

Next, the processing unit 20 performs a process of detecting a feature point (landing, stepping, taking-off, or the like) in the running exercise of the user by using the calculation data (step S310).

The processing unit 20 calculates a ground contact time and an impact time on the basis of the timing of detecting the feature point in step S310 (step S320).

Next, the processing unit 20 performs a process of computing slow turnover of the legs (a process of computing an angle of the femur of the swing leg) (step S330). An example of procedures of the process of computing the slow turnover of the legs will be described.

Next, the processing unit 20 calculates remaining items of the first analysis information by using some of the calculation data and the ground contact time and the impact time generated in step S320 as input information (step S340).

Next, the processing unit 20 calculates each item of the second analysis information by using the first analysis information (step S350).

Next, the processing unit 20 calculates a left-right difference ratio for each item of the input information, each item of the first analysis information, and each item of the second analysis information (step S360).

The processing unit 20 adds the present measurement time to each piece of the information calculated in steps S300 to S360, stores the information in the storage unit 30 (step S370), and finishes the exercise analysis information generation process.

Figure 59:
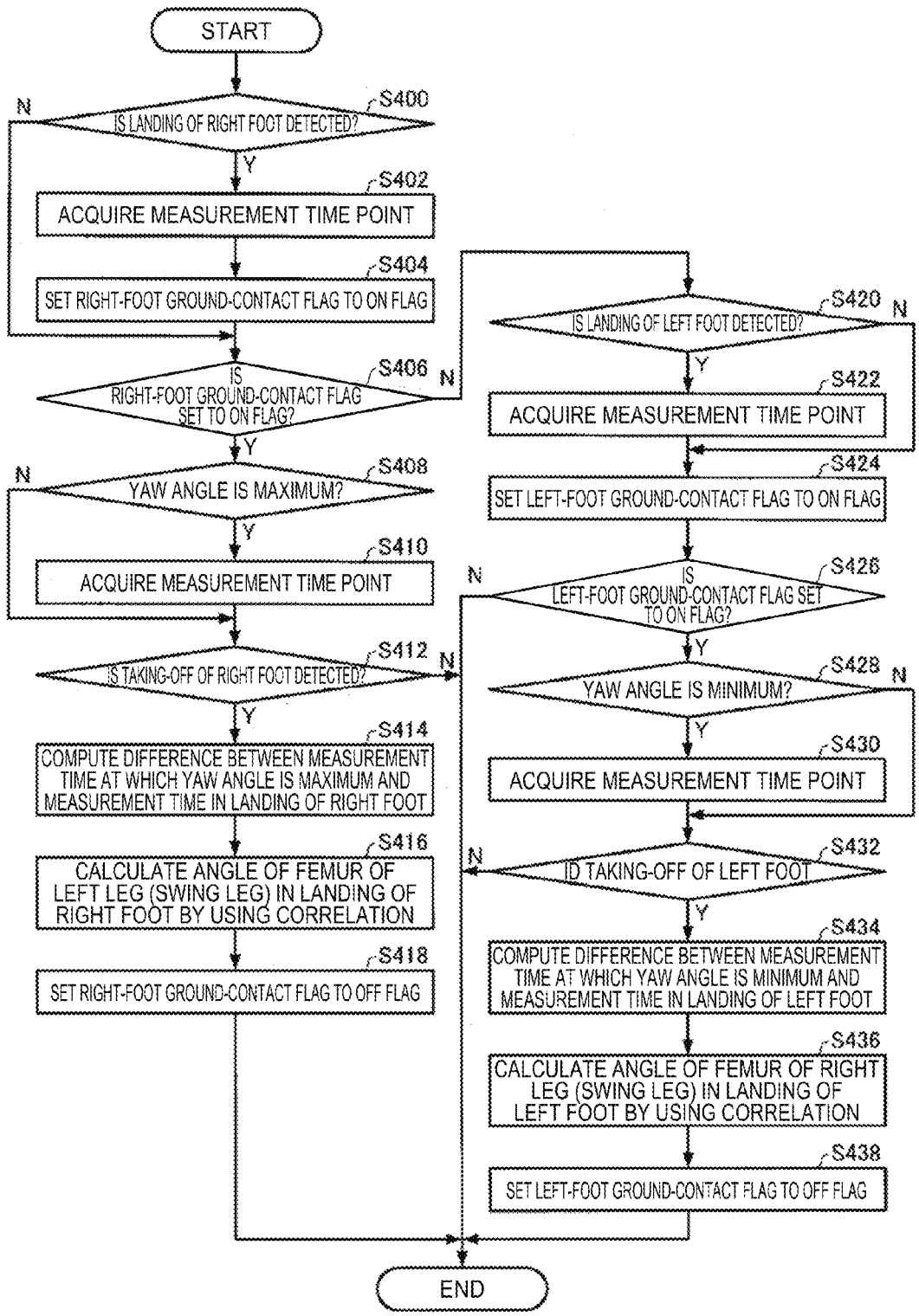
FIG. 59 is a flowchart illustrating an example of procedures of computing an index value of slow turnover of the legs.

FIG. 59 is a flowchart illustrating an example of procedures of the process of computing an index value of the slow turnover of the legs (the process of computing an angle of the femur of the swing leg) (the process in step S330 of FIG. 58). FIG. 59 is a flowchart corresponding to a case where the above-described first index is used as an index correlated with an angle of the swing leg in landing.

As illustrated in FIG. 59, if landing of the right foot is detected in the process in step S310 of FIG. 58 (Y in step S400), the processing unit 20 acquires a measurement time in landing of the right foot (step S402), and sets a right-foot ground-contact flag to an ON flag (step S404). If landing of the right foot is not detected (N in step S400), the processing unit 20 does not perform the processes in steps S402 and S404.

Next, if the right-foot ground-contact flag is an ON flag (Y in step S406), the processing unit 20 determines whether or not a yaw angle is the maximum after the right-foot ground-contact flag is set to an ON flag (step S408), and acquires a measurement time at which the yaw angle is the maximum (step S410) if the yaw angle is the maximum (Y in step S408). If the yaw angle is not the maximum (N in step S408), the processing unit 20 does not perform the process in step S410.

Next, if taking-off of the right foot is detected in the process in step S310 of FIG. 58 (Y in step S412), the processing unit 20 computes a difference between the latest measurement time at which the yaw angle is the maximum, acquired in step S410, and the latest measurement time in landing of the right foot, acquired in step S402 (step S414), and assigns the value computed in step S414 to a correlation so as to calculate an angle of the femur of the left leg (swing leg) in landing of the right foot (step S416). The processing unit 20 sets the right-foot ground-contact flag to an OFF flag (step S418), and finishes the computation process.

If taking-off of the right foot is not detected (N in step S412), the processing unit 20 does not perform the processes in steps S414 to S418 and finishes the computation process.

If the right-foot ground-contact flag is an OFF flag (N in step S406), and landing of the left foot is detected in the process in step S310 of FIG. 58 (Y in step S420), the processing unit 20 acquires a measurement time in landing of the left foot (step S422), and sets a left-foot ground-contact flag to an ON flag (step S424). If landing of the left foot is not detected (N in step S420), the processing unit 20 does not perform the processes in steps S422 and S424.

Next, if the left-foot ground-contact flag is an ON flag (Y in step S426), the processing unit 20 determines whether or not a yaw angle is the minimum after the left-foot ground-contact flag is set to an ON flag (step S428), and acquires a measurement time at which the yaw angle is the minimum (step S430) if the yaw angle is the minimum (Y in step S428). If the yaw angle is not the minimum (N in step S428), the processing unit 20 does not perform the process in step S430.

Next, if taking-off of the left foot is detected in the process in step S310 of FIG. 58 (Y in step S432), the processing unit 20 computes a difference between the latest measurement time at which the yaw angle is the minimum, acquired in step S430, and the latest measurement time in landing of the left foot, acquired in step S422 (step S434), and assigns the value computed in step S434 to a correlation so as to calculate an angle of the femur of the right leg (swing leg) in landing of the left foot (step S436). The processing unit 20 sets the left-foot ground-contact flag to an OFF flag (step S438), and finishes the computation process.

If taking-off of the left foot is not detected (N in step S432), the processing unit 20 does not perform the processes in steps S434 to S438 and finishes the computation process.

Figure 60:
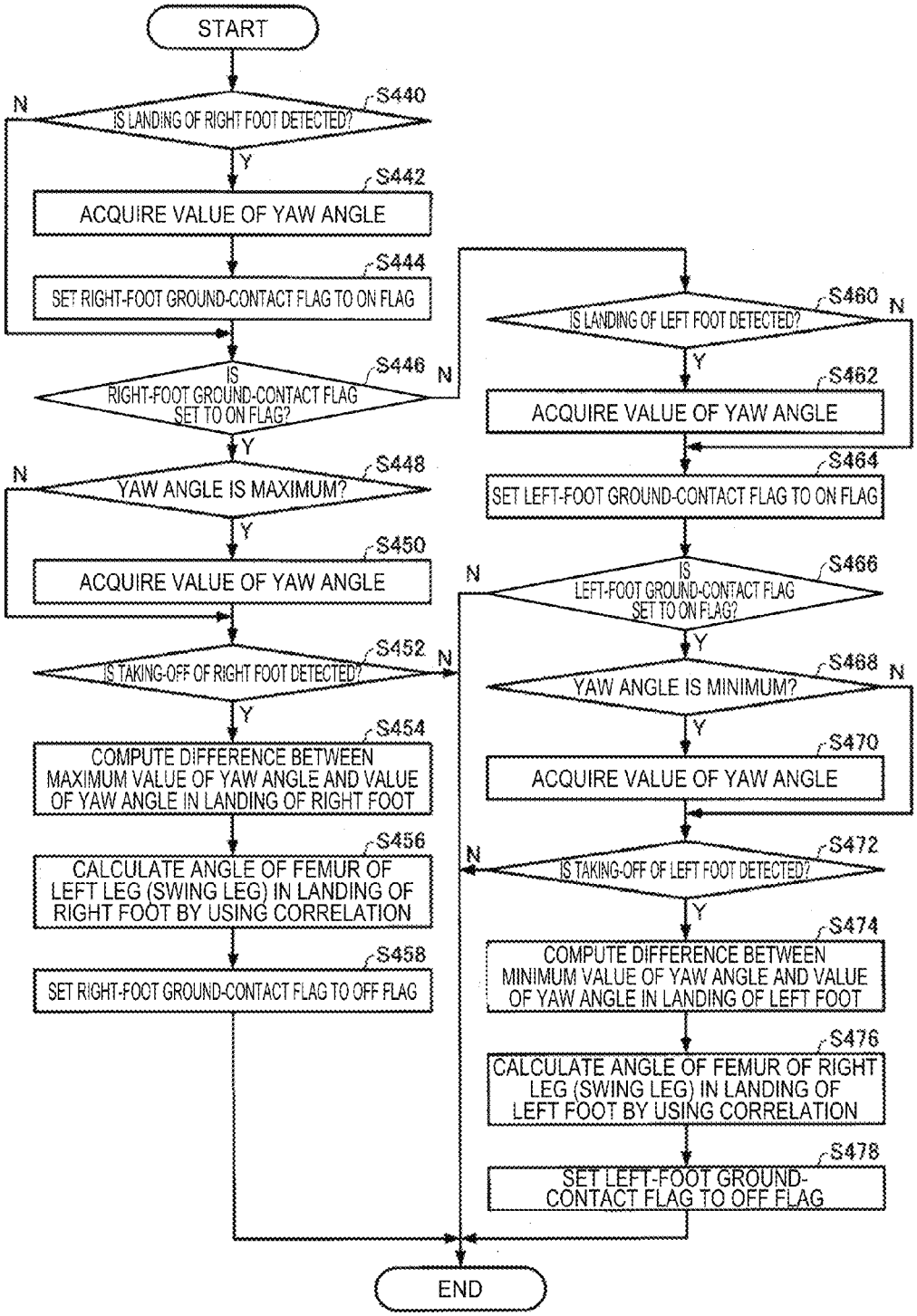
FIG. 60 is a flowchart illustrating another example of procedures of computing an index value of the slow turnover of the legs.

FIG. 60 is a flowchart illustrating another example of procedures of the process of computing an index value of the slow turnover of the legs (the process of computing an angle of the femur of the swing leg) (the process in step S330 of FIG. 58). FIG. 60 is a flowchart corresponding to a case where the above-described second index is used as an index correlated with an angle of the swing leg in landing.

As illustrated in FIG. 60, if landing of the right foot is detected in the process in step S310 of FIG. 58 (Y in step S440), the processing unit 20 acquires a value of a yaw angle in landing of the right foot (step S442), and sets a right-foot ground-contact flag to an ON flag (step S444). If landing of the right foot is not detected (N in step S440), the processing unit 20 does not perform the processes in steps S442 and S444.

Next, if the right-foot ground-contact flag is an ON flag (Y in step S446), the processing unit 20 determines whether or not a yaw angle is the maximum after the right-foot ground-contact flag is set to an ON flag (step S448), and acquires the maximum value of the yaw angle (step S450) if the yaw angle is the maximum (Y in step S448). If the yaw angle is not the maximum (N in step S448), the processing unit 20 does not perform the process in step S450.

Next, if taking-off of the right foot is detected in the process in step S310 of FIG. 58 (Y in step S452), the processing unit 20 computes a difference between the latest maximum value of the yaw angle acquired in step S450, and the latest value of the yaw angle in landing of the right foot, acquired in step S442 (step S454), and assigns the value computed in step S454 to a correlation so as to calculate an angle of the femur of the left leg (swing leg) in landing of the right foot (step S456). The processing unit 20 sets the right-foot ground-contact flag to an OFF flag (step S458), and finishes the computation process.

If taking-off of the right foot is not detected (N in step S452), the processing unit 20 does not perform the processes in steps S454 to S458 and finishes the computation process.

If the right-foot ground-contact flag is an OFF flag (N in step S446), and landing of the left foot is detected in the process in step S310 of FIG. 58 (Y in step S460), the processing unit 20 acquires a value of a yaw angle in landing of the left foot (step S462), and sets a left-foot ground-contact flag to an ON flag (step S464). If landing of the left foot is not detected (N in step S460), the processing unit 20 does not perform the processes in steps S462 and S464.

Next, if the left-foot ground-contact flag is an ON flag (Y in step S466), the processing unit 20 determines whether or not a yaw angle is the minimum after the left-foot ground-contact flag is set to an ON flag (step S468), and acquires the minimum value of the yaw angle (step S470) if the yaw angle is the minimum (Y in step S468). If the yaw angle is not the minimum (N in step S468), the processing unit 20 does not perform the process in step S470.

Next, if taking-off of the left foot is detected in the process in step S310 of FIG. 58 (Y in step S472), the processing unit 20 computes a difference between the latest minimum value of the yaw angle acquired in step S470 and the latest value of the yaw angle in landing of the left foot, acquired in step S462 (step S474), and assigns the value computed in step S474 to a correlation so as to calculate an angle of the femur of the right leg (swing leg) in landing of the left foot (step S476). The processing unit 20 sets the left-foot ground-contact flag to an OFF flag (step S478), and finishes the computation process.

If taking-off of the left foot is not detected (N in step S472), the processing unit 20 does not perform the processes in steps S474 to S478 and finishes the computation process.

Figure 61:
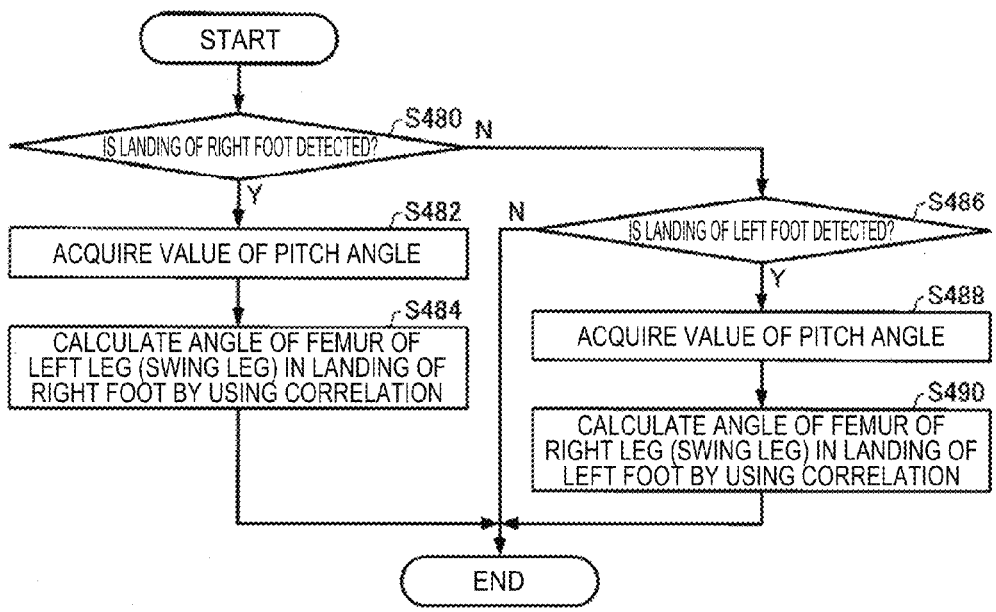
FIG. 61 is a flowchart illustrating an example of procedures of computing still another index value of the slow turnover of the legs.

FIG. 61 is a flowchart illustrating still another example of procedures of the process of computing an index value of the slow turnover of the legs (the process of computing an angle of the femur of the swing leg) (the process in step S330 of FIG. 58). FIG. 61 is a flowchart corresponding to a case where the above-described third index is used as an index correlated with an angle of the swing leg in landing.

As illustrated in FIG. 61, if landing of the right foot is detected in the process in step S310 of FIG. 58 (Y in step S480), the processing unit 20 acquires a value of a pitch angle in landing of the right foot (step S482). The processing unit 20 assigns the value of the pitch angle in landing of the right foot acquired in step S482 to a correlation so as to calculate an angle of the femur of the left leg (swing leg) in landing of the right foot (step S484), and finishes the computation process.

If landing of the right foot is not detected (N in step S480), and landing of the left foot is detected in the process in step S310 of FIG. 58 (Y in step S486), the processing unit 20 acquires a value of a pitch angle in landing of the left foot (step S488). The processing unit 20 assigns the value of the pitch angle in landing of the left foot acquired in step S488 to a correlation so as to calculate an angle of the femur of the right leg (swing leg) in landing of the left foot (step S490), and finishes the computation process.

If landing of the left foot is not detected (N in step S486), the processing unit 20 does not perform the processes in steps S488 and S490 and finishes the computation process.

2-4. Notification Apparatus 2-4-1. Configuration of Notification Apparatus

Figure 62:
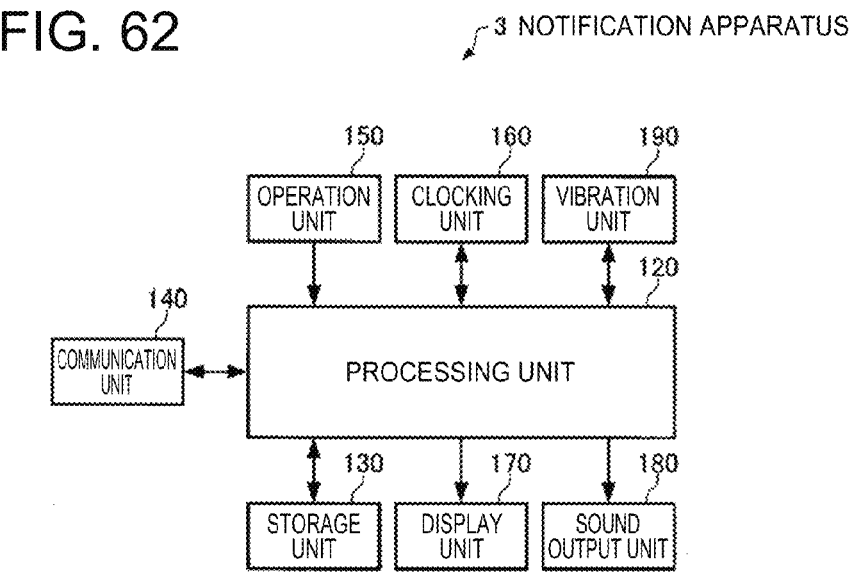
FIG. 62 is a functional block diagram illustrating a configuration example of a notification apparatus in the second embodiment.

FIG. 62 is a functional block diagram illustrating a configuration example of the notification apparatus 3 in the second embodiment. As illustrated in FIG. 62, in the same manner as in the first embodiment (FIG. 2), the notification apparatus 3 of the second embodiment includes a processing unit 120, a storage unit 130, the communication unit 140, an operation unit 150, a clocking unit 160, a display unit 170, a sound output unit 180, and a vibration unit 190. However, the notification apparatus 3 of the present embodiment may have a configuration in which some of the constituent elements are deleted or changed, or other constituent elements may be added thereto.

Respective functions of the storage unit 130, the operation unit 150, the clocking unit 160, the display unit 170, the sound output unit 180, and the vibration unit 190 are the same as in the first embodiment, and thus description thereof will be omitted here.

The communication unit 140 performs data communication with the communication unit 40 (refer to FIG. 47) of the exercise analysis apparatus 2, and performs a process of receiving a command (a command for starting or finishing measurement or the like) corresponding to operation data from the processing unit 120 and transmitting the command to the communication unit 40 of the exercise analysis apparatus 2, a process of receiving output information during running or running result information transmitted from the communication unit 40 of the exercise analysis apparatus 2 and sending the information to the processing unit 120, and the like.

The processing unit 120 is constituted of, for example, a CPU, a DSP, or an ASIC, and performs various calculation processes or control processes according to a program stored in the storage unit 130 (recording medium). For example, the processing unit 120 performs various processes (a process of sending a command for starting or finishing measurement to the communication unit 140, a process of performing display or outputting sound corresponding to the operation data, and the like) corresponding to operation data received from the operation unit 150; a process of receiving output information during running from the communication unit 140 and sending text data or image data corresponding to the exercise analysis information to the display unit 170; a process of sending sound data corresponding to the exercise analysis information to the sound output unit 180; and a process of sending vibration data corresponding to the exercise analysis information to the vibration unit 190. The processing unit 120 performs a process of generating time image data corresponding to time information received from the clocking unit 160 and sending the time image data to the display unit 170, and the like.

In the present embodiment, the processing unit 120 sets, for example, a target value of each exercise index on the basis of operation data received from the operation unit 150 before the user's running (before transmitting a measurement start command). The processing unit 120 compares a value of each exercise index included in the output information during running with each target value, generates information regarding an exercise state in the user's running on the basis of a comparison result, and notifies the user of the information via the sound output unit 180 or the vibration unit 190.

For example, the user may set a target value with a value of each exercise index in past running of the user as a reference by operating the operation unit 150; the user may set a target value with an average value of each exercise index of another member belonging to the same running team as a reference; the user may set a value of each exercise index of a desired runner or a target runner as a target value; and the user may set a value of each exercise index of another user which has cleared target time as a target value.

An exercise index which is compared with a target value may be all exercise indexes included in the output information during running, may be only a specific exercise index which is predefined, and may be selected by the user operating the operation unit 150 or the like.

Figure 63A:
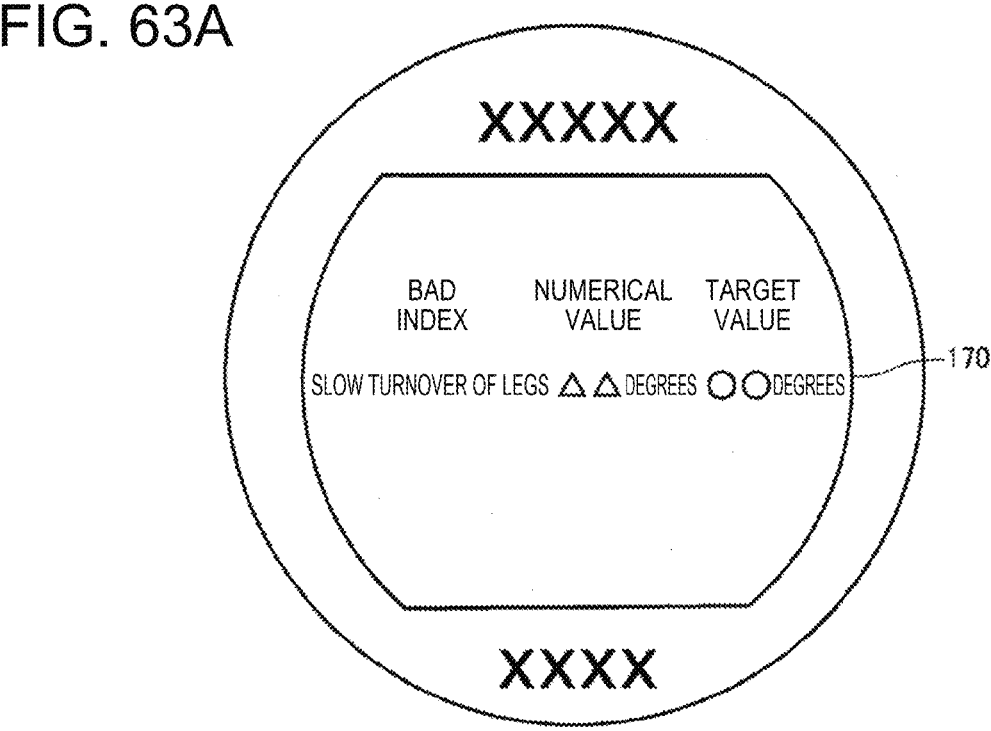
FIGS. 63A and 63B illustrate examples of information displayed on a display unit of the notification apparatus.

For example, if there is an exercise index worse than a target value, the processing unit 120 notifies the user of the exercise index by using sound or vibration, and also displays a value of the exercise index worse than the target value on the display unit 170. The processing unit 120 may generate different types of sound or vibration depending on the type of exercise index worse than a target value, and may change the type of sound or vibration according to the extent of being worse than a target value for each exercise index. In a case where there are a plurality of exercise indexes worse than a target value, the processing unit 120 may generate sound or vibration of the type corresponding to the worst exercise index, and also may display information regarding values of all exercise indexes worse than the target value, and the target value, on the display unit 170, for example, as illustrated in FIG. 63A.

Even if the user does not view the information displayed on the display unit 170, the user can continuously run while recognizing the worst exercise index and the extent of being worse on the basis of the type of sound or vibration. When viewing the information displayed on the display unit 170, the user can accurately recognize differences between values of all exercise indexes worse than target values, and the target values.

An object exercise index related to generation of sound or vibration may be selected from exercise indexes which are compared with target values, by the user operating the operation unit 150 or the like. Also in this case, for example, information regarding values of all exercise indexes worse than target values, and the target values may be displayed on the display unit 170. As an example, in a case where the user wants to run while being aware of the "slow turnover of the legs", if the user selects only the "slow turnover of the legs" as an object exercise index related to generation of sound or vibration, the user can recognize whether or not the slow turnover of the legs occurs on the basis of generation or non-generation of sound or vibration at all times.

The user performs setting (for example, setting such as generation of sound or vibration for five seconds every one minute) of a notification cycle via the operation unit 150, and may send a notification to the user according to the notification cycle which is set by the processing unit 120.

Figure 63B:
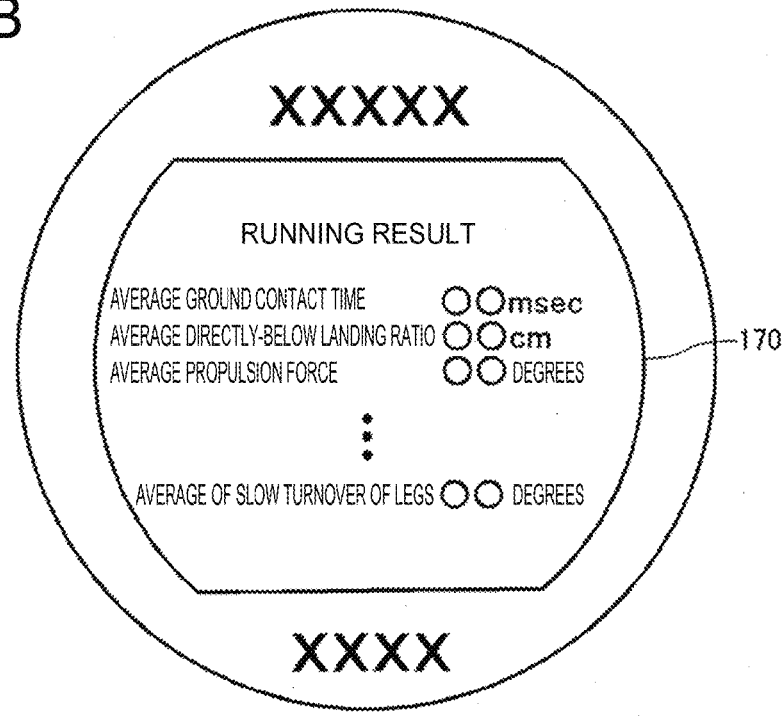

In the present embodiment, the processing unit 120 acquires running result information transmitted from the exercise analysis apparatus 2 via the communication unit 140, and displays the running result information on the display unit 170. For example, as illustrated in FIG. 63B, the processing unit 120 displays an average value of each exercise index in the user's running, included in the running result information, on the display unit 170. The user can immediately recognize goodness and badness of each exercise index while viewing the display unit 170 after the running is finished (after a measurement finishing operation is performed). For example, in a case where the user starts to run while being aware of the "slow turnover of the legs", the user can immediately check whether or not the running was performed in the way of improving the slow turnover of the legs by viewing the running result information displayed on the display unit 170 right after the running is finished.

2-4-2. Procedures of Process

Figure 64:
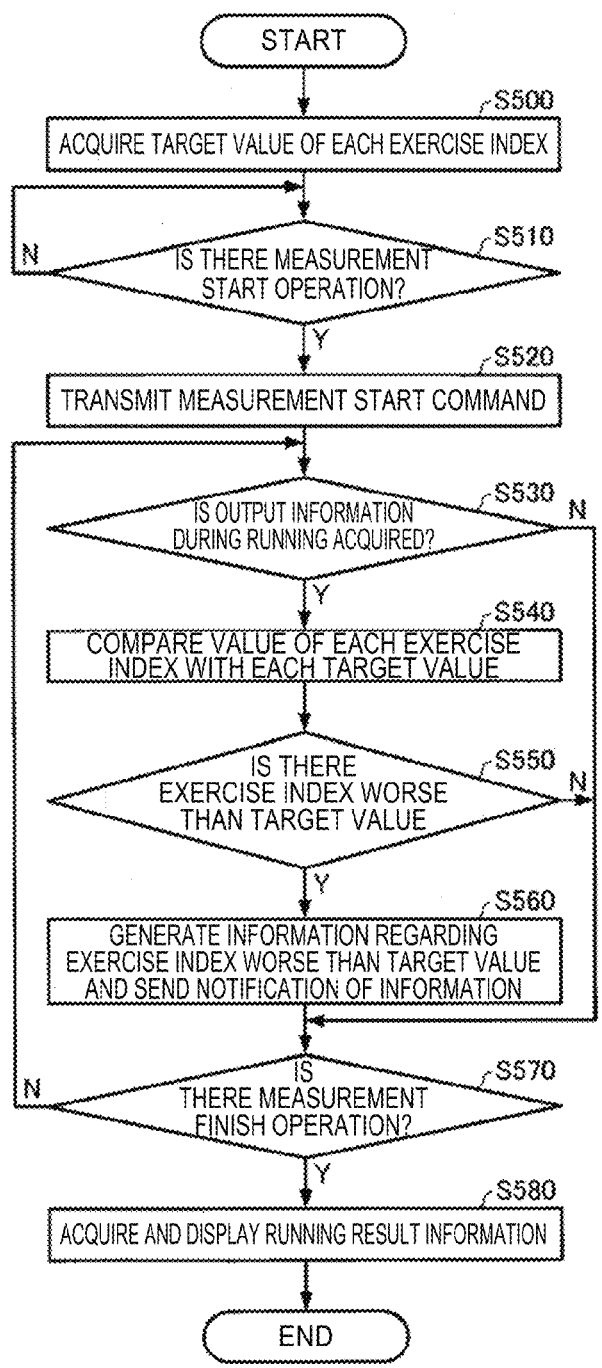
FIG. 64 is a flowchart illustrating an example of procedures of a notification process.

FIG. 64 is a flowchart illustrating an example of procedures of a notification process performed by the processing unit 120. The processing unit 120 performs the notification process according to, for example, the procedures of the flowchart illustrated in FIG. 64 by executing the program stored in the storage unit 130.

As illustrated in FIG. 64, first, the processing unit 120 acquires a target value of each exercise index on the basis of operation data from the operation unit 150 (step S500).

Next, the processing unit 120 waits for operation data for starting measurement to be acquired from the operation unit 150 (N in step S510), and if the operation data for starting measurement is acquired (Y in step S510), the processing unit 120 transmits a measurement start command to the exercise analysis apparatus 2 via the communication unit 140 (step S520).

Next, the processing unit 120 compares a value of each exercise index included in output information during running with each target value acquired in step S500 (step S540) whenever the output information during running is acquired from the exercise analysis apparatus 2 via the communication unit 140 (Y in step S530) until operation data for finishing the measurement is acquired from the operation unit 150 (N in step S570).

In a case where there is an exercise index worse than the target value (Y in step S550), the processing unit 120 generates information regarding the exercise index worse than the target value, and notifies the user of the information via the sound output unit 180, the vibration unit 190, and the display unit 170 by using sound, vibration, text, and the like (step S560).

On the other hand, if there is no exercise index worse than the target value (N in step S550), the processing unit 120 does not perform the process in step S560.

If the operation data for finishing the measurement is acquired from the operation unit 150 (Y in step S570), the processing unit 120 acquires the running result information from the exercise analysis apparatus 2 via the communication unit 140, displays the running result information on the display unit 170 (step S580), and finishes the notification process.

As mentioned above, the user can run while recognizing a running state on the basis of the information of which a notification is sent in step S550. The user can immediately recognize a running result after the running is finished on the basis of the information displayed in step S580.

Figure 65:
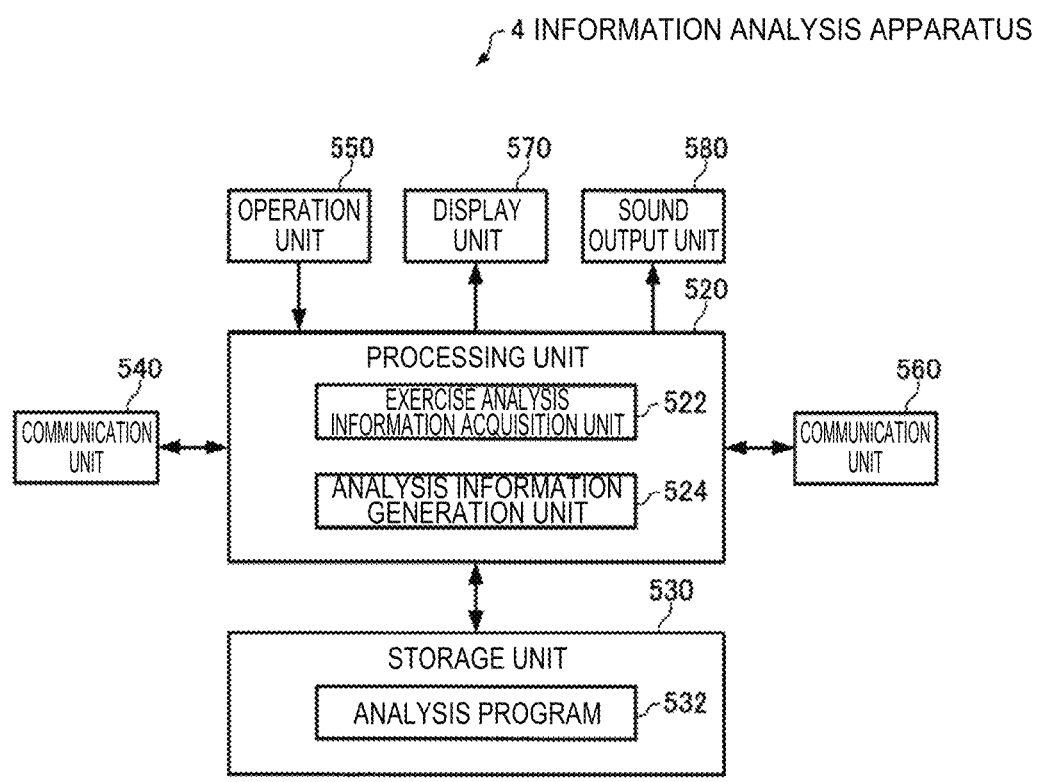
FIG. 65 is a functional block diagram illustrating a configuration example of an information analysis apparatus.

2-5. Information Analysis Apparatus 2-5-1. Configuration off Information Analysis Apparatus FIG. 65 is a functional block diagram illustrating a configuration example of the information analysis apparatus 4. As illustrated in FIG. 65, the information analysis apparatus 4 includes a processing unit 520, a storage unit 530, the communication unit 540, an operation unit 550, a communication unit 560, a display unit 570, and a sound output unit 580. However, the information analysis apparatus 4 of the present embodiment may have a configuration in which some of the constituent elements are deleted or changed, or other constituent elements may be added thereto.

The communication unit 540 performs data communication with the communication unit 40 (refer to FIG. 47) of the exercise analysis apparatus 2, and performs a process of receiving a transmission request command for requesting transmission of exercise analysis information (exercise analysis information included in running data to be registered) which is designated in response to operation data from the processing unit 520, transmitting the command to the communication unit 40 of the exercise analysis apparatus 2, receiving the exercise analysis information from the communication unit 40 of the exercise analysis apparatus 2, and sending the exercise analysis information to the processing unit 520.

The communication unit 560 performs data communication with the server 5, and performs a process of receiving running data to be registered from the processing unit 520 and transmitting the running data to the server 5 (a process of registering the running data), and a process of receiving management information corresponding to operation data such as registration, editing, and deleting of a user, and editing, deleting, and changing of running data from the processing unit 520, and transmitting the management information to the server 5.

The operation unit 550 performs a process of acquiring operation data (operation data such as registration, editing, and deleting of a user, and registration, editing, deleting, and changing of running data, and operation data for selecting a user to be analyzed) from the user, and sending the operation data to the processing unit 520. The operation unit 550 may be, for example, a touch panel type display, a button, a key, and a microphone.

The display unit 570 displays image data or text data sent from the processing unit 520 by using text, a graph, a table, animation, and other images. The display unit 570 is implemented by a display such as an LCD, an organic EL display, and an EPD, and may be a touch panel type display. The functions of the operation unit 550 and the display unit 570 may be implemented by a single touch panel type display.

The sound output unit 580 outputs sound data sent from the processing unit 520 as sound such as voice or buzzer sound. The sound output unit 580 is implemented by, for example, a speaker or a buzzer.

The storage unit 530 is constituted of, for example, recording media including a ROM, a flash ROM, a hard disk, and a memory card which store a program or data, and a RAM serving as a work area of the processing unit 520. The storage unit 530 (any one of recording media) stores an analysis program 532 which is read by the processing unit 520 and is used to perform an analysis process (refer to FIG. 66).

The processing unit 520 is constituted of, for example, a CPU, a DSP, or an ASIC, and performs various calculation processes or control processes according to a program stored in the storage unit 530 (recording medium). For example, the processing unit 520 performs a process of transmitting a transmission request command for requesting transmission of exercise analysis information which is designated in response to operation data received from the operation unit 550, to the exercise analysis apparatus 2 via the communication unit 540, and receiving the exercise analysis information from the exercise analysis apparatus 2 via the communication unit 540; and a process of generating running data (running data to be registered) including the exercise analysis information received from the exercise analysis apparatus 2 in response to operation data received from the operation unit 550, and transmitting the running data to the server 5 via the communication unit 560. The processing unit 520 performs a process of transmitting management information corresponding to operation data received from the operation unit 550, to the server 5 via the communication unit 560. The processing unit 520 performs a process of transmitting a transmission request of running data as an analysis object which is selected in response to operation data received from the operation unit 550, to the server 5 via the communication unit 560, and receiving the analysis object running data from the server 5 via the communication unit 560. The processing unit 520 performs a process of analyzing running data of a user as an analysis on the basis of which is selected in response to operation data received from the operation unit 550 so as to generate analysis information which is information regarding an analysis result, and sending the analysis information to the display unit 570 or the sound output unit 580 as text data, image data, or sound data.

Particularly, in the present embodiment, the processing unit 520 functions as an exercise analysis information acquisition unit 522 and an analysis information generation unit 524 by executing the analysis program 532 stored in the storage unit 530. However, the processing unit 520 may receive the analysis program 532 stored in any storage device (recording medium) via the network and may execute the analysis program.

The exercise analysis information acquisition unit 522 performs a process of acquiring exercise analysis information (exercise analysis information generated by the exercise analysis apparatus 2) which is information regarding an analysis result of an exercise of the user as an analysis object, from the database of the server 5 (or from the exercise analysis apparatus 2). The exercise analysis information acquired by the exercise analysis information acquisition unit 522 is stored in the storage unit 530. In the present embodiment, the exercise analysis information acquired by the exercise analysis information acquisition unit 522 includes values of various exercise indexes (various exercise indexes including the above-described "slow turnover of the legs").

The analysis information generation unit 524 performs a process of generating analysis information regarding running performance of the user as an analysis object by using the exercise analysis information acquired by the exercise analysis information acquisition unit 522. The analysis information generation unit 524 may generate analysis information by using, for example, exercise analysis information of the user as an analysis object in a time period selected by operation data received from the operation unit 550.

The analysis information generation unit 524 may generate analysis information in which running performance is comparable on each date on which the user as an analysis object performed running. For example, in a case where the user performed running three times on July 1, July 8, and July 15, analysis information may be generated in which running performance of the user is comparable on each date of July 1, July 8, and July 15.

The analysis information generation unit 524 may generate analysis information in which running performance of the user as an analysis object can be relatively evaluated, by using values of exercise indexes included in each of running data items (exercise analysis information) of a plurality of users including the user as an analysis object, registered in the database of the server 5. For example, the plurality of users may be users selected by operation data received from the operation unit 550. For example, the analysis information generation unit 524 may convert an exercise index value of the user as an analysis object into values of 0 to 10 when the highest index value is 10 and the lowest index value is 0 among exercise index values of the plurality of users, and may generate analysis information including information regarding the converted exercise index value. The analysis information generation unit 524 may compute a deviation value of an exercise index value of the user as an analysis object by using exercise index values of the plurality of users, and may generate analysis information including information regarding the deviation value.

The processing unit 520 generates display data such as text or an image or sound data such as voice by using the analysis information generated by the analysis information generation unit 524, and outputs the display data or the sound data to the display unit 570 or the sound output unit 580. Consequently, analysis results related to a plurality of users as analysis objects are presented from the display unit 570 or the sound output unit 580.

2-5-2. Procedures of Process

Figure 66:
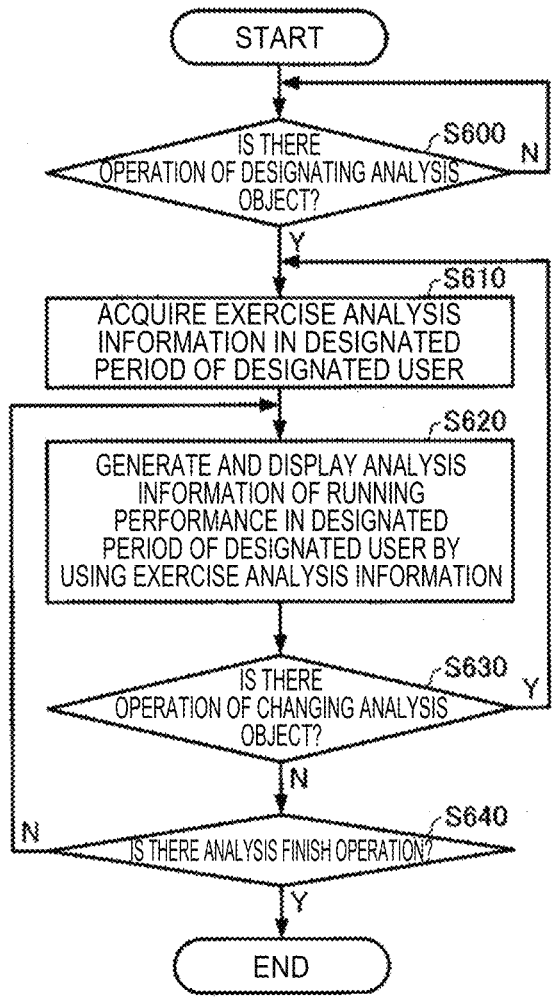
FIG. 66 is a flowchart illustrating an example of procedures of an analysis process.

FIG. 66 is a flowchart illustrating an example of procedures of the analysis process performed by the processing unit 520. The processing unit 520 performs the analysis process according to, for example, the procedures of the flowchart illustrated in FIG. 66 by executing the analysis program 532 stored in the storage unit 530.

First, the processing unit 520 waits for operation data for designating an analysis object to be acquired (N in step S600), and if the operation data for designating an analysis object is acquired (Y in step S600), the processing unit 520 acquires exercise analysis information (specifically, running data) in a designated period (analysis object period) of a user (analysis object user) designated by the operation data, from the database of the server 5 via the communication unit 560, and stores the exercise analysis information in the storage unit 530 (step S610).

Next, the processing unit 520 generates analysis information of running performance in the designated period (analysis object period) of the designated user (analysis object user) by using the exercise analysis information (running data) acquired in step S610 and displays the analysis information on the display unit 570 (step S620).

Next, if operation data for changing an analysis object or operation data for finishing the analysis is not acquired (N in step S630 and N in step S640), the processing unit 520 performs a process in step S620.

If the operation data for changing an analysis object is acquired (Y in step S630), the processing unit 520 performs the processes in steps S610 and S620 again, and if the operation data for finishing the analysis is acquired (Y in step S640), the processing unit 520 finishes the analysis process.

Figure 67:
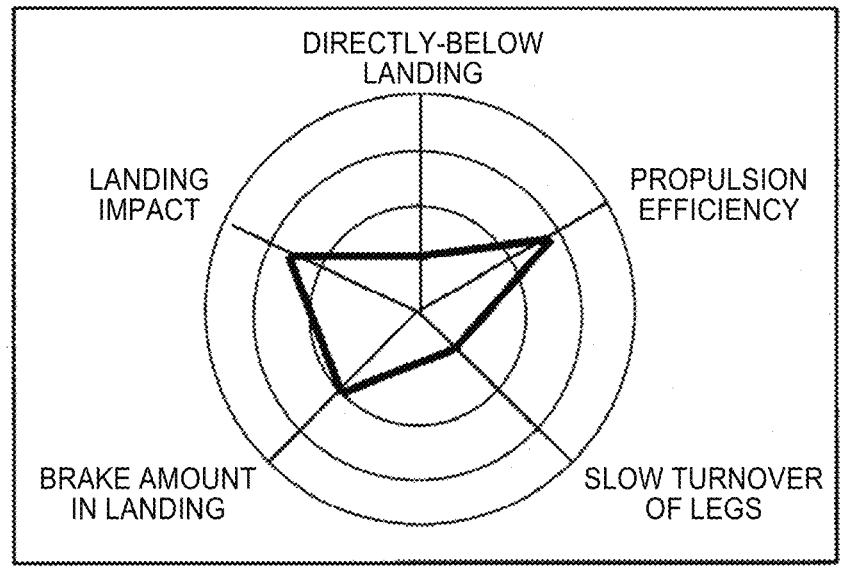
FIG. 67 is a diagram illustrating an example of information displayed on a display unit of the information analysis apparatus.

FIG. 67 is a diagram illustrating an example of the analysis information displayed on the display unit 570. In the example illustrated in FIG. 67, the analysis information displayed on the display unit 570 includes a radar chart in which average values of five exercise indexes (directly-below landing, propulsion efficiency, slow turnover of the legs, brake amount in landing, and landing impact) in running during an analysis object period of an analysis object user are compared with average values of a plurality of selected users so as to be relatively evaluated. For example, if the user selects the user and a plurality of users as analysis objects, and selects an analysis object period via the operation unit 550, the processing unit 520 acquires exercise analysis information (values of respective exercise indexes) in all running items performed in the selected period of the plurality of selected users, from the database of the server 5. The processing unit 520 computes an average value of each exercise index of each user, and converts a value of the analysis object user into a relatively evaluated value with the highest value of 10 and the lowest value of 0 for each exercise index of the plurality of users, so as to generate a radar chart as illustrated in FIG. 67. The user can relatively evaluate running performance of the user in a plurality of selected users (for example, members of the running team) on the basis of the analysis information as illustrated in FIG. 67. For example, in the example illustrated in FIG. 67, the user can understand that the "directly-below landing" or the "slow turnover of the legs" is bad (weak point), and can thus expect that a running result will improve by being aware of improvement in such an exercise index in the next running.

2-6. Effects

According to the second embodiment, since the inertial measurement unit 10 can also detect a fine motion of the user's body by using the three-axis acceleration sensor 12 and the three-axis angular velocity sensor 14, the exercise analysis apparatus 2 performs inertial navigation calculation by using a detection result in the inertial measurement unit 10 during the user's running, and can compute an index value of slow turnover of the legs (an angle of the swing leg in landing) by using a result of the inertial navigation calculation with high accuracy.

Particularly, according to the second embodiment, the exercise analysis apparatus 2 computes an index value which is highly correlated with an index value (an angle of the swing leg in landing) of slow turnover of the legs using a yaw angle of the user's waist or a pitch angle of the user's body, and assigns the correlated index value to a predefined correlation. Therefore, it is possible to compute (estimate) an index value (an angle of the swing leg in landing) of the slow turnover of the legs with high accuracy by using the exercise analysis apparatus 2 (a single inertial measurement unit 10) mounted on the user's body.

According to the second embodiment, since the notification apparatus 3 compares a value of each exercise index during the user's running with a target value and notifies the user of a comparison result by using sound or vibration, the user can recognize goodness and badness of an index value of the slow turnover of the legs in real time without the running being disturbed thereby. Therefore, the user performs running by trial and error so that the slow turnover of the legs does not occur, or can perform running while being aware that the slow turnover of the legs does not occur even in a fatigue state.

According to the second embodiment, since the information analysis apparatus 4 generates analysis information of running performance of the user after the user finishes the running, the user can acquire specific information regarding slow turnover of the legs after the running is finished.

3. Modification Examples

The invention is not limited to the above-described respective embodiments, and may be variously modified within the scope of the invention. Hereinafter, modification examples will be described. The same constituent elements as those in the respective embodiments are given the same reference numerals, and repeated description will be omitted.

3-1. Sensors

In the above-described respective embodiments, the acceleration sensor 12 and the angular velocity sensor 14 are integrally formed as the inertial measurement unit 10 and are built into the exercise analysis apparatus 2, but the acceleration sensor 12 and the angular velocity sensor 14 may not be integrally formed. Alternatively, the acceleration sensor 12 and the angular velocity sensor 14 may not be built into the exercise analysis apparatus 2, and may be directly mounted on the user. In either case, for example, a sensor coordinate system of one sensor may be set to the b frame of the embodiments, the other sensor coordinate system may be converted into the b frame, and the embodiments may be applied thereto.

In the above-described respective embodiments, a part of which the sensor (the exercise analysis apparatus 2 (the IMU 10)) is mounted on the user has been described to be the waist, but the sensor may be mounted on parts other than the waist. A preferable mounting part is the user's trunk (parts other than the limbs). However, a mounting part is not limited to the trunk, and may be mounted on, for example, the user's head or leg other than the arms. The number of sensors is not limited to one, and additional sensors may be mounted on other parts of the body. For example, the sensors may be mounted on the waist and the leg, or the waist and the arm.

3-2. Inertial Navigation Calculation

In the above-described respective embodiments, the integral processing portion 220 calculates a velocity, a position, an attitude angle, and a distance of the e frame, and the coordinate conversion portion 250 coordinate-converts the parameters into a velocity, a position, an attitude angle, and a distance of the m frame, but the integral processing portion 220 may calculate a velocity, a position, an attitude angle, and a distance of the m frame. In this case, the exercise analysis unit 24 preferably performs an exercise analysis process by using the velocity, the position, the attitude angle, and the distance of the m frame calculated by the integral processing portion 220, and thus coordinate conversion of a velocity, a position, an attitude angle, and a distance in the coordinate conversion portion 250 is not necessary. The error estimation portion 230 may estimate an error by using the extended Karman filter on the basis of the velocity, the position, and the attitude angle of the m frame.

In the above-described respective embodiments, the inertial navigation calculation unit 22 performs a part of the inertial navigation calculation by using a signal from a GPS satellite, but may use a signal from a positioning satellite of a global navigation satellite system (GNSS) other than the GPS, or a positioning satellite other than the GNSS. For example, one, or two or more satellite positioning systems such as a wide area augmentation system (WAAS), a quasi zenith satellite system (QZSS), a global navigation satellite system (GLONASS), GALILEO, a BeiDou navigation satellite system (BeiDou) may be used. An indoor messaging system (IMES) may also be used.

In the above-described respective embodiments, the running detection section 242 detects a running cycle at a timing at which a vertical acceleration (z axis acceleration) of the user becomes the maximum value which is equal to or greater than a threshold value, but the detection of a running cycle is not limited thereto, and, for example, a running cycle may be detected at a timing at which the vertical acceleration (z axis acceleration) changes from a positive value to a negative value (or a timing changes from a negative value to a positive value). Alternatively, the running detection section 242 may integrate the vertical acceleration (z axis acceleration) so as to calculate a vertical velocity (z axis velocity), and may detect a running cycle by using the calculated vertical velocity (z axis velocity). In this case, the running detection section 242 may detect a running cycle at a timing at which, for example, the velocity crosses a threshold value around a median value between the maximum value and the minimum value by increasing or decreasing a value. For example, the running detection section 242 may calculate a combined acceleration of the x axis, y axis and z axis accelerations and may detect a running cycle by using the calculated combined acceleration. In this case, the running detection section 242 may detect a running cycle at a timing at which, for example, the combined acceleration crosses a threshold value around a median value between the maximum value and the minimum value by increasing or decreasing a value.

In the above-described respective embodiments, the error estimation portion 230 uses a velocity, an attitude angle, an acceleration, an angular velocity, and a position as indexes or state variables indicating a user's state, and estimates errors of the indexes or the state variables by using the extended Karman filter, but may estimate the errors thereof by using some of the velocity, the attitude angle, the acceleration, the angular velocity, and the position as indexes or state variables indicating a user's state. Alternatively, the error estimation portion 230 may estimate the errors thereof by using parameters other than the velocity, the attitude angle, the acceleration, the angular velocity, and the position (for example, a movement distance) as indexes or state variables indicating a user's state.

In the above-described respective embodiments, the extended Karman filter is used to estimate an error in the error estimation portion 230, but other estimation filters such as a particle filter or H∞ (H infinity) may be used.

3-3. Exercise Analysis

The exercise analysis information generated by the exercise analysis unit 24 may include items other than the items described in the above-described respective embodiments. For example, the exercise analysis information may include respective items such as "air-stay time", a "ground contact distance", and an "air-stay distance". The air-stay time is computed as the air-stay time=(time per step−ground contact time). The ground contact distance is computed as the ground contact distance=(ground contact time×average velocity), (taking-off position−ground contact position), or (stride−air-stay distance). The air-stay distance is computed as the air-stay distance=(air-stay time×average velocity), (ground contact position−taking-off position), or (stride−ground contact distance). The exercise analysis information may include, for example, "air-stay time/ground contact time", "ground contact time/time per step", and, "air-stay time/time per step".

For example, the exercise analysis information may include respective items such as "stride-to-height", "vertical movement", "waist movement distance", "position of waist", and "deviation of body". The stride-to-height is computed by stride/height. The vertical movement is computed as the amplitude of a position of the waist (in the gravitational direction). The waist movement distance is computed as a movement distance between landing and taking-off. The position of the waist is computed as a displacement of a position of the waist with an upright stance as a reference. The deviation of the body is computed as a sum of an amount of change in an attitude, and the amount of change in an attitude is absolute values corresponding to three axes in a predetermined period, or an absolute value corresponding to any one of the three axes in a predetermined period. The predetermined period is, for example, time per step, a period between the start and the finish of running, or one minute.

Figure 68A:
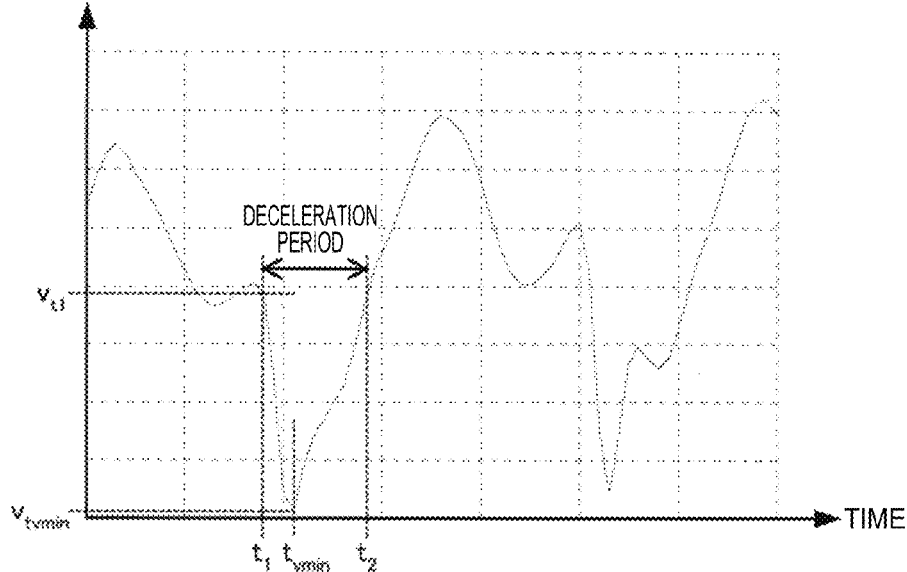
FIGS. 68A and 68B illustrate a method of computing a deceleration amount.

For example, the exercise analysis information may include an item such as a "deceleration amount". A description will be made of an example of a method of computing the deceleration amount using an advancing direction velocity with reference to FIG. 68A. In FIG. 68A, a transverse axis expresses time, and a longitudinal axis expresses an advancing direction velocity. As illustrated in FIG. 68A, when a start time point (landing time point) of a deceleration period is denoted by $t_1$, a finish time point of the deceleration period is denoted by $t_2$, the advancing direction velocity is denoted by v, and a sampling cycle is denoted by $\Delta t$, the deceleration amount may be approximately computed according to Equation (7).

$$\text{Deceleration Amount}=\int_{t_1}^{t_2} v\,dt \approx \Sigma v \Delta t \qquad (7)$$

Alternatively, when a start time point (landing time point) of a deceleration period is denoted by $t_1$, a finish time point of the deceleration period is denoted by $t_2$, a time point at which an advancing direction velocity is the minimum after landing is denoted by $t_{vmin}$, an advancing direction velocity in landing is denoted by $v_{t1}$, an advancing direction velocity when the deceleration period finishes is denoted by $v_{t2}$, and the advancing direction lowest velocity after landing is denoted by $v_{tvmin}$, the deceleration amount may also be approximately computed according to Equation (8).

$$\text{Deceleration Amount} = \int_{t_1}^{t_2} v\, dt \approx \tfrac{1}{2}(v_{tvmin} - v_{t1})(t_{vmin} - t_1) + \tfrac{1}{2}(v_{t2} - v_{tvmin})(t_2 - t_{vmin}) \quad (8)$$

Assuming that, in Equation (8), the first term of the right side is the same as the second term of the right side, the deceleration amount may also be approximately computed according to Equation (9).

$$\text{Deceleration Amount} \approx (v_{tvmin} - v_{t1})(t_{vmin} - t_1) \quad (9)$$

Alternatively, when a start time point (landing time point) of a deceleration period is denoted by $t_1$, a finish time point of the deceleration period is denoted by $t_2$, the number of data with the advancing direction velocity v between the time points $t_1$ and $t_2$ is denoted by N, and a sampling cycle is denoted by $\Delta t$, the deceleration amount may also be approximately computed according to Equation (10).

$$\text{Deceleration Amount} = v_{avg} \Delta t \cdot N = \frac{\Sigma v}{N} \Delta t \cdot N = \frac{\Sigma v}{N}(t_2 - t_1) \quad (10)$$

Figure 68B:
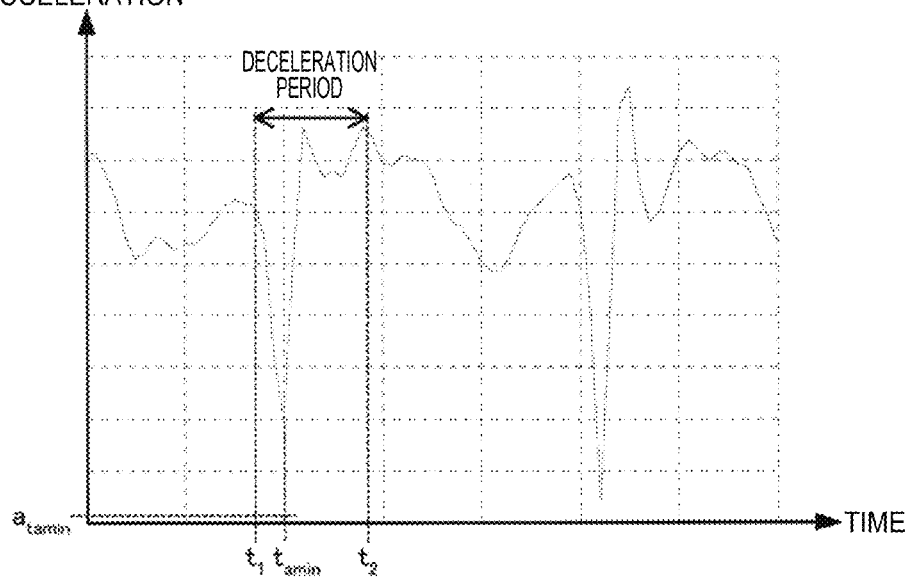

A description will be made of an example of a method of computing the deceleration amount using an advancing direction acceleration with reference to FIG. 68B. In FIG. 68B, a transverse axis expresses time, and a longitudinal axis expresses an advancing direction acceleration. As illustrated in FIG. 68B, when a start time point (landing time point) of a deceleration period is denoted by $t_1$, a finish time point of the deceleration period is denoted by $t_2$, a time point at which an advancing direction acceleration is the minimum after landing is denoted by $t_{amin}$, an advancing direction acceleration is denoted by a, and the advancing direction lowest acceleration after landing is denoted by $a_{tamin}$, the deceleration amount may also be approximately computed by using the advancing direction acceleration according to Equation (11) which is modified from Equation (9).

$$\begin{aligned}\text{Deceleration Amount} &\approx (v_{tvmin} - v_{t1})(t_{vmin} - t_1) \quad (11) \\ &= \left(\int_{t_1}^{t_{vmin}} a\, dt\right)(t_{vmin} - t_1) \\ &\approx \left(2\int_{t_1}^{t_{amin}} a\, dt\right)(t_{vmin} - t_1) \\ &= a_{tamin}(t_{amin} - t_1)(t_{vmin} - t_1)\end{aligned}$$

In Equations (7) to (11), the deceleration amounts are all computed in terms of a distance (m), but the deceleration amount may be computed in terms of a velocity (m/s) (for example, an average value of the lowest velocity in a deceleration period, or an average velocity only in a deceleration period). For example, information such as the content that the entire average velocity of the user is 10 km/h, and information such as the content that the average velocity only in the deceleration period is 2 km/h are presented together, and thus the user can easily intuitively recognize to what extent the velocity decreases in landing.

For example, the exercise analysis apparatus 2 (the exercise analysis unit 24) may generate exercise analysis information (exercise index) by using biological information of the user. The biological information may include, for example, a skin temperature, a central part temperature, oxygen consumption, variation between heart beats, a heart rate, a pulse rate, a respiratory rate, heat flow, galvanic skin response, electromyography (EMG), electroencephalogram (EEG), electro-oculogram (EOG), blood pressure, and activity. The exercise analysis apparatus 2 may be provided with a device which measures biological information, or the exercise analysis apparatus 2 may receive biological information which is measured by a measurement device. For example, the user may wear a wrist watch type pulsimeter, or may wind a heart rate sensor on the chest with a belt so as to perform running, and the exercise analysis apparatus 2 (the exercise analysis unit 24) may calculate a heart rate during the user's running as the first item of the exercise analysis information by using a value measured by the pulsimeter or the heart rate sensor.

In the above-described respective embodiments, each exercise index included in the exercise analysis information is an index regarding a technical skill of the user, but the exercise analysis information may include an exercise index regarding the endurance. For example, the exercise analysis information may include heart rate reserved (HRR) which is computed by (heart rate–stable heart rate)/(maximum heart rate–stable heart rate)×100 as an exercise index regarding the endurance. For example, each athlete may input a heart rate, the maximum heart rate, and a stable heart rate by operating the notification apparatus 3 whenever running is performed, or may perform running in a state of mounting a pulsimeter, and the exercise analysis apparatus 2 may acquire the heart rate, the maximum heart rate, and the stable heart rate from the notification apparatus 3 or the pulsimeter so as to compute a value of the heart rate reserved (HRR).

In the above-described respective embodiments, an exercise in human running is an object of analysis, but the invention is not limited thereto, and is also applicable to exercise analysis in walking or running of a moving body such as an animal or a walking robot. The invention is not limited to running, and is applicable to various exercises such as climbing, trail running, skiing (including cross-country and ski jumping), snowboarding, swimming, bicycling, skating, golf, tennis, baseball, and rehabilitation. As an example, if the invention is applied to skiing, it may be determined whether clear curving was performed or a ski board was deviated on the basis of a variation in the vertical acceleration when the ski board was pressed, and it may be determined whether or not there is a difference between the right foot and the left foot, or sliding performance may be determined on the basis of a trajectory of the variation in the vertical acceleration when the ski board is pressed and released. Alternatively, it may be determined whether or not a user can ski by analyzing to what extent a trajectory of the variation in the acceleration in the yaw direction is close to a sine wave, and it may be determined whether or not smooth sliding is performed by analyzing to what extent a trajectory of the variation in the acceleration in the roll direction is close to a sine wave.

In the above-described respective embodiments, the exercise analysis is performed separately for the left and right sides, but the exercise analysis may be performed without differentiating the left and right sides from each other. In this case, determination of the left foot and the right foot, or analysis using comparison between the left and right sides may be omitted.

In the second embodiment, the exercise analysis apparatus 2 performs a process of generating the exercise analysis information (exercise index), but the exercise analysis apparatus 2 may transmit data measured by the inertial measurement unit 10 or a result (calculation data) of the inertial navigation calculation to the server 5, and the server 5 may perform a process of generating the exercise analysis information (exercise index) (may function as the exercise analysis apparatus) by using the measured data or the calculation data and may store the exercise analysis information in the database.

In the second embodiment, the swing leg information generation section 277 computes an index correlated with an angle of the swing leg in landing of the user (right after landing) assuming that the time of a predetermined state while the user's foot contacts the ground is the time when the user's foot lands, and estimates an angle of the swing leg in landing of the user by using a value of the index, but the invention is not limited thereto. The time of a predetermined state while the user's foot contacts the ground may be, for example, the time when the user's foot is in a stepping state, or the time when the user's foot takes off (right before the user's foot takes off). In other words, the swing leg information generation section 277 may compute an index correlated with an angle of the swing leg in stepping or taking-off of the user, and may estimate an angle of the swing leg in stepping or taking-off of the user by using a value of the index.

3-4. Notification Process

In the above-described respective embodiments, the notification apparatus 3 which receives output information during running from the processing unit 20 is a wrist watch type apparatus, but is not limited thereto, and may be a portable apparatus (head mounted display (HMD)) other than the wrist watch type mounted on the user, an apparatus (which may be the exercise analysis apparatus 2) mounted on the user's waist, or a portable apparatus (a smart phone or the like) which is not a mounting type apparatus. In a case where the notification apparatus 3 is a head mounted display (HMD), a display unit thereof provides sufficiently better visibility than the display unit of the wrist watch type notification apparatus 3, and thus running is unlikely to be disturbed even if the user views the display unit. Therefore, for example, the display unit may display the present location of the user or information regarding changes in target hitherto, and may display videos in which a virtual runner created on the basis of time (time set by the user, a record of the user, a record of a celebrity, a world record, or the like) performs running. Alternatively, the processing unit 20 may transmit output information during running to a personal computer, a smart phone, or the like so that the information is fed back to people other than the user who is running.

Figure 69:
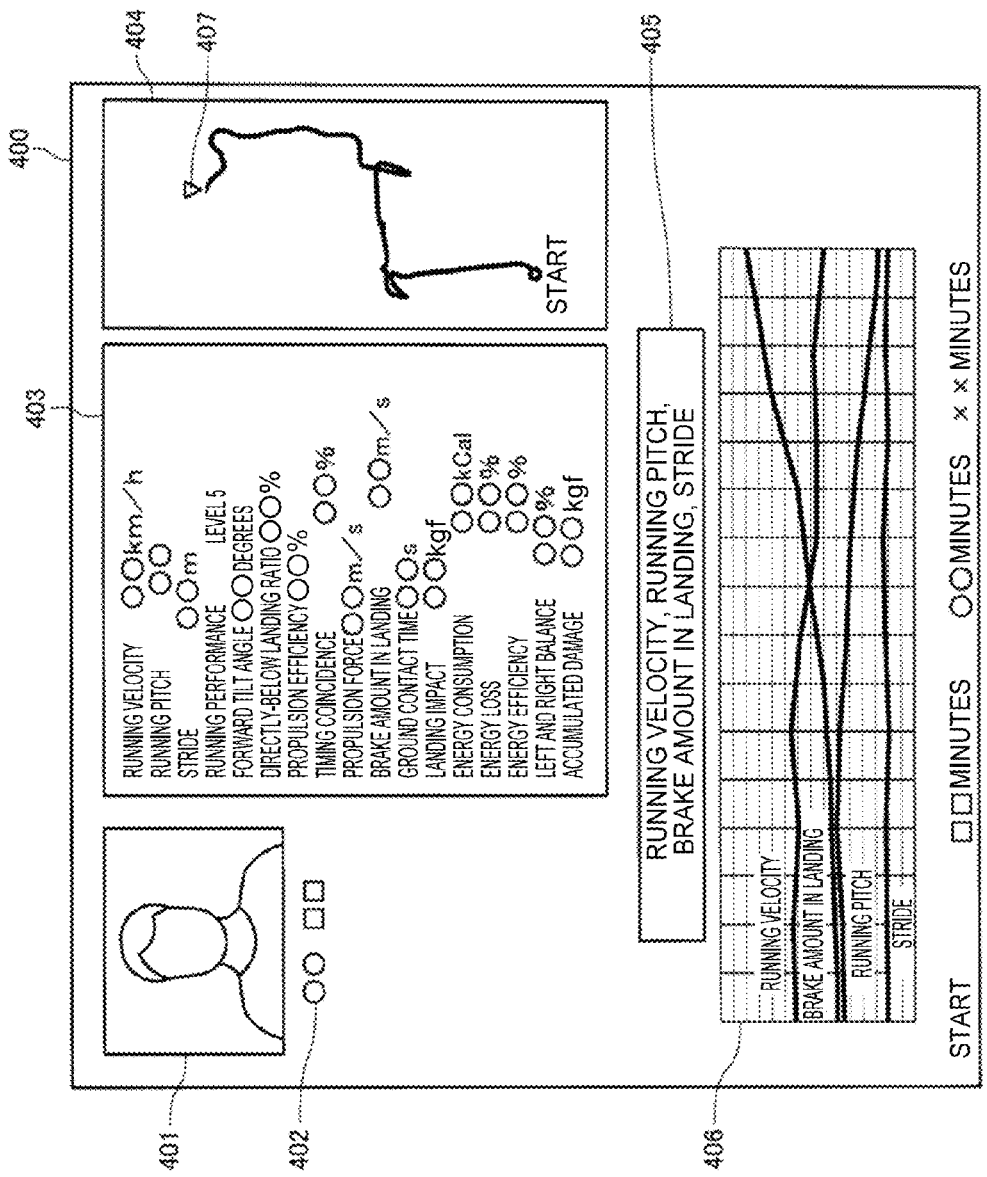
FIG. 69 is a diagram illustrating another example of a screen displayed during the user's running.

In a case where the output information during running is displayed on a head mounted display (HMD), a smart phone, or a personal computer, a display unit of such an apparatus is sufficiently larger than the display unit of the wrist watch type notification apparatus 3, and thus the information illustrated in FIGS. 34A and 34B or other information can be displayed on the same screen. FIG. 69 illustrates an example of a screen displayed on a display unit of a head mounted display (HMD), a smart phone, or a personal computer during the user's running. In the example illustrated in FIG. 69, a screen 400 is displayed on the display unit. The screen 400 includes a user image 401 and a user name 402 which are registered in advance by the user, a summary image 403 displaying a running state of the user, a running path image 404 displaying a running path from the start hitherto, an item name 405 of an item selected by the user, and time-series data 406 thereof.

The summary image 403 includes respective numerical values of the "running velocity", the "running pitch", the "stride", the "running performance", the "forward tilt angle", the "directly-below landing ratio", the "propulsion efficiency", the "timing coincidence", the "propulsion force", the "brake amount in landing", the "ground contact time", the "landing impact", the "energy consumption", the "energy loss", the "energy efficiency", the "left and right balance (left-right difference ratio)", and the "accumulated damage (burden on the body)", which are the respective items of the basic information, the first analysis information, and the second analysis information. Such numerical values are updated in real time during the user's running.

The summary image 403 may include numerical values of all the items of the basic information, the first analysis information, and the second analysis information, may include only some items selected by the user, and may include only items (for example, only an item within a reference range, or only an item out of a reference range) which satisfy a predetermined condition.

The running path image 404 is an image which displays a running path hitherto after the user starts running, and the present location is indicated by a predetermined mark 407.

The item name 405 indicates an item selected by the user from the items included in the summary image 403, and the time-series data 406 generates numerical values of the item indicated by the item name 405 as a graph in a time series. In the example illustrated in FIG. 69, the "running velocity", the "running pitch", the "brake amount in landing", and the "stride" are selected, and a time-series graph is displayed in which a transverse axis expresses time from the start of running, and a longitudinal axis expresses a numerical value of the average energy efficiency.

For example, if the user wearing the head mounted display (HMD) performs running while viewing the screen as illustrated in FIG. 69, the user can check the present running state, and can continuously perform running while being aware of the running way of causing a numerical value of each item to become better or the running way of improving an item with a bad numerical value, or while objectively recognizing a fatigue state.

A feedback timing using the head mounted display (HMD) may be the same as the feedback timing described in the first embodiment. A feedback method using the head mounted display (HMD) may be, for example, screen display such as easily understandable display with a still image, animation display, text display, or display on a map, or voice. Alternatively, information regarding a timing such as a waist rotation timing, a running pitch, or a kicking timing may be fed back in short sound such as "beep beep" or as an image.

Feedback information or feedback timing using the apparatus mounted on the user's waist may be the same as that in the first embodiment. As a feedback method using the apparatus mounted on the user's waist, information to be delivered may be fed back in voice; sound may be output in a case where all items are good; and sound may be output in a case where there is a bad item. Information regarding a good item may be fed back, and information regarding a bad item may be fed back. Alternatively, running performance or the like may be fed back by changing a musical scale according to a level thereof, and may be fed back by changing the number of types of sound such as "beep beep" for a predetermined period of time. Alternatively, information regarding a timing such as a waist rotation timing, a running pitch, or a kicking timing may be fed back in short sound such as "beep beep" or as an image.

Fed back information, a feedback timing, and a feedback method using the portable apparatus which is a mounting type apparatus may be the same as those in the first embodiment.

In the second embodiment, in a case where there is an exercise index worse than a target value, the notification apparatus 3 notifies the user of the exercise index by using sound or vibration, but in a case where there is an exercise index better than a target value, the notification apparatus 3 may notify the user of the exercise index by using sound or vibration.

In the second embodiment, the notification apparatus 3 performs a process of comparing a value of each exercise index with a target value, but the exercise analysis apparatus 2 may perform the comparison process and may control output or display of sound or vibration of the notification apparatus 3 according to a comparison result.

3-5. Analysis Process

In the first embodiment, the running analysis program 306 is executed by the exercise analysis apparatus 2 as a subroutine of the exercise analysis program 300, but may be a program which is different from the exercise analysis program 300, and may not be executed by the exercise analysis apparatus 2. For example, the exercise analysis apparatus 2 may transmit exercise analysis information which is analyzed and generated during running, to an information apparatus such as a personal computer or a smart phone after the user's running, and the information apparatus may execute the running analysis program 306 by using the received exercise analysis information and may output information regarding an analysis result to the display unit thereof or the like. Alternatively, the exercise analysis apparatus 2 may transmit exercise analysis information which is analyzed and generated during running, to an information apparatus such as a personal computer or a smart phone after the user's running, and the information apparatus may transmit the received exercise analysis information to a network server via a communication network such as the Internet. The network server may execute the running analysis program 306 by using the received exercise analysis information and may transmit information regarding an analysis result to the information apparatus, and the information apparatus may receive the information regarding the analysis result and may output the information to the display unit thereof or the like. Alternatively, the exercise analysis apparatus 2 may store exercise analysis information which is analyzed and generated during running, in a recording medium such as a memory card, and an information apparatus such as a personal computer or a smart phone may read the exercise analysis information from the memory card and may execute the running analysis program 306, or may transmit the exercise analysis information to a network server which executes the running analysis program 306.

In the first embodiment, the running analysis program 306 is a program for performing whole analysis, detail analysis, or comparison analysis with other people in terms of the running user, that is, a program for managing personal running history, but, may be a program for performing whole analysis or detail analysis of running of a plurality of members, for example, in terms of a manager of a team, that is, a program for performing group management of running history of a plurality of members.

Figure 70:
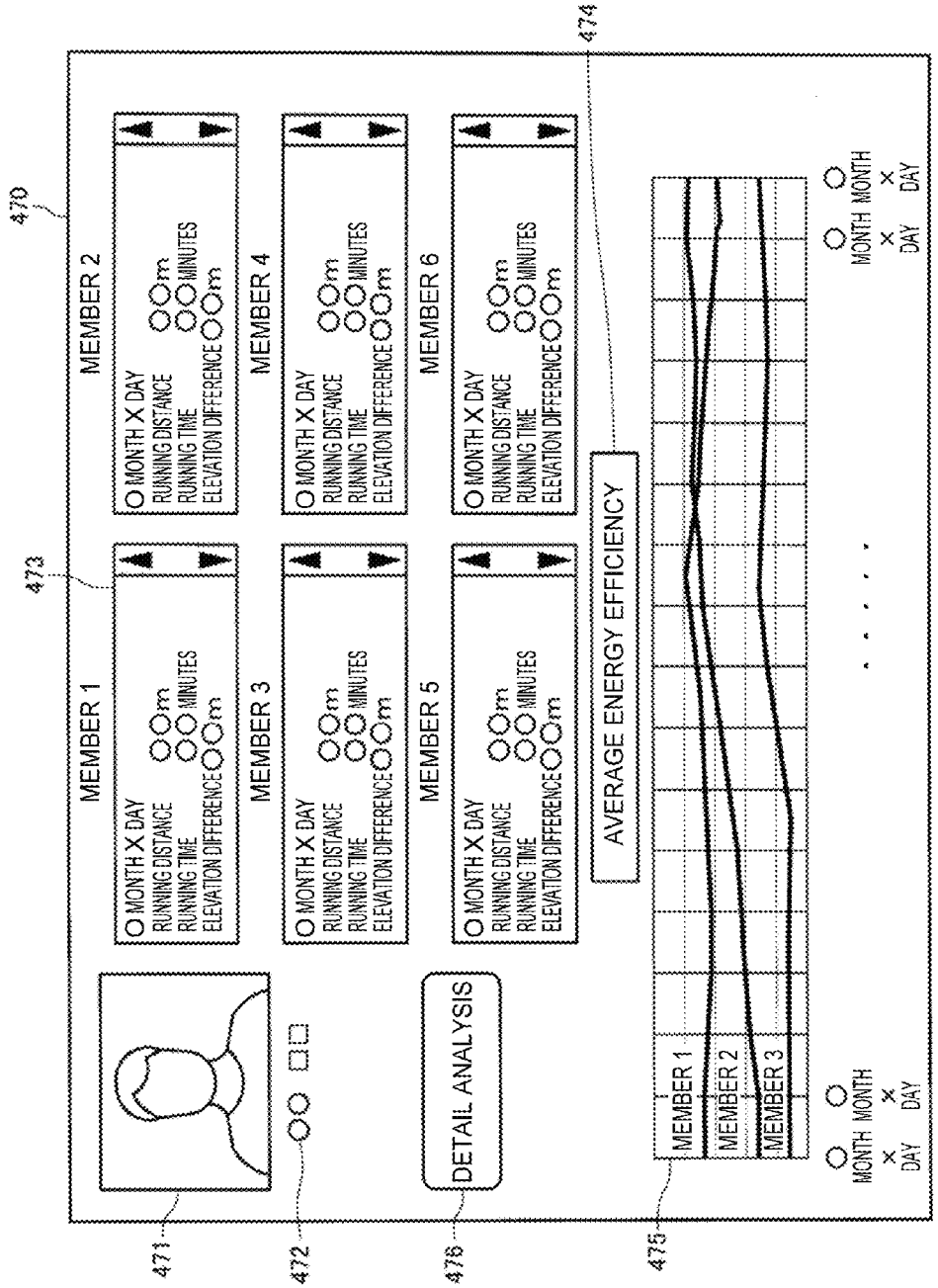
FIG. 70 is a diagram illustrating another example of the whole analysis screen.

FIG. 70 illustrates an example of a whole analysis screen in a program for performing group management of running history of a plurality of members. In the example illustrated in FIG. 70, a whole analysis screen 470 (first page) includes a user image 471 and a user name 472 which are registered in advance by a user (manager), a plurality of summary images 473 which respectively display running analysis results of members on the date selected by the user, an item name 474 of an item selected by the user, a time-series graph 475 in which a selected item for a member selected by the user is displayed in a time series, and a detail analysis button 476.

The content of each summary image 473 may be the same as the content of the summary image 413 illustrated in FIG. 35. In the example illustrated in FIG. 70, the item name 474 is "average energy efficiency", and the time-series graph 475 which has a transverse axis expressing the running date and a longitudinal axis expressing a numerical value of the average energy efficiency, and displays the average energy efficiency for members 1, 2 and 3 in a time series. If the user selects any one of the dates on the transverse axis in the time-series graph 475, a running analysis result on the selected date is displayed on each summary image 473.

The detail analysis button 476 is a button for transition from the whole analysis mode to the detail analysis mode, and if the user selects the date and a member, and performs a selection operation (pressing operation) of the detail analysis button 476, transition to the detail analysis mode occurs, and a detail analysis screen related to running on the selected date of the selected member is displayed. The detail analysis screen may be the same as the detail analysis screen illustrated in FIGS. 37 to 39, for example. A calendar image as illustrated in FIG. 36 may be displayed on the second page of the whole analysis screen.

Figure 71:
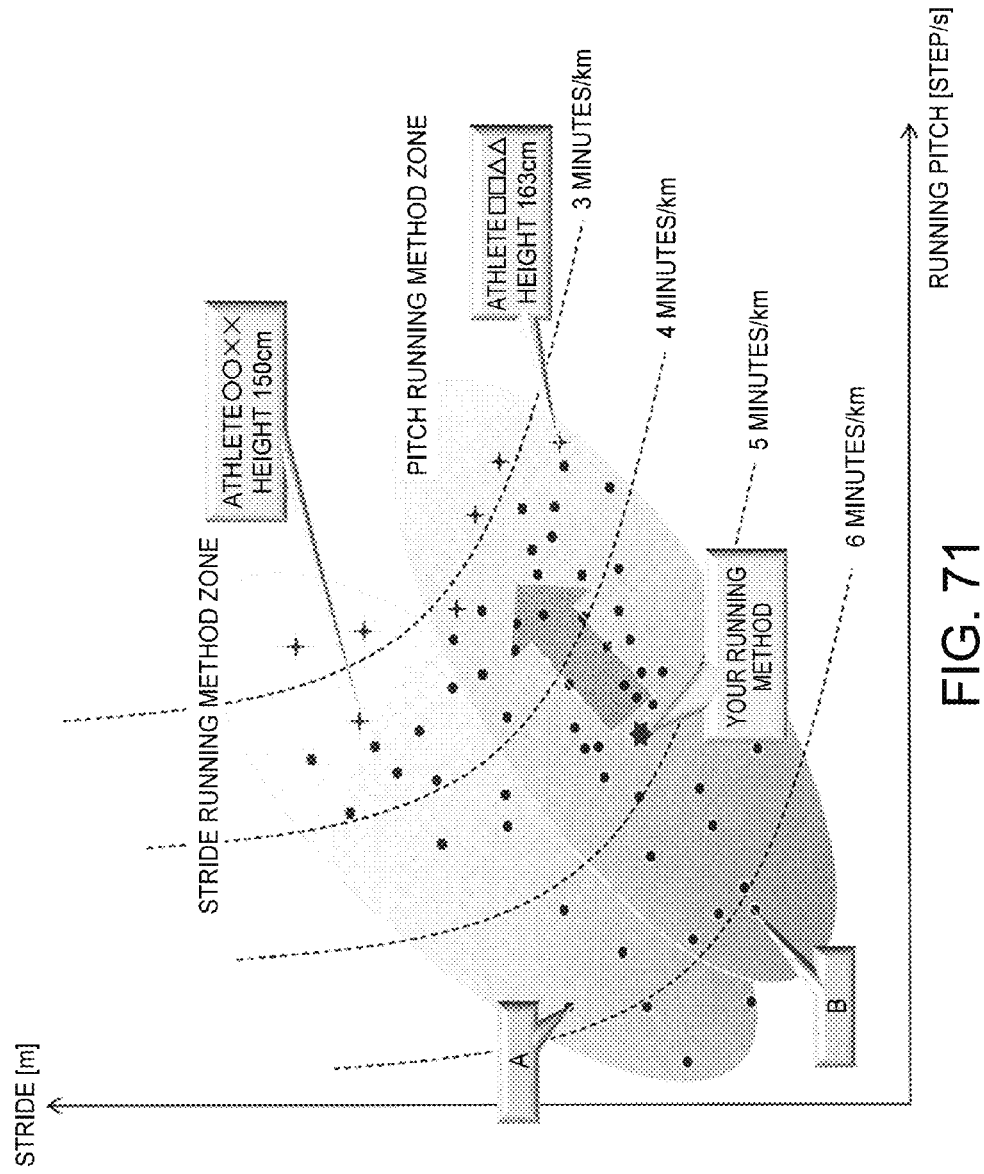
FIG. 71 is a diagram illustrating an example of comparison analysis.

Not only the comparison analysis in the first embodiment or the modification example but also various other comparison analysis may be used. For example, FIG. 71 is a graph in which relationships between running pitches and strides of a plurality of runners are plotted, in which a transverse axis expresses a running pitch [step/s], and a longitudinal axis expresses a stride [m]. FIG. 71 also illustrates a range included in a stride running method (stride running method zone) and a range included in a pitch running method (pitch running method zone). FIG. 71 also illustrates curves corresponding to running velocities of 3 min/km, 4 min/km, 5 min/km, and 6 min/km with dashed lines. A point (shown as "your running method") indicating a running pitch and a stride of the user is included in the pitch running zone, and a running velocity is located between 4 min/km and 5 min/km. The stride running method zone includes "A" who is slower than the user, and an athlete "XX" who is faster than the user, and the pitch running method zone includes "B" who is slower than the user, and an athlete "YY" who is faster than the user. The user can understand the running way at which the user aims by observing the graph having such running method distributions. For example, as indicated by an arrow in FIG. 71, the user can aim at a running velocity of 4 min/km or lower in the running way of increasing the running pitch and the stride without changing the pitch running method.

Figure 72:
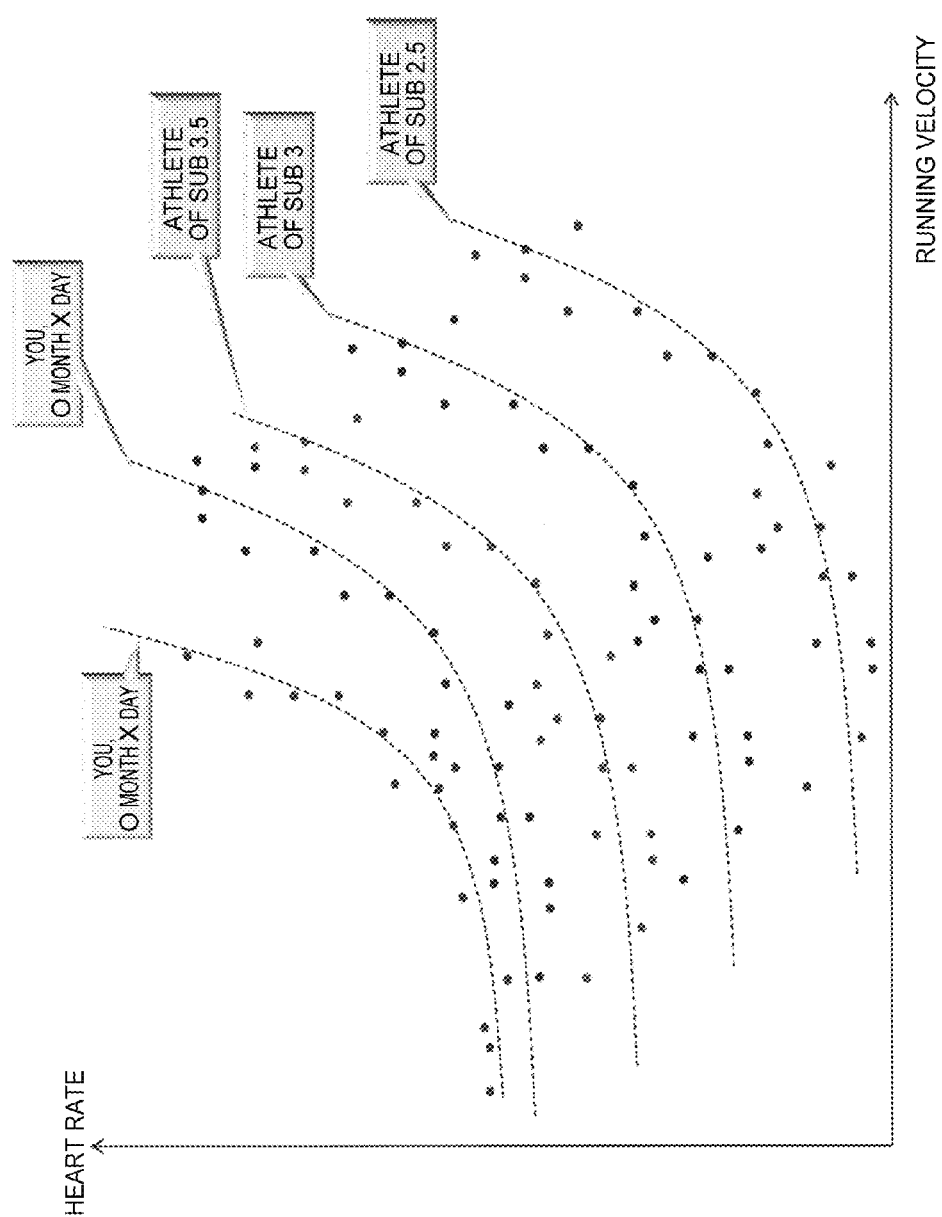
FIG. 72 is a diagram illustrating an example of comparison analysis.

For example, FIG. 72 is a graph in which a relationship between a running velocity and a heart rate in one-time running of a plurality of runners is plotted, a transverse axis expresses the running velocity, and a longitudinal axis expresses the heart rate. FIG. 72 illustrates a curve of the user (shown as "you, O month X day"), a curve of athletes who run a marathon under 3.5 hours (shown as "athletes of sub 3.5"), a curve of athletes who run a marathon under 3 hours (shown as "athletes of sub 3"), and a curve of athletes who run a marathon under 2.5 hours (shown as "athletes of sub 2.5"), obtained by approximating the running velocity and the heart rate during one-time running, with dashed lines. For example, if the curve shifts to the lower right side whenever running is repeatedly performed, the user can recognize that running performance improves since the heart rate does not increase even if the running velocity is high, and can also understand how close to an athlete with a target time the user is.

In the second embodiment, the information analysis apparatus 4 performs an analysis process, but the server 5 may perform the analysis process (may function as the information analysis apparatus) and may transmit analysis information to the notification apparatus 3 via the network.

In the second embodiment, the running data (exercise analysis information) of the user is stored in the database of the server 5, but may be stored in a database built into the storage unit 530 of the information analysis apparatus 4. In other words, the server 5 may be omitted.

3-6. Others

For example, the exercise analysis apparatus 2 or the notification apparatus 3 may compute scores of the user on the basis of the input information or the analysis information, and may notify the user of the computed scores during running or after running. For example, a numerical value of each item (each exercise index) is divided into a plurality of stages (for example, five stages or ten stages), and a score defined for each stage. A user's score in a corresponding stage may be displayed in correlation with the item of any one of the analysis screens. For example, the exercise analysis apparatus 2 or the notification apparatus 3 may score or may compute a total score according to the type or exercise index or the number of exercise indexes with favorable attainments, and may display the score.

In the first embodiment, an example of displaying the animation image 441 has been described, but display of animation or an image is not limited to an aspect of the embodiment. For example, animation for emphasizing a user's exercise tendency may be displayed. For example, in a case where the user's body tilts forward more than an ideal state, an image is displayed in which the user's body tilts forward with an angle which is greater than an actual forward tilt angle. The user can easily understand a user's exercise tendency. The animation image 441 may display information regarding parts other than the arm. A motion of the arm may be unlikely to be estimated on the basis of information from a sensor (the exercise analysis apparatus 2) mounted on the waist. By presenting information limited to body parts of which motions can be estimated on the basis of information from the sensor, the user can understand a user's motion more accurately. For example, a 3D image may be displayed, and the image may be checked from a desired angle through a user's operation.

In the above-described respective embodiments, the GPS unit 50 is provided in the exercise analysis apparatus 2 but may be provided in the notification apparatus 3. In this case, the processing unit 120 of the notification apparatus 3 may receive GPS data from the GPS unit 50 and may transmit the GPS data to the exercise analysis apparatus 2 via the communication unit 140, and the processing unit 20 of the exercise analysis apparatus 2 may receive the GPS data via the communication unit 40 and may add the received GPS data to the GPS data table 320.

In the above-described respective embodiment, the exercise analysis apparatus 2 and the notification apparatus 3 are separately provided, but an exercise analysis apparatus in which the exercise analysis apparatus 2 and the notification apparatus 3 are integrally provided may be used.

In the above-described respective embodiments, the exercise analysis apparatus 2 is mounted on the user but is not limited thereto. For example, an inertial measurement unit (inertial sensor) or a GPS unit may be mounted on the user's body or the like, the inertial measurement unit (inertial sensor) or the GPS unit may transmit a detection result to a portable information apparatus such as a smart phone, an installation type information apparatus such as a personal computer, or a server via a network, and such an apparatus may analyze an exercise of the user by using the received detection result. Alternatively, an inertial measurement unit (inertial sensor) or a GPS unit which is mounted on the user's body or the like may record a detection result on a recording medium such as a memory card, and an information apparatus such as a smart phone or a personal computer may read the detection result from the recording medium and may perform an exercise analysis process.

Figure 73:
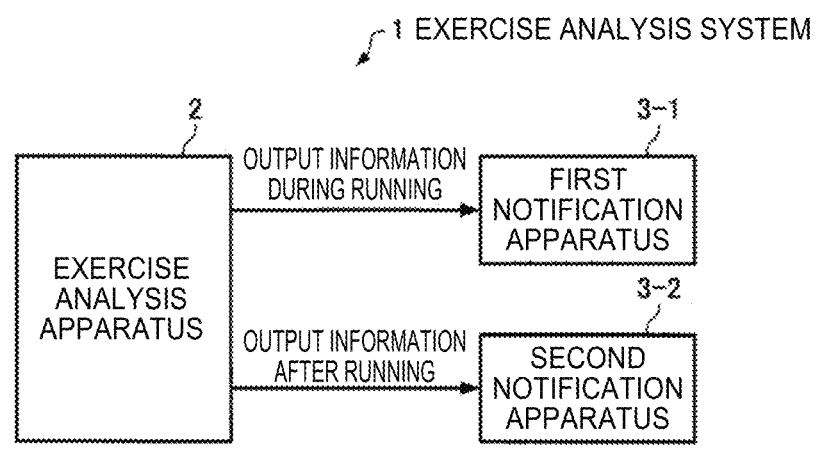
FIG. 73 is a diagram illustrating a configuration example of an exercise analysis system of a modification example.

In the first embodiment, the notification apparatus 3 receives output information during running or output information after running, generates data such as an image, sound, or vibration corresponding to the information, and presents (delivers) the data to the user via the display unit 170, the sound output unit 180, and the vibration unit 190. In other words, the notification apparatus 3 functions as a first notification apparatus (for example, a first display apparatus) which outputs the output information during running which is exercise information satisfying a predetermined condition during the user's running among a plurality of exercise information pieces of the user generated by the exercise analysis apparatus 2, and also functions as a second notification apparatus (for example, a second display apparatus) which outputs the output information after running which is at least one exercise information piece after the user finishes the running among the plurality of exercise information pieces of the user generated by the exercise analysis apparatus 2. However, for example, as illustrated in FIG. 73, the first notification apparatus and the second notification apparatus may be provided separately from each other. In FIG. 73, the exercise analysis system 1 includes the exercise analysis apparatus 2, a first notification apparatus 3-1, and a second notification apparatus 3-2. A configuration of the exercise analysis apparatus 2 may be the same as the configuration of the exercise analysis apparatus 2 illustrated in FIG. 2, and each configuration of the first notification apparatus 3-1 and the second notification apparatus 3-2 may be the same as the configuration of the notification apparatus 3 illustrated in FIG. 2. The first notification apparatus 3-1 may be, for example, a wrist apparatus such as a wrist watch type, or a portable apparatus such as a head mounted display (HMD) or a smart phone. The second notification apparatus 3-2 may be, for example, information apparatus such as a smart phone or a personal computer.

According to the exercise analysis system 1 illustrated in FIG. 73, during the user's running, the first notification apparatus 3-1 outputs output information during running which satisfies a predetermined condition corresponding to a running state among a plurality of exercise information pieces generated by the exercise analysis apparatus 2, and thus the user can easily utilize the presented information during running. The second notification apparatus 3-2 outputs output information after running which is based on some of the exercise information pieces generated by the exercise analysis apparatus 2 during the user's running, after the user finishes running, and thus the user can also easily utilize the presented information after running is finished. Therefore, it is possible to assist the user in improving running attainments.

The above-described respective embodiments and modification examples are only examples, and the invention is not limited thereto. For example, the respective embodiments and modification examples may be combined with each other as appropriate.

The invention includes the substantially same configuration (for example, a configuration having the same function, method, and result, or a configuration having the same object and effect) as the configuration described in the embodiments. The invention includes a configuration in which a non-essential part of the configuration described in the embodiments is replaced. The invention includes a configuration which achieves the same operation and effect or a configuration which can achieve the same object as the configuration described in the embodiments. The invention includes a configuration in which a well-known technique is added to the configuration described in the embodiments.

The entire disclosure of Japanese Patent Application No. 2014-157201, filed Jul. 31, 2014 and No. 2014-157208, filed Jul. 31, 2014 and No. 2015-115213, filed Jun. 5, 2015 are expressly incorporated by reference herein.

What is claimed is:

1. An exercise analysis apparatus comprising:
a feature point detection unit that detects a feature point in a user's running by using a detection result from a single inertial sensor; and
an exercise information generation unit that analyzes the user's running with a timing at which the feature point detection unit detects the feature point as a reference by using the detection result from the single inertial sensor, so as to generate exercise information of the user,
wherein the exercise analysis apparatus is configured to be worn by the user,
wherein the exercise information generation unit calculates values of a plurality of items indicating an exercise state of the user with a timing at which the feature point detection unit detects the feature point as a reference by using the detection result from the single inertial sensor, and generates the exercise information by combining the values of the plurality of items with each other, and
wherein the exercise information includes information regarding energy efficiency, an energy loss, a burden on the body in the user's running, directly-below landing ratio, propulsion efficiency, or a brake amount in landing.

2. The exercise analysis apparatus according to claim 1, wherein the exercise information generation unit generates the exercise information by using a detection result from the single inertial sensor at the timing at which the feature point detection unit detects the feature point.

3. The exercise analysis apparatus according to claim 1, wherein the exercise information generation unit generates the exercise information by using a detection result from the single inertial sensor after the feature point detection unit detects the feature point until the feature point detection unit detects a subsequent feature point.

4. The exercise analysis apparatus according to claim 1, wherein the exercise information generation unit calculates values of a plurality of items indicating an exercise state of the user with a timing at which the feature point detection unit detects the feature point as a reference by using the detection result from the single inertial sensor, and generates the exercise information by combining the values of the plurality of items with each other.

5. The exercise analysis apparatus according to claim 4, wherein the exercise information includes information regarding energy efficiency, an energy loss, or a burden on the body in the user's running.

6. The exercise analysis apparatus according to claim 4, wherein the exercise information includes information regarding directly-below landing ratio, propulsion efficiency, or a brake amount in landing.

7. The exercise analysis apparatus according to claim 1, wherein the exercise information generation unit generates the exercise information separately for left and right sides of the user's body.

8. The exercise analysis apparatus according to claim 1, wherein the exercise information includes information regarding a left and right balance of the user's body.

9. The exercise analysis apparatus according to claim 1, further comprising:
an advice information generation unit that generates information regarding an advice for improving exercise attainments of the user by using the exercise information.

10. The exercise analysis apparatus according to claim 1, wherein the feature point is at least one of landing, stepping, and taking-off.

11. An exercise analysis method comprising:
detecting a feature point in a user's running by using a detection result from a single inertial sensor;
analyzing the user's running with a timing at which the feature point is detected as a reference by using the detection result from the single inertial sensor, so as to generate exercise information of the user; and
calculating values of a plurality of items indicating an exercise state of the user with a timing at which the feature point detection unit detects the feature point as a reference by using the detection result from the single inertial sensor,
wherein the exercise information is generated by combining the values of the plurality of items with each other, and
wherein the exercise information includes information regarding energy efficiency, an energy loss, a burden on the body in the user's running, directly-below landing ratio, propulsion efficiency, or a brake amount in landing.

12. An exercise analysis program causing a computer to execute:
detecting a feature point in a user's running by using a detection result from a single inertial sensor; and
analyzing the user's running with a timing at which the feature point is detected as a reference by using the detection result from the single inertial sensor, so as to generate exercise information of the user
calculating values of a plurality of items indicating an exercise state of the user with a timing at which the feature point detection unit detects the feature point as a reference by using the detection result from the single inertial sensor,
wherein the exercise information is generated by combining the values of the plurality of items with each other, and
wherein the exercise information includes information regarding energy efficiency, an energy loss, a burden on the body in the user's running, directly-below landing ratio, propulsion efficiency, or a brake amount in landing.

* * * * *